US012747237B2

(12) United States Patent
Resnick et al.

(10) Patent No.: US 12,747,237 B2
(45) Date of Patent: Sep. 29, 2026

(54) PYRAZOLYL COMPOUNDS AS KV7 CHANNEL ACTIVATORS

(71) Applicant: Biohaven Therapeutics Ltd., New Haven, CT (US)

(72) Inventors: Lynn Resnick, Pittsburgh, PA (US); James S. Hale, Pittsburgh, PA (US); Charles A. Flentge, Mars, PA (US); Suman Pathi, Pittsburgh, PA (US); Isis J. Amaye, Pittsburgh, PA (US); David A. Mareska, McMurray, PA (US)

(*) Notice: Subject to any disclaimer, the term of this patent is extended or adjusted under 35 U.S.C. 154(b) by 0 days.

(21) Appl. No.: 19/097,371

(22) Filed: Apr. 1, 2025

(65) Prior Publication Data

US 2025/0230152 A1 Jul. 17, 2025

Related U.S. Application Data

(63) Continuation of application No. 18/839,858, filed as application No. PCT/US2023/063111 on Feb. 23, 2023.

(60) Provisional application No. 63/313,208, filed on Feb. 23, 2022.

(51) Int. Cl.

| | |
|---|---|
| ***C07D 231/40*** | (2006.01) |
| ***A61K 31/4155*** | (2006.01) |
| ***A61K 31/427*** | (2006.01) |
| ***C07D 403/04*** | (2006.01) |
| ***C07D 417/04*** | (2006.01) |

(52) U.S. Cl.

CPC ........ *C07D 417/04* (2013.01); *A61K 31/4155* (2013.01); *A61K 31/427* (2013.01); *C07D 231/40* (2013.01); *C07D 403/04* (2013.01)

(58) Field of Classification Search

None

See application file for complete search history.

(56) References Cited

U.S. PATENT DOCUMENTS

| | | | |
|---|---|---|---|
| 7,223,782 | B2 | 5/2007 | Atkinson et al. |
| 7,432,379 | B2 | 10/2008 | Tung et al. |
| 8,614,243 | B2 | 12/2013 | Moreno et al. |
| 9,067,894 | B1 | 6/2015 | Weaver |
| 2003/0105143 | A1 | 6/2003 | Ammendola et al. |
| 2004/0198799 | A1 | 10/2004 | Brondyk et al. |
| 2011/0112073 | A1 | 5/2011 | Thiele et al. |
| 2012/0110702 | A1 | 5/2012 | Yap et al. |
| 2014/0121197 | A1 | 5/2014 | Burli et al. |
| 2019/0032262 | A1 | 1/2019 | Chang |

FOREIGN PATENT DOCUMENTS

| | | | |
|---|---|---|---|
| WO | 2003026649 | A1 | 4/2003 |
| WO | 2005000304 | A1 | 1/2005 |
| WO | 2005048948 | A2 | 6/2005 |
| WO | 2005060970 | A1 | 7/2005 |
| WO | 2006071940 | A2 | 7/2006 |
| WO | 2007053346 | A1 | 5/2007 |
| WO | 2007095340 | A2 | 8/2007 |
| WO | 2008149379 | A2 | 12/2008 |
| WO | 2009065096 | A1 | 5/2009 |
| WO | 2009117080 | A8 | 9/2009 |
| WO | 2009140621 | A2 | 11/2009 |
| WO | 2012061290 | A2 | 5/2012 |
| WO | 2012064715 | A1 | 5/2012 |
| WO | 2014078408 | A1 | 5/2014 |
| WO | 2014078454 | A1 | 5/2014 |
| WO | 2020244637 | A1 | 12/2020 |

OTHER PUBLICATIONS

ACS (American Chemical Society. Chemical Abstract Service. RN 1807519-14-7. Entered into STN: Sep. 16, 2015). (Year: 2015).*

American Chemical Society. Chemical Abstract Service. RN 36198-23-9. Entered into STN: Nov. 16, 1984. (Year: 1984).*

Welsh, William J., Kortagere, Sandhya, et al. "Rapid discovery of inhibitors of Toxoplasma gondii using hybrid structure-based computational approach." J. Comput. Aided Mol. Des. (2011), vol. 25, pp. 403-411. (Year: 2011).*

Szmitko, Paul E., et al. "Plasmodium falciparum malaria occurring 8 years after leaving an endemic area." Diagnostic Microbiology and Infectious Diseases. (2009), vol. 63, pp. 105-107. (Year: 2009).*

PubChem CID 53854593, N-(1-methyl-1H-pyrazol-5-yl)acetamide, Create: Dec. 4, 2011.

Chen, et al., "Interaction of Novel Positive Allosteric Modulators of Metabotropic Glutamate Receptor 5 with the Negative Allosteric Antagonist Site Is Required for Potentiation of Receptor Responses", 2007, pp. 1389-1398, vol. 71, No. 5, Molecular Pharmacology.

De Paulis, et al., "Substituent Effects of N-(1,3-Diphenyl-1 H-pyrazol-5-yl)benzamides on Positive Allosteric Modulation of the Metabotropic Glutamate-5 Receptor in Rat Cortical Astrocytes", May 2, 2006, pp. 3332-3344, vol. 49, No. 11, XP008103364, J. Med. Chem.

Williams Jr, et al., Discovery of Positive Allosteric Modulators of Metabotropic Glutamate Receptor Subtype 5 (mGluR5), 2005, pp. 825-846, vol. 5, XP002672670, Current Topics in Medicinal Chemistry.

Borgini, et al., "Chemical modulation of Kv7 potassium channels", 2021, pp. 483-537, vol. 12, RSC Med. Chem.

Su, et al., "An Efficient One-Pot Synthesis of N-(1,3-Diphenyl-1H-Pyrazol-5-yl)amides", Jul. 2010, pp. 831-837, Wiley InterScience.

* cited by examiner

*Primary Examiner* — John S Kenyon

(74) *Attorney, Agent, or Firm* — Kimberly K. Vines; Stites & Harbison, PLLC

(57) ABSTRACT

Provided herein are optionally substituted pyrazolylacetamides, pharmaceutical compositions comprising a therapeutically effective amount of such compounds and a pharmaceutically acceptable excipient, and methods of treating diseases or disorders, such as, epilepsy, amyotrophic lateral sclerosis, various types of pain, hyperexcitability, a dyskinesia, dystonia, mania, tinnitus, neurodevelopmental diseases or disorders, a smooth muscle contractility disorder, Dravet syndrome, posttraumatic stress disorder (PTSD), with such compounds and pharmaceutical compositions.

10 Claims, No Drawings

PYRAZOLYL COMPOUNDS AS KV7 CHANNEL ACTIVATORS

CROSS-REFERENCE TO RELATED APPLICATIONS

This application claims priority to U.S. Provisional Application No. 63/313,208 filed Feb. 23, 2022, and all the benefits accruing therefrom under 35 U.S.C. § 119, the content of which is incorporated herein in its entirety by reference.

STATEMENT OF FEDERALLY FUNDED RESEARCH

This invention was made with United States Government support under Grant No. U44NS115732 awarded by the National Institute of Neurological Disorders and Stroke of the National Institutes of Health. The United States Government has certain rights in the invention.

BACKGROUND

Potassium ($K^+$) channels, present on the plasma membranes of most cell types, are the most diverse class of all ion channels and are associated with a wide range of physiological functions including the regulation of the electrical properties of excitable cells. The primary pore-forming ($\alpha$) subunits of these highly selective cation channels are divided into three primary structural classes based on the number of transmembrane (TM)-spanning regions and pore (P) regions: currently there are known to be 6TM/1P, 2TM/1P and 4TM/2P $K^+$ channels. The Kv7 genes (originally termed KCNQ, a name assigned by the HUGO Gene Nomenclature Committee (HGNC)) were assigned to a subfamily of voltage-gated $K^+$ channels by the International Union of Pharmacology (IUPHAR). The Kv7 subfamily consists of five homologous pore-forming $\alpha$ subunits, Kv7.1-7.5, that have a structure typical of voltage-gated $K^+$ channels with 6TM-spanning regions (S1-S6) flanked by intracellular N-terminal and C-terminal domains, a typical voltage-sensor domain located in S4 comprised of alternating positively-charged residues and a single P region between S5 and S6 of each subunit. The channels are formed as tetramers of the primary a subunits, either as homotetramers or heterotetramers. Neurons are known to express Kv7 channels comprised of Kv7.2-7.5 $\alpha$ subunits. Some of these gene products may be exclusively neuronal while others, such as Kv7.4 and Kv7.5, can be found in other tissues such as smooth and skeletal muscle.

Native M-channels, and the corresponding macroscopic M-current, were first characterized in amphibian sympathetic neurons. M-channels were notable because they were slowly activating and non-inactivating, active at membrane potentials at or near the resting membrane potential of neurons and muscarinic cholinergic agonists produced a reduction in the M-current, demonstrating a direct and inhibitory link between G-protein coupled receptors (GPCRs) and a physiological $K^+$ current. It was not until the cloning of this subfamily of genes that the pharmacological and biophysical identity was established between Kv7.2/7.3 (and likely Kv7.5/7.3) heteromultimers and the elusive 'M'-channel, providing significant new evidence for their importance in neuronal regulation.

The distributions of these channels, both regionally and developmentally, as well as their biophysical characteristics, support their role in providing enduring resistance to depolarizing excitatory influences. Under physiological conditions, as was demonstrated with native M-channels, they can be very effective at regulating the sub-threshold excitability of certain neuronal populations with significant roles in regulating the frequency and ultimately the pattern of action potential discharge in many types of neurons. Their importance in neuronal regulation was punctuated by the discovery that neuronal Kv7 mutations lead to benign familial neonatal convulsions (BFNC), indicating that reduction or removal of the influence of Kv7.2 and Kv7.3 channels can dramatically alter neuronal excitability. Mutation analyses demonstrated their involvement in BFNC and suggested their utility as targets for anti-epileptic drugs (AEDs).

Unlike established pharmacological terminology for GPCRs, the mode of action of $K^+$ channel modulators, in particular compounds that activate the channel, is still being refined. The application of voltage-clamp techniques to the study of ion channel pharmacology enabled detailed biophysical studies on either whole-cell currents or single channels, allowing some characterization of the nature of compound-channel interactions but not preventing ongoing confusion around the terminology. The term opener or activator is commonly used throughout the literature but does not adequately describe the mode of action of all these 'positive modulator' compounds. In general, openers or activators are expected to increase the open probability of the channel or increase macroscopic current amplitude, but this nomenclature is really too simplistic. For example, ezogabine, the first publicly disclosed Kv7 opener, has a complex and interesting profile in that it has inhibitory activity at higher membrane potentials. Neuronal Kv7 channel openers may work in concert with the activity of a channel over the 'normal' activation-voltage range and enhance currents without significantly affecting the activation threshold while others can significantly alter the activation threshold. In addition, some openers appear to remove the voltage-dependence of activation entirely. Whether these effects represent some continuum is currently unclear since the effects are often concentration-dependent. Clearly, the modes of interaction of compounds that can increase channel current are complex and in most cases not well understood and the implications of these profiles on neuronal responsiveness and systems physiology are also unclear. Ezogabine is modestly potent, not highly specific, but it is a very effective opener of Kv7.2, Kv7.5 and heteromultimeric Kv7 channels. Its effects are characterized by a significant increase in channel current over a narrow voltage range. As mentioned above, at more positive voltages the opener is less effective and under some conditions channel current significantly decreases at more positive voltages relative to control currents (this 'crossover' voltage-dependence of opener action is a characteristic of many neuronal Kv7 channel openers). This effect is also concentration-dependent and is more pronounced at higher concentrations.

There remains a need in new and selective Kv7 channel openers to effectively treat a variety of medical conditions.

SUMMARY

Provided herein are genera and compounds that can be potent for the Kv7.2/7.3 heteromultimer. These compounds may have reduced untoward side effects as compared to ezogabine.

Mutations in Kv7.2, and less commonly in Kv7.3, were reported as the cause of autosomal dominant benign neonatal seizures (BFNS), mainly by haploinsufficiency. BFNS is an idiopathic epilepsy with seizures occurring in the first days of life and is due to mutations in both Kv7.2 and Kv7.3. Kv7.2 and Kv7.3 interact to give a current larger than the individual currents obtained as homomers. In situ hybridization shows that Kv7.2 is mainly present in the cerebellar cortex, the neocortex and the hippocampal formation, including the dentate gyrus. These three structures present distinct epileptic seizure susceptibility. Kv7.3 is localized in the same areas in mouse brain. However, Kv7.2 expression appears earlier than that of Kv7.3 and rapidly increases during the first week of life. At birth, Kv7.3 is expressed in a very low amount whereas Kv7.2 is already expressed at a significant level. Accordingly, different profiles of association of Kv7.2 and Kv7.3 occur during development.

Although BFNS usually bears an excellent long-term prognosis, seizure recurrences later in life have also been described. More recently, it was found that de novo and maternal inheritance mutations in Kv7.2 are responsible for 5%-23% of early infantile epileptic encephalopathies (EIEEs). Kv7.2 encephalopathy often presents in the first week of life with a distinct electroclinical pattern characterized by frequent tonic seizures, with or without autonomic features, and burst-suppression or multifocal epileptiform abnormalities with attenuation on electroencephalography (EEG). Neuroimaging reveals frontal lobe hypoplasia or transient MRI signal abnormalities of the basal ganglia or thalamus in some cases. The neurodevelopmental outcome is poor in all children, even if seizure control with the use of AEDs is achieved in the initial months of life. It has been proposed that the clinical variability of the Kv7.2-related epilepsy could be associated with the functional consequence of mutations on M-current and could thus be predictive of the neurologic prognosis. There is a marked disparity of the impact of the known mutations on Kv7.2 function, which vary on association with Kv7.3 subunits. Density of homomeric channels may be the most reliable property relating Kv7.2 function to encephalopathy. It is hypothesized that homomeric Kv7.2 channels play an essential role for fine-tuning neuronal connections during early brain development and correlates to the severity of the dominant-negative effects of Kv7.2 mutations causative of the encephalopathy.

The compounds of Formula 1 or Table 1, or a pharmaceutically acceptable salt thereof, provided herein are efficacious activators for the Kv7.2 homotetramer, the Kv7.3 homotetramer, the Kv7.2/7.3 heterotetramer, and based on the above expression of the Kv7.2 and Kv7.3 channels, such compounds are effective in the treatment of disorders of early infant development such as Angelman syndrome, neonatal abstinence syndrome, early myoclonic encephalopathy, Landau Kleffner syndrome, electrical status epilepticus during sleep, Ohtahara syndrome, autism spectrum disorders, Dravet syndrome, Lennox-Gastaut syndrome, Rett syndrome, Hirschsprung's disease (HSCR), West syndrome, SCN8A-related epilepsy with encephalopathy (EIEE13), Epilepsy of infancy with migrating focal seizures (EIMFS), Autosomal Dominant Nocturnal Frontal Lobe Epilepsy (ADNFLE), Doose syndrome, and combinations thereof.

In certain embodiments, compounds of Formula 1 or Table 1, or a pharmaceutically acceptable salt thereof, described herein modulates Kv7.2/7.3 and does not modulate $GABA_A$. In certain embodiments, the compounds of Formula 1 or Table 1, or a pharmaceutically acceptable salt thereof, described herein are selective activators of Kv7.2/7.3, having very low or no modulation selectivity to the $\alpha1\beta3\gamma2$ $GABA_A$ receptor.

In some embodiments, the compounds of Formula 1 or Table 1, or a pharmaceutically acceptable salt thereof, described herein are superior to ezogabine as the unwanted, off-target side effects are not present. The unwanted side effects are selected from the group consisting of dizziness, fatigue, drowsiness, confusion, vertigo, tremor, ataxia, double or blurred vision, attention deficit, memory impairment, muscle weakness, skin discoloration, withdrawal seizures, QT interval changes, suicidal behavior, urinary retention, sleepiness, hallucination, confusion, and combinations thereof.

In certain embodiments, compounds of Formula 1 or Table 1, or a pharmaceutically acceptable salt thereof, described herein have increased stability to photo-oxidation as compared to ezogabine. In certain embodiments, the compounds of Formula 1 or Table 1, or a pharmaceutically acceptable salt thereof, described herein have greater potency in activating Kv7 channels as compared to ezogabine. In certain embodiments, the compounds of Formula 1 or Table 1, or a pharmaceutically acceptable salt thereof, described herein have a greater subject tolerability as compared to ezogabine.

DETAILED DESCRIPTION

Before the present compositions and methods are described, it is to be understood that any invention is not limited to the particular processes, compositions, or methodologies described, as these may vary. Moreover, the processes, compositions, and methodologies described in particular embodiments are interchangeable. Therefore, for example, a composition, dosage regimen, route of administration, and so on described in a particular embodiment may be used in any of the methods described in other particular embodiments. It is also to be understood that the terminology used in the description is for the purpose of describing the particular versions or embodiments only, and is not intended to limit the scope of the present invention, which will be limited only by the appended claims. Unless clearly defined otherwise, all technical and scientific terms used herein have the same meanings as commonly understood by one of ordinary skill in the art. Although any methods similar or equivalent to those described herein can be used in the practice or testing of embodiments of the present invention, the preferred methods are now described. All publications and references mentioned herein are incorporated by reference. Nothing herein is to be construed as an admission that the invention is not entitled to antedate such disclosure by virtue of prior invention.

It must be noted that, as used herein, and in the appended claims, the singular forms "a", "an", and "the" include plural reference unless the context clearly dictates otherwise.

As used herein, the term "about" means plus or minus 10% of the numerical value of the number with which it is being used. Therefore, about 50% means in the range of 45%-55%. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

"Administering," when used in conjunction with a therapeutic, means to administer a therapeutic directly into or onto a target tissue or to administer a therapeutic to a subject whereby the therapeutic positively impacts the tissue to which it is targeted. "Administering" a composition may be accomplished by oral administration, injection, infusion, absorption or by any method in combination with other known techniques. "Administering" may include the act of self-administration or administration by another person such as a healthcare provider or a device.

As used herein, the terms "comprising," "comprise," "comprises," and "comprised" are inclusive or open-ended and do not exclude additional, unrecited elements or method steps.

As used herein, the terms "consists of" or "consisting of" means that the composition or method includes only the elements, steps, or ingredients specifically recited in the particular embodiment or claim.

As used herein, the terms "consisting essentially of" or "consists essentially of" means that the composition or method includes only the specified materials or steps and those that do not materially affect the basic and novel characteristics of the claimed invention.

The term "improves" is used to convey that the present invention refers to the overall physical state of an individual to whom an active agent has been administered. For example, the overall physical state of an individual may "improve" if one or more symptoms of a condition, disease or disorder, such as a neurodegenerative disorder, are alleviated by administration of an active agent. "Improves" may also refer to changes in the appearance, form, characteristics, and/or physical attributes of tissue, or any combination thereof, to which it is being provided, applied, or administered.

The term "inhibit," "suppress," "decrease," "interfere," and/or "reduce" (and like terms) generally refers to the act of reducing, either directly or indirectly, a function, activity, or behavior relative to the natural, expected, or average or relative to current conditions.

As used herein, the phrase "Kv7 associated diseases" is a disease, disorder, or condition: associated with a mutation in the KCNQ2 gene; associated with a mutation in the KCNQ3 gene; associated with a mutation in the KCNQ4 gene; associated with a mutation in the KCNQ5 gene; associated with genes encoding Kv7 potassium channels; associated with a non-mutated Kv7 potassium channel, but dysfunctional Kv7 potassium channel; associated with the hyperexcitability of cells that are believed to cause the disease, disorder or condition; or a combination thereof. Regardless of causation, these Kv7 associated diseases, disorders or conditions can be treated by the activation of the Kv7 potassium channel, even though the Kv7 potassium channel may not be a direct or indirect cause of the disease, disorder or condition.

Examples of a Kv7 associated disorder in relation to a mutation in the KCNQ2 gene include but are not limited to benign familial neonatal seizures (BFNS) or KCNQ2 encephalopathy (also known as KCNQ2 neonatal epileptic encephalopathy). Examples of a Kv7 associated disorder in relation to a mutation in the KCNQ3 gene include but are not limited to BFNS or KCNQ3-related developmental disability. Examples of a Kv7 associated disorder in relation to a mutation in the KCNQ4 gene include but are not limited to autosomal dominant nonsyndromic hearing loss. Examples of a Kv7 associated disorder in relation to a mutation in the KCNQ5 gene include but are not limited to nonsyndromic intellectual disability or epileptic encephalopathy. Examples of a disorder associated with the hyperexcitability of cells that are believed to cause the disease, disorder or condition include but are not limited to focal clonic seizures, generalized tonic-clonic seizures, neuropathic pain, overactive bladder; or smooth muscle disorders, or a combination thereof.

In each of the embodiments disclosed herein, the compositions and methods may be utilized with or on a subject in need of such treatment, which may also be referred to as "in need thereof." As used herein, the phrase "in need thereof" means that the subject has been identified as having a need for the particular method or treatment and that the treatment has been given to the subject for that particular purpose.

As used herein, the term "therapeutic" means an agent utilized to treat, combat, ameliorate, or prevent, or any combination thereof, an unwanted condition, disorder or disease, or the side effect thereof, of a subject.

As used herein, the terms "patient" and "subject" are interchangeable and may be taken to mean any living organism, which may be treated with compounds of the present invention. As such, the terms "patient" and "subject" may include, but are not limited to, any non-human mammal or human. In some embodiments, the "patient" or "subject" is an adult, child, infant, or fetus. In some embodiments, the "patient" or "subject" is a human. In some embodiments, the "patient" or "subject" is a mammal, such as a mouse, a rat, other rodents, a rabbit, a dog, a cat, swine, cattle, a sheep, a horse, a non-human primate, or a human.

The terms "therapeutically effective amount" or "therapeutic dose" as used herein are interchangeable and may refer to the amount of an active agent or pharmaceutical compound or composition that elicits a clinical, biological or medicinal response in a tissue, system, animal, individual or human that is being sought by a researcher, veterinarian, medical doctor or other clinical professional. A clinical, biological or medical response may include, for example, one or more of the following: (1) preventing a disease, condition or disorder in an individual that may be predisposed to the disease, condition or disorder but does not yet experience or display pathology or symptoms of the disease, condition or disorder, (2) inhibiting a disease, condition or disorder in an individual that is experiencing or displaying the pathology or symptoms of the disease, condition or disorder or arresting further development of the pathology and/or symptoms of the disease, condition or disorder, and (3) ameliorating a disease, condition or disorder in an individual that is experiencing or exhibiting the pathology or symptoms of the disease, condition or disorder or reversing the pathology and/or symptoms experience or exhibited by the individual.

The terms "treat," "treated," or "treating" may be taken to mean prophylaxis of a specific disorder, disease or condition, alleviation of the symptoms associated with a specific disorder, disease or condition and/or prevention of the symptoms associated with a specific disorder, disease or condition. In some embodiments, the terms refers to slowing the progression of the disorder, disease or condition or alleviating the symptoms associated with the specific disorder, disease or condition. In some embodiments, the terms refer to alleviating the symptoms associated with the specific disorder, disease or condition. In some embodiments, the terms refer to alleviating the symptoms associated with the specific disorder, disease or condition. In some embodiments, the terms refer to restoring function which was impaired or lost due to a specific disorder, disorder or condition.

"Pharmaceutically acceptable salt" is meant to indicate those salts which are, within the scope of sound medical judgment, suitable for use in contact with the tissues of a patient without undue toxicity, irritation, allergic response and the like, and are commensurate with a reasonable benefit/risk ratio. Pharmaceutically acceptable salts are well known in the art. For example, Berge et al. (1977) J. Pharm. Sciences, Vol. 6, 1-19, describes pharmaceutically acceptable salts in detail. A pharmaceutically acceptable "salt" is any acid addition salt, preferably a pharmaceutically acceptable acid addition salt, including, but not limited to, halogenic acid salts such as hydrobromic, hydrochloric, hydrofluoric and hydroiodic acid salt; an inorganic acid salt such as, for example, nitric, perchloric, sulfuric and phosphoric acid salt; an organic acid salt such as, for example, sulfonic acid salts (methanesulfonic, trifluoromethanesulfonic, ethanesulfonic, benzenesulfonic or p-toluenesufonic, acetic, malic, fumaric, succinic, citric, benzoic, gluconic, lactic, mandelic, mucic, pamoic, pantothenic, oxalic and maleic acid salts; and an amino acid salt such as aspartic or glutamic acid salt. The acid addition salt may be a mono- or di-acid addition salt, such as a di-hydrohalogic, di-sulfuric, di-phosphoric or di-organic acid salt. In all cases, the acid addition salt is used as an achiral reagent which is not selected on the basis of any expected or known preference for the interaction with or precipitation of a specific optical isomer of the products of this disclosure.

Unless otherwise indicated, when a compound or chemical structural feature such as aryl is referred to as being "optionally substituted," it includes a feature that has no substituents (i.e. unsubstituted), or a feature that is "substituted," meaning that the feature has one or more substituents. The term "substituent" has the broadest meaning known to one of ordinary skill in the art, and includes a moiety that replaces one or more hydrogen atoms attached to a parent compound or structural feature. In some embodiments, a substituent may be an ordinary organic moiety known in the art, which may have a molecular weight (e.g. the sum of the atomic masses of the atoms of the substituent) of 15 g/mol to 50 g/mol, 15 g/mol to 100 g/mol, 15 g/mol to 150 g/mol, 15 g/mol to 200 g/mol, 15 g/mol to 300 g/mol, or 15 g/mol to 500 g/mol. In some embodiments, a substituent comprises, or consists of: 0-30, 0-20, 0-10, or 0-5 carbon atoms; and 0-30, 0-20, 0-10, or 0-5 heteroatoms, wherein each heteroatom may independently be: N, O, S, Si, F, Cl, Br, or I; provided that the substituent includes one C, N, O, S, Si, F, Cl, Br, or I atom. Examples of substituents include, but are not limited to, alkyl, alkenyl, alkynyl, heteroalkyl, heteroalkenyl, heteroalkynyl, aryl, heteroaryl, hydroxy, alkoxy, aryloxy, acyl, acyloxy, alkylcarboxylate, thiol, alkylthio, cyano, halo, thiocarbonyl, O-carbamyl, N-carbamyl, O-thiocarbamyl, N-thiocarbamyl, C-amido, N-amido, S-sulfonamido, N-sulfonamido, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, amino, etc. The prefix "halo" in the name of any substituent means that one or more halogen atoms may be present in the substituent.

For convenience, the term "molecular weight" is used with respect to a moiety or part of a molecule to indicate the sum of the atomic masses of the atoms in the moiety or part of a molecule, even though it may not be a complete molecule.

The structures associated with some of the chemical names referred to herein are depicted below. These structures may be unsubstituted or substituted. Unless a point of attachment is indicated by , attachment may occur at any position normally occupied by a hydrogen atom.

As used herein, the term "alkyl" has the broadest meaning generally understood in the art, and may include a moiety composed of carbon and hydrogen containing no double or triple bonds. Alkyl may be linear alkyl, branched alkyl, cycloalkyl, or a combination thereof, and in some embodiments, may contain from one to thirty-five carbon atoms. In some embodiments, alkyl may include $C_{1-10}$ linear alkyl, such as methyl ($—CH_3$), methylene ($—CH_2—$), ethyl ($—CH_2CH_3$), ethylene ($—C_2H_4—$), n-propyl ($—CH_2CH_2CH_3$), propylene ($—C_3H_6—$), n-butyl ($—CH_2CH_2CH_2CH_3$), n-pentyl ($—CH_2CH_2CH_2CH_2CH_3$), pentylene ($—CH_2CH_2CH_2CH_2CH_2—$), n-hexyl ($—CH_2CH_2CH_2CH_2CH_2CH_3$), hexylene ($—CH_2CH_2CH_2CH_2CH_2CH_2—$) etc.; $C_{3-10}$ branched alkyl, such as $C_3H_7$ (e.g. iso-propyl), $C_4H_9$ (e.g. branched butyl isomers), $C_5H_{11}$ (e.g. branched pentyl isomers), $C_6H_{13}$ (e.g. branched hexyl isomers), $C_7H_{15}$ (e.g. branched heptyl isomers), etc.; $C_{3-10}$ cycloalkyl, such as $C_3H_5$ (e.g. cyclopropyl), $C_4H_7$ (e.g. cyclobutyl isomers such as cyclobutyl, methylcyclopropyl, etc.), $C_5H_9$ (e.g. cyclopentyl isomers such as cyclopentyl, methylcyclobutyl, dimethylcyclopropyl, etc.), $C_6H_{11}$ (e.g. cyclohexyl isomers), $C_7H_{13}$ (e.g. cycloheptyl isomers), bicyclo[1.1.1]pentane, norborane, etc.; and the like.

With respect to an optionally substituted moiety such as optionally substituted alkyl, a phrase such as "optionally substituted $C_{1-12}$ alkyl" refers to a $C_{1-12}$ alkyl that may be unsubstituted, or may have 1 or more substituents, and does not limit the number of carbon atoms in any substituent. Thus, for example, $CH_2(CH_2)_{11}OCH_3$ is optionally substituted $C_{1-12}$ alkyl because the parent alkyl group has 12 carbon atoms. A phrase such as "$C_{1-12}$ optionally substituted alkyl" refers to unsubstituted $C_{1-12}$ alkyl, or substituted alkyl wherein the alkyl parent and all substituents together have from 1-12 carbon atoms. For example, $CH_2CH_2OCH_3$ is $C_{1-12}$ optionally substituted alkyl because the alkyl group (e.g. ethyl) and the substituent (e.g. methoxy) together contain 3 carbon atoms. Similar conventions may be applied to other optionally substituted moieties such as aryl and heterocyclyl.

Substituents on alkyl may be the same as those described generally above. In some embodiments, substituents on alkyl are independently selected from F, Cl, Br, I, CN, $CO_2H$, —O— alkyl, ester groups, acyl, amine groups, amide groups, phenyl (including fused phenyl resulting optionally substituted alkyl such as indenyl, where the phenyl substituent is fused to the parent alkyl moiety), and may have a molecular weight of about 15 to about 100 or about 500.

As used herein the term "haloalkyl" has the broadest meaning understood in the art, and may include an alkyl group, as defined above, in which at least one hydrogen is replaced with a halogen selected from fluorine, chlorine, bromine and iodine. Examples of "haloalkyl" may include fluoromethyl, difluoromethyl, trifluoromethyl, fluoroethyl, difluoroethyl, trifluoroethyl, etc.

As used herein, the term "hydroxyalkyl" has the broadest meaning understood in the art, and may include an alkyl group, as defined above, in which at least one hydrogen is replaced with hydroxyl (—OH). Examples of "hydroxyalkyl" may include hydroxymethyl, hydroxyethyl, hydroxypropyl, etc.

As used herein, the term "cycloalkyl" has the broadest meaning understood in the art, and may include a group having one or more saturated rings in which all ring members are carbon, such as cyclopropyl, cyclobutyl, cyclopentyl, cyclohexyl, etc.

As used herein, the term "halocycloalkyl" has the broadest meaning understood in the art, and may include a cycloalkyl group, as defined above, in which at least one hydrogen is replaced with a halogen selected from fluorine, chlorine, bromine and iodine. Examples of "halocycloalkyl" may include fluorocyclopropyl, difluorocyclopropyl, fluorocyclobutyl, difluorocyclobutyl, etc.

As used herein, the term "alkanoyl" has the broadest meaning understood in the art, and may include a group having formula "alkyl-C(═O)—", wherein "alkyl" is an alkyl group defined above. Examples of "alkanoyl" may include methylcarbonyl, ethylcarbonyl, propylcarbonyl, etc.

As used herein, the term "alkenyl" has the broadest meaning understood in the art, and may include a straight or branched chain, monovalent hydrocarbon group having at least one carbon-carbon double bond. Examples of "alkenyl" may include ethenyl, propenyl, butenyl, butadienyl, etc.

As used herein, the term "aryl" has the broadest meaning generally understood in the art, and may include an aromatic ring or aromatic ring system such as phenyl, naphthyl, dihydroindene, etc.

As used herein, the term "haloaryl" has the broadest meaning generally understood in the art, and may include an aryl group, as defined above, in which at least one hydrogen is replaced with a halogen selected from fluorine, chlorine, bromine and iodine. Examples of "haloaryl" may include fluorophenyl, chlorophenyl, iodophenyl, etc.

The term "heterocyclyl" includes any ring or ring system containing a heteroatom such as N, O, S, P, etc. Heterocyclyl includes heteroaryl rings or ring systems (such as those listed below) and non-aromatic rings or ring systems. Examples of non-aromatic heterocyclyl include azetidinyl, oxatanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxalanyl, dithiolanyl, tetrahydropyranyl, piperidinyl, piperazinyl, morpholino, etc.

The term "heteroaryl" also has the meaning understood by a person of ordinary skill in the art, and includes an "aryl" which has one or more heteroatoms in the ring or ring system, such as pyridinyl, furyl, thienyl, oxazolyl, thiazolyl, imidazolyl, thiophenyl, pyrazolyl, triazolyl, oxadiazolyl, isoxazolyl, indolyl, indazolyl, indenyl, thiodiazolyl, quinolinyl, benzofuranyl, benzothienyl, benzooxazolyl, benzothiazolyl, benzoimidazolyl, benzoisoxazolyl, pyridinyl, methylpyridinone, etc.

As used herein, the term "carbocyclyl" has the broadest meaning generally understood in the art and includes rings free of heteroatoms, such as cycloalkyl, e.g. cyclopropyl, cyclobutyl, cyclopentyl, cyclohexyl, etc.; cycloalkenyl, e.g. cyclopropenyl, cyclobutenyl, cyclopentenyl, cyclohexenyl; cycloalkynyl, e.g. cyclopropynyl, cyclobutynyl, cyclopentynyl, cyclohexynyl; bridged cycloalkyl, e.g. bicyclo[1.1.1]pentane, norborane, etc.; as well as aryl rings free of heteroatoms.

The recited group ranges include all groups contained therein having a specific number of carbon atoms. For example, the term "$C_{1-4}$alkyl" includes $C_1$ alkyl, $C_2$ alkyl, $C_3$ alkyl, and $C_4$ alkyl groups, the term "$C_{3-8}$ cycloalkyl" includes $C_3$ cycloalkyl, $C_4$ cycloalkyl, $C_5$ cycloalkyl, $C_6$ cycloalkyl, $C_7$ cycloalkyl, and $C_8$ cycloalkyl groups, and the term "$C_{2-8}$ heterocyclyl" includes $C_2$ heterocyclyl, $C_3$ heterocyclyl, $C_4$ heterocyclyl, $C_5$ heterocyclyl, $C_6$ heterocyclyl, $C_7$ heterocyclyl, and $C_8$ heterocyclyl groups. It is therefore understood that the recitation "$C_{1-4}$ alkyl" is equivalent to the recitation "$C_1$ alkyl, $C_2$ alkyl, $C_3$ alkyl, $C_4$ alkyl", the recitation "$C_{3-8}$ cycloalkyl" is equivalent to the recitation "$C_3$ cycloalkyl, $C_4$ cycloalkyl, $C_5$ cycloalkyl, $C_6$ cycloalkyl, $C_7$ cycloalkyl, $C_8$ cycloalkyl", and the recitation "$C_{2-8}$ heterocyclyl" is equivalent to the recitation "$C_2$ heterocyclyl, $C_3$ heterocyclyl, $C_4$ heterocyclyl, $C_5$ heterocyclyl, $C_6$ heterocyclyl, $C_7$ heterocyclyl, $C_8$ heterocyclyl".

If stereochemistry is not indicated, a name or structural representation includes any stereoisomer or any mixture of stereoisomers and Applicant reserves the right to specifically identify and claim a compound as a single stereoisomer or any particular mixture of stereoisomers.

Compounds described herein may contain an asymmetric center and may thus exist as enantiomers. Where the compounds according to embodiments herein possess two or more asymmetric centers, they may additionally exist as diastereomers. Embodiments herein include all such possible stereoisomers as substantially pure resolved enantiomers, racemic mixtures thereof, as well as mixtures of diastereomers. In some embodiments, the formulas are shown without a definitive stereochemistry at certain positions. Embodiments herein include all stereoisomers of such formulas and pharmaceutically acceptable salts thereof. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general formula may be obtained by stereospecific or stereoselective synthesis using optically pure or enantioenriched starting materials or reagents of known configuration. The scope of embodiments herein as described and claimed encompasses the racemic forms of the compounds as well as the individual enantiomers, diastereomers, and stereoisomer-enriched mixtures and Applicant reserves the right to specifically identify and claim a compound in any such form.

The compounds disclosed herein can exist as and therefore include all stereoisomers, conformational isomers and mixtures thereof in all proportions as well as isotopic forms such as deuterated compounds and Applicant reserves the right to specifically identify and claim a compound in any such form.

In some embodiments of the invention, one or more hydrogen atoms is replaced by a deuterium. It is well established that deuteration of physiologically active compounds offer the advantage of retaining the pharmacological profile of their hydrogen counterparts while positively impacting their metabolic outcome. Selective replacement of one or more hydrogen with deuterium, in a compound of the present invention, could improve the safety, tolerability and efficacy of the compound when compared to its all hydrogen counterpart.

Methods for incorporation of deuterium into compounds are well established. Using metabolic studies established in the art, the compound of the present invention can be tested to identify sites for selective placement of a deuterium isotope, wherein the isotope will not be metabolized. Moreover these studies identify sites of metabolism as the location where a deuterium atom would be placed.

Compounds

Some embodiments of the present invention include a compound represented by Formula 1:

Formula 1

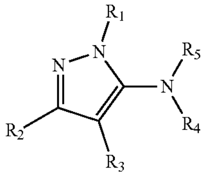

wherein:

$R_1$ is optionally substituted $C_{1-4}$ alkyl, optionally substituted $C_{3-8}$ cycloalkyl, optionally substituted $C_{5-10}$ aryl, optionally substituted $C_{2-8}$ heteroaryl, optionally substituted $C_{2-8}$ heterocyclyl, or optionally substituted —C(O)NH$C_{1-4}$ alkyl, wherein each optional substituent is independently selected from the group consisting of halogen, OH, CN, —C(O)$NH_2$, —N($C_{1-4}$ alkyl)$_2$, $C_{1-4}$ alkyl, $C_{5-10}$ aryl, and $C_{5-10}$ haloaryl;

$R_2$ is H, halogen, optionally substituted $C_{1-8}$ alkyl, optionally substituted $C_{1-8}$ haloalkyl, optionally substituted —O$C_{1-8}$ alkyl, optionally substituted $C_{2-8}$ alkanoyl, optionally substituted $C_{3-10}$ cycloalkyl, optionally substituted benzo($C_{3-8}$ cycloalkyl), optionally substituted $C_{5-10}$ aryl, optionally substituted benzoyl, optionally substituted —O$C_{5-10}$ aryl, optionally substituted $C_{2-8}$ heteroaryl, or optionally substituted —O$C_{2-8}$ heteroaryl, wherein each optional substituent is independently selected from the group consisting of halogen, OH, CN, $CO_2H$, $C_{1-4}$ alkyl, $C_{1-4}$ hydroxyalkyl, $C_{1-4}$ haloalkyl, —O$C_{1-4}$ alkyl, —O$C_{1-4}$ haloalkyl, $C_{3-8}$ cycloalkyl, $C_{3-8}$ halocycloalkyl, —$CO_2H$, —$SO_2C_{1-4}$ alkyl, —$SO_2C_{1-4}$ haloalkyl, $C_{5-10}$ aryl, and $C_{5-10}$ haloaryl, —N($C_{1-4}$ alkyl)$_2$, —N$C_{1-4}$ alkyl, or optionally substituted $C_{2-8}$ heterocyclyl;

$R_3$ is H, halogen, optionally substituted $C_{1-6}$ alkyl, optionally substituted $C_{3-8}$ cycloalkyl, optionally substituted $C_{2-8}$ heterocyclyl, or optionally substituted $C_{5-10}$ aryl, wherein each optional substituent is independently selected from the group consisting of halogen, OH, N($R_7$)($R_8$) wherein $R_7$ and $R_8$ are independently H or $C_{1-4}$ alkyl and wherein $R_7$ and $R_8$ are optionally connected to form a ring, CN, $C_{1-4}$ alkyl, $C_{1-4}$ hydroxyalkyl, and $C_{1-4}$ haloalkyl;

$R_4$ is H, $C_{1-3}$ alkyl, $C_{3-6}$ cycloalkyl, or $C_{1-4}$ hydroxyalkyl;

$R_5$ is

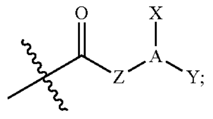

A is $C_{1-8}$ alkyl, $C_{2-8}$ alkenyl, $C_{3-8}$ cycloalkyl, $C_{5-10}$ bicycloalkyl, $C_{2-5}$ heterocyclyl, $C_{5-10}$ aryl, or $C_{2-8}$ heteroaryl;

X is H, F, Cl, optionally substituted $C_{1-6}$ alkyl, optionally substituted $C_{3-8}$ cycloalkyl, optionally substituted —O$C_{1-6}$ alkyl, optionally substituted $C_{2-5}$ heterocyclyl, or optionally substituted $C_{5-10}$ aryl, wherein each optional substituent is independently selected from the group consisting of halogen, OH, $C_{1-3}$ alkyl, $C_{1-3}$ haloalkyl, —O$C_{1-3}$ alkyl, $C_{3-8}$ cycloalkyl, $C_{3-8}$ halocycloalkyl, and CN.

Y is H, halogen, OH, optionally substituted $C_{1-3}$ alkyl, optionally substituted $C_{3-6}$ cycloalkyl, optionally substituted —O$C_{1-3}$ alkyl, optionally substituted $C_{1-3}$haloalkyl, or optionally substituted —O$C_{1-3}$ haloalkyl, wherein each optional substituent is independently selected from the group consisting of halogen, OH, $C_{1-3}$ alkyl, $C_{1-3}$ haloalkyl, —O$C_{1-3}$ alkyl, $C_{3-8}$ cycloalkyl, $C_{3-8}$ halocycloalkyl, and CN;

Z is a bond, C($R_6$)$_2$, N$R_6$, O, C($R_6$)$_2$N$R_6$, C($R_6$)$_2$O, N$R_6$C($R_6$)$_2$, or OC($R_6$)$_2$; and $R_6$ is H, $C_{1-3}$ alkyl, or $C_{1-4}$ hydroxyalkyl;

or a pharmaceutically acceptable salt thereof.

In some embodiments of Formula 1, $R_1$ may be $C_{1-4}$ alkyl or $C_{3-8}$ cycloalkyl, each optionally substituted as stated above.

In some embodiments, $R_2$ may be optionally substituted $C_{3-10}$ cycloalkyl.

In some embodiments, $R_3$ may be $C_{1-6}$ alkyl or $C_{3-8}$ cycloalkyl, each optionally substituted as stated above.

In some embodiments, $R_4$ may be H.

In some embodiments, $R_5$ may be

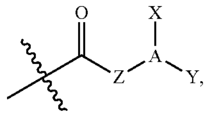

wherein A may be $C_{1-8}$ alkyl or $C_{3-8}$ cycloalkyl.

In some embodiments of Formula 1, $R_1$ may be optionally substituted $C_{1-4}$ alkyl or optionally substituted $C_{3-8}$ cycloalkyl;

$R_2$ may be optionally substituted $C_{3-6}$ cycloalkyl;

$R_3$ may be optionally substituted $C_{1-4}$ alkyl or optionally substituted $C_{3-6}$ cycloalkyl;

$R_4$ may be H; and $R_5$ may be

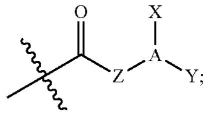

wherein

A may be $C_{1-4}$ alkyl or $C_{3-6}$ cycloalkyl;

X may be H, F, optionally substituted $C_{1-6}$ alkyl or optionally substituted $C_{3-8}$ cycloalkyl, Y may be H or halogen; and Z may be a bond, C($R_6$)$_2$, N$R_6$, and O, wherein $R_6$ may be as defined above.

In some of these embodiments of Formula 1, $R_1$ may be optionally substituted $C_{1-4}$ alkyl. In some other embodiments, $R_1$ may be optionally substituted $C_{3-8}$ cycloalkyl. $R_2$ may be $C_{3-6}$ cycloalkyl substituted with at least one F. $R_3$ may be $C_{1-4}$ alkyl or $C_{3-6}$ cycloalkyl.

As far as the scope of Formula 1 is concerned, each chemical group listed in the definition of any of the substituents $R_1$, $R_2$, $R_3$, $R_4$, $R_5$, $R_6$, $R_7$, $R_8$, A, X, Y, and Z may be combined with any chemical group listed for any other substituent selected from $R_1$, $R_2$, $R_3$, $R_4$, $R_5$, $R_6$, $R_7$, $R_8$, A, X, Y, and Z. Thus, any groups selected from each of $R_1$, $R_2$, $R_3$, $R_4$, $R_5$, $R_6$, $R_7$, $R_8$, A, X, Y, and Z based on their definitions may form a subgenus of Formula 1 which falls within the scope of the present inventive concept. Even though, for practical reasons, all possibilities of such combinations are not explicitly recited herein, based on the description of Formula 1, a person of ordinary skill in the art would readily understand that any subgenus of Formula 1 including any possible combination of substituents $R_1$, $R_2$, $R_3$, $R_4$, $R_5$, $R_6$, $R_7$, $R_8$, A, X, Y, and Z is within the scope of Formula 1, and is therefore, a part of the present inventive concept.

Some embodiments of Formula 1 are further illustrated by Compounds 1-574 shown in Table 1, or a pharmaceutically acceptable salt thereof.

In some embodiments, provided herein are any one of Compounds 1-574 shown in Table 1, or a pharmaceutically acceptable salt thereof.

Pharmaceutical Compositions

Embodiments herein are directed to pharmaceutical compositions comprising a therapeutically effective amount of a compound described herein or acceptable salts thereof, such as a compound of Formula 1 or Table 1, or pharmaceutically acceptable salts thereof. Pharmaceutical formulations containing such compounds and a suitable carrier can be in various forms including, but not limited to, solids, solutions, powders, fluid emulsions, fluid suspensions, semi-solids, and dry powders including an effective amount of a compound of the invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, antioxidants, preservatives and the like. The means and methods for administration are known in the art and an artisan can refer to various pharmacologic references for guidance. For example, Modern Pharmaceutics, Banker & Rhodes, Marcel Dekker, Inc. (1979); and Goodman & Gilman's, The Pharmaceutical Basis of Therapeutics, 6th Edition, MacMillan Publishing Co., New York (1980) both of which are hereby incorporated by reference in their entireties can be consulted.

In some embodiments, a single unit dose of a compound of Formula 1 or Table 1, or a pharmaceutically acceptable salt thereof, is selected from the group consisting of about 0.1 mg to about 1,500 mg, about 1 mg to about 1,500 mg, about 10 mg to about 1,500 mg, about 50 mg to about 1,500 mg, about 75 mg to about 1,500 mg, about 100 mg to about 1,500 mg, about 125 mg to about 1,500 mg, about 150 mg to about 1,500 mg, about 175 mg to about 1,500 mg, about 200 mg to about 1,500 mg, about 225 mg to about 1,500 mg, about 250 mg to about 1,500 mg, about 275 mg to about 1,500 mg, about 300 mg to about 1,500 mg, about 400 mg to about 1,500 mg, about 450 mg to about 1,500 mg, about 500 mg to about 1,500 mg, about 600 mg to about 1,500 mg, about 700 mg to about 1,500 mg, about 800 mg to about 1,500 mg, about 1,000 mg to about 1,500 mg, and about 1,200 mg to about 1,500 mg.

In some embodiments, a single unit dose amount of a compound of Formula 1 or Table 1, or a pharmaceutically acceptable salt thereof, is selected from group consisting of about 25 mg to about 5,000 mg, about 50 mg to about 5,000 mg, about 100 mg to about 5,000 mg, about 150 mg to about 5,000 mg, about 200 mg to about 5,000 mg, about 250 mg to about 5,000 mg, about 300 mg to about 5,000 mg, about 400 mg to about 5,000 mg, about 450 mg to about 5,000 mg, about 100 mg to about 3,000 mg, about 150 mg to about 3,000 mg, about 200 mg to about 3,000 mg, about 250 mg to about 3,000 mg, about 300 mg to about 3,000 mg, about 400 mg to about 3,000 mg, 450 mg to about 3,000 mg, about 100 mg to about 1,000 mg, about 150 mg to about 1,000 mg, about 200 mg to about 1,000 mg, about 250 mg to about 1,000 mg, about 300 mg to about 1,000 mg, about 400 mg to about 1,000 mg, about 450 mg to about 1,000 mg, about 500 mg to about 1000 mg, and about 600 mg to about 1,000 mg. In some embodiments, the single unit dose amount may be 10 mg/day to 1,500 mg/day, or about 100 mg/day to 600 mg/day. In some embodiments, such single unit doses may be administered once per day or multiple times per day, such as twice per day or three times per day.

In some embodiments, the single unit dose further comprises a pharmaceutically acceptable carrier.

The compounds can be formulated for parenteral or intravenous administration by injection, e.g., by bolus injection or continuous infusion. Formulations for injection can be presented in unit dosage form, e.g., in ampoules or in multi-dose containers, with an added preservative. The compositions can take such forms as suspensions, solutions, or emulsions in oily or aqueous vehicles, and can contain formulatory agents such as suspending, stabilizing, and/or dispersing agents.

Injectable preparations may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution.

Other embodiments include a compound prepared as described above which are formulated as a solid dosage form for oral administration including capsules, tablets, pills, powders, and granules. In such embodiments, the active compound may be admixed with one or more inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents and can additionally be prepared with enteric coatings.

Preparation of a composition of the invention in solid dosage form may vary. For example, in one embodiment, a liquid or gelatin formulation may be prepared by combining a compound, such as those described above, and adding a thickening agent to the liquid mixture to form a gelatin. The gelatin may then be encapsulated in unit dosage form to form a capsule. In another exemplary embodiment, an oily preparation of a compound prepared as described above may be lyophilized to for a solid that may be mixed with one or more pharmaceutically acceptable excipient, carrier or diluent to form a tablet.

Further embodiments which may be useful for oral administration of a compound for the invention include liquid dosage forms. In such embodiments, a liquid dosage may include a pharmaceutically acceptable emulsion, solution, suspension, syrup, and elixir containing inert diluents commonly used in the art, such as water. Such compositions may also comprise adjuvants, such as wetting agents, emulsifying and suspending agents, and sweetening, flavoring, and perfuming agents.

In still further embodiments, the compounds described herein can be formulated as a depot preparation. Such long-acting formulations can be administered by implantation (for example, subcutaneously or intramuscularly) or by intramuscular injection. Depot injections can be administered at about 1 to about 6 months or longer intervals. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Methods of Use

Some embodiments of the present invention relate to a method of treating a disease or disorder comprising administering a therapeutically effective amount of a compound of Formula 1 or Table 1, or pharmaceutically acceptable salt thereof, to a subject in need thereof, wherein the disease or disorder is selected from a Kv7 associated disorder, a disorder associated with a KCNQ subunit, a disorder associated with a mutation in a KCNQ subunit, a neurodegenerative disease, a disease or disorder that would benefit from the activation of a Kv7.2 homomer, a neurodevelopmental disease or disorder, or a disease or disorder of Group CA.

Some embodiments of the present invention relate to a method of treating a Kv7 associated disorder comprising administering a therapeutically effective amount of a compound of Formula 1 or Table 1, or a pharmaceutically acceptable salt thereof, to a subject in need thereof. The Kv7 associated disorder is selected from the group consisting of epilepsy, neonatal spasms, pain, migraine, a disorder of neurotransmitter release, a smooth muscle contractility disorder, a dyskinesia, dystonia, mania, a hearing disorder, neuropathic pain, inflammatory pain, persistent pain, cancer pain, postoperative pain, anxiety, substance abuse, schizophrenia, a bladder disorder, a vasculature disorder, tinnitus, benign familial neonatal seizures, epilepsy, neurological disease via reduced basal M-current (and subsequent neuronal hyperexcitability), sensorineural hearing impairment, intellectual disability, epileptic encephalopathy, treatment-resistant epilepsy, cortical atrophy, neurological impairment, infantile spasms with hypsarrhythmia, myoclonic-tonic seizures, myoclonic seizures, tonic seizures, absence and focal-onset seizures with impaired awareness, congenital neurological disorder with intellectual disability or epileptic encephalopathy, benign familial neonatal convulsions, severe epileptic encephalopathies, congenital neurodevelopmental disorder with phenotypes of nonsyndromic intellectual disability or epileptic encephalopathy, neonatal spasms, neonatal seizures, epileptic encephalopathy, benign familial neonatal convulsions type 1, benign familial neonatal seizures 1, neonatal seizures associated with hypoxic-ischemic injury, epileptic spasms, epileptic encephalopathy, early infantile epileptic encephalopathy 7, early infantile epileptic encephalopathy with delayed psychomotor development, generalized tonic seizures, abnormal globus pallidus morphology, apnea, cerebral edema, dystonia, facial erythema, muscular hypotonia, febrile seizures, hypoplasia of the corpus callosum, hypsarrhythmia, focal clonic seizure, generalized tonic-clonic seizures, myokymia, spastic tetraparesis, gynecological system disorders, and combinations thereof. In some embodiments, the wherein the Kv7 associated disorder is selected from epilepsy, neonatal spasms, pain, migraine, a disorder of neurotransmitter release, a smooth muscle contractility disorder, a dyskinesia, dystonia, mania, a hearing disorder, neuropathic pain, inflammatory pain, persistent pain, cancer pain, postoperative pain, anxiety, substance abuse, schizophrenia, a bladder disorder, a vasculature disorder, tinnitus, frontotemporal dementia (FTD), familial FTD, or amyotrophic lateral sclerosis. In embodiments, such compound may be administered in a pharmaceutical composition as described herein.

In some embodiments, the gynecological system disorders are selected from the group consisting of pre-term labor, post-partum hemorrhage, uterine atony, uterine perforation, uterine hyper-stimulation, menorrhagia, metrorrhagia, menometrorrhagia, dysmenorrhea and endometriosis.

KCNQ genes encode five Kv7 potassium channel subunits (1-5). A functional Kv7 potassium channel can be assembled using a combination of these five subunits arranged as homotetramers or heterotetramers. KCNQ2, KCNQ3, KCNQ4, and KCNQ5 are expressed in the nervous system and have been associated with a range of disorders involving neuronal excitability.

Embodiments herein are directed to methods of treating a disorder associated with a KCNQ subunit comprising administering a therapeutically effective amount of a compound of Formula 1 or Table 1, or a pharmaceutically acceptable salt thereof, to a subject in need thereof. Embodiments herein are directed to methods of treating a disorder associated with a KCNQ2 subunit comprising administering a therapeutically effective amount of a compound of Formula 1 or Table 1, or a pharmaceutically acceptable salt thereof, to a subject in need thereof. Embodiments herein are directed to methods of treating a disorder associated with a KCNQ3 subunit comprising administering a therapeutically effective amount of a compound of Formula 1 or Table 1, or a pharmaceutically acceptable salt thereof, to a subject in need thereof. Embodiments herein are directed to methods of treating a disorder associated with a KCNQ4 subunit comprising administering a therapeutically effective amount of a compound of Formula 1 or Table 1, or a pharmaceutically acceptable salt thereof, to a subject in need thereof. Embodiments herein are directed to methods of treating a disorder associated with a KCNQ5 subunit comprising administering a therapeutically effective amount of a compound of Formula 1 or Table 1, or a pharmaceutically acceptable salt thereof, to a subject in need thereof.

Embodiments herein are directed to methods of treating a disorder associated with a mutation in a KCNQ subunit comprising administering a therapeutically effective amount of a compound of Formula 1 or Table 1, or a pharmaceutically acceptable salt thereof, to a subject in need thereof. In some embodiments the disorder associated with a mutation in a KCNQ subunit is a disorder associated with a KCNQ2 mutation. In some embodiments the disorder associated with a mutation in a KCNQ subunit is a disorder associated with a KCNQ3 mutation. In some embodiments the disorder associated with a mutation in a KCNQ subunit is a disorder associated with a KCNQ4 mutation. In some embodiments the disorder associated with a mutation in a KCNQ subunit is a disorder associated with a KCNQ5 mutation. In some embodiments the disorder associated with a mutation in a KCNQ subunit wherein the disorder associated with a mutation in a KCNQ subunit is selected from the group consisting of a disorder associated with a KCNQ2 mutation, a disorder associated with a KCNQ3 mutation, a disorder associated with a KCNQ4 mutation, or a disorder associated with a KCNQ5 mutation, and combinations thereof.

Embodiments herein are directed to methods of treating a disorder associated with a mutation in a KCNQ2 subunit comprising administering a therapeutically effective amount of a compound of Formula 1 or Table 1, or a pharmaceutically acceptable salt thereof, to a subject in need thereof. Embodiments herein are directed to methods of treating a disorder associated with a mutation in a KCNQ3 subunit comprising administering a therapeutically effective amount of a compound of Formula 1 or Table 1, or a pharmaceutically acceptable salt thereof, to a subject in need thereof.

Embodiments herein are directed to methods of treating a disorder associated with a mutation in a KCNQ4 subunit comprising administering a therapeutically effective amount of a compound of Formula 1 or Table 1, or a pharmaceutically acceptable salt thereof, to a subject in need thereof. Embodiments herein are directed to methods of treating a disorder associated with a mutation in a KCNQ5 subunit comprising administering a therapeutically effective amount of a compound of Formula 1 or Table 1, or a pharmaceutically acceptable salt thereof, to a subject in need thereof.

Compounds described herein have been shown to activate the Kv7 potassium channel. Mutations in the gene, KCNQ3, which encodes the Kv7 potassium channel result in a wide range of disorders. Embodiments herein are directed to methods of treating a disorder associated with a KCNQ3 mutation comprising administering a therapeutically effective amount of a compound of Formula 1 or Table 1, or a pharmaceutically acceptable salt thereof, to a subject in need thereof. The disorder associated with a KCNQ3 mutation is selected from the group consisting of benign familial neonatal seizures, epilepsy, neurological disease via reduced basal M-current (and subsequent neuronal hyperexcitability), and any combination thereof.

Compounds described herein have been shown to activate the Kv7 potassium channel. Mutations in the gene, KCNQ4, which encodes the Kv7 potassium channel result in a wide range of disorders. Embodiments herein are directed to methods of treating a disorder associated with a KCNQ4 mutation comprising administering a therapeutically effective amount of a compound of Formula 1 or Table 1, or a pharmaceutically acceptable salt thereof, to a subject in need thereof. The disorder associated with a KCNQ4 mutation is sensorineural hearing impairment.

Compounds described herein have been shown to activate the Kv7 potassium channel. Mutations in the gene, KCNQ5, which encodes the Kv7 potassium channel result in a wide range of disorders. Embodiments herein are directed to methods of treating a disorder associated with a KCNQ5 mutation comprising administering a therapeutically effective amount of a compound of Formula 1 or Table 1, or a pharmaceutically acceptable salt thereof, to a subject in need thereof. The disorder associated with a KCNQ5 mutation is selected from the group consisting of intellectual disability, epileptic encephalopathy, treatment-resistant epilepsy, cortical atrophy, neurological impairment, infantile spasms with hypsarrhythmia, myoclonic-tonic seizures, myoclonic seizures, tonic seizures, absence and focal-onset seizures with impaired awareness, congenital neurological disorder with intellectual disability or epileptic encephalopathy, benign familial neonatal convulsions, severe epileptic encephalopathies, congenital neurodevelopmental disorder with phenotypes of nonsyndromic intellectual disability or epileptic encephalopathy, and any combination thereof.

Compounds described herein have been shown to activate the Kv7 potassium channel. Mutations in the gene, KCNQ2, which encodes the Kv7 potassium channel result in a wide range of disorders. Embodiments herein are directed to methods of treating a disorder associated with a KCNQ2 mutation comprising administering a therapeutically effective amount of a compound of Formula 1 or Table 1, or a pharmaceutically acceptable salt thereof, to a subject in need thereof. The disorder associated with a KCNQ2 mutation is selected from the group consisting of neonatal spasms, neonatal seizures, epilepsy, benign familial neonatal epilepsy (KCNQ2-BFNE), epileptic encephalopathy (KCNQ2-NEE), benign familial neonatal convulsions type 1 (BFNC), benign familial neonatal seizures 1 (BFNS1), neonatal seizures associated with hypoxic-ischemic injury, epileptic spasms, epileptic encephalopathy, early infantile epileptic encephalopathy 7 (EIEE7), early infantile epileptic encephalopathy with delayed psychomotor development, generalized tonic seizures, abnormal globus pallidus morphology, apnea, cerebral edema, dystonia, facial erythema, muscular hypotonia, febrile seizures, hypoplasia of the corpus callosum, hypsarrhythmia, focal clonic seizure, generalized tonic-clonic seizures, myokymia, spastic tetraparesis, and combinations thereof. In embodiments, such compound may be administered in a pharmaceutical composition as described herein.

Embodiments are directed to methods for treating conditions associated with hyperexcitability of cells in a subject comprising administering to the subject a therapeutically effective amount of a compound of Formula 1 or Table 1, or a pharmaceutically acceptable salt thereof, wherein the hyperexcitability is treated.

Embodiments are directed to methods for treating a Kv7 associated disorder in a subject comprising administering to the subject a therapeutically effective amount of a compound of Formula 1 or Table 1, or a pharmaceutically acceptable salt thereof, wherein the symptoms of the disorder are alleviated or improved due to the activation of Kv7 potassium channel.

Embodiments are directed to methods for treating neurodegenerative disease in a subject comprising administering to the subject a therapeutically effective amount of a compound of Formula 1 or Table 1, or a pharmaceutically acceptable salt thereof, wherein the neurodegenerative disease is treated. The compound of Formula 1 or Table 1, or a pharmaceutically acceptable salt thereof, may be administered to any individual exhibiting the symptoms of a neurodegenerative disease or to individuals predisposed to a neurodegenerative disease. Non-limiting examples of neurodegenerative diseases that may be treated using a compound of Formula 1 or Table 1, or a pharmaceutically acceptable salt thereof, include amyotrophic lateral sclerosis (ALS), Huntington's disease, metabolically induced neurological damage, Alzheimer's disease, Pick's disease, senile dementia, age associated cognitive dysfunction, vascular dementia, multi-infarct dementia, Lewy body dementia, neurodegenerative dementia, frontotemporal dementia (FTD), familial FTD, neurodegenerative movement disorder, ataxia, Friedreich's ataxia, multiple sclerosis, spinal muscular atrophy, primary lateral sclerosis, seizure disorders, motor neuron disorder or disease, inflammatory demyelinating disorder, Parkinson's disease, hepatic encephalopathy, chronic encephalopathy, chronic encephalitis, or any combination thereof.

Embodiments are directed to methods for treating neurodegenerative disease, such as amyotrophic lateral sclerosis, in a subject in need thereof comprising: administering to the subject a therapeutically effective amount of a compound of Formula 1 or Table 1, or a pharmaceutically acceptable salt thereof, wherein the neurodegenerative disease is treated. In embodiments, the subject is a subject with definite ALS, has amyotrophic lateral sclerosis symptom onset duration of less than about 18 months, plasma creatinine levels of about 72 μM/L or greater, concomitant riluzole administration, concomitant dexpramipexole administration, and combinations thereof.

Embodiments are directed to methods for treating amyotrophic lateral sclerosis in a subject in need thereof comprising: administering to the subject a therapeutically effective amount of a compound of Formula 1 or Table 1, or a pharmaceutically acceptable salt thereof, wherein the amyotrophic lateral sclerosis is treated.

Embodiments are directed to methods for treating amyotrophic lateral sclerosis in a subject diagnosed with definite amyotrophic lateral sclerosis comprising administering to the subject a therapeutically effective amount of a compound of Formula 1 or Table 1, or a pharmaceutically acceptable salt thereof, wherein the amyotrophic lateral sclerosis is treated. In embodiments, the definite amyotrophic lateral sclerosis is as defined by the E1 Escorial diagnosis criteria. In embodiments, the subject is a subject with definite ALS, amyotrophic lateral sclerosis symptom onset duration of less than about 18 months, plasma creatinine levels of about 72 μM/L or greater, concomitant riluzole administration, concomitant dexpramipexole administration, and combinations thereof.

Embodiments are directed to methods for treating amyotrophic lateral sclerosis in a subject in need thereof comprising administering to the subject a therapeutically effective amount of a compound of Formula 1 or Table 1, or a pharmaceutically acceptable salt thereof, wherein the subject is selected from a subject with definite amyotrophic lateral sclerosis, a subject with limb-onset amyotrophic lateral sclerosis, a subject with bulbar-onset amyotrophic lateral sclerosis, a subject with amyotrophic lateral sclerosis symptom onset duration of less than about 18 months, a subject with a high level of serum creatinine, a subject with low bicarbonate levels, a subject with concomitant riluzole administration, a subject with concomitant dexpramipexole administration, and combinations thereof, and wherein the amyotrophic lateral sclerosis is treated. In certain embodiments, the method further comprises monitoring said subject for any clinical features associated with amyotrophic lateral sclerosis. In certain embodiments, the method further comprises initiating therapy with a therapeutically effective amount of a compound of Formula 1 or Table 1, or a pharmaceutically acceptable salt thereof upon diagnosis of amyotrophic lateral sclerosis. In certain embodiments, the subject exhibits symptoms of amyotrophic lateral sclerosis. In certain embodiments, the subject has definite amyotrophic lateral sclerosis, probable amyotrophic lateral sclerosis, possible amyotrophic lateral sclerosis or suspected amyotrophic lateral sclerosis.

Embodiments are directed to methods for treating amyotrophic lateral sclerosis in a subject diagnosed with definite amyotrophic lateral sclerosis comprising administering to the subject a therapeutically effective amount of a compound of Formula 1 or Table 1, or a pharmaceutically acceptable salt thereof, wherein the amyotrophic lateral sclerosis is treated. In some embodiments definite amyotrophic lateral sclerosis is the presence of the E1 Escorial diagnosis criteria, amyotrophic lateral sclerosis symptom onset duration of less than about 18 months, limb-onset amyotrophic lateral sclerosis, plasma creatinine levels of about 72 μM/L or greater, concomitant riluzole administration, concomitant dexpramipexole administration, an ALSFRS-R score of greater than 36.0, a pre-study progression rate greater than or equal to 0.8 points per month, a percentage predicted relaxed (slow) vital capacity (SVC) of less than or equal to 102.0, an ALSFRS-R fine motor domain score of greater than 10.0 points, ALSFRS-R bulbar domain score or greater than 9.0 points, an ALSFRS-R gross motor domain score of greater than 8.0 points, an abnormal neurological exam of the tongue, an abnormal neurological exam of the pharynx, larynx and swallowing, an abnormal neurological exam of the lower extremities, an abnormal neurological exam of the upper extremities, an abnormal neurological exam of the triceps, an abnormal neurological exam of the muscle mass and bulk, an abnormal neurological exam of the bicep, an abnormal neurological exam, a pulse rate of greater than 81.0 beats per minute, a diastolic blood pressure of greater than 82.0 mmHg, a systolic blood pressure of less than or equal to 117.0 mmHg, a creatinine value of greater than 72.0 μmol/L, a phosphorous value of less than or equal to 1.090 μmol/L, a platelet count of less than or equal to $248.0\times10^9$ cells/L, a cholesterol value of less than or equal to 5.3 mmol/L, a lactate dehydrogenase value of less than or equal to 161.0 U/L, a creatine phosphokinase value of less than or equal to 184.0 U/L, a bicarbonate value of less than or equal to 21.6 mmol/L, a triglyceride level of less than or equal to 1.4 mmol/L, a uric acid level of greater than 320.0 μmol/L, a gamma-glutamyltransferase (GGT) level of greater than 37.0 U/L, a total bilirubin level of less than or equal to 6.0 μmol/L, a urine pH of less than or equal to 5.5, or any combination thereof.

Embodiments are directed to methods for treating amyotrophic lateral sclerosis in a subject exhibiting symptoms of amyotrophic lateral sclerosis comprising administering to the subject a therapeutically effective amount of a compound of Formula 1 or Table 1, or a pharmaceutically acceptable salt thereof, wherein the symptoms of amyotrophic lateral sclerosis are treated. In some embodiments, the subject exhibits clinical characteristics selected from definite amyotrophic lateral sclerosis, amyotrophic lateral sclerosis symptom onset duration of less than about 18 months, limb-onset amyotrophic lateral sclerosis, plasma creatinine levels of about 72 μM/L or greater, concomitant riluzole administration, concomitant dexpramipexole administration, an ALSFRS-R score of greater than 36.0, a re-study progression rate greater than or equal to 0.8 points per month, a percentage predicted relaxed (slow) vital capacity (SVC) of less than or equal to 102.0, an ALSFRS-R fine motor domain score of greater than 10.0 points, ALSFRS-R bulbar domain score or greater than 9.0 points, an ALSFRS-R gross motor domain score of greater than 8.0 points, an abnormal neurological exam of the tongue, an abnormal neurological exam of the pharynx, larynx and swallowing, an abnormal neurological exam of the lower extremities, an abnormal neurological exam of the upper extremities, an abnormal neurological exam of the triceps, an abnormal neurological exam of the muscle mass and bulk, an abnormal neurological exam of the bicep, an abnormal neurological exam, a pulse rate of greater than 81.0 beats per minute, a diastolic blood pressure of greater than 82.0 mmHg, a systolic blood pressure of less than or equal to 117.0 mmHg, a creatinine value of greater than 72.0 μmol/L, a phosphorous value of less than or equal to 1.090 μmol/L, a platelet count of less than or equal to 248.0×109 cells/L, a cholesterol value of less than or equal to 5.3 mmol/L, a lactate dehydrogenase value of less than or equal to 161.0 U/L, a creatine phosphokinase value of less than or equal to 184.0 U/L, a bicarbonate value of less than or equal to 21.6 mmol/L, a triglyceride level of less than or equal to 1.4 mmol/L, a uric acid level of greater than 320.0 μmol/L, a gamma-glutamyltransferase (GGT) level of greater than 37.0 U/L, a total bilirubin level of less than or equal to 6.0 μmol/L, a urine pH of less than or equal to 5.5, or any combination thereof.

Embodiments described herein are directed to methods of treating a disease or disorder that would benefit from the activation of a Kv7.2 homomer comprising administering to a subject in need thereof a therapeutically effective amount of a compound of Formula 1 or Table 1, or a pharmaceutically acceptable salt thereof. In some embodiments, the disease or disorder is developmental and diagnosed during prenatally, neonatally, infancy, during early childhood, during adolescence, and during early adulthood. In certain embodiments, a human subject is diagnosed before birth. In certain embodiments, a neonate is diagnosed at about birth to about 1 week, or at about 1 week to about 1 month. In certain embodiments, an infant is diagnosed at about birth to about 1 week, about 1 week to about 1 month, about 1 month to about 12 months. In certain embodiments, the subject is an infant from about birth to about 12 months. In certain embodiments, the subject is a fetus and is treated in utero. In certain embodiments, the subject is a child of about 1 year to about 12 years old.

Embodiments described herein are directed to methods of treating a neurodevelopmental disease or disorder comprising administering to a subject in need thereof a therapeutically effective amount of a compound of Formula 1 or Table 1, or a pharmaceutically acceptable salt thereof. In embodiments, the diseases or disorders are occurring early in life, between about 0 days to about 1 yr. The neonatal brain is undergoing changes early in development and is more susceptible to alterations during this sensitive time. Studies in rodents show that KCNQ2 expression predominates over KCNQ3 early in life. The delayed expression of KCNQ3 leads to the greater formation of KCNQ2 homomers relative to KCNQ2/KCNQ3 heteromers. In embodiments described herein, the method of treating developmental diseases or disorders is effective at restoring the electrical balance of the cells or normalizing the hyperexcitibility caused by genes or mechanisms unrelated to KCNQ2. In certain embodiments, the neurodevelopmental disease or disorder is selected from the group consisting of Angelman syndrome, neonatal abstinence syndrome, early myoclonic encephalopathy, Landau Kleffner syndrome, electrical status epilepticus during sleep, Ohtahara syndrome, autism spectrum disorders, Dravet syndrome, Lennox-Gastaut syndrome, Rett syndrome, Hirschsprung's disease (HSCR), West syndrome, SCN8A-related epilepsy with encephalopathy (EIEE13), Epilepsy of infancy with migrating focal seizures (EIMFS), Autosomal Dominant Nocturnal Frontal Lobe Epilepsy (ADNFLE), Doose syndrome, and combinations thereof.

Embodiments described herein are directed to methods of treating Angelman syndrome comprising administering to a subject in need thereof a therapeutically effective amount of a compound of Formula 1 or Table 1, or a pharmaceutically acceptable salt thereof. Angelman syndrome is caused by loss of function of the UBE3A gene which plays a role in the normal development of the nervous system. Patients exhibit mental retardation, abnormal gait, speech impairment, seizures, and an inappropriate happy demeanor that includes frequent laughing, smiling, and excitability. They are typically treated with anticonvulsants. Compounds described herein are effective in treating the seizures associated with Angleman syndrome.

Embodiments described herein are directed to methods of treating neonatal abstinence syndrome comprising administering to a subject in need thereof a therapeutically effective amount of a compound of Formula 1 or Table 1, or a pharmaceutically acceptable salt thereof. Neonatal abstinence syndrome is seen in infants born with a dependence on drugs due to exposure in utero. At birth they may experience withdrawal symptoms including seizures. Withdrawal from opiates may cause changes in excitatory transmission. Compounds described herein reverse the excitability and ameliorate the withdrawal symptoms.

Embodiments described herein are directed to methods of treating early myoclonic encephalopathy, Landau Kleffner syndrome, and electrical status epilepticus during sleep comprising administering to a subject in need thereof a therapeutically effective amount of a compound of Formula 1 or Table 1, or a pharmaceutically acceptable salt thereof. Early myoclonic encephalopathy is diagnosed in infants that present with seizures early in life with multiple contributing factors. Seizures are treatment resistant with standard therapy and prognosis is poor. Compounds described herein are effective in treating early myoclonic encephalopathy.

Embodiments described herein are directed to methods of treating Ohtahara syndrome comprising administering to a subject in need thereof a therapeutically effective amount of a compound of Formula 1 or Table 1, or a pharmaceutically acceptable salt thereof. Ohtahara syndrome (OS) or early infantile epileptic encephalopathy (EIEE) is a rare type of epilepsy that typically becomes apparent during the first 1-3 months of life. OS may be caused by brain malformations, metabolic disorders and gene mutations, including KCNQ2. Infants have primarily tonic seizures, but may also experience partial seizures, and rarely, myoclonic seizures. Most infants with the disorder show significant underdevelopment of part or all of the cerebral hemispheres. The EEGs of infants with Ohtahara syndrome reveal a characteristic pattern of high voltage spike wave discharge followed by little activity. This pattern is known as "burst suppression." The course of Ohtahara syndrome is severely progressive. Seizures become more frequent, accompanied by delays in physical and cognitive development. Some children will die in infancy; others will survive but be profoundly handicapped. As they grow, some children will progress into other epileptic disorders, such as West syndrome or Lennox-Gestaut syndrome. Due to the early onset of disease, Kv7 channel activators are effective treatment options for this disease.

Embodiments described herein are directed to methods of treating autism spectrum disorders comprising administering to a subject in need thereof a therapeutically effective amount of a compound of Formula 1 or Table 1, or a pharmaceutically acceptable salt thereof. Several voltage gated potassium channels have been implicated in autistic patients including mutations and truncation in KCNQ3 gene. Dysregulation of Kv7 function facilitates seizures and impairs normal development which may result in an autistic phenotype. Autism spectrum disorder (ASD) is a developmental disorder that affects communication and behavior. Although autism can be diagnosed at any age, it is said to be a "developmental disorder" because symptoms generally appear in the first two years of life. According to the Diagnostic and Statistical Manual of Mental Disorders (DSM-5), a guide created by the American Psychiatric Association used to diagnose mental disorders, people with ASD have: 1) difficulty with communication and interaction with other people, 2) restricted interests and repetitive behaviors, and 3) symptoms that hurt the person's ability to function properly in school, work, and other areas of life. Autism is known as a "spectrum" disorder because there is wide variation in the type and severity of symptoms people experience. Compounds described herein restore synaptic transmission required for normal development.

Embodiments described herein are directed to methods of treating Dravet syndrome comprising administering to a subject in need thereof a therapeutically effective amount of a compound of Formula 1 or Table 1, or a pharmaceutically acceptable salt thereof. Mutations in the SCN1A gene which encodes a voltage-gated sodium channel are common in Dravet syndrome. Mutations cause reductions in sodium current leading to hyper-excitability of GABAergic inhibitory neurons, leading to epilepsy. More recently KCNQ2 mutations have been found to contribute to the clinical presentation of Dravet syndrome. Dravet syndrome, previously known as severe myoclonic epilepsy of infancy (SMEI), is a rare, treatment-resistant developmental epileptic encephalopathy with onset in infancy and significant neurodevelopmental, motor, cognitive, and behavioral consequences that persist into adulthood. Dravet syndrome has been characterized by prolonged febrile and non-febrile seizures within the first year of a child's life. The disease progresses to other seizure types, such as myoclonic and partial seizures, psychomotor delay, and ataxia. It is characterized by cognitive impairment, behavioral disorders, and motor deficits. Behavioral deficits often include hyperactivity and impulsiveness, and in more rare cases, autistic-like behaviors. The seizures experienced by people with Dravet syndrome become worse as the patient ages. Compounds described herein are effective in Dravet syndrome by restoring the balance of excitation and inhibition in these neurons.

Embodiments described herein are directed to methods of treating Lennox-Gastaut syndrome comprising administering to a subject in need thereof a therapeutically effective amount of a compound of Formula 1 or Table 1, or a pharmaceutically acceptable salt thereof. Lennox-Gastaut syndrome (LGS) is a severe, complex, and rare childhood-onset epilepsy with multifactorial cause. Evidence suggests that cortical excitability during development contributes to the disease. Changes in excitability may be secondary to brain damage. The symptoms of Lennox-Gastaut syndrome usually begin during infancy or childhood, most often between 3 to 5 years of age. Affected children experience several different types of seizures, most commonly atonic, tonic and atypical absence seizures. Tonic seizures cause an increase muscle tone and muscle stiffness. They are characterized by sustained muscle contractions that can cause mild abnormalities, such as a slight bend of the body and brief interruption of breathing, or more significant problems, such as muscle spasms of the face and flexion or extension of the arms and legs. Tonic seizures are usually brief (lasting between a few seconds and a minute) and are especially prevalent at night during sleep, but can also occur during the day. Atonic seizures cause a sudden loss of muscle tone and limpness. They can cause the head to drop or nod, problems with posture, or sudden falls. Atonic seizures are also known as drop attacks. Atonic seizures may only partially affect consciousness and usually last only a few seconds. Atypical absence seizures are associated with a period of unconsciousness usually marked by unresponsive staring. Absence seizures usually begin and end abruptly and the affected individual usually resumes activity with no memory of the episode. Absence seizures do not cause convulsions and may be so mild that they go unnoticed. They usually last only a few seconds. Children with Lennox-Gastaut syndrome may also develop cognitive dysfunction, delays in reaching developmental milestones, and behavioral problems ranging from hyperactivity and irritability to autistic symptoms and psychosis. The prognosis for LGS is poor, with a 5% mortality in childhood and persistent seizures into adulthood (80%-90%). Generally, three findings are necessary for the diagnosis: multiple generalized seizure types; a slow spike-and-wave pattern (less than 2.5 Hz) on EEG; and cognitive dysfunction. Compounds described herein normalize brain excitability, reduce seizures, and may improve development outcomes and reduce behavioral problems.

Embodiments described herein are directed to methods of treating Rett syndrome comprising administering to a subject in need thereof a therapeutically effective amount of a compound of Formula 1 or Table 1, or a pharmaceutically acceptable salt thereof. Rett syndrome is a rare genetic neurological disorder that occurs primarily in girls. Patients appear normal early in life, but then growth and development slow later along with the emergence of problems with walking, seizures and intellectual disability. Many cases involve mutations in the MECP2 gene which is believed to control the function of many other genes and disrupts the normal functioning of nerve cells. Upon clinical diagnosis, patients were found to have mutations in other genes including KCNQ2. Compounds described herein are an effective treatment for Rett syndrome.

Embodiments described herein are directed to methods of treating Hirschsprung's disease (HSCR) comprising administering to a subject in need thereof a therapeutically effective amount of a compound of Formula 1 or Table 1, or a pharmaceutically acceptable salt thereof. Hirschsprung's disease is a condition that affects a newborn's ability to have bowel movements. The cause is unknown but believed to be associated with genetic mutations causing the nerve cells in the colon to not form appropriately, thus leading to poor contractions and less bowel movements. Kv7 channels are expressed in smooth muscle and contribute to the control of excitation of these cells. More recently it has been observed that Kv7 expression is reduced in HSCR patients. Compounds described herein activate these cells, restoring nerve function enabling normal contractility.

Embodiments described herein are directed to methods of treating West syndrome comprising administering to a subject in need thereof a therapeutically effective amount of a compound of Formula 1 or Table 1, or a pharmaceutically acceptable salt thereof. West syndrome is characterized by epileptic spasms and intellectual disability occurring early in life. In many cases infantile spams also includes hypsarrhythmia, a chaotic and disorganized brain activity. The diagnosis is clinical and is a combination of myoclonic jerks, developmental regression and a characteristic EEG pattern. There are many underlying causes including structural, metabolic and genetic causes all which produce a seizure disorder. Due to the early onset of disease, compounds described herein are an effective treatment option for this disease.

Embodiments described herein are directed to methods of treating SCN8A-related epilepsy with encephalopathy (EIEE13) comprising administering to a subject in need thereof a therapeutically effective amount of a compound of Formula 1 or Table 1, or a pharmaceutically acceptable salt thereof. EIEE13 is characterized by recurrent seizures, abnormal brain function, and intellectual disability; symptoms begin in infancy. Seizure frequency can be as high as hundreds per day and do not respond to current anti-epileptic medications. EIEE13 is caused by mutations in the SCN8A gene, resulting in increased Nav1.6 function. Increased Nav1.6 activity leads to excitation of neurons in the brain. Compounds described herein reduce excitability in the brain and restore normal brain function during the critical neurodevelopmental period.

Embodiments described herein are directed to methods of treating Epilepsy of infancy with migrating focal seizures (EIMFS) comprising administering to a subject in need thereof a therapeutically effective amount of a compound of Formula 1 or Table 1, or a pharmaceutically acceptable salt thereof. Epilepsy of infancy with migrating focal seizures (EIMFS) is also referred to as migrating partial epilepsy in infancy, migrating partial seizures of infancy, and malignant migrating partial seizures in infancy. EIMFS is a rare epilepsy syndrome where seizures begin within the first weeks of life. Seizures are focal but will migrate to different parts of the brain. Autonomic changes (stop breathing, turning blue, sweating, and hiccups) can frequently be seen during the seizures. EIMFS is associated with mutations in several genes including the KCNT1 potassium channel which accounts for 40% of EIMFS cases. KCNT1 channels contribute to the resting membrane potential and neuronal firing. Compounds described herein are effective in treating EIMFS.

Embodiments described herein are directed to methods of treating Autosomal Dominant Nocturnal Frontal Lobe Epilepsy (ADNFLE) comprising administering to a subject in need thereof a therapeutically effective amount of a compound of Formula 1 or Table 1, or a pharmaceutically acceptable salt thereof. ADNFLE is an uncommon form of epilepsy beginning early in childhood. Seizures typically occur at night while the person is sleeping. Seizures tend to cluster and may present with sudden repetitive movements and vocalization. ADNFLE is caused by mutations in genes encoding nicotinic acetylcholine receptors which play and important role in signaling between nerve cells and the brain. Disruption in neuronal network is associated with seizures. Kv7 activation could restore normal brain function and prevent seizures during this critical developmental period. Compounds described herein are effective in treating ADNFLE.

Embodiments described herein are directed to methods of treating Doose syndrome comprising administering to a subject in need thereof a therapeutically effective amount of a compound of Formula 1 or Table 1, or a pharmaceutically acceptable salt thereof. Doose syndrome, also known as myoclonic astatic epilepsy (MAE), is an epilepsy syndrome of early childhood that more commonly affects boys than girls with onset commonly occurring between ages 2 to 6. Children with Doose syndrome develop multiple seizure types, including drop attacks. About a third of children may have episodes of non-convulsive status epilepticus. Childhood development prior to the onset of seizures is usually normal. With frequent seizures, development slows and may regress. Compounds described herein are effective in treating Doose syndrome.

Some embodiments of the present invention relate to a method of treating a disease or disorder of Group CA comprising administering a therapeutically effective amount of a compound of Formula 1 or Table 1, or a pharmaceutically acceptable salt thereof, to a subject in need thereof. The disease or disorder of Group CA is selected from the group consisting of alcohol use disorders, Dravet syndrome, traumatic brain injury, cerebral vasospasm following subarachnoid hemorrhage, stroke, gout pain, temporomandibular joint (TMJ) pain, chronic cough, asthma or chronic obstructive pulmonary disease, trigeminal neuralgia (TN), atypical facial pain, cluster headache, neuropathic pain induced by chemotherapy drugs, orofacial cold hyperalgesia, depression, major depressive disorder, peripheral nerve hyperexcitability (PNH) syndromes, neuromyotonia, cramp-fasciculation syndrome (CFS), Morvan's syndrome, diseases involving hypoxic pulmonary vasoconstriction (HPV), hypoxia-induced pulmonary hypertension and high altitude pulmonary edema, pre-eclampsia, paroxysmal dystonia, psychostimulant addiction, bipolar disorder, posttraumatic stress disorder (PTSD), noise induced tinnitus, salicylate induced hearing loss and tinnitus, and combinations thereof. In embodiments, such compound may be administered in a pharmaceutical composition as described herein.

Some embodiments of the present invention relate to a method of treating alcohol use disorder comprising administering a therapeutically effective amount of a compound of Formula 1 or Table 1, or a pharmaceutically acceptable salt thereof, to a subject in need thereof. Ethanol has been shown to reduce M-current in hippocampal neurons, which increases their excitability and ultimately contributes to the reinforcing effects of ethanol. Compounds described herein are effective by reversing the ethanol induce excitability and reducing ethanol consumption.

Some embodiments of the present invention relate to a method of treating Dravet syndrome comprising administering a therapeutically effective amount of a compound of Formula 1 or Table 1, or a pharmaceutically acceptable salt thereof, to a subject in need thereof. Mutations cause reductions in sodium current leading to hyper-excitability of GABAergic inhibitory neurons, leading to epilepsy. More recently KCNQ2 mutations have been found to contribute to the clinical presentation of Dravet syndrome. Dravet Syndrome, previously known as severe myoclonic epilepsy of infancy (SMEI), is a rare, treatment-resistant developmental epileptic encephalopathy with onset in infancy and significant neurodevelopmental, motor, cognitive, and behavioral consequences that persist into adulthood. Dravet syndrome has been characterized by prolonged febrile and non-febrile seizures within the first year of a child's life. The disease progresses to other seizure types, such as myoclonic and partial seizures, psychomotor delay, and ataxia. It is characterized by cognitive impairment, behavioral disorders, and motor deficits. Behavioral deficits often include hyperactivity and impulsiveness, and in more rare cases, autistic-like behaviors. The seizures experienced by people with Dravet syndrome become worse as the patient ages. Compounds described herein are effective in Dravet syndrome by restoring the balance of excitation and inhibition in these neurons.

Some embodiments of the present invention relate to a method of treating traumatic brain injury comprising administering a therapeutically effective amount of a compound of Formula 1 or Table 1, or a pharmaceutically acceptable salt thereof, to a subject in need thereof. Seizures are very common in traumatic brain injury (TBI) patients due to TBI-induced hyperexcitability which ultimately leads to cell death. This hyperexcitability is due to compromised activity of the GABAergic inhibitory network. Compounds described herein can reverse neuronal excitability and reverse or prevent post-TBI brain damage.

Some embodiments of the present invention relate to a method of treating cerebral vasospasm following subarachnoid hemorrhage comprising administering a therapeutically effective amount of a compound of Formula 1 or Table 1, or a pharmaceutically acceptable salt thereof, to a subject in need thereof. Cerebral vasospasm following subarachnoid hemorrhage (SAH) is typically a result of a head injury or cerebral aneurysm. Cerebral vasospasm is constriction and narrowing of the arteries and the leading cause of death after the initial insult. Compounds described herein can dilate arteries and reduce ischemia.

Some embodiments of the present invention relate to a method of treating stroke comprising administering a therapeutically effective amount of a compound of Formula 1 or Table 1, or a pharmaceutically acceptable salt thereof, to a subject in need thereof. Acute ischemic stroke causes damage to blood vessels and surrounding tissue, including neurons, due to low blood supply. In addition, post-ischemic hyperexcitability contributes to inflammatory responses and behavioral deficits. KCNQ channels are expressed in CNS neurons and in cerebrovascular smooth muscle and therefore administration of the compounds described herein after stroke reduce stroke induced injury and functional impairment.

Some embodiments of the present invention relate to a method of treating gout pain comprising administering a therapeutically effective amount of a compound of Formula 1 or Table 1, or a pharmaceutically acceptable salt thereof, to a subject in need thereof. Gout pain is an inflammatory pain caused by the buildup of urate/uric acid crystals in joints. Peripheral inflammation increases the sensitivity of the receptors at the site of inflammation and increases the excitability of spinal cord neurons. KCNQ channels are expressed in both the CNS and PNS and compounds described herein reverse this excitability and pain response.

Some embodiments of the present invention relate to a method of treating temporomandibular joint (TMJ) pain comprising administering a therapeutically effective amount of a compound of Formula 1 or Table 1, or a pharmaceutically acceptable salt thereof, to a subject in need thereof. Temporomandibular joint (TMJ) pain is an inflammatory pain which can evolve into central sensitization leading to neuronal excitability and spontaneous pain. Compounds described herein suppress abnormal firing and control neuronal excitability reducing pain.

Some embodiments of the present invention relate to a method of treating trigeminal neuralgia (TN), atypical facial pain, cluster headache, neuropathic pain induced by chemotherapy drugs, and orofacial cold hyperalgesia comprising administering a therapeutically effective amount of a compound of Formula 1 or Table 1, or a pharmaceutically acceptable salt thereof, to a subject in need thereof. Some embodiments of the present invention relate to a method of treating trigeminal neuralgia (TN), atypical facial pain, or neuropathic pain induced by chemotherapy drugs comprising administering a therapeutically effective amount of a compound of Formula 1 or Table 1, or a pharmaceutically acceptable salt thereof, to a subject in need thereof. These are types of neuropathic pain which can be caused by many factors, including: compression of the trigeminal nerve caused by a tumor, injury to the nerve itself, or damage to the myelin sheath as in multiple sclerosis. Injuries to the trigeminal afferent neurons generate hyperexcitability of the cell. Trigeminal nerves convey thermal, mechanical, and nociceptive signals from the periphery to the central nervous system. Kv7 channels play an important role in regulating neuronal excitability and are expressed in trigeminal ganglia. Compounds described herein are useful in treating these types of pain.

Some embodiments of the present invention relate to a method of treating chronic cough, asthma or chronic obstructive pulmonary disease comprising administering a therapeutically effective amount of a compound of Formula 1 or Table 1, or a pharmaceutically acceptable salt thereof, to a subject in need thereof. Chronic cough is a pulmonary inflammatory disease with increased excitability of vagal sensory C-fibers. KCNQ is expressed in mouse nodose ganglion neurons and therefore can regulate the activity the fibers which innervate the lungs. The expression of KCNQ in airway smooth muscle cells may relax the airway in cases of histamine-induced constriction. Compounds described herein are effective in treating chronic cough and other inflammatory airway diseases including asthma and chronic obstructive pulmonary disease (COPD).

Some embodiments of the present invention relate to a method of treating depression and major depressive disorder comprising administering a therapeutically effective amount of a compound of Formula 1 or Table 1, or a pharmaceutically acceptable salt thereof, to a subject in need thereof. Upregulated K+ channels stabilize ventral tegmental area (VTA) dopaminergic (DA) neurons by counteracting the pathologic hyperactivity of these neurons. The firing rate of Dopaminergic neurons in the VTA is important for regulating dopamine levels in the brain. Compounds described herein, through exerting baseline changes in connectivity to the ventral striatum, the brain "rewards center," effectively treats major depressive disorder and its accompanying eating and sleeping disorders.

Some embodiments of the present invention relate to a method of treating peripheral nerve hyperexcitability (PNH) syndrome, neuromyotonia, cramp-fasciculation syndrome (CFS), and Morvan's syndrome comprising administering a therapeutically effective amount of a compound of Formula 1 or Table 1, or a pharmaceutically acceptable salt thereof, to a subject in need thereof. PNH is caused by spontaneous muscle fiber cramps and contractility due to overactive motor neurons. Mutations in KNCQ2 resulting in a reduction of potassium current have been described in patients with PNH. Compounds described herein effectively treat these diseases because of their general increase in nerve fiber excitability.

Some embodiments of the present invention relate to a method of treating diseases involving Hypoxic pulmonary vasoconstriction (HPV), hypoxia-induced pulmonary hypertension, and high altitude pulmonary edema comprising administering a therapeutically effective amount of a compound of Formula 1 or Table 1, or a pharmaceutically acceptable salt thereof, to a subject in need thereof. HPV is a mechanism that diverts blood to better ventilated areas by restricting blood flow. Hypoxic smooth muscle cells have reduced Kv7 mRNA which contributes to cell depolarization and the development of hypoxia induced pulmonary hypertension. Compounds described herein are protective in pulmonary vascular diseases by relaxing the vascular smooth muscle cells.

Some embodiments of the present invention relate to a method of treating pre-eclampsia comprising administering a therapeutically effective amount of a compound of Formula 1 or Table 1, or a pharmaceutically acceptable salt thereof, to a subject in need thereof. Pre-eclampsia contributes to complications in pregnancy by reducing placental blood flow causing hypoxia and inflammation. A reduction in KCNQ protein expression was observed in arteries from women with pre-eclampsia. Compounds described herein effectively, in smooth muscle, modulate contractility to facilitate blood flow.

Some embodiments of the present invention relate to a method of treating paroxysmal dystonia comprising administering a therapeutically effective amount of a compound of Formula 1 or Table 1, or a pharmaceutically acceptable salt thereof, to a subject in need thereof. Paroxysmal dystonia is a movement disorder where patients suffer from periods of dystonic movements and muscle spasms. A clinical diagnosis differentiates it from epilepsy, but anticonvulsants are used as treatment. Channelopathies are believed to play a causative role in paroxysmal dystonia. Compounds described herein are effective in treating paroxysmal dystonia.

Some embodiments of the present invention relate to a method of treating psychostimulant addiction comprising administering a therapeutically effective amount of a compound of Formula 1 or Table 1, or a pharmaceutically acceptable salt thereof, to a subject in need thereof. Drugs like cocaine, methylphenidate and phencyclidine act by stimulating regions of the brain including Dopaminergic (DA) neurons which reinforce the impact of these drugs promoting addiction. Kv7 channels expressed in these brain regions can directly reduce the activity of these neurons.

Additionally, Kv7 channels have been shown to reduce cortical excitability which would indirectly inhibit the release of dopamine. Compounds described herein are effective to treat addiction.

Some embodiments of the present invention relate to a method of treating bipolar disorder (BD) comprising administering a therapeutically effective amount of a compound of Formula 1 or Table 1, or a pharmaceutically acceptable salt thereof, to a subject in need thereof. Bipolar disorder is a brain disorder characterized by unusual shifts in energy. Ion channel dysregulation has been implicated in the aberrant excitability of the brain and altered dopaminergic tone associated with mania and depression. In addition, accumulating evidence suggests that variants in KCNQ may also be associated with BD and therefore compounds described herein are useful in treating BD by reducing the hyperexcitability.

Some embodiments of the present invention relate to a method of treating posttraumatic stress disorder (PTSD) comprising administering a therapeutically effective amount of a compound of Formula 1 or Table 1, or a pharmaceutically acceptable salt thereof, to a subject in need thereof. The body responds to stress by altering synaptic inputs and neuroendocrine function through an alteration in ion channel activity. Kv7 channel expression is reduced in response to acute stress increasing the activity of the hypothalamic-pituitary-adrenal (HPA) axis. Chronic stress is also associated HPA axis over-activity. Compounds described herein effectively enhance M-current and reduce HPA axis activity.

Some embodiments of the present invention relate to a method of treating noise induced tinnitus comprising administering a therapeutically effective amount of a compound of Formula 1 or Table 1, or a pharmaceutically acceptable salt thereof, to a subject in need thereof. Noise overexposure can be damaging and cause changes in cochlear neurons. These changes lead to abnormal hyperactive firing patterns and the phantom perception of sound, or tinnitus. This hyperactivity is caused in part by decreased Kv7 currents in cochlear neurons. Compounds described herein can restore normal function of these neurons and provide relief from tinnitus.

Some embodiments of the present invention relate to a method of treating salicylate induced hearing loss and tinnitus comprising administering a therapeutically effective amount of a compound of Formula 1 or Table 1, or a pharmaceutically acceptable salt thereof, to a subject in need thereof. High doses of salicylate, the active ingredient in aspirin, is known to induce hearing loss and tinnitus. Electromotility of outer hair cells (OHCs) is driven by membrane potential and is essential for control of hearing sensitivity. Salicylate induced reduction in Kv7.4 currents contributes to disrupted eletromotile response of outer hair cells (OHCs). In addition, salicylate increases the spontaneous activity of the auditory nerve. Compounds described herein reverse the salicylate induced changes by improving elelctomotility in OHCs and reducing auditory nerve activity.

In some embodiments, the compounds of Formula 1 or Table 1, or a pharmaceutically acceptable salt thereof, are superior to ezogabine. In some embodiments, the compounds of Formula 1 or Table 1, or a pharmaceutically acceptable salt thereof, have greater potency compared with ezogabine.

In certain embodiments, the compounds of Formula 1 or Table 1, or a pharmaceutically acceptable salt thereof, described herein have increased stability to photo-oxidation as compared to ezogabine. In certain embodiments, the compounds of Formula 1 or Table 1, or a pharmaceutically acceptable salt thereof, described herein have greater potency in activating Kv7 channels as compared to ezogabine. In certain embodiments, the compounds of Formula 1 or Table 1, or a pharmaceutically acceptable salt thereof, described herein have a greater subject tolerability as compared to ezogabine.

In certain embodiments, the compounds of Formula 1 or Table 1, or a pharmaceutically acceptable salt thereof, described herein modulates Kv7.2/7.3 and does not modulate $GABA_A$. In certain embodiments, the compounds of Formula 1 or Table 1, or a pharmaceutically acceptable salt thereof, described herein are selective to modulating Kv7.2/7.3, having very low or no activity to the $\alpha 1\beta 3\gamma 2$ $GABA_A$ receptor.

In some embodiments, the therapeutically effective amount of a compound of Formula 1 or Table 1, or a pharmaceutically acceptable salt thereof, have a decrease in unwanted side effects. The unwanted side effects are selected from the group consisting of dizziness, fatigue, drowsiness, confusion, vertigo, tremor, ataxia, double or blurred vision, attention deficit, memory impairment, muscle weakness, skin discoloration, withdrawal seizures, QT interval changes, suicidal behavior, urinary retention, sleepiness, hallucination, confusion, and combinations thereof. In some embodiments, the therapeutically effective amount of a compound of Formula 1 or Table 1, or a pharmaceutically acceptable salt thereof, have greater subject tolerability due to its selectivity and little to no side effects.

In some embodiments, administering a therapeutically effective amount of a compound of Formula 1 or Table 1, or a pharmaceutically acceptable salt thereof, may include administering daily doses of about 0.1 mg to about 1,500 mg, about 1 mg to about 1,500 mg, about 10 mg to about 1,500 mg, about 50 mg to about 1,500 mg, about 75 mg to about 1,500 mg, about 100 mg to about 1,500 mg, about 125 mg to about 1,500 mg, about 150 mg to about 1,500 mg, about 175 mg to about 1,500 mg, about 200 mg to about 1,500 mg, about 225 mg to about 1,500 mg, about 250 mg to about 1,500 mg, about 275 mg to about 1,500 mg, about 300 mg to about 1,500 mg, about 400 mg to about 1,500 mg, about 450 mg to about 1,500 mg, about 500 mg to about 1,500 mg, about 600 mg to about 1,500 mg, about 700 mg to about 1,500 mg, about 800 mg to about 1,500 mg, about 1,000 mg to about 1,500 mg, and about 1,200 mg to about 1,500 mg.

In some embodiments, the therapeutically effective amount of a compound of Formula 1 or Table 1, or a pharmaceutically acceptable salt thereof, is selected from the group consisting of from about 0.1 mg to about 1,000 mg, about 50 mg to about 1,000 mg per day, about 100 mg to about 1,000 mg per day, about 150 mg to about 1,000 mg per day, about 300 mg to about 1,000 mg per day, about 50 mg to about 300 mg per day, and about 150 mg to about 300 mg per day.

Such therapeutically effective amounts may be administered once a day or in equal, divided doses twice a day, three times a day, or four times a day. In some embodiments, administering a therapeutically effective amount comprises administering a dose equal to about half of a daily dose twice per day. In some embodiments, the dose is administered every about 12 hours. In some embodiments, administering a therapeutically effective amount comprises administering about 25 mg two times per day, about 75 mg two times per day, about 150 mg two times per day, or about 300 mg two times per day.

The invention is further illustrated by the following non-limiting examples.

Experimental Section and Examples

The schemes below show general methodologies for the synthesis of the compounds of the present invention.

As shown in Scheme 1, an appropriately substituted ester 1.1 is reacted with an alkyl cyano and a base such as LDA, LiHMDS, NaH, or NaOMe to afford β-ketonitriles 1.2. This compound is reacted with appropriately substituted alkyl hydrazine or alkyl hydrazine hydrochloride salt in the presence or absence of an acid such as acetic acid or hydrochloric acid or a base such as NaOH or triethylamine to afford N-alkylpyrazole 1.3 as the major product and N-alkylpyrazole 1.4 as the minor product.

Scheme 1

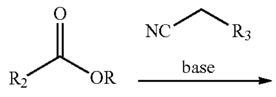

1.1

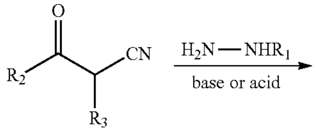

1.2

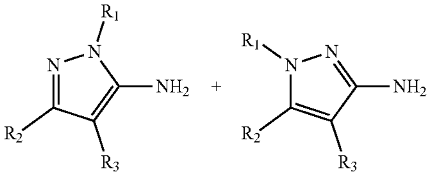

1.3 (major product) 1.4 (minor product)

An alternative method to prepare N-alkylpyrazoles 1.3 is described in Scheme 2.

β-Ketonitrile 1.2 is reacted with hydrazine in a solvent such as EtOH to provide pyrazole 2.1. This compound is reacted with phthalic anhydride and acetic acid to provide phthalimide 2.2. Alkylation in the presence of an alkyl halide and a base such as potassium carbonate or sodium hydride affords N-1 alkylated pyrazole 2.3 as the minor product and regioisomer N-2 alkylated pyrazole as the major product. Treatment of 2.3 with hydrazine hydrate affords amino pyrazole 1.3.

Scheme 2

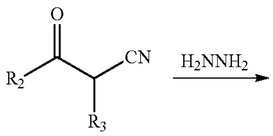

1.2

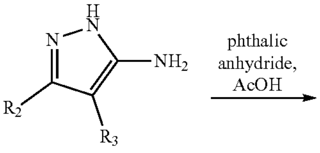

2.1

-continued

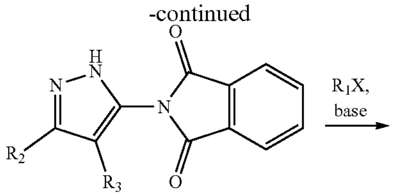

2.2

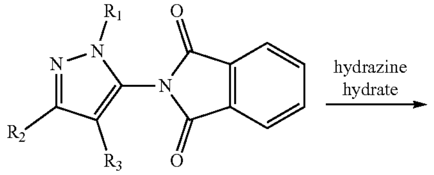

2.3

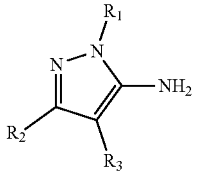

1.3

An alternative method to prepare pyrazole 1.3 is described in Scheme 3. Amino pyrazole 2.1 is reacted with alkyl halide in the presence of a base such as sodium hydride to provide to N-alkylpyrazole 1.3. Typically, the major regioisomer formed is pyrazole 1.4. These regioisomers can be separated by chromatography.

Scheme 3

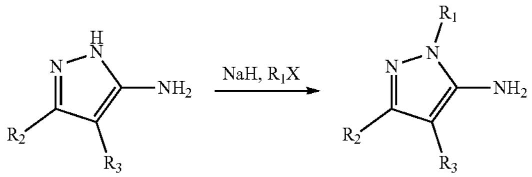

2.1 1.3

As shown in Scheme 4, reacting 1.3 with an appropriate carboxylic acid in the presence of an amino acid coupling reagent such as HATU, BTFFH (1-(fluoro(pyrrolidin-1-yl)methylene)pyrrolidin-1-ium hexafluorophosphate(V)) or T3P (propylphosphonic anhydride) and a base, such as Hunig's base or pyridine, affords N-alkylpyrazole amide 4.1. Alternatively, amide formation is prepared from 1.3 by reacting it with an appropriate acyl chloride in the presence of base such as triethylamine or Hunig's base.

Scheme 4

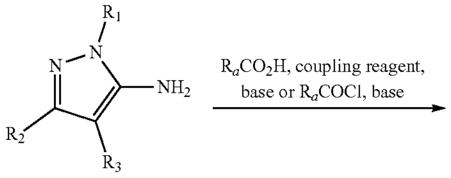

1.3

-continued

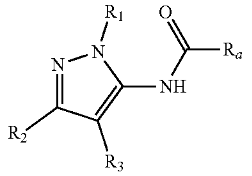

4.1

As shown in Scheme 5, reaction of 1.3 with phenylchloroformate to form phenylcarbamate 5.1 followed by reaction with an appropriate alcohol or amine and an appropriate base, such as Hunig's base, potassium carbonate or potassium tert-butoxide, affords N-alkylpyrazole carbamate or N-alkylpyrazole urea 5.2 or 5.3, respectively. Alternatively, carbamate 5.2 can be prepared by reacting aminopyrazole 1.3 with an appropriately substituted chloroformate 5.4. Alternatively, urea 5.2 can be prepared by reacting 1.3 with a substituted isocyanate in the presence of a base such as triethylamine. Alternatively, ureas 5.3 are prepared by reacting aminopyrazoles 1.3 with a substituted isocyanate such as 5.6.

Scheme 5

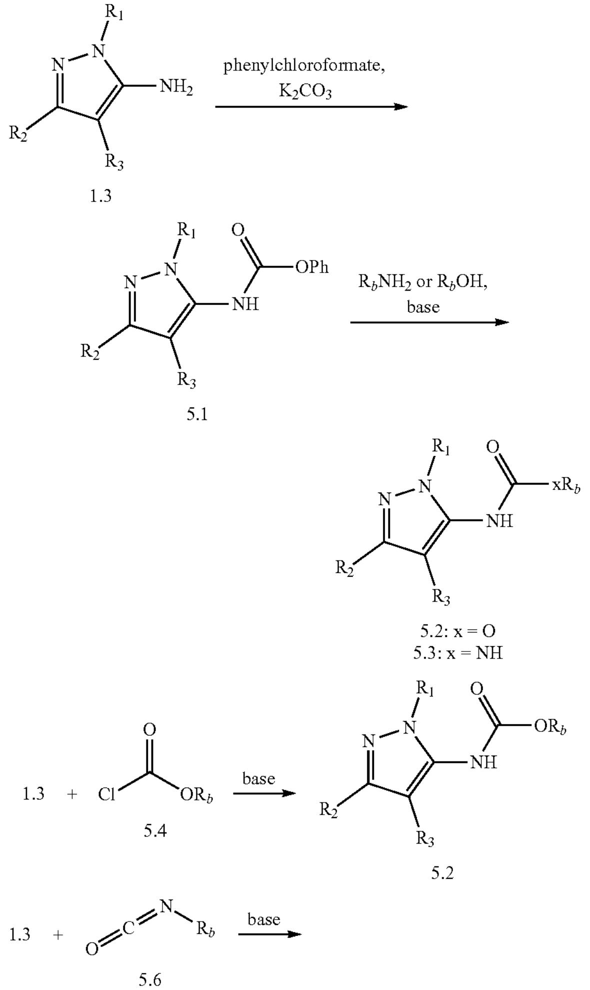

1.3

5.1

5.2: x = O
5.3: x = NH 5.4

5.2

5.6

-continued

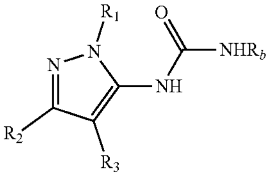

5.2

As shown in Scheme 6, treatment of silyloxyl 6.1 (prepared as described in methods above) with TBAF provides alcohols 6.2.

Scheme 6

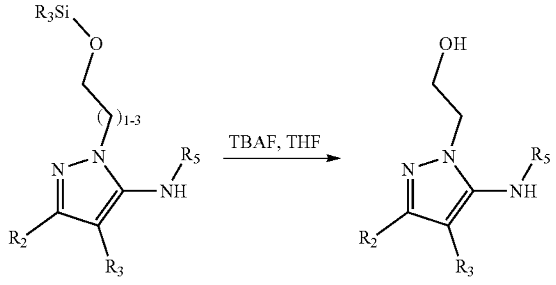

6.1

6.2

As shown in Scheme 7, pyrazole amine 7.5 is prepared by reacting diethyl oxalate 7.1 with alkyl nitrile 7.2 in the presence of a base such as potassium tert-butoxide with or without 18-crown-6 in an appropriate solvent to provide hydroxyacrylates 7.3. This compound is then treated with appropriately substituted hydrazine to form the amino ester pyrazole 7.4, which is treated with alkyl or aryl magnesium halide to provide pyrazole amines 7.5.

Scheme 7

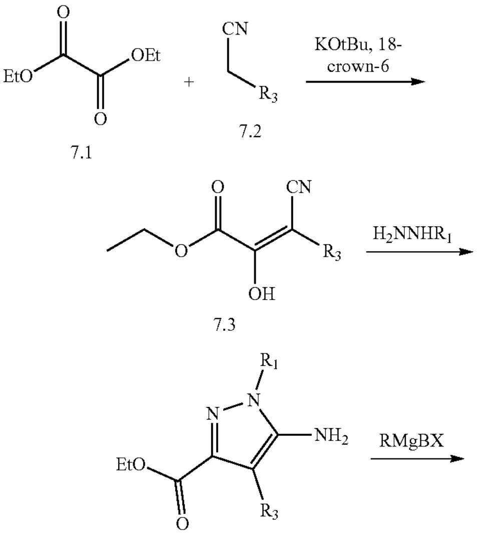

7.1

7.2

7.3

7.4

-continued

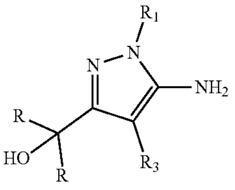

7.5

As shown in Scheme 8, alcohol 8.2 is prepared by lithiation of aryl halide 8.1 with t-BuLi or n-BuLi in the presence or absence of i-PrMgCl, followed by quenching with ketone.

Scheme 8

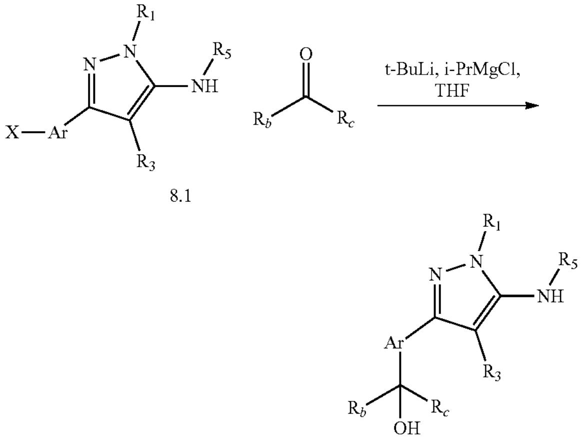

8.1 8.2

As shown in Scheme 9, carbamate 5.2 can be alkylated in the presence of an alkyl halide and a base such as sodium hydride to obtain alkylated carbamate 9.1.

Scheme 9

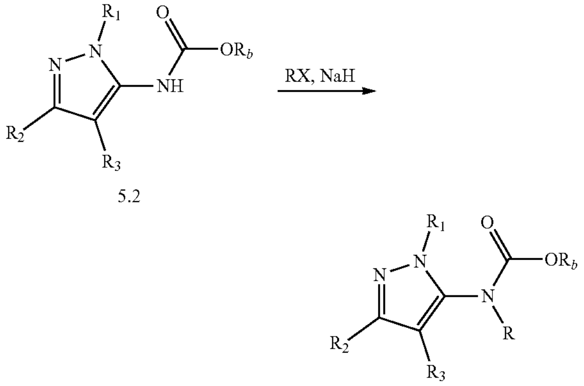

5.2 9.1

As shown in Scheme 10, ketal 10.1 can be treated with and acid such as p-toluenesulfonic acid or hydrochloric acid to form ketone 10.2. Subsequently, ketone 10.2 can be reacted with alkyl magnesium halide to form alkyl hydroxy cyclobutyl 10.3. Alternatively, ketone 10.2 can be treated with a reducing agent such as sodium borohydride to obtain cyclobutyl alcohol 10.4

Scheme 10

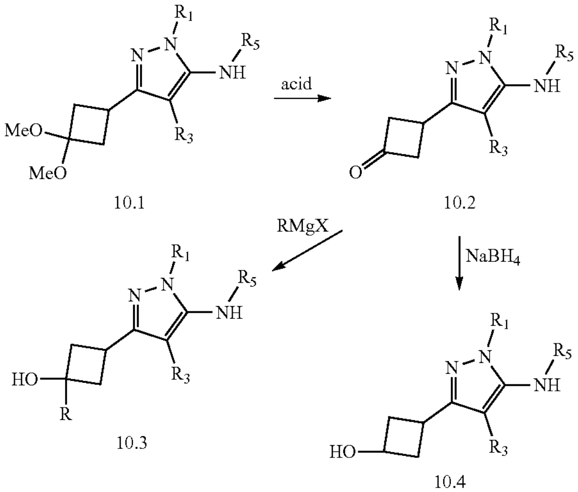

10.1 10.2 10.3 10.4

As shown in Scheme 11 aryloxy pyrazole 11.2 can be prepared from the appropriate hydroxy pyrazole in the presence of an arylboronic acid, copper acetate, a base such as pyridine, with or without molecular sieves in an appropriate solvent such as dichloroethane. Starting material 11.1 is prepared by methods described in Table 1.

Scheme 11

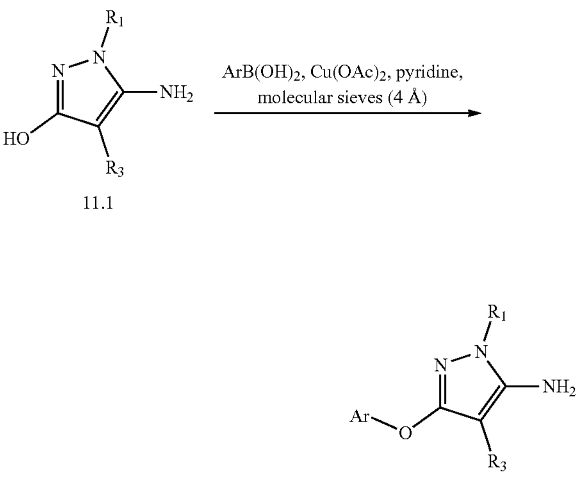

11.1 11.2

As shown in Scheme 12, ester 12.1 can be treated with alkyl or aryl substituted magnesium halide in an appropriate solvent such as THF to form alcohol 12.2.

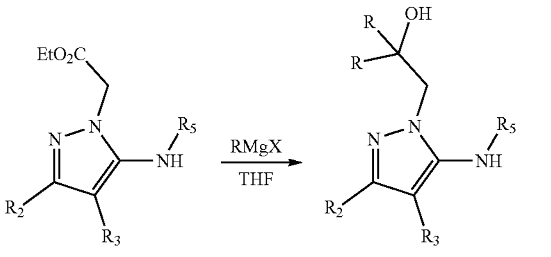

12.1 12.2

LC-MS Methods:

LC-MS Method A

Instrument: Shimadzu LCMS 2020 with LC-40D and SPD-M30A diode array detector Column: Shimadzu Nexcol C18, 50×3.0 mm, 5 mm Solvent A: 0.1% formic acid in water Solvent B: acetonitrile Flow rate: 0.4 mL/min 0-3 min, gradient from B=5% to B=95%

3-4 min, hold B=95%

4-4.2 min, gradient from B=95% to B=10%

4.2-5 min, hold B=10%

LC-MS Method B

Column: X Bridge C18 3.5 um 4.6*50 mm; Mobile Phase-A: 10 mm Ammonium acetate B: 100% ACN; Gradient 0/10, 0.5/10, 4/90, 8/90, 8.10/10, 10/10; Flow rate: 0.6 mL/min Synthetic methods: The methods listed below are representative methods that can be used with appropriate starting materials to synthesize described compounds in Table 1 with methods specified in the table.

1. Synthetic Methods: β-Ketonitriles

Method A

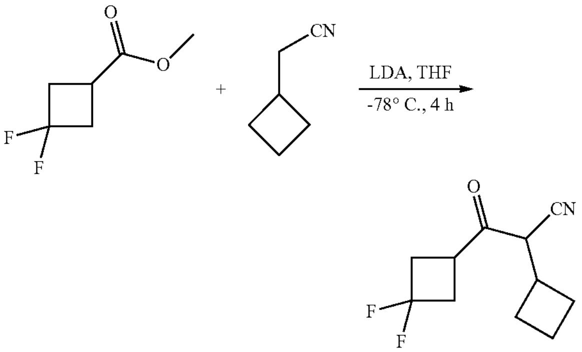

To a stirred solution of N,N-diisopropylamine (4.9 mL, 34.7 mmol) in THF (0.5 M, 63.0 mL) at −78° C. was added n-BuLi solution (13.2 mL, 33.1 mmol, 2.5 M in hexanes). The mixture was stirred at 0° C. for 30 min, then cooled to −78° C., and then cyclobutylacetonitrile (3.0 g, 31.5 mmol) was added slowly. The reaction mixture was warmed to 0° C. and stirred for 30 min, then cooled to −78° C. Methyl 3,3-difluoro cyclobutane-1-carboxylate (5.7 g, 37.8 mmol) was slowly added and the reaction mixture was stirred at −78° C. for 2.5 h. The mixture was then quenched with sat. aqueous $NH_4Cl$, warmed to room temperature, and extracted with ethyl acetate (2×). The combined organic layers were washed with brine (1×) and water (1×), then dried over anhydrous $Na_2SO_4$ and concentrated under reduced pressure. The resulting residue was purified by chromatography (silica gel, 0-50% ethyl acetate/hexanes) to furnish 2-cyclobutyl-3-(3,3-difluorocyclobutyl)-3-oxopropanenitrile as a colorless liquid (4.0 g, 60%). LC-MS (Method A, ESI): m/z, 212 $(M-H)^-$; $t_R$=3.8 min.

Method B

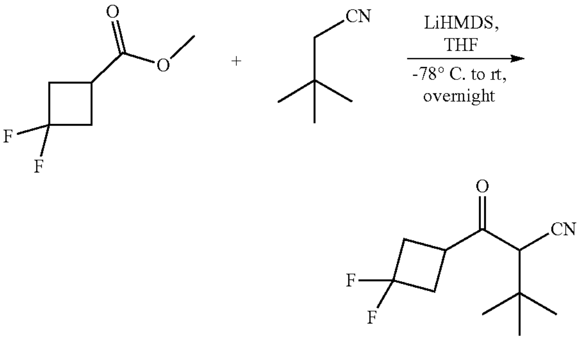

To a solution of 3,3-dimethylbutanenitrile (1.0 g, 10.3 mmol) in THF (0.4 M, 26 mL) at −78° C., was added LiHMDS (15.4 mL, 15.5 mmol, 1.0 M in THF) slowly and the reaction mixture was stirred for 30 min. Then methyl 3,3-difluorocyclobutane-1-carboxylate (1.85 g, 12.4 mmol) was added to the reaction mixture, and it was stirred for 2 h, and then warmed to room temperature and stirred overnight. The reaction mixture was quenched with sat. aqueous $NH_4Cl$ and extracted with ethyl acetate (2×). The combined organic layers were washed with brine (1×), dried over anhydrous $Na_2SO_4$, and concentrated under reduced pressure. The resulting residue was purified by flash chromatography (silica gel, 0-30% ethyl acetate/hexanes) to furnish 2-(3,3-difluorocyclobutane-1-carbonyl)-3,3-dimethylbutanenitrile as a pale-yellow thick liquid (780 mg, 35%). LC-MS (Method A, ESI): m/z, 214 $(M-H)^-$; $t_R$=3.9 min.

Method C

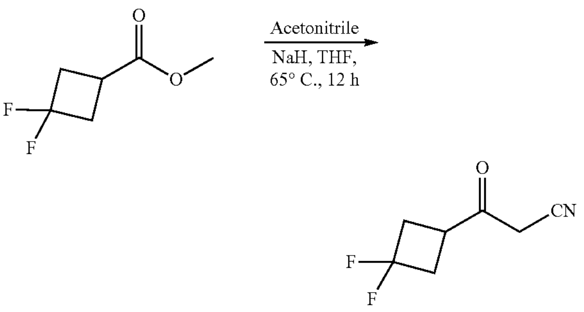

To a slurry of sodium hydride (1.10 g, 26.7 mmol) in THF (0.2 M, 67 mL) at 0° C., were added acetonitrile (1.4 mL, 26.7 mmol) followed by methyl 3,3-difluorocyclobutane-1-carboxylate (2.0 g, 13.2 mmol) dropwise. The reaction mixture was stirred at 65° C. for 12 h. Then the reaction mixture was quenched with dropwise addition of sat. aqueous $NH_4Cl$ until hydrogen evolution ceased. The reaction mixture was extracted with ethyl acetate (2×). The combined organic layers were washed with brine (1×), dried over $Na_2SO_4$, filtered, and concentrated under reduced pressure at 25° C. The resulting residue was purified by chromatography (silica gel, 0-50% ethyl acetate/hexanes) to obtain 3-(3,3-difluorocyclobutyl)-3-oxopropanenitrile as a colorless thick liquid (1.4 g, 67%). LC-MS (Method A, ESI): m/z, 159 $(M-H)^-$; $t_R$=3.2 min.

Method D

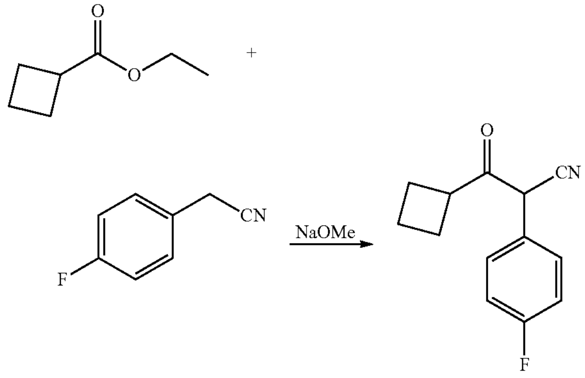

To a sealed tube was added ethyl cyclobutane carboxylate (431 μL, 3.1 mmol), 3-cyclobutyl-2-(4-fluorophenyl)-3-oxopropanenitrile (468 μL, 3.9 mmol) and 25% sodium methoxide solution (714 μL, 3.1 mmol). The tube was sealed and stirred at 85° C. overnight. The cooled mixture was diluted with $H_2O$ and conc. hydrochloric acid was added to adjust pH to 6. The mixture was extracted with EtOAc (3×), the extracts were combined, washed with brine, dried ($Na_2SO_4$), filtered and concentrated. The crude material was purified on a 40 g silica gel column eluting with 0-30% EtOAc/hexane to give the desired product (367.9 mg, 54%). LC-MS (Method A, ESI): m/z, 216 $(M-H)^-$; $t_R$=4.0 min.

2. Synthetic Methods: N-alkyl Pyrazoles

Method E

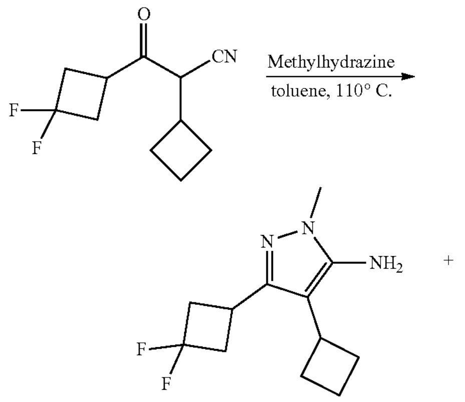

-continued

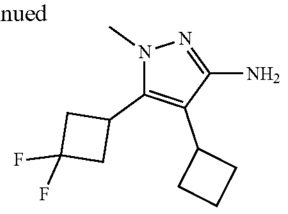

Methylhydrazine (740 μL, 7.04 mmol) was added to a solution of 2-cyclobutyl-3-(3,3-difluorocyclobutyl)-3-oxo-propanenitrile (1.5 g, 7.0 mmol) in toluene (0.4 M, 18 mL) in a pressure tube and heated to 110° C. overnight. The volatiles were removed under reduced pressure and the resulting residue was purified by silica gel chromatography to afford 4-cyclobutyl-3-(3,3-difluorocyclobutyl)-1-methyl-1H-pyrazol-5-amine (eluted with 0-100% ethyl acetate/hexanes, isolated as a pale-yellow solid, 1.2 g, 85% yield, LC-MS (ESI): m/z, 242 $(M+H)^+$; $t_R$=3.0); and 4-cyclobutyl-5-(3,3-difluorocyclobutyl)-1-methyl-1H-pyrazol-3-amine (eluted with 0-15% methanol/dichloromethane, isolated as a pale brown solid, 0.2 g, 15% yield, LC-MS (Method A, ESI): m/z, 242 $(M+H)^+$; $t_R$=3.2).

Method F

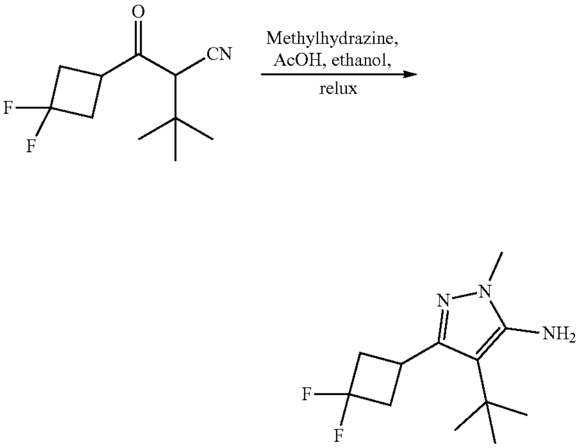

To a solution of methylhydrazine (200 μL, 3.83 mmol) and 2-(3,3-difluorocyclobutane-1-carbonyl)-3,3-dimethylbutanenitrile (412 mg, 1.91 mmol) in ethanol (6.4 mL) in a 15 mL pressure tube was added acetic acid (162 μL, 2.87 mmol). The mixture was heated to reflux overnight. After complete consumption of starting compound (LC-MS), the volatiles were removed under reduced pressure. The resulting residue was diluted with cold water and the pH was adjusted to 10 with aqueous ammonium hydroxide (25-30% in $H_2O$) and then extracted with ethyl acetate (2×). The combined organic layers were washed with sat. aqueous $NaHCO_3$ (1×), brine (1×), and water (1×), then dried over anhydrous $Na_2SO_4$, and concentrated under reduced pressure. The resulting residue was purified by chromatography (silica gel, 0-100% ethyl acetate/hexanes) to provide 4-(tert-butyl)-3-(3,3-difluorocyclobutyl)-1-methyl-1H-pyrazol-5-amine as beige solid (80 mg, 17%). LC-MS (Method A, ESI): m/z, 244 $(M+H)^+$; $t_R$=3.2 min.

Method G

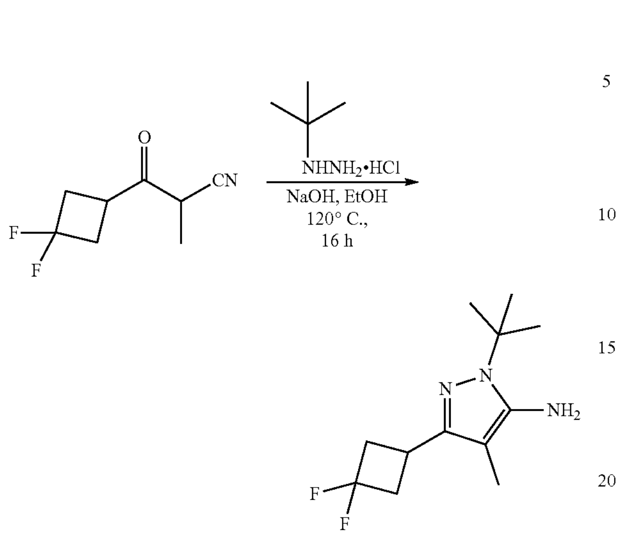

A solution of tert-butyl hydrazine hydrochloride (2.88 g, 23.1 mmol) and NaOH (920 mg, 23.1 mmol) in EtOH (20 mL) was stirred at room temperature for 10 min. To this mixture, a solution of 3-(3,3-difluorocyclobutyl)-2-methyl-3-oxopropanenitrile (2.00 g, 11.6 mmol) in EtOH (5 mL) was added dropwise and the mixture was stirred at 120° C. in a sealed tube for 16 h. The progress of the reaction was monitored by TLC. After completion of the reaction, the volatiles were removed under reduced pressure, the resulting residue was diluted with water (100 mL), and then extracted with EtOAc (2×100 mL). The combined organic layers were washed with brine (100 mL), dried over anhydrous $Na_2SO_4$ and concentrated under reduced pressure. Silica-gel column chromatography, eluting with 15%-20% EtOAc/hexane gradient afforded 1-(tert-butyl)-3-(3,3-difluorocyclobutyl)-4-methyl-1H-pyrazol-5-amine (1.20 g, 43%) as a light brown solid. LC-MS (Method B, $^{+}$ve mode): m/z, 244.1 $(M+H)^+$; $t_R$=4.99 min.

Method H

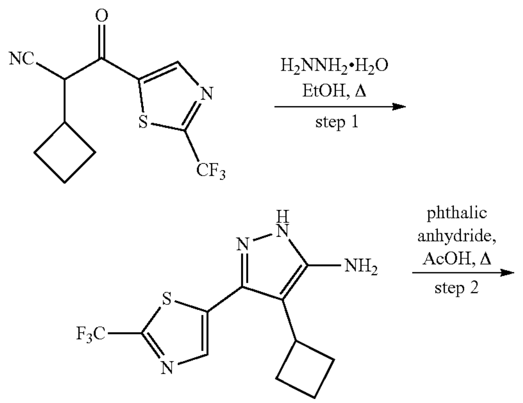

-continued

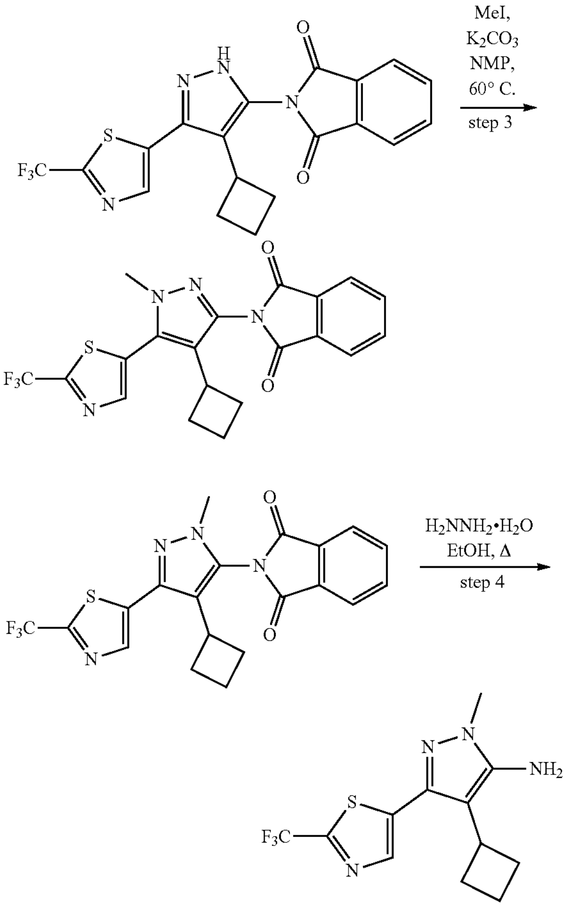

Step 1. 2-Cyclobutyl-3-oxo-3-(2-(trifluoromethyl)thiazol-5-yl)propanenitrile (0.700 g, 2.55 mmol) and hydrazine hydrate (0.149 mL, 3.06 mmol) were combined in EtOH (5 mL) and refluxed overnight. The volatiles were removed and the crude material was purified via chromatography (silica gel, 0-10% MeOH/DCM) to give 620 mg (84%) of 4-cyclobutyl-3-(2-(trifluoromethyl)thiazol-5-yl)-1H-pyrazol-5-amine. Confirmed by LC-MS (Method A, ESI): m/z, 289 $(M+H)^+$; $t_R$=3.6 min.

Step 2. 4-Cyclobutyl-3-(2-(trifluoromethyl)thiazol-5-yl)-1H-pyrazol-5-amine (0.620 g, 2.15 mmol) and phthalic anhydride (0.478 g, 3.23 mmol) were refluxed in acetic acid (4.0 mL) for 1 h. Most of the acetic acid was removed in vacuo and the remaining residue was taken up in EtOAc and washed with sat. aqueous $NaHCO_3$ several times until gas evolution ceased. The organic portion was dried ($Na_2SO_4$) and the volatiles were removed to give crude material that was purified via chromatography (silica gel, 0-100% EtOAc/hexanes) to give 410 mg (46%) of 2-(4-cyclobutyl-3-(2-(trifluoromethyl)thiazol-5-yl)-1H-pyrazol-5-yl)isoindoline-1,3-dione. Confirmed by LC-MS (Method A, ESI): m/z, 419 $(M+H)^+$; $t_R$=4.2 min.

Step 3. Potassium carbonate (0.406 g, 2.94 mmol), followed by iodomethane (0.122 mL, 1.96 mmol), was added to a solution of 2-(4-cyclobutyl-3-(2-(trifluoromethyl)thiazol-5-yl)-1H-pyrazol-5-yl)isoindoline-1,3-dione (0.410, 0.980 mmol) in NMP (1.4 mL) and the resulting reaction mixture was stirred at 60° C. overnight. Complete conversion of the starting material to product was confirmed by LC-MS. The reaction mixture was diluted in EtOAc and the organic portion was washed ($H_2O$ 3×, brine 1×), dried ($Na_2SO_4$), and concentrated to give a crude residue that was purified by chromatography (silica gel, 0-100% $Et_2O$/hexanes) to give 2-(4-cyclobutyl-1-methyl-3-(2-(trifluoromethyl)thiazol-5-yl)-1H-pyrazol-5-yl)isoindoline-1,3-dione (0.150 g, LC-MS (Method A, ESI): m/z, 433 $(M+H)^+$; $t_R$=4.7), 2-(4-cyclobutyl-1-methyl-5-(2-(trifluoromethyl)thiazol-5-yl)-1H-pyrazol-3-yl)isoindoline-1,3-dione (0.070 g, LC-MS (Method A, ESI): m/z, 433 $(M+H)^+$; $t_R$=4.2) and 0.040 g of a mixture of N-Me regioisomers (61% combined yield).

Step 4. 2-(4-Cyclobutyl-1-methyl-3-(2-(trifluoromethyl)thiazol-5-yl)-1H-pyrazol-5-yl)isoindoline-1,3-dione (0.100 g, 0.231 mmol) and hydrazine hydrate (0.056 mL, 1.16 mmol) were combined in EtOH (1.2 mL) and refluxed overnight. After cooling to ambient temperature, the white solid was removed by filtration, washed with EtOH, and discarded. The volatiles were removed from the filtrate and the resulting crude residue was loaded directly onto a silica gel column and eluted (0-10% MeOH/DCM) to give 0.040 mg (57%) of 4-cyclobutyl-1-methyl-3-(2-(trifluoromethyl)thiazol-5-yl)-1H-pyrazol-5-amine. Confirmed by LC-MS (Method A, ESI): m/z, 303 $(M+H)^+$; $t_R$=3.9 min.

Method I

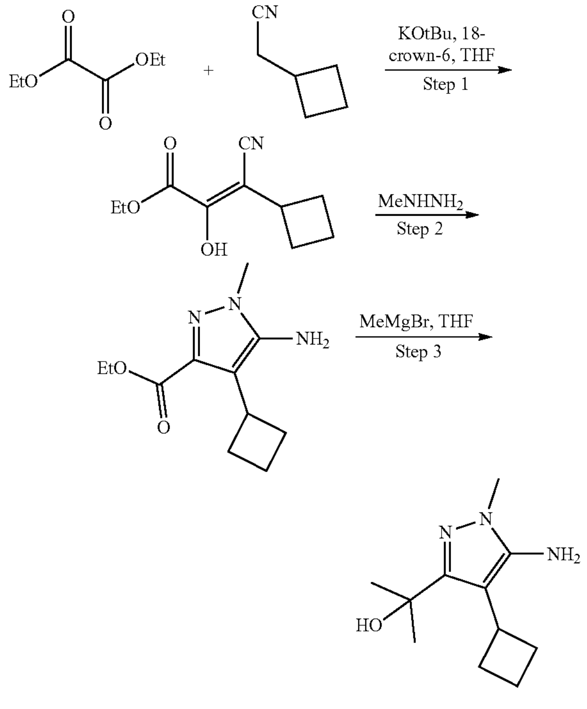

Step 1. To a round bottom flask containing anhydrous THF (3.4 ml) was added 18-crown-6 (72 mg, 0.27 mmol). The mixture was cooled to 0° C. and potassium tert-butoxide (383 mg, 3.41 mmol) was added. To the 0° C. mixture was added diethyl oxalate (465 μL, 3.4 mmol) dropwise. Once the addition was complete, the mixture was heated to 60° C. To the mixture was added dropwise cyclobutyl acetonitrile (409 μL, 3.4 mmol) and heating was continued for 30 min. The mixture was added to aqueous 1N HCl and the mixture was then extracted with EtOAc (3×). The combined extracts were dried ($Na_2SO_4$), filtered, and concentrated to a light-yellow oil to provide ethyl (E)-3-cyano-3-cyclobutyl-2-hydroxyacrylate (741.0 mg, 93%). LC-MS (Method A, ESI): m/z, 194 $(M-H)^-$; $t_R$=3.5 min.

Step 2. To ethyl (E)-3-cyano-3-cyclobutyl-2-hydroxyacrylate (455 mg, 2.3 mmol) in EtOH (5.0 ml) was added methyl hydrazine (123 μL, 2.3 mmol) followed by conc. hydrochloric acid (180 μL). The mixture was refluxed for 6 h, at which time the LCMS showed completion of the reaction. The mixture was cooled and diluted with $H_2O$. The mixture was extracted with EtOAc (3×) and the combined extracts were washed with sat. aqueous $NaHCO_3$ and brine, then dried ($Na_2SO_4$), filtered and concentrated. The crude residue was purified on a 24 g silica gel column eluting with 0-100% EtOAc/hexane to give ethyl 5-amino-4-cyclobutyl-1-methyl-1H-pyrazole-3-carboxylate (41.1 mg, 8%). LC-MS (Method A, ESI): m/z, 224 $(M+H)^+$; $t_R$=3.1 min.

Step 3. To ethyl 5-amino-4-cyclobutyl-1-methyl-1H-pyrazole-3-carboxylate (100 mg, 0.45 mmol) in THF (2.2 ml) at 0° C. was added a solution of methyl magnesium bromide (746 μL, 2.2 mmol, 3M in THF) dropwise. The mixture was stirred at 0° C. for 10 min, then warmed to room temperature over 1 h. LCMS indicated the reaction was complete. The reaction was quenched with sat. aqueous $NH_4Cl$, diluted with $H_2O$ and extracted (3×) with EtOAc. The extracts were combined, dried ($Na_2SO_4$), filtered and concentrated. Purification (12 g silica gel column eluting with 0-10% $CH_3OH$/DCM) provided 2-(5-amino-4-cyclobutyl-1-methyl-1H-pyrazol-3-yl)propan-2-ol (65 mg, 70%). LC-MS (Method A, ESI): m/z, 210 $(M+H)^+$; $t_R$=2.4 min.

Method J

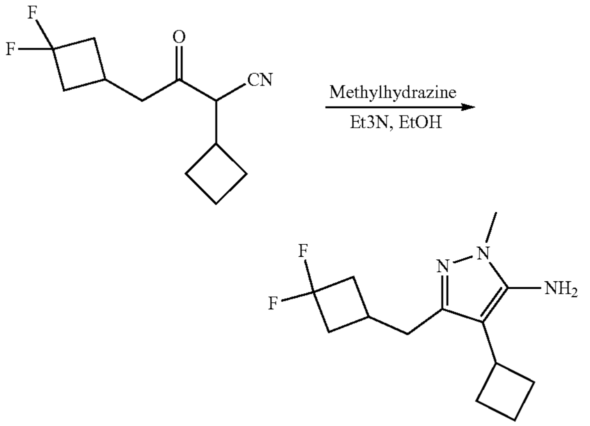

To 2-cyclobutyl-4-(3,3-difluorocyclobutyl)-3-oxobutanenitrile (500 mg, 2.2 mmol) in EtOH (4.4 mL) was added triethylamine (1.2 ml, 8.8 mmol) and methylhydrazine (232 μL, 4.4 mmol). The mixture was heated to reflux for 3 h, cooled to room temperature, and concentrated. The resulting residue was dissolved in EtOAc. The mixture was washed with $H_2O$ and brine, dried ($Na_2SO_4$), filtered and concentrated. The crude material was purified on a 24 g silica gel column eluting with 0-30% EtOAc/hexane to give 4-cyclobutyl-3-((3,3-difluorocyclobutyl)methyl)-1-methyl-1H-pyrazol-5-amine (195.8 mg, 35%). LC-MS (Method A, ESI): m/z, 256 $(M+H)^+$; $t_R$=2.9 min.

Method T

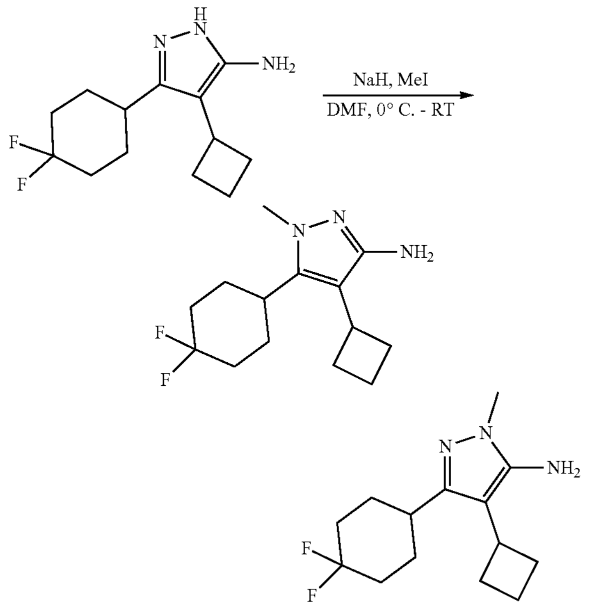

Sodium hydride (0.108 g, 2.70 mmol; 60 wt %) was added to a solution of 4-cyclobutyl-3-(4,4-difluorocyclohexyl)-1H-pyrazol-5-amine (0.420 g, 1.50 mmol) in DMF (1.5 mL) at 0° C. and the resulting reaction mixture was stirred at that temperature for 30 min. Iodomethane (0.103 mL, 1.65 mmol) was added, the reaction mixture was removed from the ice bath, and stirred at ambient temperature for 2 h. LC-MS shows consumption of starting material and two major products with desired mass (m/z+1=270). The reaction mixture was treated with EtOAc, washed ($H_2O$ 3×, brine 1×), the organic portion dried ($Na_2SO_4$), and the volatiles removed to give crude material that was purified via chromatography (silica gel, 0-100% EtOAc/hexanes) to give 4-cyclobutyl-3-(4,4-difluorocyclohexyl)-1-methyl-1H-pyrazol-5-amine (160 mg, 40%, confirmed by LC-MS (Method A, ESI): m/z, 270 $(M+H)^+$; $t_R$=2.8) and 4-cyclobutyl-5-(4,4-difluorocyclohexyl)-1-methyl-1H-pyrazol-3-amine (140 mg, 35%, confirmed by LC-MS (Method A, ESI): m/z, 270 $(M+H)^+$; $t_R$=3.2 min).

Method V

Method V is analogous to Method A with addition of 1.2 equivalents of diisopropylethylamine to the reaction mixture.

Method DD

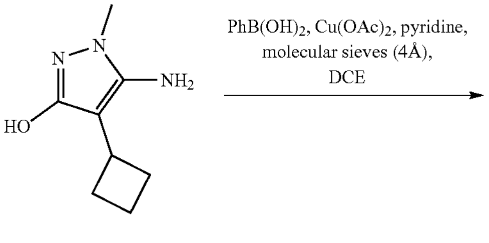

-continued

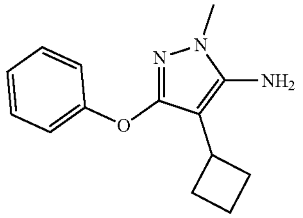

A mixture of 5-amino-4-cyclobutyl-1-methyl-1H-pyrazol-3-ol (155 mg, 0.927 mmol), phenylboronic acid (283 mg, 2.32 mol), $Cu(OAc)_2$, (253 mg, 1.39 mmol), pyridine (229 μL, 2.78 mmol), and molecular sieves (4 Å, 150 mg) in dichloroethane (9 mL) was stirred at room temperature for 2 days. The mixture was diluted with EtOAc and washed with $H_2O$. The organic layer was dried ($Na_2SO_4$), concentrated, and chromatographed (silica column, 0-10% MeOH/DCM) to provide 4-cyclobutyl-1-methyl-3-phenoxy-1H-pyrazol-5-amine (75.5 mg, 33%).

3. Synthetic Method: Amine Functionalization/Final Step

Method K

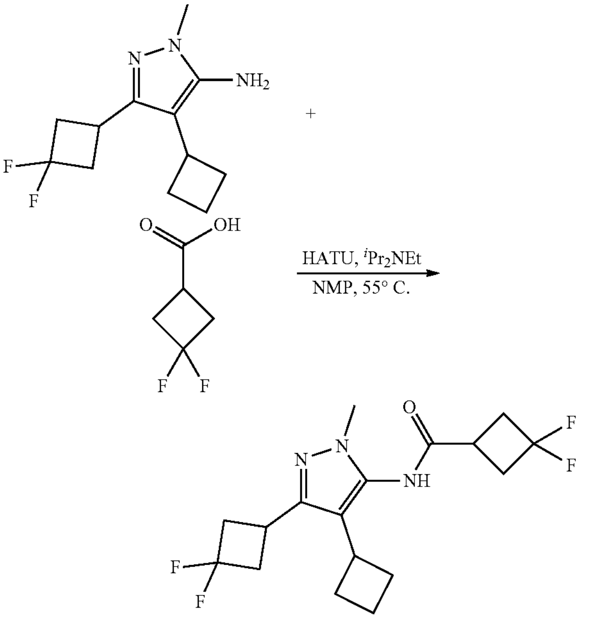

To a solution of 3,3-difluorocyclobutane-1-carboxylic acid (40 mg, 0.16 mmol) in NMP (0.6 mL) were added HATU (113 mg, 0.30 mmol) and N,N-diisopropylethylamine (58 μL, 0.33 mmol and the resulting reaction mixture was stirred for 5 min before addition of 4-cyclobutyl-3-(3,3-difluorocyclobutyl)-1-methyl-1H-pyrazol-5-amine (27 mg, 0.19 mmol). The reaction mixture was heated to 55° C. and stirred at that temperature overnight. The resulting reaction mixture was injected directly onto a reverse phase HPLC column (C18, 10-100% acetonitrile/water and monitoring with 220 nm wavelength) to give N-(4-cyclobutyl-3-(3,3-difluorocyclobutyl)-1-methyl-1H-pyrazol-5-yl)-3,3-difluorocyclobutane-1-carboxamide as white solid (31 mg, 52%); $^1$H-NMR (400 MHz, $CDCl_3$): δ 6.75 (s, 1H), 3.63 (s, 3H), 3.20-3.6 (m, 2H), 2.94-3.05 (m, 2H), 2.78-2.91 (m, 6H), 2.43-2.72 (m, 1H), 2.17-2.27 (m, 2H), 1.98-2.08 (m, 3H), 1.76-1.88 (m, 1H); LC-MS (Method A, ESI): m/z, 360 $(M+H)^+$; $t_R$=3.8 min.

Method L

Example 243: 3,3-difluorocyclobutyl (4-cyclobutyl-3-(3,3-difluorocyclobutyl)-1-methyl-1H-pyrazol-5-yl)carbamate Step 1, Option 1

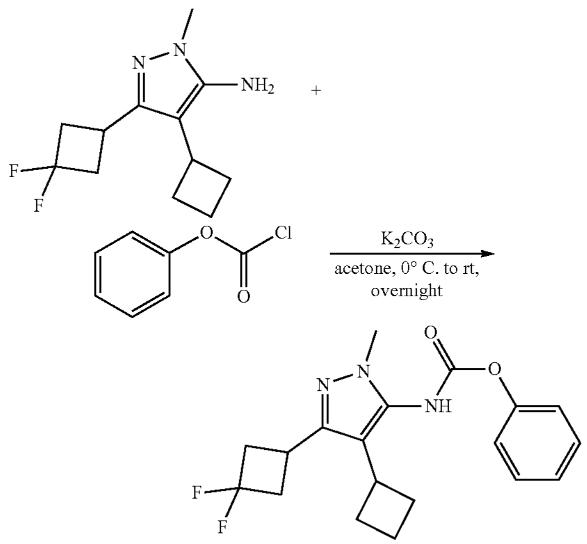

To a stirred solution of 4-cyclobutyl-3-(3,3-difluorocyclobutyl)-1-methyl-1H-pyrazol-5-amine (50 mg, 0.21 mmol) in acetone (3 mL) at 0° C., were added $K_2CO_3$ (43 mg, 0.32 mmol) and phenyl chloroformate (29 μL, 0.23 mmol), and the reaction mixture was stirred at room temperature overnight. The LC-MS indicated that the starting material was consumed, and the desired product was formed. Solvent was removed under reduced pressure and the resulting residue was diluted with water, sonicated for 2 min, and extracted with ethyl acetate (2×). The combined organic layers were washed with sat. aqueous $NaHCO_3$ (1×), brine (1×), and water (1×), then dried over $Na_2SO_4$ and concentrated. The resulting residue was purified by chromatography (silica gel, 0-100% ethyl acetate/hexanes) to furnish phenyl (4-cyclobutyl-3-(3,3-difluorocyclobutyl)-1-methyl-1H-pyrazol-5-yl)carbamate as a white solid (61 mg, 82%). LC-MS (Method A, ESI): m/z, 362 $(M+H)^+$; $t_R$=4.1 min.

Step 1, Option 2

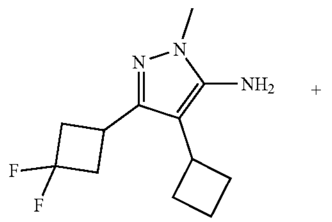

-continued

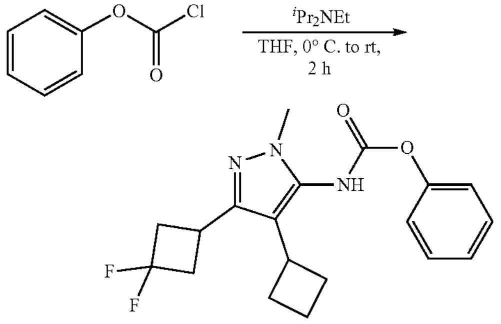

To a stirred solution of 4-cyclobutyl-3-(3,3-difluorocyclobutyl)-1-methyl-1H-pyrazol-5-amine (520 mg, 2.15 mmol) in THF at 0° C., were added N,N-diisopropylethylamine (0.75 mL, 4.3 mmol) and phenyl chloroformate (332 μL, 2.59 mmol) and the reaction mixture was stirred at room temperature for 2 h. The LC-MS indicated that the starting material was consumed. Then the reaction mixture was quenched with sat. aqueous $NH_4Cl$ and extracted with ethyl acetate (2×). The combined organic layers were washed with brine (1×), dried over anhydrous $Na_2SO_4$, and concentrated under reduced pressure. The resulting residue was purified by chromatography (silica gel, 0-100% ethyl acetate/hexanes) to obtain phenyl (4-cyclobutyl-3-(3,3-difluorocyclobutyl)-1-methyl-1H-pyrazol-5-yl)carbamate as a white solid (613 mg, 79%). LC-MS (Method A, ESI): m/z, 362 $(M+H)^+$; $t_R$=4.1 min.

Step 2

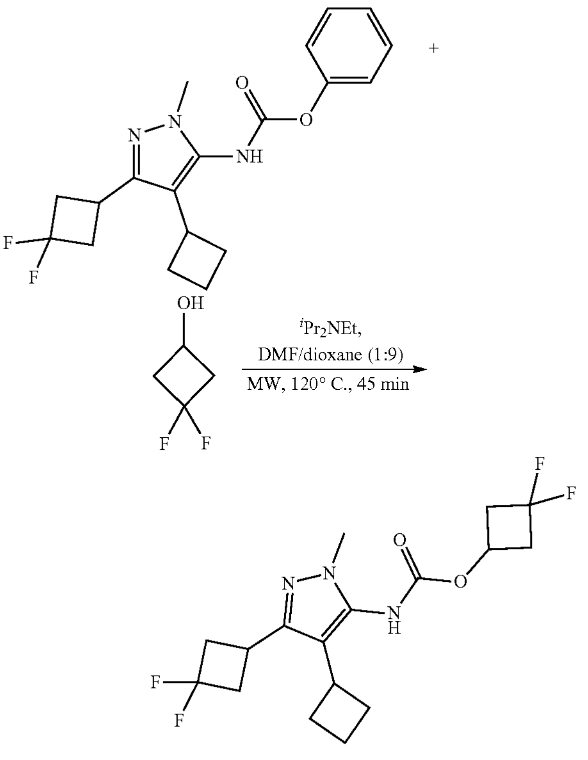

To a solution of phenyl (4-cyclobutyl-3-(3,3-difluorocyclobutyl)-1-methyl-1H-pyrazol-5-yl)carbamate (100 mg, 0.28 mmol) and 3,3-difluorocyclobutanol (36 mg, 0.33 mmol) in dry N,N-dimethylformamide/dioxane (0.1 M, 2.8 mL) in a microwave tube (2.0-5.0 mL) was added N,N-diisopropylethylamine (96 μL, 0.55 mmol). The reaction mixture was irradiated for 45 min at 120° C. under microwave conditions. The resulting reaction mixture was injected onto a reverse phase HPLC column (C18, 10-100% acetonitrile/water and monitoring with 220 nm wavelength) to obtain 3,3-difluorocyclobutyl(4-cyclobutyl-3-(3,3-difluorocyclobutyl)-1-methyl-1H-pyrazol-5-yl)carbamate (Example 243, 35 mg, 34%); $^{1}$H-NMR (400 MHz, $CDCl_3$): δ 6.05 (s, 1H), 5.0 (s, 1H), 3.66 (s, 3H), 3.20-3.36 (m, 2H), 2.98-3.16 (m, 2H), 2.54-2.96 (m, 6H), 2.18-2.31 (m, 2H), 1.93-2.17 (m, 3H), 1.77-1.89 (m, 1H); LC-MS (Method A, ESI): m/z, 376 $(M+H)^+$; $t_R$=4.0 min.

Method M

Example 374: 1-(4-cyclobutyl-3-(3,3-difluorocyclobutyl)-1-methyl-1H-pyrazol-5-yl)-3-(2,2-difluoroethyl)urea

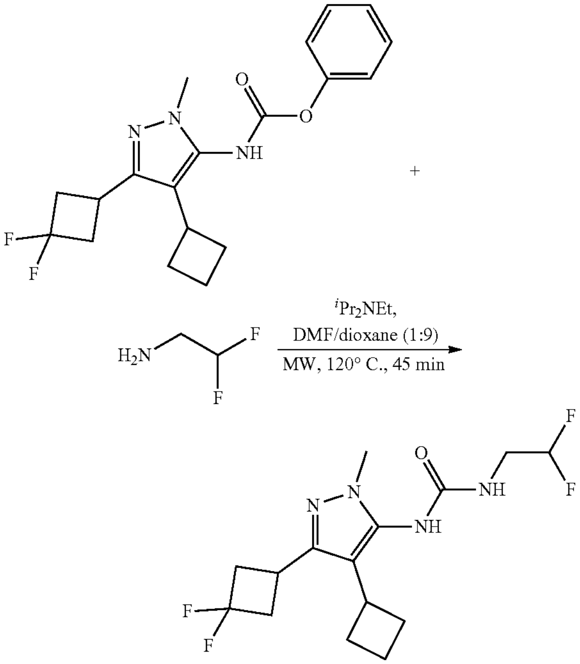

To a solution of phenyl (4-cyclobutyl-3-(3,3-difluorocyclobutyl)-1-methyl-1H-pyrazol-5-yl)carbamate (40 mg, 0.11 mmol) and 2,2-difluoroethylamine (11 mg, 0.13 mmol) in dry N,N-dimethylformamide/dioxane (0.2 M, 0.6 mL) in a microwave tube (2.0-5.0 mL) was added N,N-diisopropylethylamine (38 μL, 0.22 mmol). The reaction mixture was irradiated for 45 min at 120° C. under microwave conditions. The resulting reaction mixture was injected onto a reverse phase HPLC column (C18, 10-100% acetonitrile/water and monitoring with 220 nm wavelength) to obtain 1-(4-cyclobutyl-3-(3,3-difluorocyclobutyl)-1-methyl-1H-pyrazol-5-yl)-3-(2,2-difluoroethyl)urea (Example 374, 22 mg, 57%); $^{1}$H-NMR (400 MHz, $CDCl_3$): δ 5.98 (s, 1H), 5.70-6.05 (m, 1H), 4.70 (bs, 1H), 3.69 (s, 3H), 3.37-3.50 (m, 2H), 3.25-3.37 (m, 2H), 2.80-2.99 (m, 4H), 2.19-2.29 (m, 2H), 2.07-2.17 (m, 2H), 1.93-2.06 (m, 1H), 1.77-1.88 (m, 1H); LC-MS (Method A, ESI): m/z, 349 $(M+H)^+$; $t_R$=3.5 min.

Method N

Example 483: N-(1-cyclobutyl-3-(cyclobutylmethyl)-4-methyl-1H-pyrazol-5-yl)-3,3-difluorocyclobutane-1-carboxamide

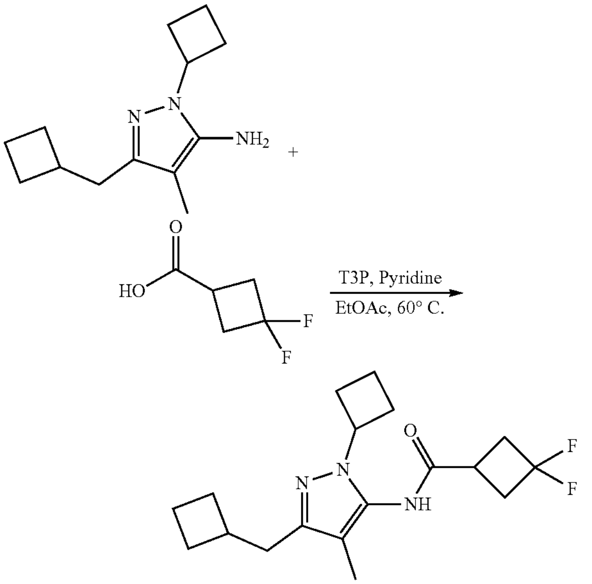

To a solution of the 1-cyclobutyl-3-(cyclobutylmethyl)-4-methyl-1H-pyrazol-5-amine (0.030 g, 0.118 mmol) in EtOAc was added the 3,3-difluorocyclobutane-1-carboxylic acid (0.026 g, 0.176 mmol), pyridine (0.019 g, 0.019 mL, 0.235 mmol) and propylphosphonic anhydride solution (>50 wt. % in ethyl acetate, 0.070 mL, 0.235 mmol). The mixture was stirred at 60° C. overnight, then diluted with DCM, washed with 0.5 M HCl, $H_2O$, sat. aqueous $NaHCO_3$, and brine, then dried ($Na_2SO_4$), filtered and concentrated. The crude material was purified on a 12 g silica gel column eluting with 0-40% EtOAc/hexane to give N-(1-cyclobutyl-3-(cyclobutylmethyl)-4-methyl-1H-pyrazol-5-yl)-3,3-difluorocyclobutane-1-carboxamide (Example 483, 23 mg, 50% yield). LC-MS (Method A, ESI): m/z, 388 $(M+H)^+$; $t_R$=3.9 min.

Method O

Example 372: N-(4-cyclobutyl-3-((3,3-difluorocyclobutyl)methyl)-1-methyl-1H-pyrazol-5-yl)-3,3-dimethylbutanamide

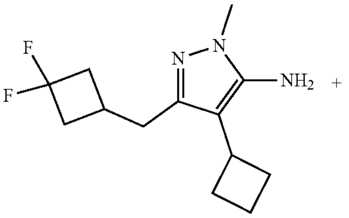

-continued

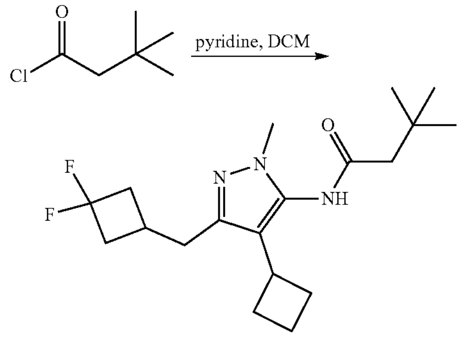

To 4-cyclobutyl-3-((3,3-difluorocyclobutyl)methyl)-1-methyl-1H-pyrazol-5-amine (25 mg, 0.10 mmol) in DCM (0.39 mL) was added pyridine (40 μL, 0.49 mmol) and 3,3-dimethylbutanoyl chloride (41 μL, 0.29 mmol). The mixture was stirred at room temperature for 3 h. Solvents were removed and the residue was dissolved in 3M ammonia in $CH_3OH$ (1 mL). The mixture was stirred at 50° C. for 1 h and concentrated. To the crude material was added sat. aqueous $NH_4Cl$ and the mixture was extracted with EtOAc. The extracts were combined and concentrated. The crude material was purified on a 4 g silica gel column eluting with 0-100% EtOAc/hexane. The product was re-purified by HPLC (C18 column, eluting with 10-100% $CH_3CN/H_2O$) to give N-(4-cyclobutyl-3-((3,3-difluorocyclobutyl)methyl)-1-methyl-1H-pyrazol-5-yl)-3,3-dimethylbutanamide (Example 372, 9.3 mg, 27%).

Method P

Example 127: Ethyl (4-cyclobutyl-3-cyclohexyl-1-methyl-1H-pyrazol-5-yl)carbamate

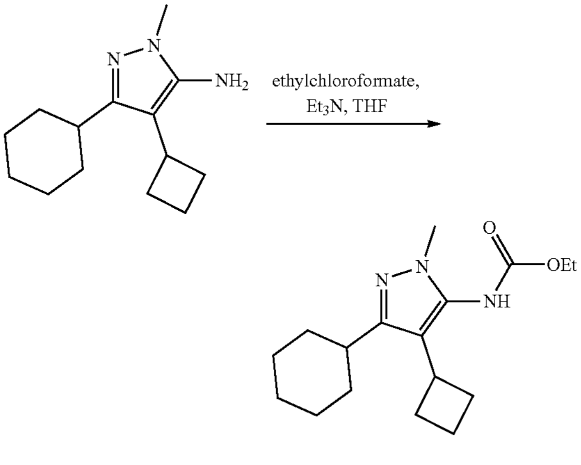

To 4-cyclobutyl-3-cyclohexyl-1-methyl-1H-pyrazol-5-amine (10.5 mg, 0.045 mmol) in THF was added triethylamine (19 μL, 0.14 mmol) and ethyl chloroformate (10 μL, 0.11 mmol). The mixture was stirred overnight and by LCMS it was determined that the reaction did not go to completion. To the mixture was added additional triethylamine (40 μL, 0.29 mmol) and ethyl chloroformate (20 μL, 0.21 mmol) and it was stirred overnight. The mixture was diluted with EtOAc, then washed with sat. aqueous $NaHCO_3$, dried over $Na_2SO_4$, then concentrated. Purification by column chromatography (0-100% EtOAc/hexane) provided ethyl (4-cyclobutyl-3-cyclohexyl-1-methyl-1H-pyrazol-5-yl)carbamate (Example 127, 4.7 mg, 35%).

Method Q

Example 542: Phenyl (1s,3s)-3-fluorocyclobutyl (1-(tert-butyl)-3-(3,3-difluorocyclobutyl)-4-methyl-1H-pyrazol-5-yl) carbamate

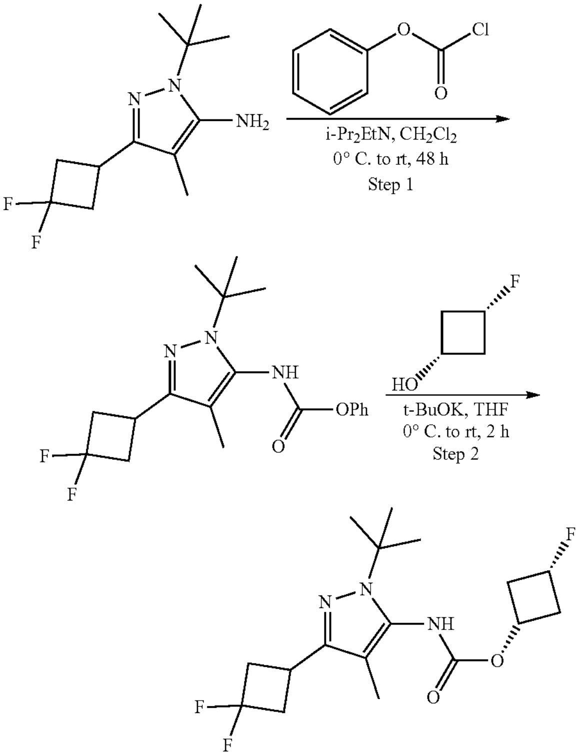

Step 1. To a solution of 1-(tert-butyl)-3-(3,3-difluorocyclobutyl)-4-methyl-1H-pyrazol-5-amine (500 mg, 2.06 mmol) and N, N-diisopropylethylamine (1.79 mL, 10.3 mmol) in $CH_2Cl_2$ (20 mL) at 0° C. was added phenyl chloroformate (0.5 mL, 4.1 mmol) dropwise over 5 min and the solution was stirred at room temperature for 48 h. The progress of the reaction was monitored by TLC. After completion of the reaction, the volatiles were removed under reduced pressure and the resulting residue was purified by silica-gel column chromatography eluting with 15%-20% EtOAc/hexane gradient to afford (1-(tert-butyl)-3-(3,3-difluorocyclobutyl)-4-methyl-1H-pyrazol-5-yl) carbamate (600 mg, 81%) as an off-white solid. LC-MS (Method B, -ve mode): m/z, 364 $(M+H)^+$; $t_R$=5.4 min Step 2. To a mixture of potassium tert-butoxide (155 mg, 1.39 mmol) in THF (3 mL), a solution of (1s,3s)-3-fluorocyclobutan-1-ol (93.8 mg, 1.04 mmol) in dry THF was added dropwise at 0° C. and the mixture was stirred for 30 min. (1-(tert-butyl)-3-(3,3-difluorocyclobutyl)-4-methyl-1H-pyrazol-5-yl) carbamate (250 mg, 0.694 mmol) in THF (3 mL) was added dropwise to the above reaction mixture at 0° C. and then stirred for 2 h. The progress of the reaction was monitored by TLC. After completion of the reaction, the volatiles were removed under reduced pressure and the resulting residue was purified by silica-gel column chromatography eluting with 15% EtOAc/hexane to afford (1s,3s)-3-fluorocyclobutyl (1-(tert-butyl)-3-(3,3-difluorocyclobutyl)-4-methyl-1H-pyrazol-5-yl) carbamate (85 mg, 34%) as an off-white solid.

$^1$H NMR (300 MHz, DMSO-$D_6$): δ 8.80-9.04 (m, 1H), 4.70-4.97 (m, 1H), 4.50-4.56 (m, 1H), 3.23-3.29 (m, 1H), 2.67-2.96 (m, 6H), 1.92-2.27 (m, 2H), 1.70 (s, 3H), 1.48 (s, 9H); LC-MS (Method B, −ve mode): m/z, 358 $(M-H)^-$; $t_R$=4.9 min.

Method R

Example 180: N-(4-cyclobutyl-1-methyl-3-(2-(trifluoromethyl)thiazol-5-yl)-1H-pyrazol-5-yl)-1-(trifluoromethyl)cyclopropane-1-carboxamide

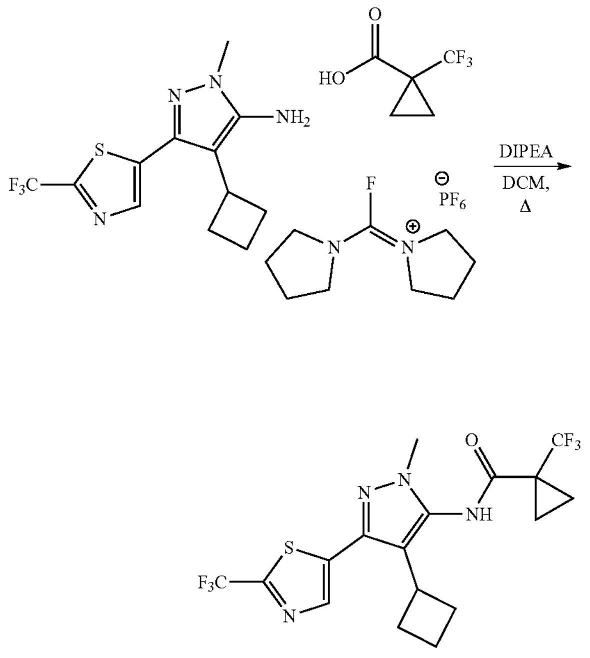

1-(Trifluoromethyl)cyclopropane-1-carboxylic acid (0.027 g, 0.172 mmol), 1-(fluoro(pyrrolidin-1-yl)methylene)pyrrolidin-1-ium hexafluorophosphate(V) (0.063 g, 0.198 mmol), and diisopropylethylamine (0.104 mL, 0.595 mmol) were stirred in DCM (0.5 mL) in a vial at ambient temperature for 30 min followed by addition of 4-cyclobutyl-1-methyl-3-(2-(trifluoromethyl)thiazol-5-yl)-1H-pyrazol-5-amine (0.040 g, 0.132 mmol). The vial was capped and sealed with parafilm and electrical tape and the reaction mixture was heated at reflux overnight. LCMS indicates desired product and complete consumption of amine. DCM was removed in vacuo and the reaction mixture was diluted with MeOH, loaded onto a C18 HPLC column and eluted with 10-100% MeCN/$H_2O$ to give 8 mg (14%) of N-(4-cyclobutyl-1-methyl-3-(2-(trifluoromethyl)thiazol-5-yl)-1H-pyrazol-5-yl)-1-(trifluoromethyl)cyclopropane-1-carboxamide as confirmed by $^1$H-NMR (400 MHz, $CDCl_3$) δ 7.90 (s, 1H), 7.47 (s, 1H), 3.70 (s, 3H), 3.60-3.64 (m, 1H), 2.29-2.33 (m, 2H), 2.08-2.17 (m, 2H), 2.00-2.05 (m, 1H), 1.81-2.00 (m, 1H), 1.43 (bs, 2H); LC-MS (Method A, ESI): m/z, 439 $(M+H)^+$; $t_R$=4.2 min.

Method S

Example 217: 1-(4-cyclobutyl-3-(3,3-difluorocyclobutyl)-1-methyl-H-pyrazol-5-yl)-3-phenylurea

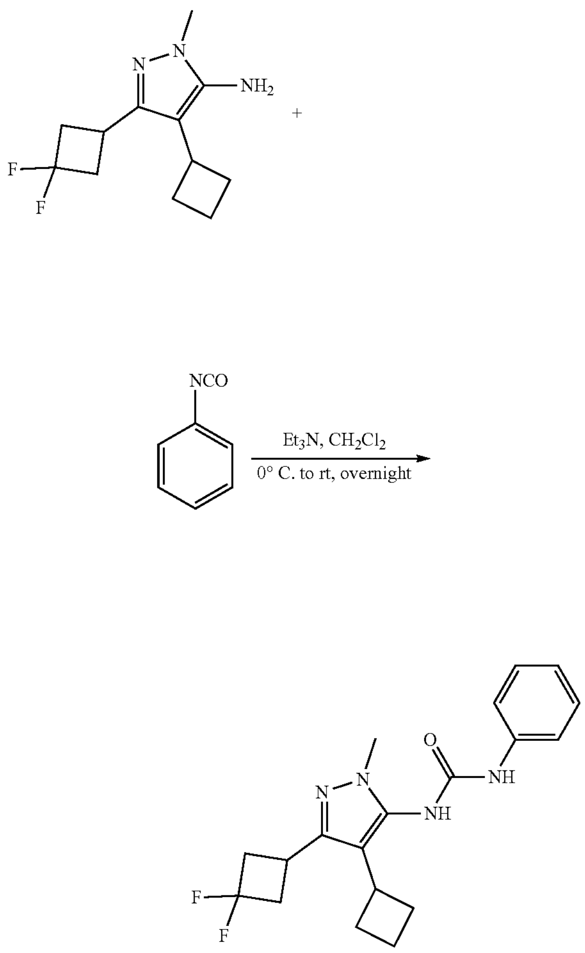

To a solution of 4-cyclobutyl-3-(3,3-difluorocyclobutyl)-1-methyl-1H-pyrazol-5-amine (30 mg, 0.12 mmol) in dichloromethane (2.0 mL) at 0° C., were added phenyl isocyanate (20 μL, 0.18 mmol) and triethylamine (35 μL, 0.24 mmol). Then the reaction mixture was allowed to stir at room temperature overnight. The volatiles were removed under reduced pressure, the resulting residue was dissolved in acetonitrile and purified by reverse phase HPLC column (C18, 10-100% acetonitrile/water and monitoring with 220 nm wavelength) to give 1-(4-cyclobutyl-3-(3,3-difluorocyclobutyl)-1-methyl-1H-pyrazol-5-yl)-3-phenylurea as white solid (Example 217, 14 mg, 32%); $^1$H-NMR (400 MHz, $CDCl_3$): δ 7.29-7.37 (m, 4H), 7.08-7.15 (m, 1H), 6.30 (s, 1H), 6.0 (s, 1H), 3.74 (s, 3H), 3.28-3.40 (m, 2H), 2.80-3.01 (m, 4H), 2.10-2.30 (m, 4H), 1.91-2.05 (m, 1H), 1.77-1.88 (m, 1H); LC-MS (Method A, ESI): m/z, 361 $(M+H)^+$; $t_R$=3.9 min.

Method W

Example 102: (R)—N-(4-cyclobutyl-3-(4-fluorophenyl)-1-(2-hydroxyethyl)-1H-pyrazol-5-yl)-2-(2,2,3,3-tetrafluorocyclobutyl)acetamide

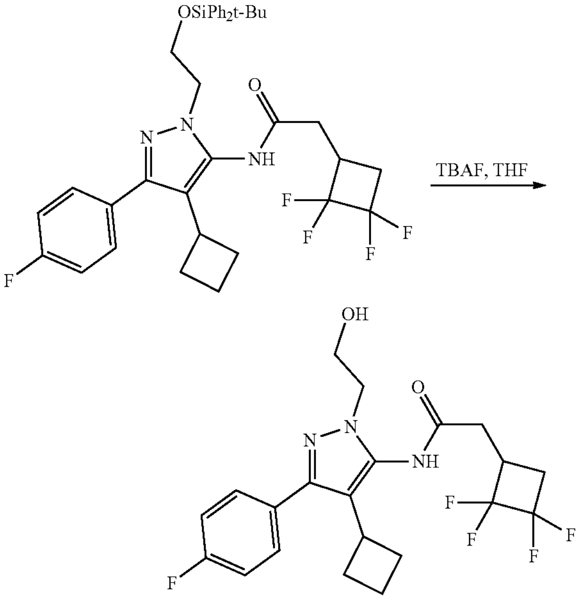

To (R)—N-(1-(2-((tert-butyldiphenylsilyl)oxy)ethyl)-4-cyclobutyl-3-(4-fluorophenyl)-1H-pyrazol-5-yl)-2-(2,2,3,3-tetrafluorocyclobutyl)acetamide (17 mg, 0.025 mmol) in THF (1 mL) was added TBAF solution (50 μL, 0.05 mmol, 1 M in THF). After 2 h, TLC indicated consumption of starting material. The mixture was purified by direct application on reverse phase HPLC column (10-100% ACN/$H_2O$) to provide (R)—N-(4-cyclobutyl-3-(4-fluorophenyl)-1-(2-hydroxyethyl)-1H-pyrazol-5-yl)-2-(2,2,3,3-tetrafluorocyclobutyl)acetamide (Example 102, 8.3 mg, 75%).

Method X

Example 294: 3,3-difluorocyclobutyl (4-cyclobutyl-3-(3,3-difluorocyclobutyl)-1-methyl-1H-pyrazol-5-yl)(methyl)carbamate

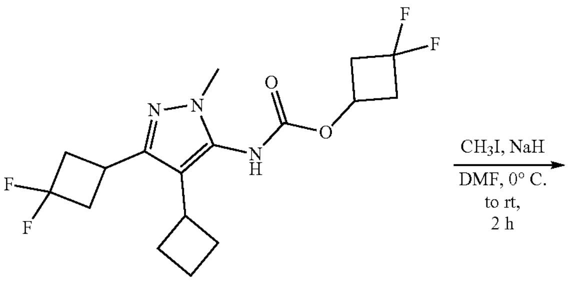

-continued

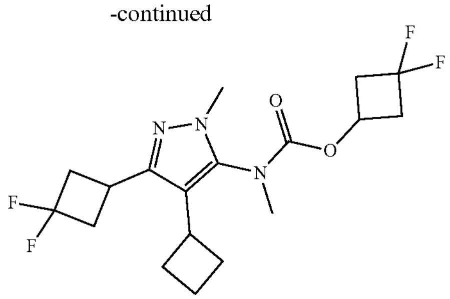

To a slurry of sodium hydride (4 mg, 0.16 mmol) in DMF (0.3 mL) at 0° C. was added a solution of 3,3-difluorocyclobutyl (4-cyclobutyl-3-(3,3-difluorocyclobutyl)-1-methyl-1H-pyrazol-5-yl)carbamate (20 mg, 0.053 mmol; in 0.6 mL DMF). The mixture was allowed to stir for 30 min, then iodomethane (4 μL, 0.069 mmol) was added. The reaction mixture was warmed to ambient temperature and stirred for 2 h, at which point the reaction mixture was cooled to 0° C. and was quenched with careful dropwise addition of sat. aq. $NH_4Cl$ until hydrogen evolution ceased. The reaction mixture was diluted with ethyl acetate and the organic portion was washed with cold water (4×) and brine (1×), then dried ($Na_2SO_4$), and concentrated under reduced pressure. The resulting residue was purified by chromatography (silica gel, 0-100% ethyl acetate/hexanes) to afford 3,3-difluorocyclobutyl (4-cyclobutyl-3-(3,3-difluorocyclobutyl)-1-methyl-1H-pyrazol-5-yl)(methyl)carbamate as an oil (11 mg, 53%); $^1$H-NMR (400 MHz, $CDCl_3$): δ 5.04 (bs, 1H), 3.60 (s, 3H), 3.19-3.35 (m, 2H), 3.15 (s, 3H), 2.93-3.05 (m, 2H), 2.76-2.91 (m, 4H), 2.45-2.60 (m, 1H), 2.11-2.26 (m, 2H), 1.92-2.10 (m, 3H), 1.75-1.88 (m, 1H); LC-MS (Method A, ESI): m/z, 390 $(M+H)^+$; $t_R$=4.3 min.

Method Y

Example 77: N-(4-cyclobutyl-3-(4-(2-hydroxypropan-2-yl)phenyl)-1-methyl-1H-pyrazol-5-yl)-3,3-dimethylbutanamide

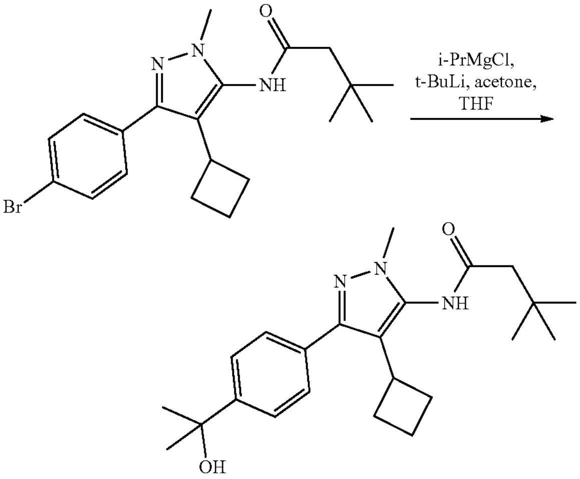

N-(3-(4-bromophenyl)-4-cyclobutyl-1-methyl-1H-pyrazol-5-yl)-3,3-dimethylbutanamide (20 mg, 0.05 mmol) was dissolved in THF (1.6 mL) and cooled to 0° C. in an ice bath.

To this solution was added, dropwise, i-PrMgCl (42 μL, 0.08 mmol, 2M in THF). The solution was stirred at 0° C. for 10 min, then cooled to −78° C. and t-BuLi (125 μL, 0.21 mmol, 1M in hexane) was added dropwise. The solution was stirred at −78° C. for 15 min, then acetone (36 μL, 0.50 mmol) was added and the solution was allowed to warm to room temperature over 1 h. The mixture was quenched with saturated aqueous $NH_4Cl$, then extracted with EtOAc. The extracts were combined, washed with brine, dried ($MgSO_4$), filtered and concentrated. This residue was dissolved in 0.5 mL of ACN and purified by reverse phase HPLC, (C18 column, eluting with 10-100% $CH_3CN/H_2O$) to provide N-(4-cyclobutyl-3-(4-(2-hydroxypropan-2-yl)phenyl)-1-methyl-1H-pyrazol-5-yl)-3,3-dimethylbutanamide (Example 77, 3.1 mg, 16%).

Method Z

Example 442: 1-(4-(azetidin-3-yl)-3-(3,3-difluoro-cyclobutyl)-1-methyl-1H-pyrazol-5-yl)-3-(2,2,2-trifluoroethyl)urea hydrochloride

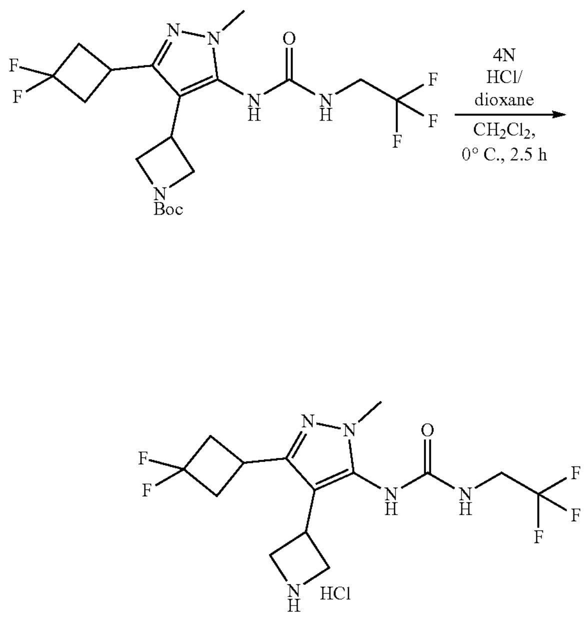

To a solution of tert-butyl 3-(3-(3,3-difluorocyclobutyl)-1-methyl-5-(3-(2,2,2-trifluoroethyl)ureido)-1H-pyrazol-4-yl)azetidine-1-carboxylate (50 mg, 0.11 mmol) in dichloromethane (2 mL) at 0° C., was added 4N HCl/dioxane (654 μL) dropwise. The reaction mixture was stirred at 0° C. for 2.5 h. The LC-MS indicated that the starting compound was consumed. The volatiles were removed under reduced pressure and the resulting residue was triturated with methanol/diethyl ether (1:9). The precipitate was collected by filtration, and dried in vacuo to furnish 1-(4-(azetidin-3-yl)-3-(3,3-difluorocyclobutyl)-1-methyl-H-pyrazol-5-yl)-3-(2,2,2-trifluoroethyl)urea hydrochloride as white solid (38 mg, 88%); $^1$H-NMR (400 MHz, DMSO-$d_6$): δ 9.14 (bs, 1H), 8.60-8.85 (m, 2H), 7.38 (s, 1H), 3.98-4.12 (m, 4H), 3.79-3.95 (m, 3H), 3.55 (s, 3H), 2.70-3.01 (m, 5H); LC-MS (ESI): m/z, 368 $(M+H)^+$; $t_R$=2.3 min.

Method AA

Example 251: 5-amino-4-cyclobutyl-N-(3,3-difluorocyclobutyl)-3-(4-fluorophenyl)-1H-pyrazole-1-carboxamide

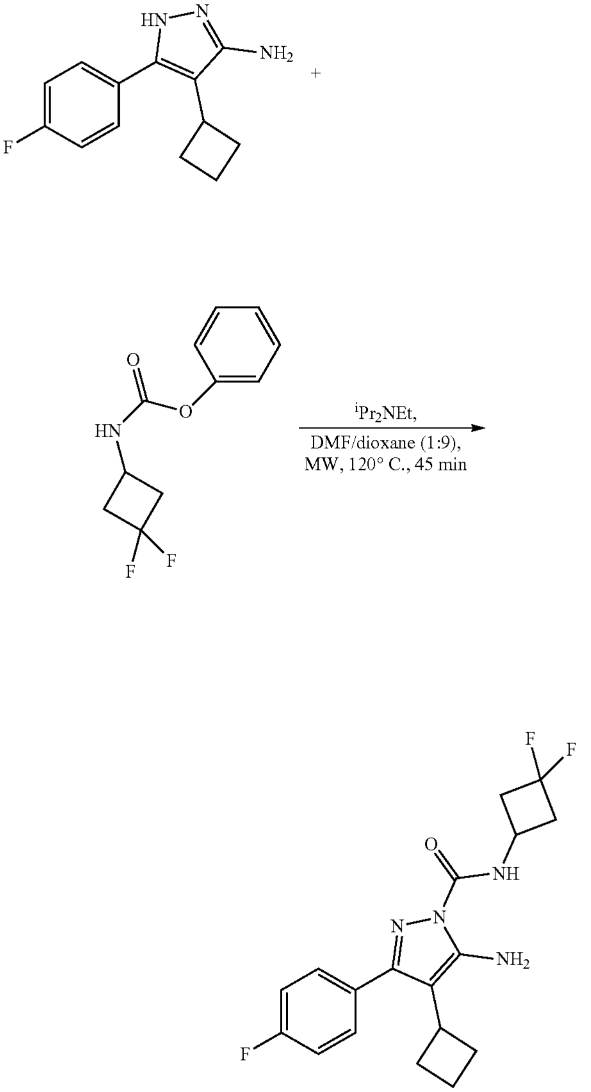

To a solution of 4-cyclobutyl-5-(4-fluorophenyl)-1H-pyrazol-3-amine (30 mg, 0.13 mmol) and phenyl (3,3-difluorocyclobutyl)carbamate (44 mg, 0.19 mmol) in DMF/dioxane (0.7 mL, 1:9) in a microwave tube (2.0-5.0 mL) was added N,N-diisopropylethylamine (45 μL, 0.26 mmol). The reaction mixture was irradiated for 45 min at 120° C. under microwave conditions. The resulting reaction mixture was injected directly onto a reverse phase HPLC column (C18, 10-100% acetonitrile/water and monitoring with 220 nm wavelength) to obtain 5-amino-4-cyclobutyl-N-(3,3-difluorocyclobutyl)-3-(4-fluorophenyl)-1H-pyrazole-1-carboxamide as a white solid (Example 251, 12 mg, 25%); $^1$H-NMR (400 MHz, $CDCl_3$): δ 7.40-7.51 (m, 2H), 7.30-7.37 (m, 1H), 7.04-7.18 (m, 2H), 5.39 (s, 2H), 4.21-4.37 (m, 1H), 3.39-3.54 (m, 1H), 2.95-3.14 (m, 2H), 2.55-2.75 (m, 2H), 2.03-2.22 (m, 4H), 1.84-1.99 (m, 1H), 1.77-1.83 (m, 1H); LC-MS (ESI): m/z, 365 $(M+H)^+$; $t_R$=4.5 min.

Method BB

Example 555: 2-(3,3-difluorocyclobutyl)-N-(3-(3,3-difluorocyclobutyl)-1-(2-hydroxy-2-methylpropyl)-4-methyl-1H-pyrazol-5-yl)acetamide

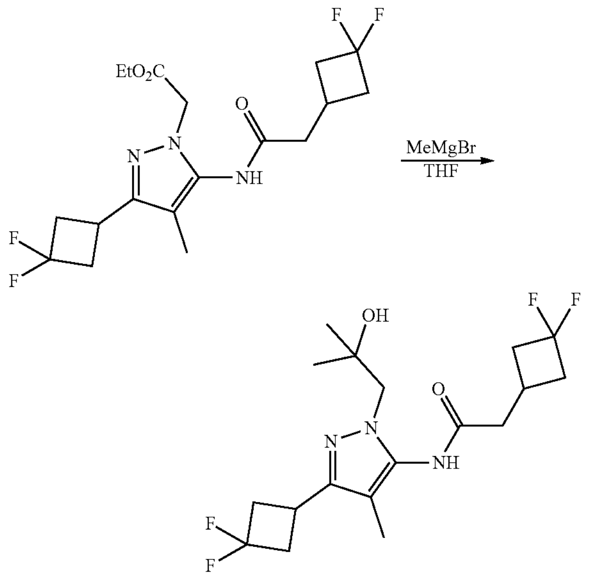

Methylmagnesium bromide (0.658, 1.97 mmol; 3.0 M in $Et_2O$) was added to a solution of ethyl 2-(3-(3,3-difluorocyclobutyl)-5-(2-(3,3-difluorocyclobutyl)acetamido)-4-methyl-1H-pyrazol-1-yl)acetate (0.080 g, 0.197 mmol) in 1.0 mL THF and the reaction mixture stirred overnight. The reaction was quenched with 1 N HCl, extracted (EtOAc 2×), the combined organics dried ($Na_2SO_4$), and the volatiles removed to give a crude residue that was purified via preparatory HPLC (C18 column, 10-100% $MeCN/H_2O$) to give 12 mg (16%) of 2-(3,3-difluorocyclobutyl)-N-(3-(3,3-difluorocyclobutyl)-1-(2-hydroxy-2-methylpropyl)-4-methyl-1H-pyrazol-5-yl)acetamide as confirmed by $^1$H-NMR (400 MHz, $CDCl_3$) δ 8.03 (s, 1H), 3.92 (s, 2H), 3.25-3.30 (m, 1H), 2.78-2.91 (m, 6H), 2.61 (bs, 3H), 2.46 (s, 1H), 2.22-2.39 (m, 2H), 1.92 (s, 3H), 1.22 (s, 6H); LC-MS (ESI): m/z, 392 $(M+H)^+$; $t_R$=3.6 min.

Method CC

Example 238: N-(4-cyclobutyl-3-(3-hydroxy-3-phenylcyclobutyl)-1-methyl-1H-pyrazol-5-yl)-3,3-difluorocyclobutane-1-carboxamide

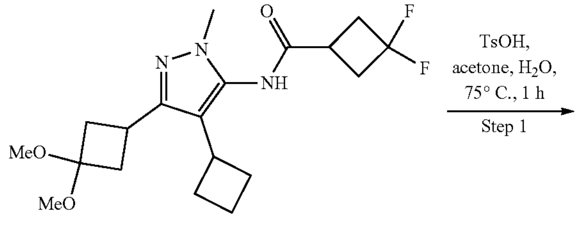

-continued

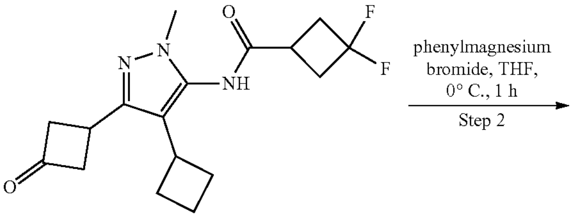

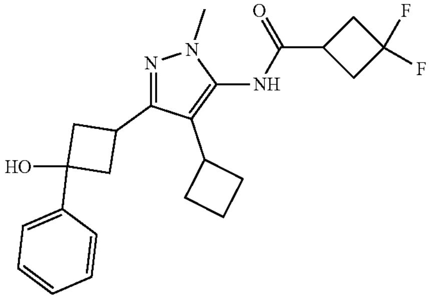

Step 1. N-(4-cyclobutyl-3-(3,3-dimethoxycyclobutyl)-1-methyl-1H-pyrazol-5-yl)-3,3-difluorocyclobutane-1-carboxamide (0.097 g, 0.253 mmol) was dissolved in acetone/water (4 mL, 3:1) and p-toluene sulfonic acid monohydrate (0.048 g, 0.253 mmol) was added. The mixture was stirred at 75° C. for 1 h. The mixture was cooled to room temperature and concentrated. The resulting solid was taken up in DCM, washed with sat. aqueous $NaHCO_3$ and dried over $MgSO_4$. The organics were then concentrated to give N-(4-cyclobutyl-1-methyl-3-(3-oxocyclobutyl)-1H-pyrazol-5-yl)-3,3-difluorocyclobutane-1-carboxamide as a white solid (73.9 mg, 87% yield) that was used in the next step without further purification. LC-MS (ESI): m/z, 338 $(M+H)^+$; $t_R$=3.4 min.

Step 2. N-(4-cyclobutyl-1-methyl-3-(3-oxocyclobutyl)-1H-pyrazol-5-yl)-3,3-difluorocyclobutane-1-carboxamide (0.097 g, 0.147 mmol) was dissolved in THF (0.500 mL) and phenylmagnesium bromide solution (0.134 mL, 0.741 mmol) was added. The mixture was stirred at 0° C. for 1 h. The reaction was quenched with sat. $NH_4Cl$ and allowed to warm to room temperature. The mixture was extracted with EtOAc (2×10 mL), dried over $Na_2SO_4$ and concentrated. The crude material was purified on a 12 g silica gel column eluting with MeOH/DCM (0-10%) to give N-(4-cyclobutyl-3-(3-hydroxy-3-phenylcyclobutyl)-1-methyl-1H-pyrazol-5-yl)-3,3-difluorocyclobutane-1-carboxamide (30 mg, 62% yield). LC-MS (ESI): m/z, 416 $(M+H)^+$; $t_R$=3.7 min. $^1$H NMR (400 MHz, MeOH-$D_4$): δ 7.60-7.62 (m, 2H), 7.37-7.41 (m, 2H), 7.28-7.30 (m, 1H), 3.59 (s, 3H), 3.01-3.18 (m, 2H), 2.81-2.98 (m, 6H), 2.60-2.66 (m, 2H), 2.12-2.18 (m, 4H), 2.0-2.09 (m, 1H), 1.96-1.98 (m, 1H).

Method DD

Example 332: 1-(4-cyclobutyl-3-(3-hydroxycyclobutyl)-1-methyl-1H-pyrazol-5-yl)-3-(3,3-difluorocyclobutyl)urea

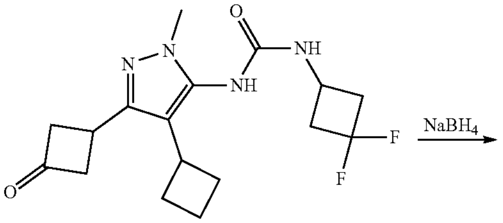

-continued

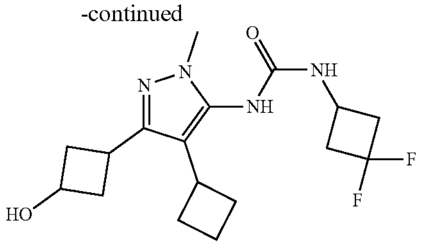

1-(4-cyclobutyl-1-methyl-3-(3-oxocyclobutyl)-1H-pyrazol-5-yl)-3-(3,3-difluorocyclobutyl)urea (0.016 g, 0.045 mmol)) was dissolved in anhydrous methanol (2 mL) at 0° C. and $NaBH_4$ (0.003 g, 0.091 mmol) was added under $N_2$ and the reaction mixture was stirred for 1 h. LCMS confirmed product formation. The mixture was allowed to warm to room temperature and concentrated. The resulting solid was taken up in DCM and washed with aq. $NaHCO_3$ and dried over $Na_2SO_4$. The organics were concentrated and the crude material was purified on a 12 g silica gel column eluting with MeOH/DCM (0-10%) to give a white solid 1-(4-cyclobutyl-3-(3-hydroxycyclobutyl)-1-methyl-1H-pyrazol-5-yl)-3-(3,3-difluorocyclobutyl)urea. (9 mg, 56%). LC-MS (ESI): m/z, 355 $(M+H)^+$; $t_R$=2.9 min.

Compounds made by these methods are shown in Table 1.

TABLE 1

List of Compounds and Characterization Data

| Cmpd # | Structure | Name | LCMS RT (min)* | m/z $(M + H)^+$ |
|---|---|---|---|---|
| 1 | 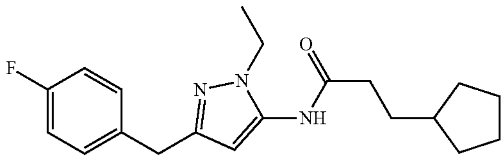 [SMILES: CCn1nc(Cc2ccc(F)cc2)cc1NC(=O)CCC1CCCC1] | 3-cyclopentyl-N-(1-ethyl-3-(4-fluorobenzyl)-1H-pyrazol-5-yl)propenamide | 4.1 | 344 |
| 2 | 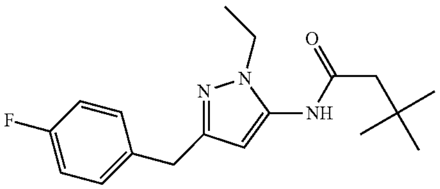 [SMILES: CCn1nc(Cc2ccc(F)cc2)cc1NC(=O)CC(C)(C)C] | N-(1-ethyl-3-(4-fluorobenzyl)-1H-pyrazol-5-yl)-3,3-dimethylbutanamide | 3.8 | 318 |
| 3 | 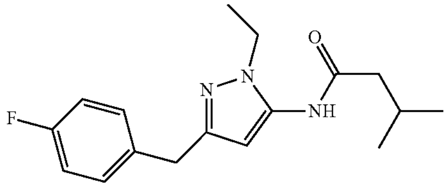 [SMILES: CCn1nc(Cc2ccc(F)cc2)cc1NC(=O)CC(C)C] | N-(1-ethyl-3-(4-fluorobenzyl)-1H-pyrazol-5-yl)-3-methylbutanamide | 3.6 | 304 |
| 4 | 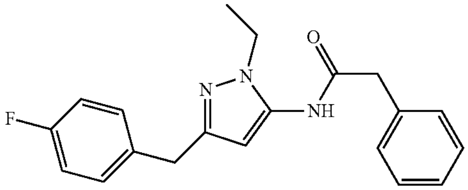 [SMILES: CCn1nc(Cc2ccc(F)cc2)cc1NC(=O)Cc1ccccc1] | N-(1-ethyl-3-(4-fluorobenzyl)-1H-pyrazol-5-yl)-2-phenylacetamide | 3.8 | 338 |

TABLE 1-continued
List of Compounds and Characterization Data
| Cmpd # | Structure | Name | LCMS RT (min)* | m/z $(M + H)^+$ |
|---|---|---|---|---|
| 5 | 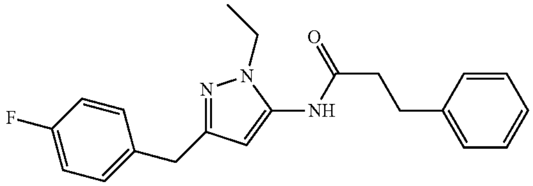 [SMILES: CCn1nc(Cc2ccc(F)cc2)cc1NC(=O)CCc1ccccc1] | N-(1-ethyl-3-(4-fluorobenzyl)-1H-pyrazol-5-yl)-3-phenylpropanamide | 3.9 | 352 |
| 6 | 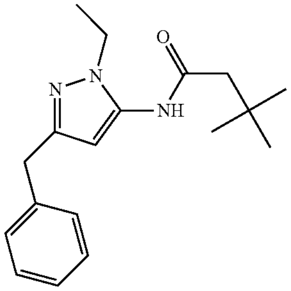 [SMILES: CCn1nc(Cc2ccccc2)cc1NC(=O)CC(C)(C)C] | N-(3-benzyl-1-ethyl-1H-pyrazol-5-yl)-3,3-dimethylbutanamide | 3.8 | 300 |
| 7 | 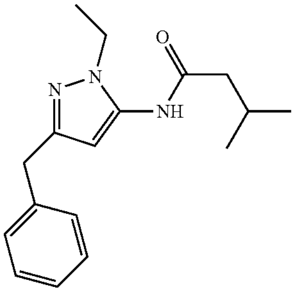 [SMILES: CCn1nc(Cc2ccccc2)cc1NC(=O)CC(C)C] | N-(3-benzyl-1-ethyl-1H-pyrazol-5-yl)-3-methylbutanamide | 3.6 | 286 |
| 8 | 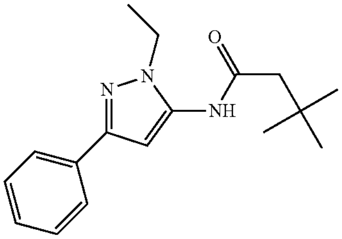 [SMILES: CCn1nc(-c2ccccc2)cc1NC(=O)CC(C)(C)C] | N-(1-ethyl-3-phenyl-1H-pyrazol-5-yl)-3,3-dimethylbutanamide | 3.9 | 286 |
| 9 | 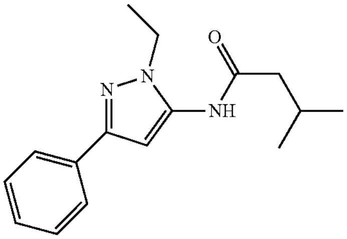 [SMILES: CCn1nc(-c2ccccc2)cc1NC(=O)CC(C)C] | N-(1-ethyl-3-phenyl-1H-pyrazol-5-yl)-3-methylbutanamide | 3.7 | 272 |

TABLE 1-continued

| List of Compounds and Characterization Data | | | | |
|---|---|---|---|---|
| Cmpd # | Structure | Name | LCMS RT (min)* | m/z $(M + H)^+$ |
| 10 | 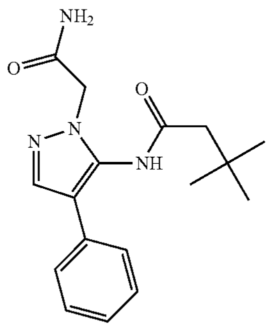 [SMILES: CC(C)(C)CC(=O)Nc1c(-c2ccccc2)cnn1CC(N)=O] | N-(1-(2-amino-2-oxoethyl)-4-phenyl-1H-pyrazol-5-yl)-3,3-dimethylbutanamide | 3.2 | 315 |
| 11 | 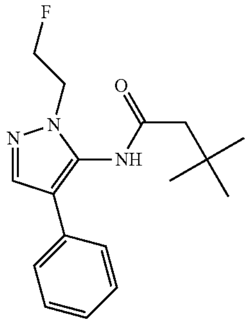 [SMILES: CC(C)(C)CC(=O)Nc1c(-c2ccccc2)cnn1CCF] | N-(1-(2-fluoroethyl)-4-phenyl-1H-pyrazol-5-yl)-3,3-dimethylbutanamide | 3.6 | 304 |
| 12 | 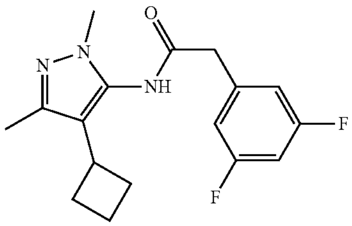 [SMILES: Cc1nn(C)c(NC(=O)Cc2cc(F)cc(F)c2)c1C1CCC1] | N-(4-cyclobutyl-1,3-dimethyl-1H-pyrazol-5-yl)-2-(3,5-difluorophenyl)acetamide | 4.3 | 320 |
| 13 | 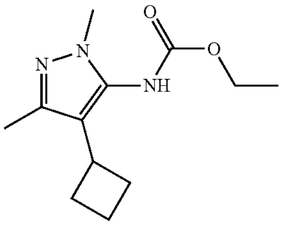 [SMILES: CCOC(=O)Nc1c(C2CCC2)c(C)nn1C] | ethyl (4-cyclobutyl-1,3-dimethyl-1H-pyrazol-5-yl)carbamate | 3 | 238 |
| 14 | 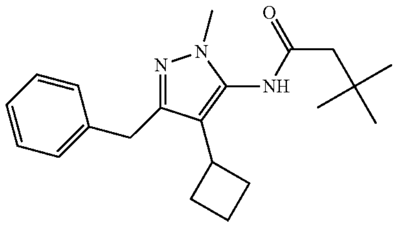 [SMILES: Cn1nc(Cc2ccccc2)c(C2CCC2)c1NC(=O)CC(C)(C)C] | N-(3-benzyl-4-cyclobutyl-1-methyl-1H-pyrazol-5-yl)-3,3-dimethylbutanamide | 4.1 | 340 |

TABLE 1-continued

| List of Compounds and Characterization Data | | | | |
|---|---|---|---|---|
| Cmpd # | Structure | Name | LCMS RT (min)* | m/z (M + H)+ |
| 15 | 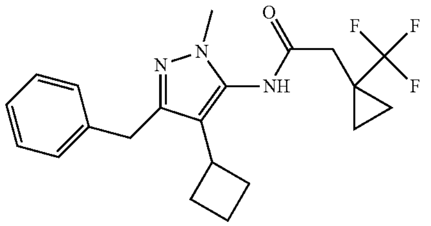 [SMILES: Cn1nc(Cc2ccccc2)c(C2CCC2)c1NC(=O)CC1(C(F)(F)F)CC1] | N-(3-benzyl-4-cyclobutyl-1-methyl-1H-pyrazol-5-yl)-2-(1-(trifluoromethyl)cyclopropyl)acetamide | 4 | 392 |
| 16 | 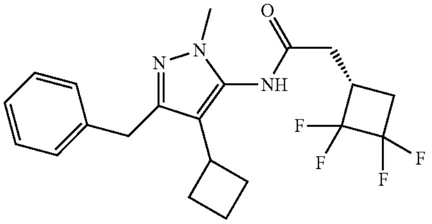 [SMILES: Cn1nc(Cc2ccccc2)c(C2CCC2)c1NC(=O)C[C@@H]1CC(F)(F)C1(F)F] | (R)-N-(3-benzyl-4-cyclobutyl-1-methyl-1H-pyrazol-5-yl)-2-(2,2,3,3-tetrafluorocyclobutyl)acetamide | 4 | 410 |
| 17 | 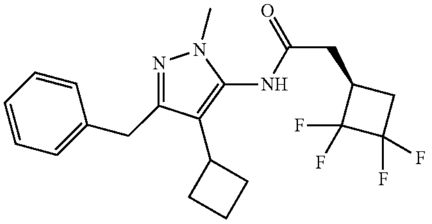 [SMILES: Cn1nc(Cc2ccccc2)c(C2CCC2)c1NC(=O)C[C@H]1CC(F)(F)C1(F)F] | (S)-N-(3-benzyl-4-cyclobutyl-1-methyl-1H-pyrazol-5-yl)-2-(2,2,3,3-tetrafluorocyclobutyl)acetamide | 4 | 410 |
| 18 | 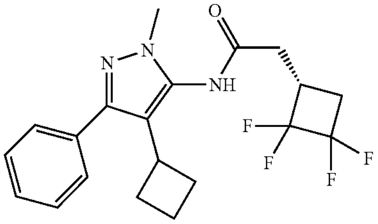 [SMILES: Cn1nc(-c2ccccc2)c(C2CCC2)c1NC(=O)C[C@@H]1CC(F)(F)C1(F)F] | (R)-N-(4-cyclobutyl-1-methyl-3-phenyl-1H-pyrazol-5-yl)-2-(2,2,3,3-tetrafluorocyclobutyl)acetamide | 4.1 | 396 |
| 19 | 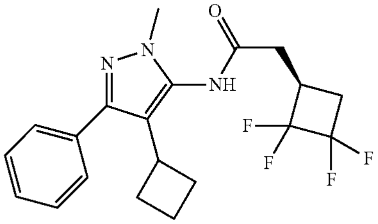 [SMILES: Cn1nc(-c2ccccc2)c(C2CCC2)c1NC(=O)C[C@H]1CC(F)(F)C1(F)F] | (S)-N-(4-cyclobutyl-1-methyl-3-phenyl-1H-pyrazol-5-yl)-2-(2,2,3,3-tetrafluorocyclobutyl)acetamide | 4.1 | 396 |
| 20 | 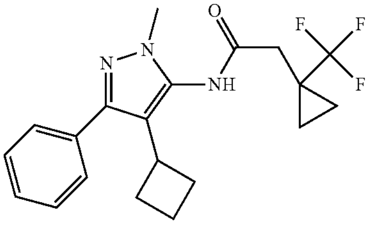 [SMILES: Cn1nc(-c2ccccc2)c(C2CCC2)c1NC(=O)CC1(C(F)(F)F)CC1] | N-(4-cyclobutyl-1-methyl-3-phenyl-1H-pyrazol-5-yl)-2-(1-(trifluoromethyl)cyclopropyl)acetamide | 4 | 378 |

TABLE 1-continued

| List of Compounds and Characterization Data | | | | |
|---|---|---|---|---|
| Cmpd # | Structure | Name | LCMS RT (min)* | m/z (M + H)+ |
| 21 | 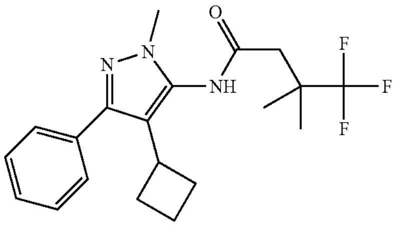 [SMILES: Cn1nc(-c2ccccc2)c(C2CCC2)c1NC(=O)CC(C)(C)C(F)(F)F] | N-(4-cyclobutyl-1-methyl-3-phenyl-1H-pyrazol-5-yl)-4,4,4-trifluoro-3,3-dimethylbutanamide | 4.3 | 380 |
| 22 | 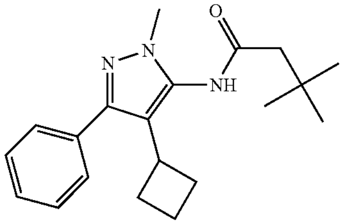 [SMILES: Cn1nc(-c2ccccc2)c(C2CCC2)c1NC(=O)CC(C)(C)C] | N-(4-cyclobutyl-1-methyl-3-phenyl-1H-pyrazol-5-yl)-3,3-dimethylbutanamide | 4.1 | 326 |
| 23 | 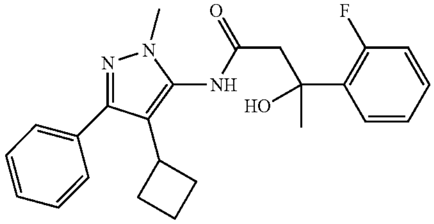 [SMILES: Cn1nc(-c2ccccc2)c(C2CCC2)c1NC(=O)CC(C)(O)c1ccccc1F] | (R)-N-(4-cyclobutyl-1-methyl-3-phenyl-1H-pyrazol-5-yl)-3-(2-fluorophenyl)-3-hydroxybutanamide | 4.1 | 408 |
| 24 | 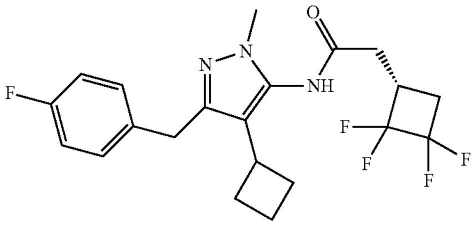 [SMILES: Cn1nc(Cc2ccc(F)cc2)c(C2CCC2)c1NC(=O)C[C@@H]1CC(F)(F)C1(F)F] | (R)-N-(4-cyclobutyl-3-(4-fluorobenzyl)-1-methyl-1H-pyrazol-5-yl)-2-(2,2,3,3-tetrafluorocyclobutyl)acetamide | 4.1 | 428 |
| 25 | 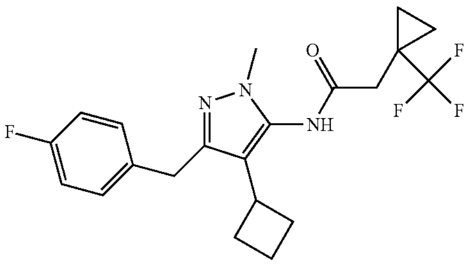 [SMILES: Cn1nc(Cc2ccc(F)cc2)c(C2CCC2)c1NC(=O)CC1(C(F)(F)F)CC1] | N-(4-cyclobutyl-3-(4-fluorobenzyl)-1-methyl-1H-pyrazol-5-yl)-2-(1-(trifluoromethyl)cyclopropyl)acetamide | 4.1 | 410 |
| 26 | 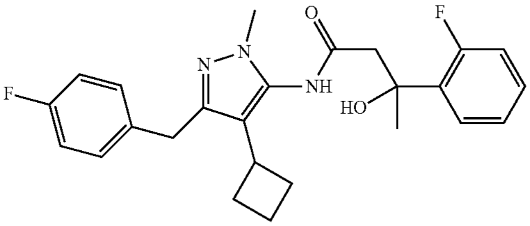 [SMILES: Cn1nc(Cc2ccc(F)cc2)c(C2CCC2)c1NC(=O)CC(C)(O)c1ccccc1F] | (R)-N-(4-cyclobutyl-3-(4-fluorobenzyl)-1-methyl-1H-pyrazol-5-yl)-3-(2-fluorophenyl)-3-hydroxybutanamide | 4.2 | 440 |

TABLE 1-continued

List of Compounds and Characterization Data

| Cmpd # | Structure | Name | LCMS RT (min)* | m/z (M + H)+ |
|---|---|---|---|---|
| 27 | 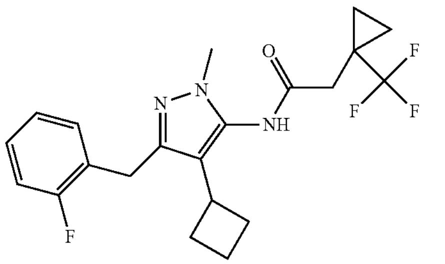 [SMILES: Cn1nc(Cc2ccccc2F)c(C2CCC2)c1NC(=O)CC1(C(F)(F)F)CC1] | N-(4-cyclobutyl-3-(2-fluorobenzyl)-1-methyl-1H-pyrazol-5-yl)-2-(1-(trifluoromethyl)cyclopropyl)acetamide | 4.1 | 410 |
| 28 | 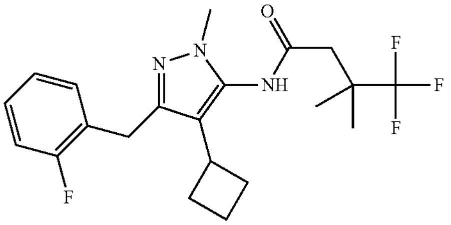 [SMILES: Cn1nc(Cc2ccccc2F)c(C2CCC2)c1NC(=O)CC(C)(C)C(F)(F)F] | N-(4-cyclobutyl-3-(2-fluorobenzyl)-1-methyl-1H-pyrazol-5-yl)-4,4,4-trifluoro-3,3-dimethylbutanamide | 4.3 | 412 |
| 29 | 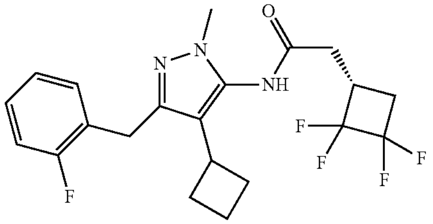 [SMILES: Cn1nc(Cc2ccccc2F)c(C2CCC2)c1NC(=O)C[C@@H]1CC(F)(F)C1(F)F] | (R)-N-(4-cyclobutyl-3-(2-fluorobenzyl)-1-methyl-1H-pyrazol-5-yl)-2-(2,2,3,3-tetrafluorocyclobutyl)acetamide | 4.1 | 428 |
| 30 | 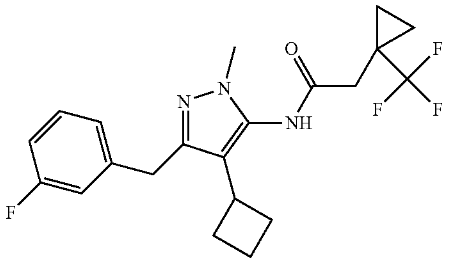 [SMILES: Cn1nc(Cc2cccc(F)c2)c(C2CCC2)c1NC(=O)CC1(C(F)(F)F)CC1] | N-(4-cyclobutyl-3-(3-fluorobenzyl)-1-methyl-1H-pyrazol-5-yl)-2-(1-(trifluoromethyl)cyclopropyl)acetamide | 4.1 | 410 |
| 31 | 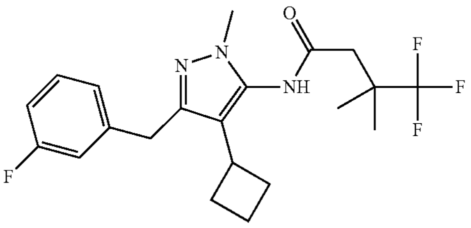 [SMILES: Cn1nc(Cc2cccc(F)c2)c(C2CCC2)c1NC(=O)CC(C)(C)C(F)(F)F] | N-(4-cyclobutyl-3-(3-fluorobenzyl)-1-methyl-1H-pyrazol-5-yl)-4,4,4-trifluoro-3,3-dimethylbutanamide | 4.3 | 412 |
| 32 | 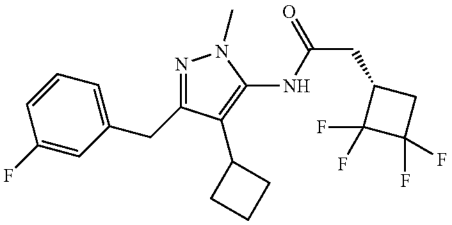 [SMILES: Cn1nc(Cc2cccc(F)c2)c(C2CCC2)c1NC(=O)C[C@@H]1CC(F)(F)C1(F)F] | (R)-N-(4-cyclobutyl-3-(3-fluorobenzyl)-1-methyl-1H-pyrazol-5-yl)-2-(2,2,3,3-tetrafluorocyclobutyl)acetamide | 4.1 | 428 |

TABLE 1-continued

| List of Compounds and Characterization Data | | | | |
|---|---|---|---|---|
| Cmpd # | Structure | Name | LCMS RT (min)* | m/z $(M + H)^+$ |
| 33 | 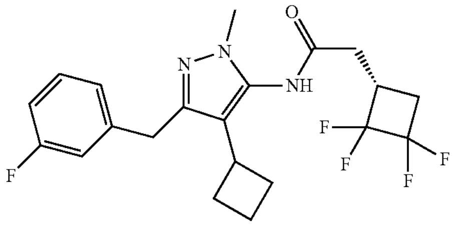 [SMILES: Cn1nc(Cc2cccc(F)c2)c(C2CCC2)c1NC(=O)C[C@@H]1CC(F)(F)C1(F)F] | (S)-N-(4-cyclobutyl-3-(2-fluorobenzyl)-1-methyl-1H-pyrazol-5-yl)-2-(2,2,3,3-tetrafluorocyclo-butyl)acetamide | 4.1 | 428 |
| 34 | 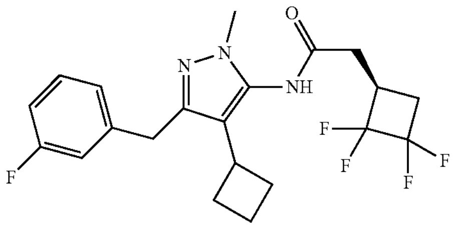 [SMILES: Cn1nc(Cc2cccc(F)c2)c(C2CCC2)c1NC(=O)C[C@H]1CC(F)(F)C1(F)F] | (S)-N-(4-cyclobutyl-3-(3-fluorobenzyl)-1-methyl-1H-pyrazol-5-yl)-2-(2,2,3,3-tetrafluorocyclo-butyl)acetamide | 4.1 | 428 |
| 35 | 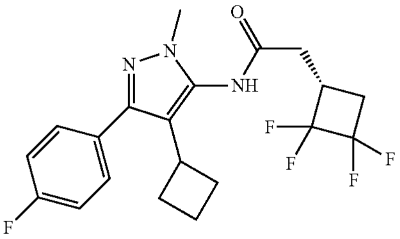 [SMILES: Cn1nc(-c2ccc(F)cc2)c(C2CCC2)c1NC(=O)C[C@@H]1CC(F)(F)C1(F)F] | (R)-N-(4-cyclobutyl-3-(4-fluorophenyl)-1-methyl-1H-pyrazol-5-yl)-2-(2,2,3,3-tetrafluorocyclo-butyl)acetamide | 4.1 | 414 |
| 36 | 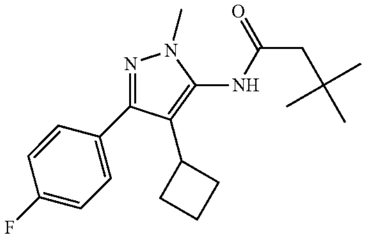 [SMILES: Cn1nc(-c2ccc(F)cc2)c(C2CCC2)c1NC(=O)CC(C)(C)C] | N-(4-cyclobutyl-3-(4-fluorophenyl)-1-methyl-1H-pyrazol-5-yl)-3,3-dimethylbutanamide | 4.2 | 344 |
| 37 | 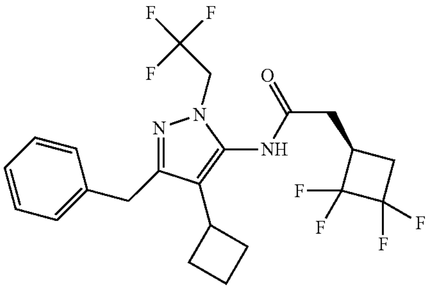 [SMILES: O=C(C[C@H]1CC(F)(F)C1(F)F)Nc1c(C2CCC2)c(Cc2ccccc2)nn1CC(F)(F)F] | (S)-N-(3-benzyl-4-cyclobutyl-1-(2,2,2-trifluoroethyl)-1H-pyrazol-5-yl)-2-(2,2,3,3-tetrafluorocyclo-butyl)acetamide | 4.3 | 478 |
| 38 | 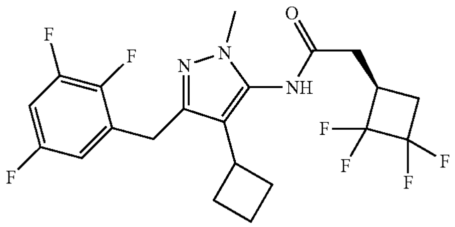 [SMILES: Cn1nc(Cc2cc(F)cc(F)c2F)c(C2CCC2)c1NC(=O)C[C@H]1CC(F)(F)C1(F)F] | (S)-N-(4-cyclobutyl-1-methyl-3-(2,3,5-trifluorobenzyl)-1H-pyrazol-5-yl)-2-(2,2,3,3-tetrafluorocyclo-butyl)acetamide | 4.2 | 464 |

TABLE 1-continued

List of Compounds and Characterization Data

| Cmpd # | Structure | Name | LCMS RT (min)* | m/z (M + H)+ |
|---|---|---|---|---|
| 39 | 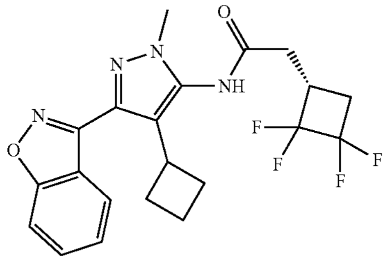 [SMILES: Cn1nc(-c2noc3ccccc23)c(C2CCC2)c1NC(=O)C[C@@H]1CC(F)(F)C1(F)F] | (R)-N-(3-(benzo[d]isoxazol-3-yl)-4-cyclobutyl-1-methyl-1H-pyrazol-5-yl)-2-(2,2,3,3-tetrafluorocyclobutyl)acetamide | 4.3 | 437 |
| 40 | 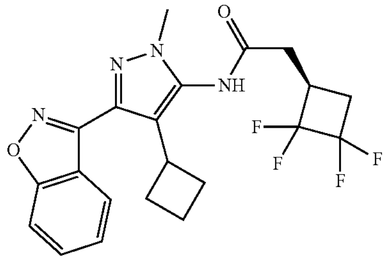 [SMILES: Cn1nc(-c2noc3ccccc23)c(C2CCC2)c1NC(=O)C[C@H]1CC(F)(F)C1(F)F] | (S)-N-(3-(benzo[d]isoxazol-3-yl)-4-cyclobutyl-1-methyl-1H-pyrazol-5-yl)-2-(2,2,3,3-tetrafluorocyclobutyl)acetamide | 4.1 | 437 |
| 41 | 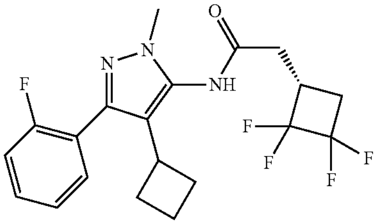 [SMILES: Cn1nc(-c2ccccc2F)c(C2CCC2)c1NC(=O)C[C@@H]1CC(F)(F)C1(F)F] | (R)-N-(4-cyclobutyl-3-(2-fluorophenyl)-1-methyl-1H-pyrazol-5-yl)-2-(2,2,3,3-tetrafluorocyclobutyl)acetamide | 4.1 | 414 |
| 42 | 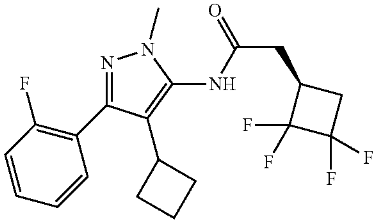 [SMILES: Cn1nc(-c2ccccc2F)c(C2CCC2)c1NC(=O)C[C@H]1CC(F)(F)C1(F)F] | (S)-N-(4-cyclobutyl-3-(2-fluorophenyl)-1-methyl-1H-pyrazol-5-yl)-2-(2,2,3,3-tetrafluorocyclobutyl)acetamide | 4.1 | 414 |
| 43 | 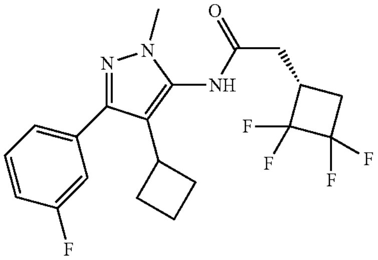 [SMILES: Cn1nc(-c2cccc(F)c2)c(C2CCC2)c1NC(=O)C[C@@H]1CC(F)(F)C1(F)F] | (R)-N-(4-cyclobutyl-3-(3-fluorophenyl)-1-methyl-1H-pyrazol-5-yl)-2-(2,2,3,3-tetrafluorocyclobutyl)acetamide | 4.1 | 414 |
| 44 | 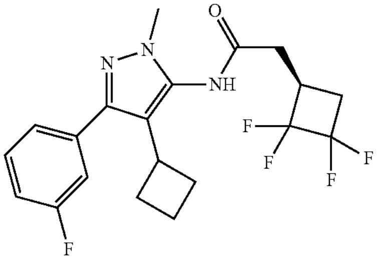 [SMILES: Cn1nc(-c2cccc(F)c2)c(C2CCC2)c1NC(=O)C[C@H]1CC(F)(F)C1(F)F] | (S)-N-(4-cyclobutyl-3-(3-fluorophenyl)-1-methyl-1H-pyrazol-5-yl)-2-(2,2,3,3-tetrafluorocyclobutyl)acetamide | 4.1 | 414 |

TABLE 1-continued

| List of Compounds and Characterization Data | | | | |
|---|---|---|---|---|
| Cmpd # | Structure | Name | LCMS RT (min)* | m/z (M + H)$^+$ |
| 45 | 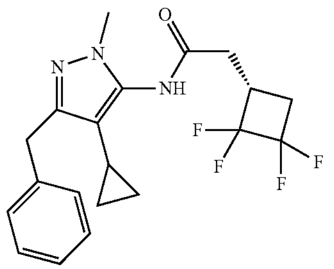 [SMILES: Cn1nc(Cc2ccccc2)c(C2CC2)c1NC(=O)C[C@@H]1CC(F)(F)C1(F)F] | (R)-N-(3-benzyl-4-cyclopropyl-1-methyl-1H-pyrazol-5-yl)-2-(2,2,3,3-tetrafluorocyclo-butyl)acetamide | 3.9 | 396 |
| 46 | 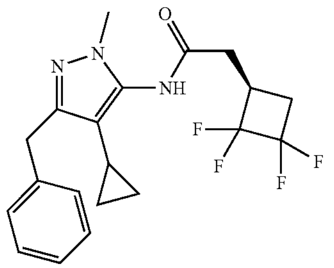 [SMILES: Cn1nc(Cc2ccccc2)c(C2CC2)c1NC(=O)C[C@H]1CC(F)(F)C1(F)F] | (S)-N-(3-benzyl-4-cyclopropyl-1-methyl-1H-pyrazol-5-yl)-2-(2,2,3,3-tetrafluorocyclo-butyl)acetamide | 3.9 | 396 |
| 47 | 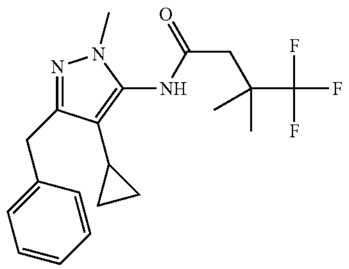 [SMILES: Cn1nc(Cc2ccccc2)c(C2CC2)c1NC(=O)CC(C)(C)C(F)(F)F] | N-(3-benzyl-4-cyclopropyl-1-methyl-1H-pyrazol-5-yl)-4,4,4-trifluoro-3,3-dimethylbutanamide | 4.1 | 380 |
| 48 | 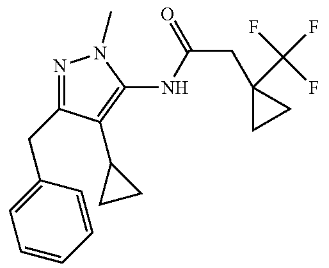 [SMILES: Cn1nc(Cc2ccccc2)c(C2CC2)c1NC(=O)CC1(C(F)(F)F)CC1] | N-(3-benzyl-4-cyclopropyl-1-methyl-1H-pyrazol-5-yl)-2-(1-(trifluoromethyl)cyclo-propyl)acetamide | 3.9 | 378 |
| 49 | 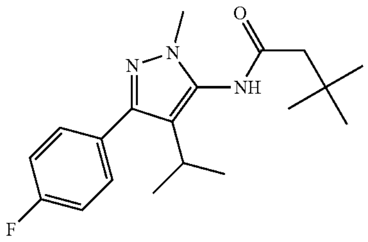 [SMILES: CC(C)c1c(-c2ccc(F)cc2)nn(C)c1NC(=O)CC(C)(C)C] | N-(3-(4-fluorophenyl)-4-isopropyl-1-methyl-1H-pyrazol-5-yl)-3,3-dimethylbutanamide | 4.1 | 332 |

TABLE 1-continued

List of Compounds and Characterization Data

| Cmpd # | Structure | Name | LCMS RT (min)* | m/z (M + H)+ |
|---|---|---|---|---|
| 50 | 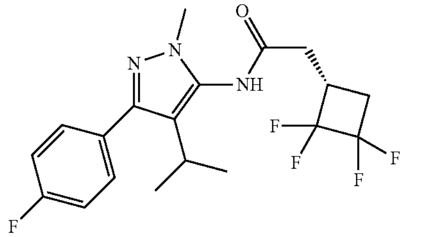 [SMILES: CC(C)c1c(-c2ccc(F)cc2)nn(C)c1NC(=O)C[C@@H]1CC(F)(F)C1(F)F] | (R)-N-(3-(4-fluorophenyl)-4-isopropyl-1-methyl-1H-pyrazol-5-yl)-2-(2,2,3,3-tetrafluorocyclobutyl)acetamide | 4 | 402 |
| 51 | 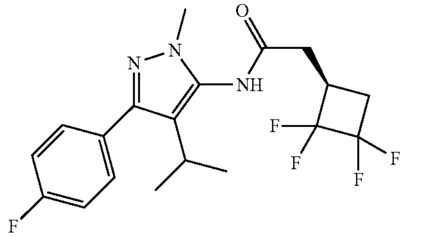 [SMILES: CC(C)c1c(-c2ccc(F)cc2)nn(C)c1NC(=O)C[C@H]1CC(F)(F)C1(F)F] | (S)-N-(3-(4-fluorophenyl)-4-isopropyl-1-methyl-1H-pyrazol-5-yl)-2-(2,2,3,3-tetrafluorocyclobutyl)acetamide | 4 | 402 |
| 52 | 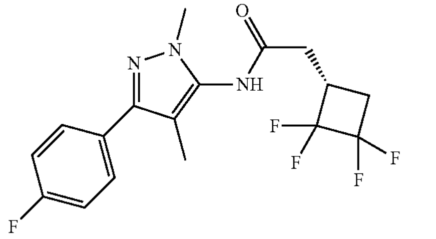 [SMILES: Cc1c(-c2ccc(F)cc2)nn(C)c1NC(=O)C[C@@H]1CC(F)(F)C1(F)F] | (R)-N-(3-(4-fluorophenyl)-1,4-dimethyl-1H-pyrazol-5-yl)-2-(2,2,3,3-tetrafluorocyclobutyl)acetamide | 3.8 | 374 |
| 53 | 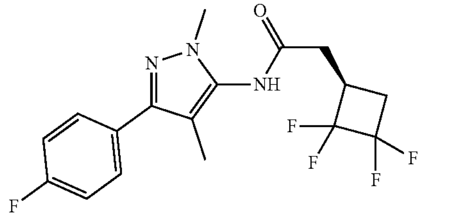 [SMILES: Cc1c(-c2ccc(F)cc2)nn(C)c1NC(=O)C[C@H]1CC(F)(F)C1(F)F] | (S)-N-(3-(4-fluorophenyl)-1,4-dimethyl-1H-pyrazol-5-yl)-2-(2,2,3,3-tetrafluorocyclobutyl)acetamide | 3.8 | 374 |
| 54 | 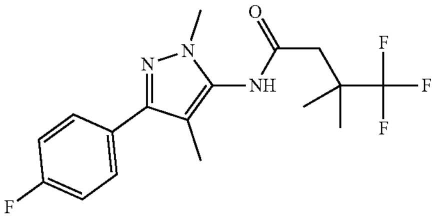 [SMILES: Cc1c(-c2ccc(F)cc2)nn(C)c1NC(=O)CC(C)(C)C(F)(F)F] | 4,4,4-trifluoro-N-(3-(4-fluorophenyl)-1,4-dimethyl-1H-pyrazol-5-yl)-3,3-dimethylbutanamide | 4 | 358 |
| 55 | 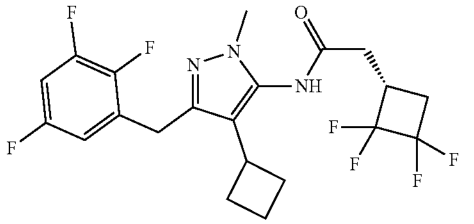 [SMILES: Cn1nc(Cc2cc(F)cc(F)c2F)c(C2CCC2)c1NC(=O)C[C@@H]1CC(F)(F)C1(F)F] | (R)-N-(4-cyclobutyl-1-methyl-3-(2,3,5-trifluorobenzyl)-1H-pyrazol-5-yl)-2-(2,2,3,3-tetrafluorocyclobutyl)acetamide | 4.2 | 464 |

TABLE 1-continued

| List of Compounds and Characterization Data | | | | |
|---|---|---|---|---|
| Cmpd # | Structure | Name | LCMS RT (min)* | m/z (M + H)$^+$ |
| 56 | 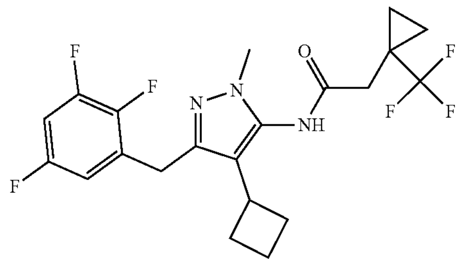 [SMILES: Cn1nc(Cc2cc(F)cc(F)c2F)c(C2CCC2)c1NC(=O)CC1(C(F)(F)F)CC1] | N-(4-cyclobutyl-1-methyl-3-(2,3,5-trifluorobenzyl)-1H-pyrazol-5-yl)-2-(1-(trifluoromethyl)cyclopropyl)acetamide | 4.2 | 446 |
| 57 | 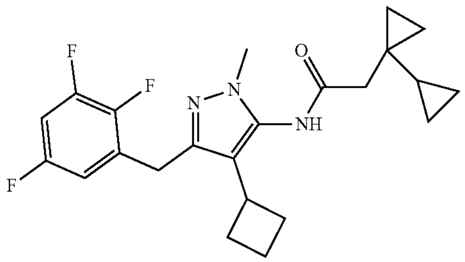 [SMILES: Cn1nc(Cc2cc(F)cc(F)c2F)c(C2CCC2)c1NC(=O)CC1(C2CC2)CC1] | 2-([1,1'-bi(cyclopropan)]-1-yl)-N-(4-cyclobutyl-1-methyl-3-(2,3,5-trifluorobenzyl)-1H-pyrazol-5-yl)acetamide | 4.4 | 418 |
| 58 | 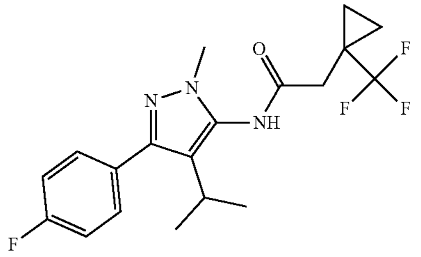 [SMILES: CC(C)c1c(-c2ccc(F)cc2)nn(C)c1NC(=O)CC1(C(F)(F)F)CC1] | N-(3-(4-fluorophenyl)-4-isopropyl-1-methyl-1H-pyrazol-5-yl)-2-(1-(trifluoromethyl)cyclopropyl)acetamide | 4 | 384 |
| 59 | 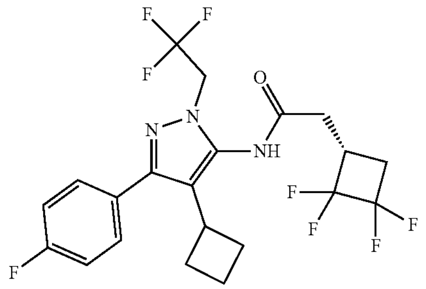 [SMILES: O=C(C[C@@H]1CC(F)(F)C1(F)F)Nc1c(C2CCC2)c(-c2ccc(F)cc2)nn1CC(F)(F)F] | (R)-N-(4-cyclobutyl-3-(4-fluorophenyl)-1-(2,2,2-trifluoroethyl)-1H-pyrazol-5-yl)-2-(2,2,3,3-tetrafluorocyclobutyl)acetamide | 4.3 | 482 |
| 60 | 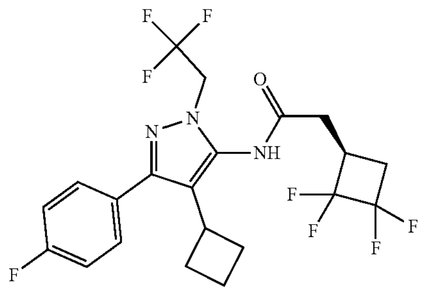 [SMILES: O=C(C[C@H]1CC(F)(F)C1(F)F)Nc1c(C2CCC2)c(-c2ccc(F)cc2)nn1CC(F)(F)F] | (S)-N-(4-cyclobutyl-3-(4-fluorophenyl)-1-(2,2,2-trifluoroethyl)-1H-pyrazol-5-yl)-2-(2,2,3,3-tetrafluorocyclobutyl)acetamide | 4.3 | 482 |

TABLE 1-continued

List of Compounds and Characterization Data

| Cmpd # | Structure | Name | LCMS RT (min)* | m/z $(M + H)^+$ |
|---|---|---|---|---|
| 61 | 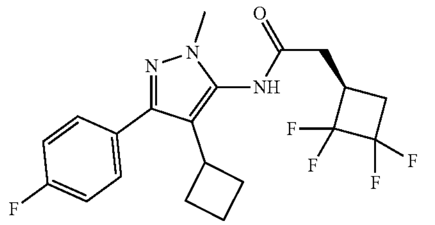 [SMILES: Cn1nc(-c2ccc(F)cc2)c(C2CCC2)c1NC(=O)C[C@H]1CC(F)(F)C1(F)F] | (S)-N-(4-cyclobutyl-3-(4-fluorophenyl)-1-methyl-1H-pyrazol-5-yl)-2-(2,2,3,3-tetrafluorocyclobutyl)acetamide | 4.1 | 414 |
| 62 | 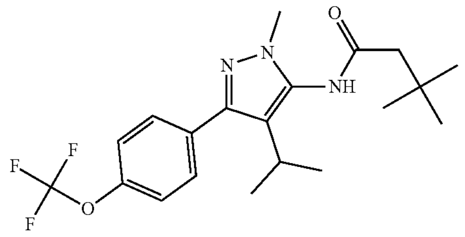 [SMILES: CC(C)c1c(-c2ccc(OC(F)(F)F)cc2)nn(C)c1NC(=O)CC(C)(C)C] | N-(4-isopropyl-1-methyl-3-(4-(trifluoromethoxy)phenyl)-1H-pyrazol-5-yl)-3,3-dimethylbutanamide | 4.5 | 398 |
| 63 | 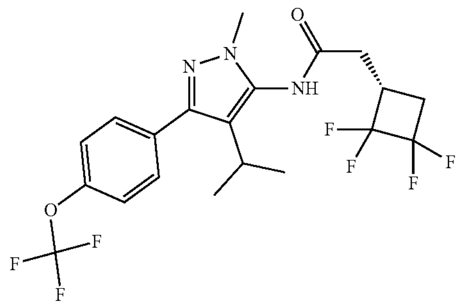 [SMILES: CC(C)c1c(-c2ccc(OC(F)(F)F)cc2)nn(C)c1NC(=O)C[C@@H]1CC(F)(F)C1(F)F] | (R)-N-(4-isopropyl-1-methyl-3-(4-(trifluoromethoxy)phenyl)-1H-pyrazol-5-yl)-2-(2,2,3,3-tetrafluorocyclobutyl)acetamide | 4.3 | 468 |
| 64 | 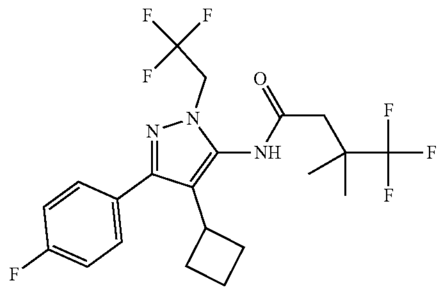 [SMILES: CC(C)(CC(=O)Nc1c(C2CCC2)c(-c2ccc(F)cc2)nn1CC(F)(F)F)C(F)(F)F] | N-(4-cyclobutyl-3-(4-fluorophenyl)-1-(2,2,2-trifluoroethyl)-1H-pyrazol-5-yl)-4,4,4-trifluoro-3,3-dimethylbutanamide | 4.5 | 466 |
| 65 | 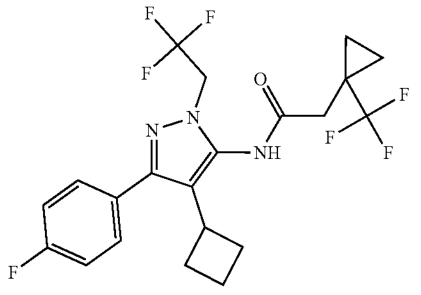 [SMILES: O=C(CC1(C(F)(F)F)CC1)Nc1c(C2CCC2)c(-c2ccc(F)cc2)nn1CC(F)(F)F] | N-(4-cyclobutyl-3-(4-fluorophenyl)-1-(2,2,2-trifluoroethyl)-1H-pyrazol-5-yl)-2-(1-(trifluoromethyl)cyclopropyl)acetamide | 4.3 | 464 |

TABLE 1-continued

List of Compounds and Characterization Data

| Cmpd # | Structure | Name | LCMS RT (min)* | m/z (M + H)$^+$ |
|---|---|---|---|---|
| 66 | 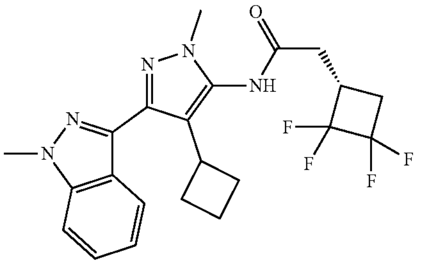 [SMILES: Cn1nc(-c2nn(C)c3ccccc23)c(C2CCC2)c1NC(=O)C[C@@H]1CC(F)(F)C1(F)F] | (R)-N-(4-cyclobutyl-1-methyl-3-(1-methyl-1H-indazol-3-yl)-1H-pyrazol-5-yl)-2-(2,2,3,3-tetrafluorocyclobutyl)acetamide | 4.1 | 450 |
| 67 | 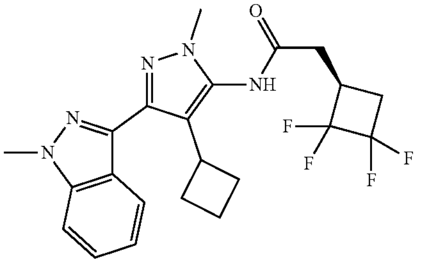 [SMILES: Cn1nc(-c2nn(C)c3ccccc23)c(C2CCC2)c1NC(=O)C[C@H]1CC(F)(F)C1(F)F] | (S)-N-(4-cyclobutyl-1-methyl-3-(1-methyl-1H-indazol-3-yl)-1H-pyrazol-5-yl)-2-(2,2,3,3-tetrafluorocyclobutyl)acetamide | 4.1 | 450 |
| 68 | 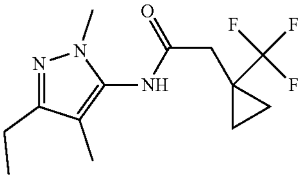 [SMILES: CCc1nn(C)c(NC(=O)CC2(C(F)(F)F)CC2)c1C] | N-(3-ethyl-1,4-dimethyl-1H-pyrazol-5-yl)-2-(1-(trifluoromethyl)cyclopropyl)acetamide | 3.3 | 290 |
| 69 | 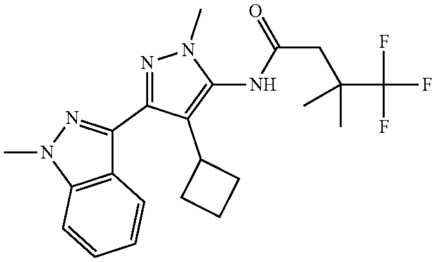 [SMILES: Cn1nc(-c2nn(C)c3ccccc23)c(C2CCC2)c1NC(=O)CC(C)(C)C(F)(F)F] | N-(4-cyclobutyl-1-methyl-3-(1-methyl-1H-indazol-3-yl)-1H-pyrazol-5-yl)-4,4,4-trifluoro-3,3-dimethylbutanamide | 4.3 | 434 |
| 70 | 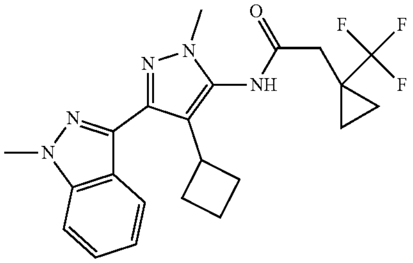 [SMILES: Cn1nc(-c2nn(C)c3ccccc23)c(C2CCC2)c1NC(=O)CC1(C(F)(F)F)CC1] | N-(4-cyclobutyl-1-methyl-3-(1-methyl-1H-indazol-3-yl)-1H-pyrazol-5-yl)-2-(1-(trifluoromethyl)cyclopropyl)acetamide | 4.1 | 432 |
| 71 | 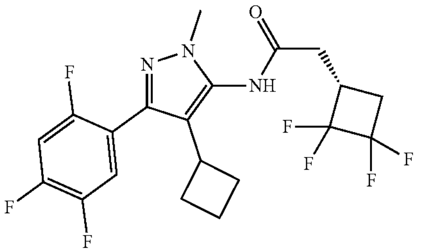 [SMILES: Cn1nc(-c2cc(F)c(F)cc2F)c(C2CCC2)c1NC(=O)C[C@@H]1CC(F)(F)C1(F)F] | (R)-N-(4-cyclobutyl-1-methyl-3-(2,4,5-trifluorophenyl)-1H-pyrazol-5-yl)-2-(2,2,3,3-tetrafluorocyclobutyl)acetamide | 4.2 | 450 |

TABLE 1-continued

List of Compounds and Characterization Data

| Cmpd # | Structure | Name | LCMS RT (min)* | m/z (M + H)+ |
|---|---|---|---|---|
| 72 | 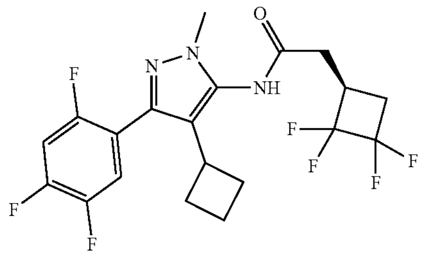 [SMILES: Cn1nc(-c2cc(F)c(F)cc2F)c(C2CCC2)c1NC(=O)C[C@H]1CC(F)(F)C1(F)F] | (S)-N-(4-cyclobutyl-1-methyl-3-(2,4,5-trifluorophenyl)-1H-pyrazol-5-yl)-2-(2,2,3,3-tetrafluorocyclobutyl)acetamide | 4.2 | 450 |
| 73 | 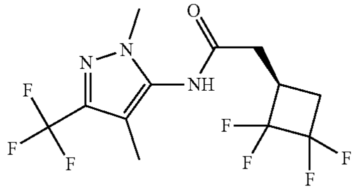 [SMILES: Cc1c(C(F)(F)F)nn(C)c1NC(=O)C[C@H]1CC(F)(F)C1(F)F] | (S)-N-(1,4-dimethyl-3-(trifluoromethyl)-1H-pyrazol-5-yl)-2-(2,2,3,3-tetrafluorocyclobutyl)acetamide | 3.7 | 348 |
| 74 | 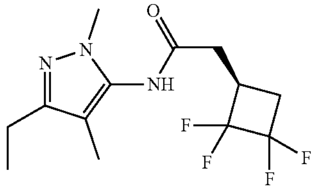 [SMILES: CCc1nn(C)c(NC(=O)C[C@H]2CC(F)(F)C2(F)F)c1C] | (S)-N-(3-ethyl-1,4-dimethyl-1H-pyrazol-5-yl)-2-(2,2,3,3-tetrafluorocyclobutyl)acetamide | 3.4 | 308 |
| 75 | 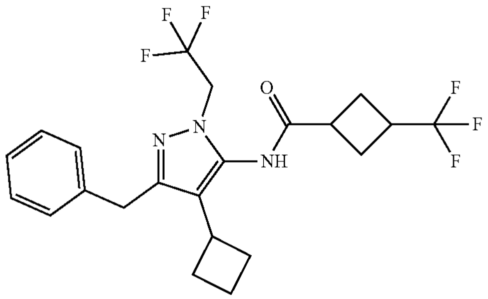 [SMILES: O=C(Nc1c(C2CCC2)c(Cc2ccccc2)nn1CC(F)(F)F)C1CC(C(F)(F)F)C1] | N-(3-benzyl-4-cyclobutyl-1-(2,2,2-trifluoroethyl)-1H-pyrazol-5-yl)-3-(trifluoromethyl)cyclobutane-1-carboxamide | 4.3 | 460 |
| 76 | 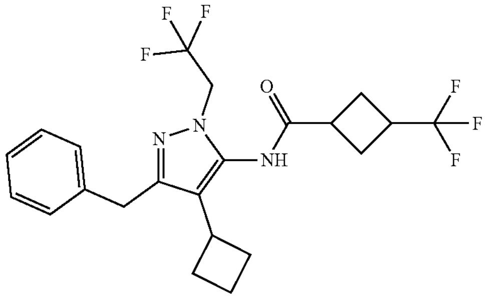 [SMILES: O=C(Nc1c(C2CCC2)c(Cc2ccccc2)nn1CC(F)(F)F)C1CC(C(F)(F)F)C1] | N-(3-benzyl-4-cyclobutyl-1-(2,2,2-trifluoroethyl)-1H-pyrazol-5-yl)-3-(trifluoromethyl)cyclobutane-1-carboxamide | 4.4 | 460 |
| 77 | 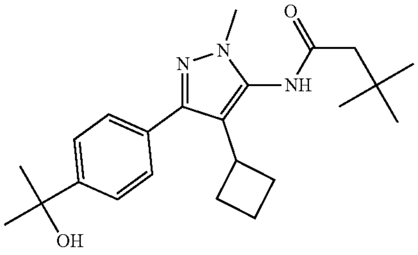 [SMILES: Cn1nc(-c2ccc(C(C)(C)O)cc2)c(C2CCC2)c1NC(=O)CC(C)(C)C] | N-(4-cyclobutyl-3-(4-(2-hydroxypropan-2-yl)phenyl)-1-methyl-1H-pyrazol-5-yl)-3,3-dimethylbutanamide | 3.7 | 384 |

TABLE 1-continued

| List of Compounds and Characterization Data | | | | |
|---|---|---|---|---|
| Cmpd # | Structure | Name | LCMS RT (min)* | m/z (M + H)+ |
| 78 | 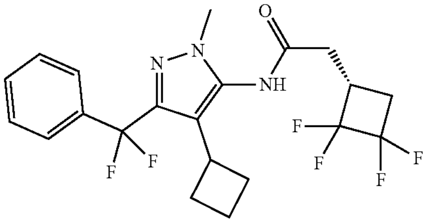 [SMILES: Cn1nc(C(F)(F)c2ccccc2)c(C2CCC2)c1NC(=O)C[C@@H]1CC(F)(F)C1(F)F] | (R)-N-(4-cyclobutyl-3-(difluoro(phenyl)methyl)-1-methyl-1H-pyrazol-5-yl)-2-(2,2,3,3-tetrafluorocyclobutyl)acetamide | 4.3 | 446 |
| 79 | 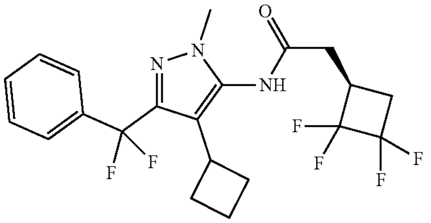 [SMILES: Cn1nc(C(F)(F)c2ccccc2)c(C2CCC2)c1NC(=O)C[C@H]1CC(F)(F)C1(F)F] | (S)-N-(4-cyclobutyl-3-(difluoro(phenyl)methyl)-1-methyl-1H-pyrazol-5-yl)-2-(2,2,3,3-tetrafluorocyclobutyl)acetamide | 4.3 | 446 |
| 80 | 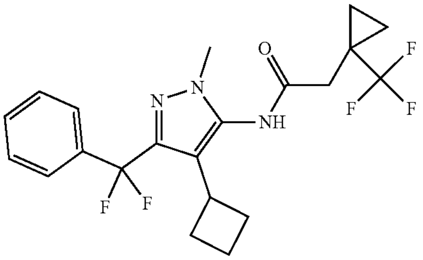 [SMILES: Cn1nc(C(F)(F)c2ccccc2)c(C2CCC2)c1NC(=O)CC1(C(F)(F)F)CC1] | N-(4-cyclobutyl-3-(difluoro(phenyl)methyl)-1-methyl-1H-pyrazol-5-yl)-2-(1-(trifluoromethyl)cyclopropyl)acetamide | 3.9 | 428 |
| 81 | 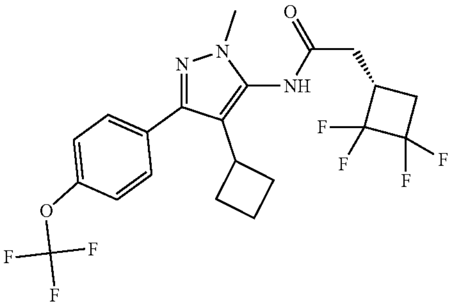 [SMILES: Cn1nc(-c2ccc(OC(F)(F)F)cc2)c(C2CCC2)c1NC(=O)C[C@@H]1CC(F)(F)C1(F)F] | (R)-N-(4-cyclobutyl-1-methyl-3-(4-(trifluoromethoxy)phenyl)-1H-pyrazol-5-yl)-2-(2,2,3,3-tetrafluorocyclobutyl)acetamide | 4.4 | 480 |
| 82 | 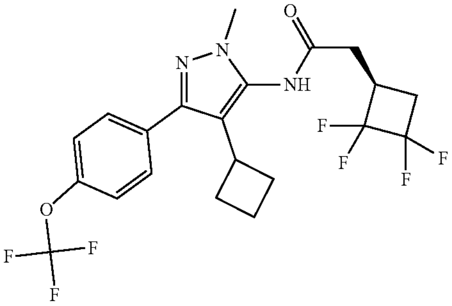 [SMILES: Cn1nc(-c2ccc(OC(F)(F)F)cc2)c(C2CCC2)c1NC(=O)C[C@H]1CC(F)(F)C1(F)F] | (S)-N-(4-cyclobutyl-1-methyl-3-(4-(trifluoromethoxy)phenyl)-1H-pyrazol-5-yl)-2-(2,2,3,3-tetrafluorocyclobutyl)acetamide | 4.4 | 480 |

TABLE 1-continued

List of Compounds and Characterization Data

| Cmpd # | Structure | Name | LCMS RT (min)* | m/z $(M + H)^+$ |
|---|---|---|---|---|
| 83 | 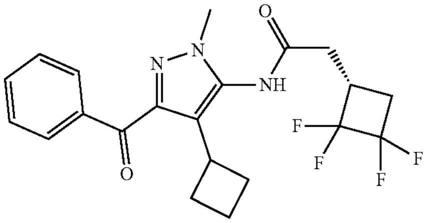 [SMILES: Cn1nc(C(=O)c2ccccc2)c(C2CCC2)c1NC(=O)C[C@@H]1CC(F)(F)C1(F)F] | (R)-N-(3-benzoyl-4-cyclobutyl-1-methyl-1H-pyrazol-5-yl)-2-(2,2,3,3-tetrafluorocyclobutyl)acetamide | 4.1 | 424 |
| 84 | 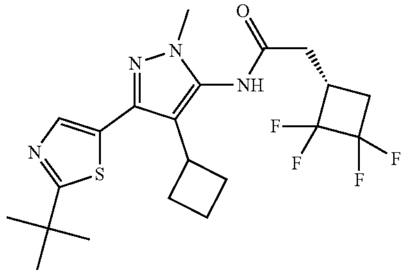 [SMILES: Cn1nc(-c2cnc(C(C)(C)C)s2)c(C2CCC2)c1NC(=O)C[C@@H]1CC(F)(F)C1(F)F] | (R)-N-(3-(2-(tert-butyl)thiazol-5-yl)-4-cyclobutyl-1-methyl-1H-pyrazol-5-yl)-2-(2,2,3,3-tetrafluorocyclobutyl)acetamide | 4.4 | 459 |
| 85 | 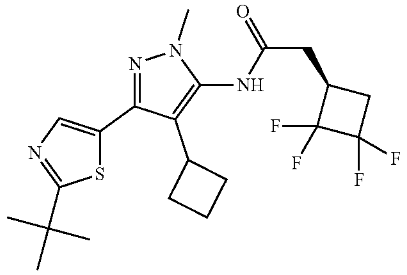 [SMILES: Cn1nc(-c2cnc(C(C)(C)C)s2)c(C2CCC2)c1NC(=O)C[C@H]1CC(F)(F)C1(F)F] | (S)-N-(3-(2-(tert-butyl)thiazol-5-yl)-4-cyclobutyl-1-methyl-1H-pyrazol-5-yl)-2-(2,2,3,3-tetrafluorocyclobutyl)acetamide | 4.4 | 459 |
| 86 | 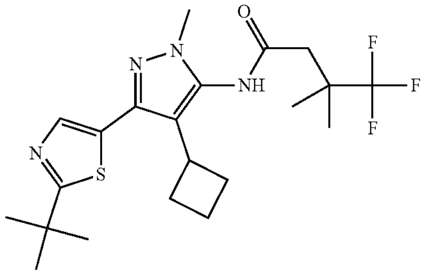 [SMILES: Cn1nc(-c2cnc(C(C)(C)C)s2)c(C2CCC2)c1NC(=O)CC(C)(C)C(F)(F)F] | N-(3-(2-(tert-butyl)thiazol-5-yl)-4-cyclobutyl-1-methyl-1H-pyrazol-5-yl)-4,4,4-trifluoro-3,3-dimethylbutanamide | 4.7 | 443 |
| 87 | 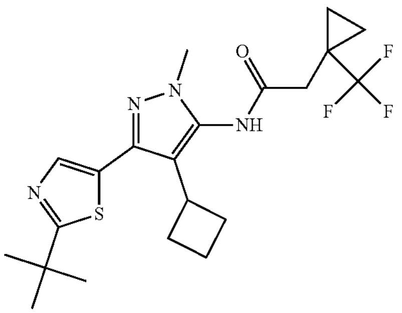 [SMILES: Cn1nc(-c2cnc(C(C)(C)C)s2)c(C2CCC2)c1NC(=O)CC1(C(F)(F)F)CC1] | N-(3-(2-(tert-butyl)thiazol-5-yl)-4-cyclobutyl-1-methyl-1H-pyrazol-5-yl)-2-(1-(trifluoromethyl)cyclopropyl)acetamide | 4.4 | 441 |

TABLE 1-continued

List of Compounds and Characterization Data

| Cmpd # | Structure | Name | LCMS RT (min)* | m/z (M + H)$^+$ |
|---|---|---|---|---|
| 88 | 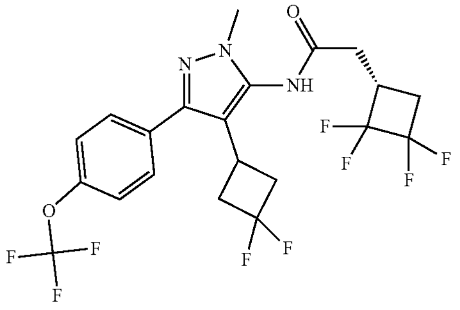 [SMILES: Cn1nc(-c2ccc(OC(F)(F)F)cc2)c(C2CC(F)(F)C2)c1NC(=O)C[C@@H]1CC(F)(F)C1(F)F] | (R)-N-(4-(3,3-difluorocyclobutyl)-1-methyl-3-(4-(trifluoromethoxy)phenyl)-1H-pyrazol-5-yl)-2-(2,2,3,3-tetrafluorocyclobutyl)acetamide | 4.3 | 516 |
| 89 | 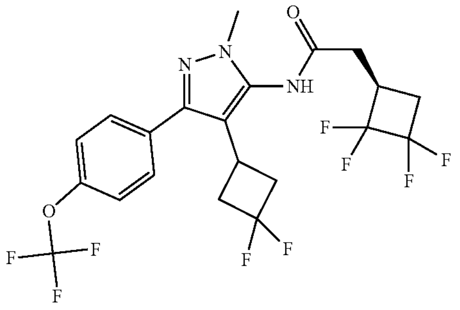 [SMILES: Cn1nc(-c2ccc(OC(F)(F)F)cc2)c(C2CC(F)(F)C2)c1NC(=O)C[C@H]1CC(F)(F)C1(F)F] | (S)-N-(4-(3,3-difluorocyclobutyl)-1-methyl-3-(4-(trifluoromethoxy)phenyl)-1H-pyrazol-5-yl)-2-(2,2,3,3-tetrafluorocyclobutyl)acetamide | 4.3 | 516 |
| 90 | 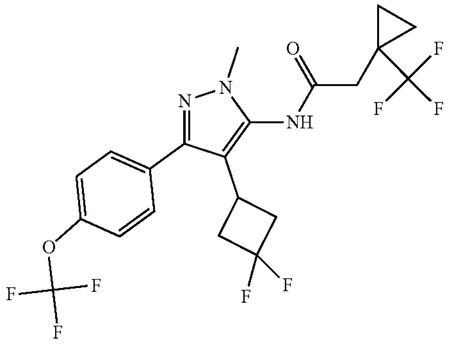 [SMILES: Cn1nc(-c2ccc(OC(F)(F)F)cc2)c(C2CC(F)(F)C2)c1NC(=O)CC1(C(F)(F)F)CC1] | N-(4-(3,3-difluorocyclobutyl)-1-methyl-3-(4-(trifluoromethoxy)phenyl)-1H-pyrazol-5-yl)-2-(1-(trifluoromethyl)cyclopropyl)acetamide | 4.3 | 498 |
| 91 | 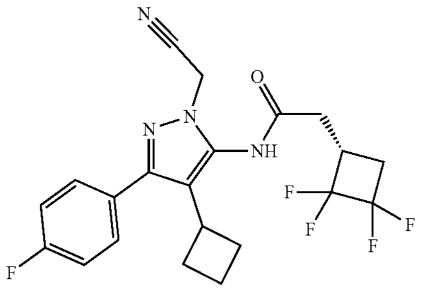 [SMILES: N#CCn1nc(-c2ccc(F)cc2)c(C2CCC2)c1NC(=O)C[C@@H]1CC(F)(F)C1(F)F] | (R)-N-(1-(cyanomethyl)-4-cyclobutyl-3-(4-fluorophenyl)-1H-pyrazol-5-yl)-2-(2,2,3,3-tetrafluorocyclobutyl)acetamide | 4.2 | 439 |

TABLE 1-continued

| List of Compounds and Characterization Data | | | | |
|---|---|---|---|---|
| Cmpd # | Structure | Name | LCMS RT (min)* | m/z $(M + H)^+$ |
| 92 | 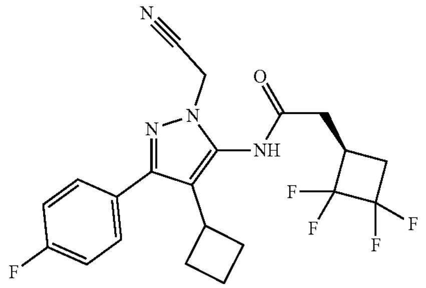 [SMILES: N#CCn1nc(-c2ccc(F)cc2)c(C2CCC2)c1NC(=O)C[C@H]1CC(F)(F)C1(F)F] | (S)-N-(1-(cyanomethyl)-4-cyclobutyl-3-(4-fluorophenyl)-1H-pyrazol-5-yl)-2-(2,2,3,3-tetrafluorocyclobutyl)acetamide | 4.2 | 439 |
| 93 | 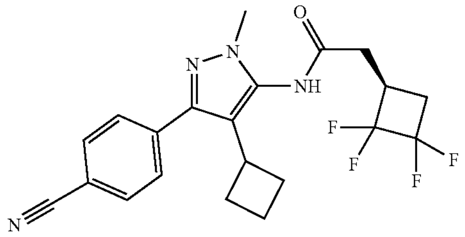 [SMILES: Cn1nc(-c2ccc(C#N)cc2)c(C2CCC2)c1NC(=O)C[C@H]1CC(F)(F)C1(F)F] | (S)-N-(3-(4-cyanophenyl)-4-cyclobutyl-1-methyl-1H-pyrazol-5-yl)-2-(2,2,3,3-tetrafluorocyclobutyl)acetamide | 3.9 | 421 |
| 94 | 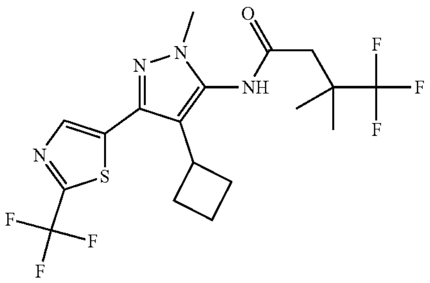 [SMILES: Cn1nc(-c2cnc(C(F)(F)F)s2)c(C2CCC2)c1NC(=O)CC(C)(C)C(F)(F)F] | N-(4-cyclobutyl-1-methyl-3-(2-(trifluoromethyl)thiazol-5-yl)-1H-pyrazol-5-yl)-4,4,4-trifluoro-3,3-dimethylbutanamide | 45 | 455 |
| 95 | 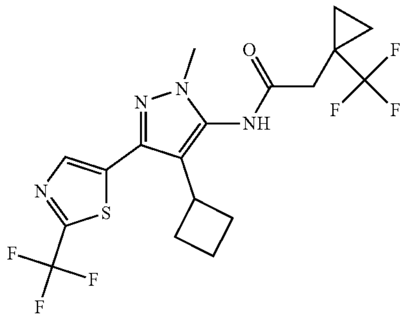 [SMILES: Cn1nc(-c2cnc(C(F)(F)F)s2)c(C2CCC2)c1NC(=O)CC1(C(F)(F)F)CC1] | N-(4-cyclobutyl-1-methyl-3-(2-(trifluoromethyl)thiazol-5-yl)-1H-pyrazol-5-yl)-2-(1-(trifluoromethyl)cyclopropyl)acetamide | 4.4 | 453 |
| 96 | 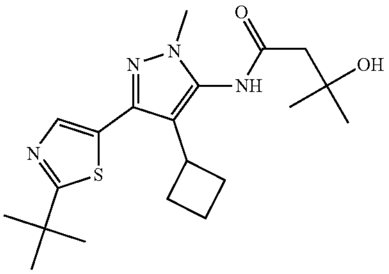 [SMILES: Cn1nc(-c2cnc(C(C)(C)C)s2)c(C2CCC2)c1NC(=O)CC(C)(C)O] | N-(3-(2-(tert-butyl)thiazol-5-yl)-4-cyclobutyl-1-methyl-1H-pyrazol-5-yl)-3-hydroxy-3-methylbutanamide | 3.8 | 391 |

TABLE 1-continued

| List of Compounds and Characterization Data | | | | |
|---|---|---|---|---|
| Cmpd # | Structure | Name | LCMS RT (min)* | m/z (M + H)$^+$ |
| 97 | 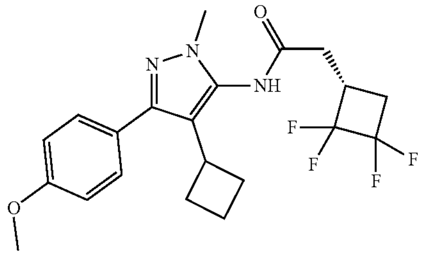 [SMILES: COc1ccc(-c2nn(C)c(NC(=O)C[C@@H]3CC(F)(F)C3(F)F)c2C2CCC2)cc1] | (R)-N-(4-cyclobutyl-3-(4-methoxyphenyl)-1-methyl-1H-pyrazol-5-yl)-2-(2,2,3,3-tetrafluorocyclobutyl)acetamide | 4 | 426 |
| 98 | 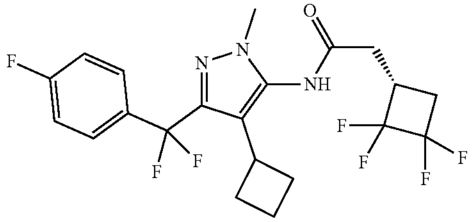 [SMILES: Cn1nc(C(F)(F)c2ccc(F)cc2)c(C2CCC2)c1NC(=O)C[C@@H]1CC(F)(F)C1(F)F] | (R)-N-(4-cyclobutyl-3-(difluoro(4-fluorophenyl)methyl)-1-methyl-1H-pyrazol-5-yl)-2-(2,2,3,3-tetrafluorocyclobutyl)acetamide | 4.3 | 464 |
| 99 | 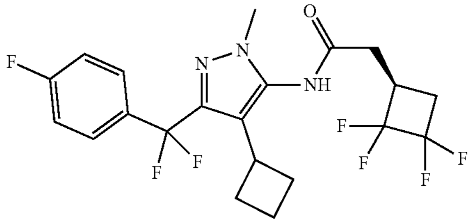 [SMILES: Cn1nc(C(F)(F)c2ccc(F)cc2)c(C2CCC2)c1NC(=O)C[C@H]1CC(F)(F)C1(F)F] | (S)-N-(4-cyclobutyl-3-(difluoro(4-fluorophenyl)methyl)-1-methyl-1H-pyrazol-5-yl)-2-(2,2,3,3-tetrafluorocyclobutyl)acetamide | 4.3 | 464 |
| 100 | 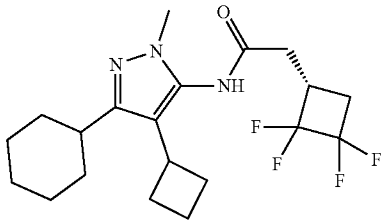 [SMILES: Cn1nc(C2CCCCC2)c(C2CCC2)c1NC(=O)C[C@@H]1CC(F)(F)C1(F)F] | (R)-N-(4-cyclobutyl-3-cyclohexyl-1-methyl-1H-pyrazol-5-yl)-2-(2,2,3,3-tetrafluorocyclobutyl)acetamide | 4.4 | 402 |
| 101 | 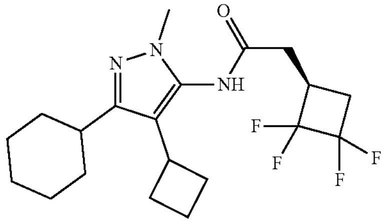 [SMILES: Cn1nc(C2CCCCC2)c(C2CCC2)c1NC(=O)C[C@H]1CC(F)(F)C1(F)F] | (S)-N-(4-cyclobutyl-3-cyclohexyl-1-methyl-1H-pyrazol-5-yl)-2-(2,2,3,3-tetrafluorocyclobutyl)acetamide | 4.4 | 402 |
| 102 | 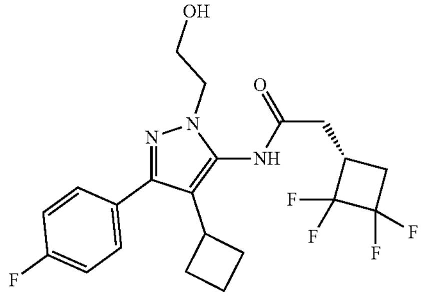 [SMILES: O=C(C[C@@H]1CC(F)(F)C1(F)F)Nc1c(C2CCC2)c(-c2ccc(F)cc2)nn1CCO] | (R)-N-(4-cyclobutyl-3-(4-fluorophenyl)-1-(2-hydroxyethyl)-1H-pyrazol-5-yl)-2-(2,2,3,3-tetrafluorocyclobutyl)acetamide | 3.9 | 444 |

TABLE 1-continued

List of Compounds and Characterization Data

| Cmpd # | Structure | Name | LCMS RT (min)* | m/z (M + H)+ |
|---|---|---|---|---|
| 103 | 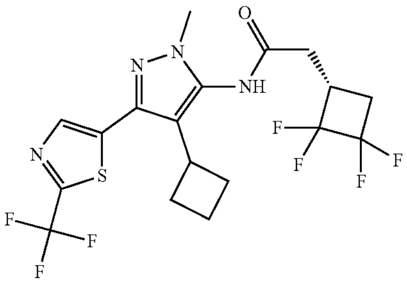 [SMILES: Cn1nc(-c2cnc(C(F)(F)F)s2)c(C2CCC2)c1NC(=O)C[C@@H]1CC(F)(F)C1(F)F] | (R)-N-(4-cyclobutyl-1-methyl-3-(2-(trifluoromethyl)thiazol-5-yl)-1H-pyrazol-5-yl)-2-(2,2,3,3-tetrafluorocyclobutyl)acetamide | 4.3 | 471 |
| 104 | 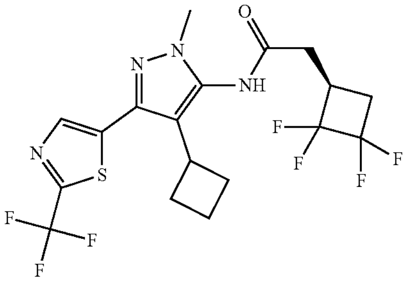 [SMILES: Cn1nc(-c2cnc(C(F)(F)F)s2)c(C2CCC2)c1NC(=O)C[C@H]1CC(F)(F)C1(F)F] | (S)-N-(4-cyclobutyl-1-methyl-3-(2-(trifluoromethyl)thiazol-5-yl)-1H-pyrazol-5-yl)-2-(2,2,3,3-tetrafluorocyclobutyl)acetamide | 4.3 | 471 |
| 105 | 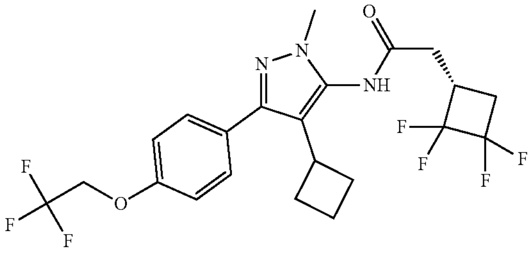 [SMILES: Cn1nc(-c2ccc(OCC(F)(F)F)cc2)c(C2CCC2)c1NC(=O)C[C@@H]1CC(F)(F)C1(F)F] | (R)-N-(4-cyclobutyl-1-methyl-3-(4-(2,2,2-trifluoroethoxy)phenyl)-1H-pyrazol-5-yl)-2-(2,2,3,3-tetrafluorocyclobutyl)acetamide | 4.1 | 494 |
| 106 | 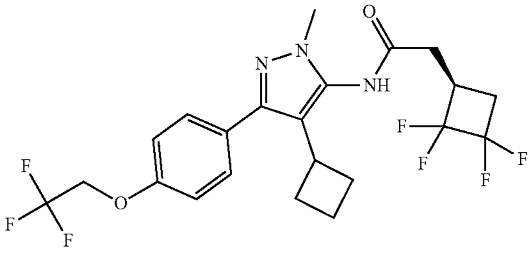 [SMILES: Cn1nc(-c2ccc(OCC(F)(F)F)cc2)c(C2CCC2)c1NC(=O)C[C@H]1CC(F)(F)C1(F)F] | (S)-N-(4-cyclobutyl-1-methyl-3-(4-(2,2,2-trifluoroethoxy)phenyl)-1H-pyrazol-5-yl)-2-(2,2,3,3-tetrafluorocyclobutyl)acetamide | 4.1 | 494 |
| 107 | 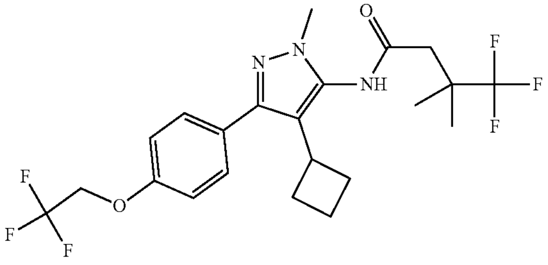 [SMILES: Cn1nc(-c2ccc(OCC(F)(F)F)cc2)c(C2CCC2)c1NC(=O)CC(C)(C)C(F)(F)F] | N-(4-cyclobutyl-1-methyl-3-(4-(2,2,2-trifluoroethoxy)phenyl)-1H-pyrazol-5-yl)-4,4,4-trifluoro-3,3-dimethylbutanamide | 4.3 | 478 |

TABLE 1-continued

| List of Compounds and Characterization Data | | | | |
|---|---|---|---|---|
| Cmpd # | Structure | Name | LCMS RT (min)* | m/z $(M + H)^+$ |
| 108 | 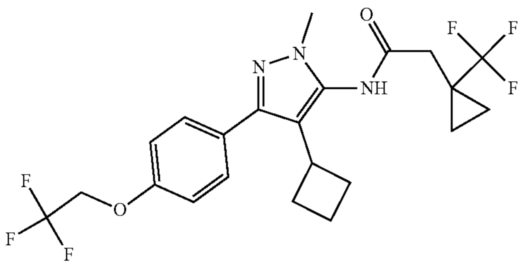 [SMILES: Cn1nc(-c2ccc(OCC(F)(F)F)cc2)c(C2CCC2)c1NC(=O)CC1(C(F)(F)F)CC1] | N-(4-cyclobutyl-1-methyl-3-(4-(2,2,2-trifluoroethoxy)phenyl)-1H-pyrazol-5-yl)-2-(1-(trifluoromethyl)cyclopropyl)acetamide | 4.1 | 476 |
| 109 | 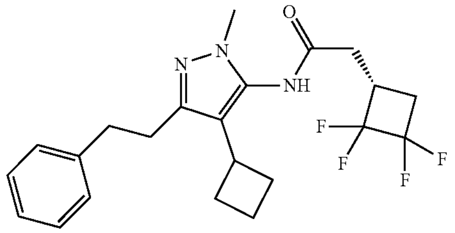 [SMILES: Cn1nc(CCc2ccccc2)c(C2CCC2)c1NC(=O)C[C@@H]1CC(F)(F)C1(F)F] | (R)-N-(4-cyclobutyl-1-methyl-3-phenethyl-1H-pyrazol-5-yl)-2-(2,2,3,3-tetrafluorocyclobutyl)acetamide | 4.2 | 424 |
| 110 | 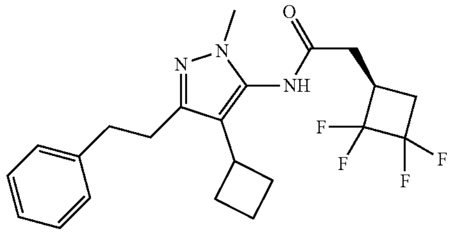 [SMILES: Cn1nc(CCc2ccccc2)c(C2CCC2)c1NC(=O)C[C@H]1CC(F)(F)C1(F)F] | (S)-N-(4-cyclobutyl-1-methyl-3-phenethyl-1H-pyrazol-5-yl)-2-(2,2,3,3-tetrafluorocyclobutyl)acetamide | 4.2 | 424 |
| 111 | 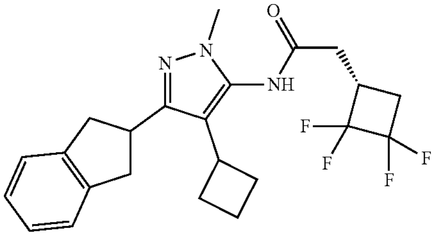 [SMILES: Cn1nc(C2Cc3ccccc3C2)c(C2CCC2)c1NC(=O)C[C@@H]1CC(F)(F)C1(F)F] | (R)-N-(4-cyclobutyl-3-(2,3-dihydro-1H-inden-2-yl)-1-methyl-1H-pyrazol-5-yl)-2-(2,2,3,3-tetrafluorocyclobutyl)acetamide | 4.4 | 436 |
| 112 | 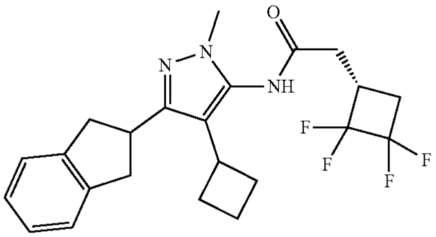 [SMILES: Cn1nc(C2Cc3ccccc3C2)c(C2CCC2)c1NC(=O)C[C@@H]1CC(F)(F)C1(F)F] | (R)-N-(4-cyclobutyl-3-(2,3-dihydro-1H-inden-2-yl)-1-methyl-1H-pyrazol-5-yl)-2-(2,2,3,3-tetrafluorocyclobutyl)acetamide | 4.4 | 436 |
| 113 | 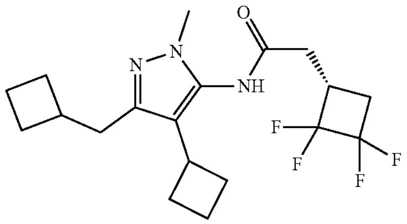 [SMILES: Cn1nc(CC2CCC2)c(C2CCC2)c1NC(=O)C[C@@H]1CC(F)(F)C1(F)F] | (R)-N-(4-cyclobutyl-3-(cyclobutylmethyl)-1-methyl-1H-pyrazol-5-yl)-2-(2,2,3,3-tetrafluorocyclobutyl)acetamide | 4.2 | 388 |

TABLE 1-continued

| List of Compounds and Characterization Data | | | | |
|---|---|---|---|---|
| Cmpd # | Structure | Name | LCMS RT (min)* | m/z (M + H)$^+$ |
| 114 | 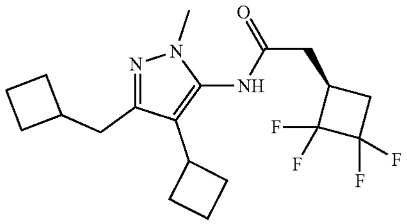 [SMILES: Cn1nc(CC2CCC2)c(C2CCC2)c1NC(=O)C[C@H]1CC(F)(F)C1(F)F] | (S)-N-(4-cyclobutyl-3-(cyclobutylmethyl)-1-methyl-1H-pyrazol-5-yl)-2-(2,2,3,3-tetrafluorocyclobutyl)acetamide | 4.2 | 388 |
| 115 | 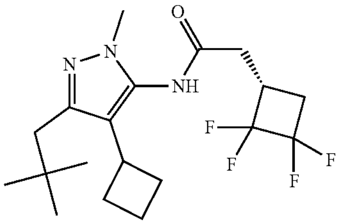 [SMILES: Cn1nc(CC(C)(C)C)c(C2CCC2)c1NC(=O)C[C@@H]1CC(F)(F)C1(F)F] | (R)-N-(4-cyclobutyl-1-methyl-3-neopentyl-1H-pyrazol-5-yl)-2-(2,2,3,3-tetrafluorocyclobutyl)acetamide | 4.2 | 390 |
| 116 | 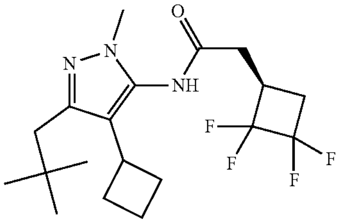 [SMILES: Cn1nc(CC(C)(C)C)c(C2CCC2)c1NC(=O)C[C@H]1CC(F)(F)C1(F)F] | (S)-N-(4-cyclobutyl-1-methyl-3-neopentyl-1H-pyrazol-5-yl)-2-(2,2,3,3-tetrafluorocyclobutyl)acetamide | 4.2 | 390 |
| 117 | 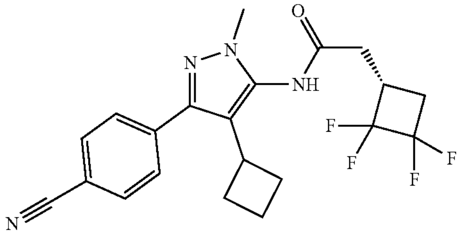 [SMILES: Cn1nc(-c2ccc(C#N)cc2)c(C2CCC2)c1NC(=O)C[C@@H]1CC(F)(F)C1(F)F] | (R)-N-(3-(4-cyanophenyl)-4-cyclobutyl-1-methyl-1H-pyrazol-5-yl)-2-(2,2,3,3-tetrafluorocyclobutyl)acetamide | 3.9 | 421 |
| 118 | 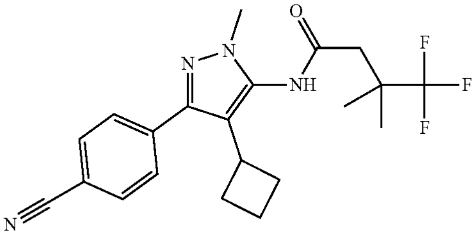 [SMILES: Cn1nc(-c2ccc(C#N)cc2)c(C2CCC2)c1NC(=O)CC(C)(C)C(F)(F)F] | N-(3-(4-cyanophenyl)-4-cyclobutyl-1-methyl-1H-pyrazol-5-yl)-4,4,4-trifluoro-3,3-dimethylbutanamide | 4.1 | 405 |
| 119 | 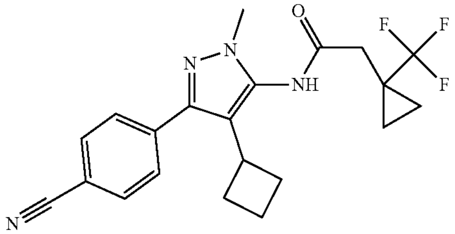 [SMILES: Cn1nc(-c2ccc(C#N)cc2)c(C2CCC2)c1NC(=O)CC1(C(F)(F)F)CC1] | N-(3-(4-cyanophenyl)-4-cyclobutyl-1-methyl-1H-pyrazol-5-yl)-2-(1-(trifluoromethyl)cyclopropyl)acetamide | 3.9 | 403 |

TABLE 1-continued

List of Compounds and Characterization Data

| Cmpd # | Structure | Name | LCMS RT (min)* | m/z (M + H)+ |
|---|---|---|---|---|
| 120 | 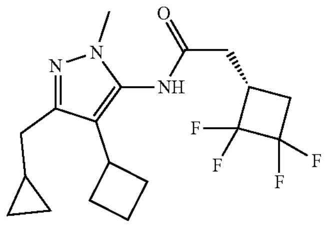 [SMILES: Cn1nc(CC2CC2)c(C2CCC2)c1NC(=O)C[C@@H]1CC(F)(F)C1(F)F] | (R)-N-(4-cyclobutyl-3-(cyclopropylmethyl)-1-methyl-1H-pyrazol-5-yl)-2-(2,2,3,3-tetrafluorocyclobutyl)acetamide | 3.9 | 374 |
| 121 | 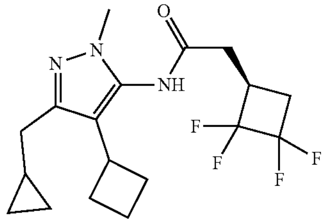 [SMILES: Cn1nc(CC2CC2)c(C2CCC2)c1NC(=O)C[C@H]1CC(F)(F)C1(F)F] | (S)-N-(4-cyclobutyl-3-(cyclopropylmethyl)-1-methyl-1H-pyrazol-5-yl)-2-(2,2,3,3-tetrafluorocyclobutyl)acetamide | 3.9 | 374 |
| 122 | 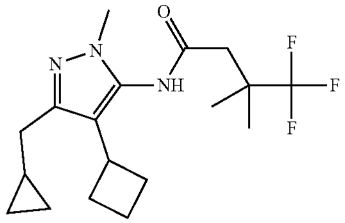 [SMILES: Cn1nc(CC2CC2)c(C2CCC2)c1NC(=O)CC(C)(C)C(F)(F)F] | N-(4-cyclobutyl-3-(cyclopropylmethyl)-1-methyl-1H-pyrazol-5-yl)-4,4,4-trifluoro-3,3-dimethylbutanamide | 4.1 | 358 |
| 123 | 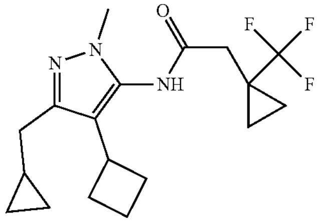 [SMILES: Cn1nc(CC2CC2)c(C2CCC2)c1NC(=O)CC1(C(F)(F)F)CC1] | N-(4-cyclobutyl-3-(cyclopropylmethyl)-1-methyl-1H-pyrazol-5-yl)-2-(1-(trifluoromethyl) cyclopropyl)acetamide | 3.9 | 356 |
| 124 | 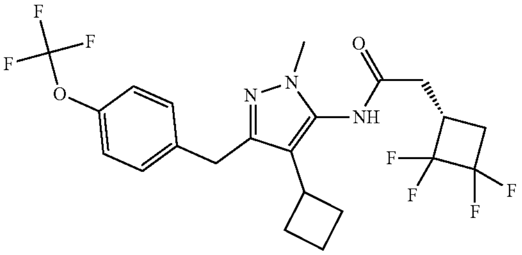 [SMILES: Cn1nc(Cc2ccc(OC(F)(F)F)cc2)c(C2CCC2)c1NC(=O)C[C@@H]1CC(F)(F)C1(F)F] | (R)-N-(4-cyclobutyl-1-methyl-3-(4-(trifluoromethoxy)benzyl)-1H-pyrazol-5-yl)-2-(2,2,3,3-tetrafluorocyclobutyl)acetamide | 4.4 | 494 |
| 125 | 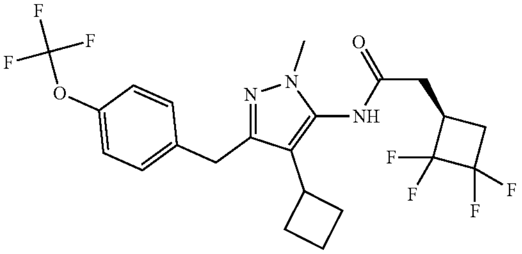 [SMILES: Cn1nc(Cc2ccc(OC(F)(F)F)cc2)c(C2CCC2)c1NC(=O)C[C@H]1CC(F)(F)C1(F)F] | (S)-N-(4-cyclobutyl-1-methyl-3-(4-(trifluoromethoxy)benzyl)-1H-pyrazol-5-yl)-2-(2,2,3,3-tetrafluorocyclobutyl)acetamide | 4.4 | 494 |

TABLE 1-continued

List of Compounds and Characterization Data

| Cmpd # | Structure | Name | LCMS RT (min)* | m/z (M + H)+ |
|---|---|---|---|---|
| 126 | 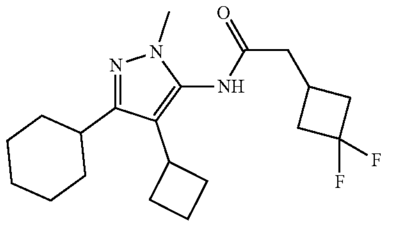 [SMILES: Cn1nc(C2CCCCC2)c(C2CCC2)c1NC(=O)CC1CC(F)(F)C1] | N-(4-cyclobutyl-3-cyclohexyl-1-methyl-1H-pyrazol-5-yl)-2-(3,3-difluorocyclobutyl)acetamide | 4.2 | 366 |
| 127 | 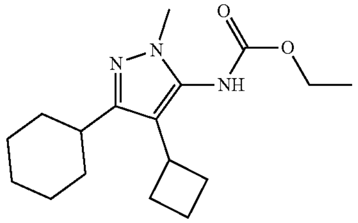 [SMILES: CCOC(=O)Nc1c(C2CCC2)c(C2CCCCC2)nn1C] | ethyl (4-cyclobutyl-3-cyclohexyl-1-methyl-1H-pyrazol-5-yl)carbamate | 4.2 | 306 |
| 128 | 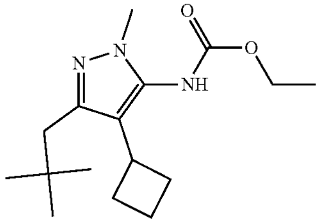 [SMILES: CCOC(=O)Nc1c(C2CCC2)c(CC(C)(C)C)nn1C] | ethyl (4-cyclobutyl-1-methyl-3-neopentyl-1H-pyrazol-5-yl)carbamate | 4.1 | 294 |
| 129 | 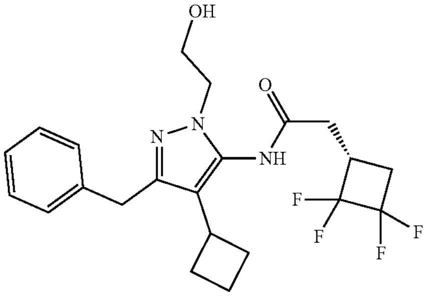 [SMILES: O=C(C[C@@H]1CC(F)(F)C1(F)F)Nc1c(C2CCC2)c(Cc2ccccc2)nn1CCO] | (R)-N-(3-benzyl-4-cyclobutyl-1-(2-hydroxyethyl)-1H-pyrazol-5-yl)-2-(2,2,3,3-tetrafluorocyclobutyl)acetamide | 3.9 | 440 |
| 130 | 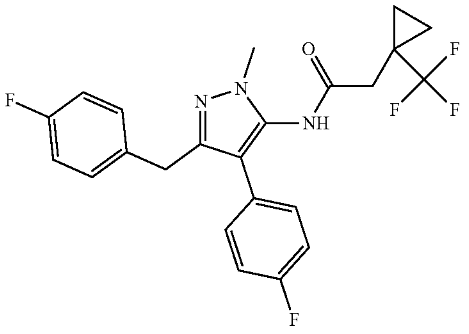 [SMILES: Cn1nc(Cc2ccc(F)cc2)c(-c2ccc(F)cc2)c1NC(=O)CC1(C(F)(F)F)CC1] | N-(3-(4-fluorobenzyl)-4-(4-fluorophenyl)-1-methyl-1H-pyrazol-5-yl)-2-(1-(trifluoromethyl)cyclopropyl)acetamide | 4.1 | 450 |

TABLE 1-continued

List of Compounds and Characterization Data

| Cmpd # | Structure | Name | LCMS RT (min)* | m/z (M + H)+ |
|---|---|---|---|---|
| 131 | 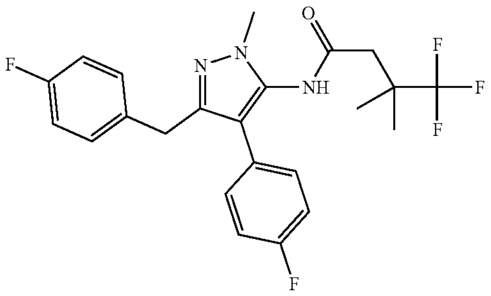 [SMILES: Cn1nc(Cc2ccc(F)cc2)c(-c2ccc(F)cc2)c1NC(=O)CC(C)(C)C(F)(F)F] | 4,4,4-trifluoro-N-(3-(4-fluorobenzyl)-4-(4-fluorophenyl)-1-methyl-1H-pyrazol-5-yl)-3,3-dimethylbutanamide | 4.3 | 452 |
| 132 | 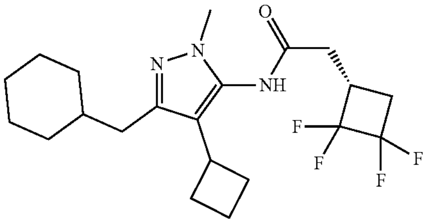 [SMILES: Cn1nc(CC2CCCCC2)c(C2CCC2)c1NC(=O)C[C@@H]1CC(F)(F)C1(F)F] | (R)-N-(4-cyclobutyl-3-(cyclohexylmethyl)-1-methyl-1H-pyrazol-5-yl)-2-(2,2,3,3-tetrafluorocyclobutyl)acetamide | 4.5 | 416 |
| 133 | 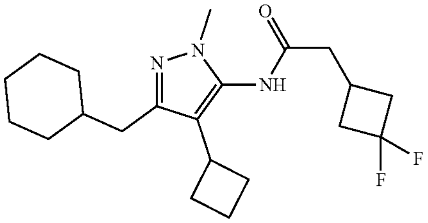 [SMILES: Cn1nc(CC2CCCCC2)c(C2CCC2)c1NC(=O)CC1CC(F)(F)C1] | N-(4-cyclobutyl-3-(cyclohexylmethyl)-1-methyl-1H-pyrazol-5-yl)-2-(3,3-difluorocyclobutyl)acetamide | 4.4 | 380 |
| 134 | 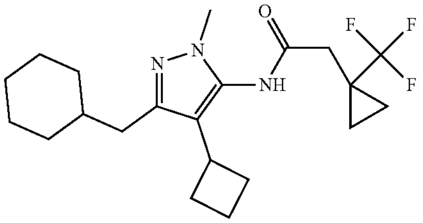 [SMILES: Cn1nc(CC2CCCCC2)c(C2CCC2)c1NC(=O)CC1(C(F)(F)F)CC1] | N-(4-cyclobutyl-3-(cyclohexylmethyl)-1-methyl-1H-pyrazol-5-yl)-2-(1-(trifluoromethyl)cyclopropyl)acetamide | 4.6 | 398 |
| 135 | 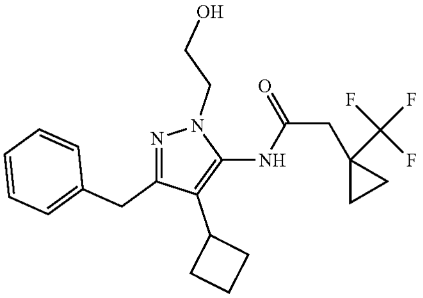 [SMILES: O=C(CC1(C(F)(F)F)CC1)Nc1c(C2CCC2)c(Cc2ccccc2)nn1CCO] | N-(3-benzyl-4-cyclobutyl-1-(2-hydroxyethyl)-1H-pyrazol-5-yl)-2-(1-(trifluoromethyl)cyclopropyl)acetamide | 3.8 | 422 |

TABLE 1-continued

List of Compounds and Characterization Data

| Cmpd # | Structure | Name | LCMS RT (min)* | m/z (M + H)+ |
| --- | --- | --- | --- | --- |
| 136 | 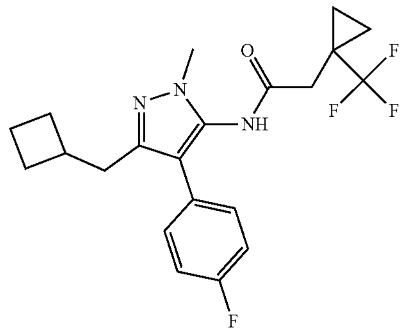 [SMILES: Cn1nc(CC2CCC2)c(-c2ccc(F)cc2)c1NC(=O)CC1(C(F)(F)F)CC1] | N-(3-(cyclobutylmethyl)-4-(4-fluorophenyl)-1-methyl-1H-pyrazol-5-yl)-2-(1-(trifluoromethyl)cyclopropyl)acetamide | 4.2 | 410 |
| 137 | 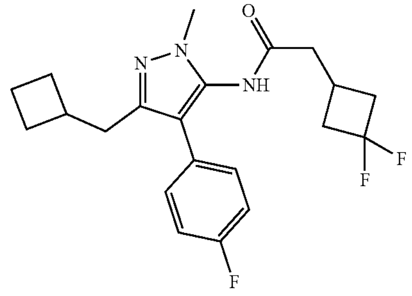 [SMILES: Cn1nc(CC2CCC2)c(-c2ccc(F)cc2)c1NC(=O)CC1CC(F)(F)C1] | N-(3-(cyclobutylmethyl)-4-(4-fluorophenyl)-1-methyl-1H-pyrazol-5-yl)-2-(3,3-difluorocyclobutyl)acetamide | 4.1 | 392 |
| 138 | 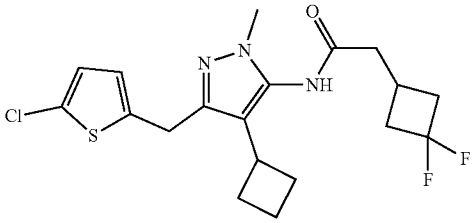 [SMILES: Cn1nc(Cc2ccc(Cl)s2)c(C2CCC2)c1NC(=O)CC1CC(F)(F)C1] | N-(3-((5-chlorothiophen-2-yl)methyl)-4-cyclobutyl-1-methyl-1H-pyrazol-5-yl)-2-(3,3-difluorocyclobutyl)acetamide | 4.2 | 414 |
| 139 | 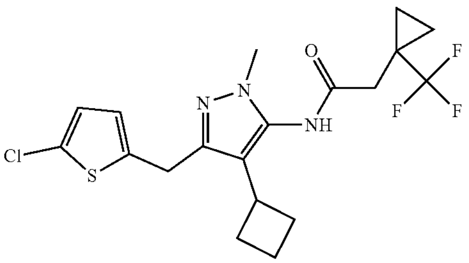 [SMILES: Cn1nc(Cc2ccc(Cl)s2)c(C2CCC2)c1NC(=O)CC1(C(F)(F)F)CC1] | N-(3-((5-chlorothiophen-2-yl)methyl)-4-cyclobutyl-1-methyl-1H-pyrazol-5-yl)-2-(1-(trifluoromethyl)cyclopropyl)acetamide | 4.3 | 432 |
| 140 | 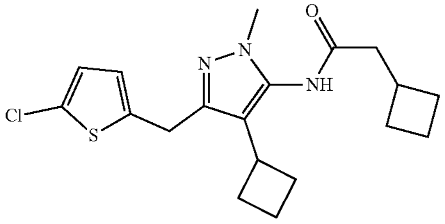 [SMILES: Cn1nc(Cc2ccc(Cl)s2)c(C2CCC2)c1NC(=O)CC1CCC1] | N-(3-((5-chlorothiophen-2-yl)methyl)-4-cyclobutyl-1-methyl-1H-pyrazol-5-yl)-2-cyclobutylacetamide | 3.3 | 378 |

TABLE 1-continued

List of Compounds and Characterization Data

| Cmpd # | Structure | Name | LCMS RT (min)* | m/z (M + H)$^+$ |
| --- | --- | --- | --- | --- |
| 141 | 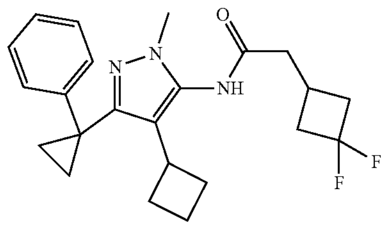 [SMILES: Cn1nc(C2(c3ccccc3)CC2)c(C2CCC2)c1NC(=O)CC1CC(F)(F)C1] | N-(4-cyclobutyl-1-methyl-3-(1-phenylcyclopropyl)-1H-pyrazol-5-yl)-2-(3,3-difluorocyclobutyl)acetamide | 4.1 | 400 |
| 142 | 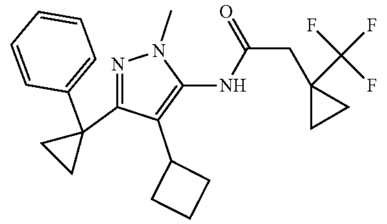 [SMILES: Cn1nc(C2(c3ccccc3)CC2)c(C2CCC2)c1NC(=O)CC1(C(F)(F)F)CC1] | N-(4-cyclobutyl-1-methyl-3-(1-phenylcyclopropyl)-1H-pyrazol-5-yl)-2-(1-(trifluoromethyl)cyclopropyl)acetamide | 4.2 | 418 |
| 143 | 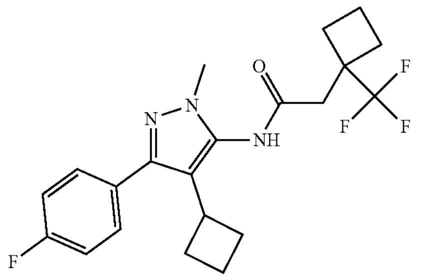 [SMILES: Cn1nc(-c2ccc(F)cc2)c(C2CCC2)c1NC(=O)CC1(C(F)(F)F)CCC1] | N-(4-cyclobutyl-3-(4-fluorophenyl)-1-methyl-1H-pyrazol-5-yl)-2-(1-(trifluoromethyl)cyclobutyl)acetamide | 4.3 | 410 |
| 144 | 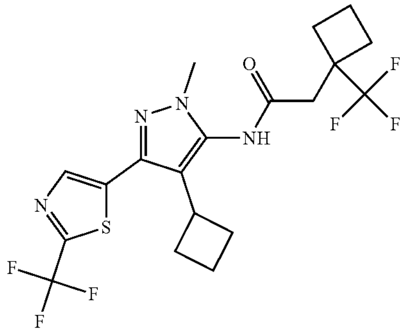 [SMILES: Cn1nc(-c2cnc(C(F)(F)F)s2)c(C2CCC2)c1NC(=O)CC1(C(F)(F)F)CCC1] | N-(4-cyclobutyl-1-methyl-3-(2-(trifluoromethyl)thiazol-5-yl)-1H-pyrazol-5-yl)-2-(1-(trifluoromethyl)cyclobutyl)acetamide | 4.4 | 467 |
| 145 | 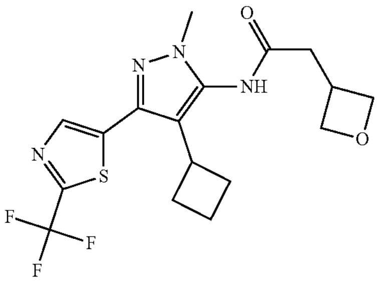 [SMILES: Cn1nc(-c2cnc(C(F)(F)F)s2)c(C2CCC2)c1NC(=O)CC1COC1] | N-(4-cyclobutyl-1-methyl-3-(2-(trifluoromethyl)thiazol-5-yl)-1H-pyrazol-5-yl)-2-(oxetan-3-yl)acetamide | 3.5 | 401 |

TABLE 1-continued

| List of Compounds and Characterization Data | | | | |
|---|---|---|---|---|
| Cmpd # | Structure | Name | LCMS RT (min)* | m/z (M + H)+ |
| 146 | 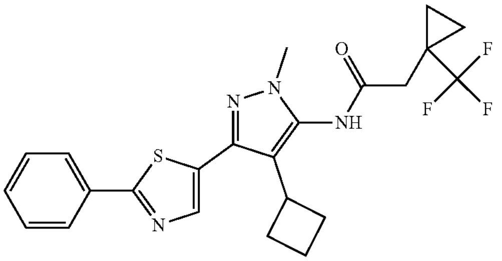 [SMILES: Cn1nc(-c2cnc(-c3ccccc3)s2)c(C2CCC2)c1NC(=O)CC1(C(F)(F)F)CC1] | N-(4-cyclobutyl-1-methyl-3-(2-phenylthiazol-5-yl)-1H-pyrazol-5-yl)-2-(1-(trifluoromethyl)cyclopropyl)acetamide | 4.3 | 461 |
| 147 | 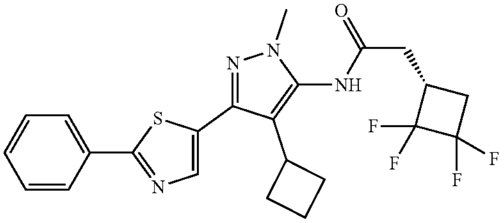 [SMILES: Cn1nc(-c2cnc(-c3ccccc3)s2)c(C2CCC2)c1NC(=O)C[C@@H]1CC(F)(F)C1(F)F] | (R)-N-(4-cyclobutyl-1-methyl-3-(2-phenylthiazol-5-yl)-1H-pyrazol-5-yl)-2-(2,2,3,3-tetrafluorocyclobutyl)acetamide | 4.3 | 479 |
| 148 | 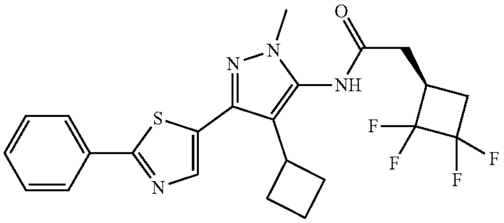 [SMILES: Cn1nc(-c2cnc(-c3ccccc3)s2)c(C2CCC2)c1NC(=O)C[C@H]1CC(F)(F)C1(F)F] | (S)-N-(4-cyclobutyl-1-methyl-3-(2-phenylthiazol-5-yl)-1H-pyrazol-5-yl)-2-(2,2,3,3-tetrafluorocyclobutyl)acetamide | 4.3 | 479 |
| 149 | 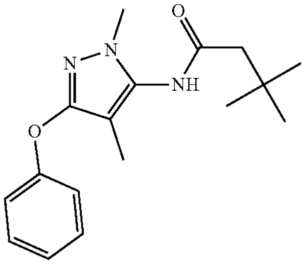 [SMILES: Cc1c(Oc2ccccc2)nn(C)c1NC(=O)CC(C)(C)C] | N-(1,4-dimethyl-3-phenoxy-1H-pyrazol-5-yl)-3,3-dimethylbutanamide | 3.2 | 302 |
| 150 | 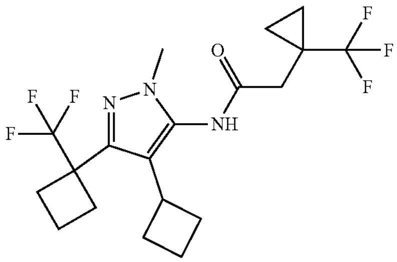 [SMILES: Cn1nc(C2(C(F)(F)F)CCC2)c(C2CCC2)c1NC(=O)CC1(C(F)(F)F)CC1] | N-(4-cyclobutyl-1-methyl-3-(1-(trifluoromethyl)cyclobutyl)-1H-pyrazol-5-yl)-2-(1-(trifluoromethyl)cyclopropyl)acetamide | 4.3 | 424 |
| 151 | 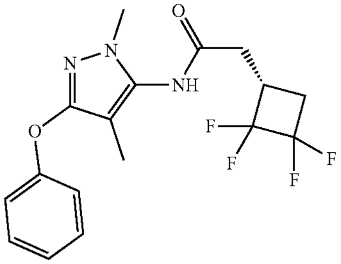 [SMILES: Cc1c(Oc2ccccc2)nn(C)c1NC(=O)C[C@@H]1CC(F)(F)C1(F)F] | (R)-N-(1,4-dimethyl-3-phenoxy-1H-pyrazol-5-yl)-2-(2,2,3,3-tetrafluorocyclobutyl)acetamide | 3.3 | 372 |

TABLE 1-continued

List of Compounds and Characterization Data

| Cmpd # | Structure | Name | LCMS RT (min)* | m/z (M + H)+ |
|---|---|---|---|---|
| 152 | 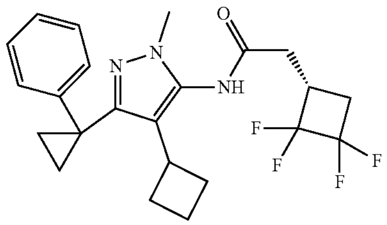 [SMILES: Cn1nc(C2(c3ccccc3)CC2)c(C2CCC2)c1NC(=O)C[C@@H]1CC(F)(F)C1(F)F] | (R)-N-(4-cyclobutyl-1-methyl-3-(1-phenylcyclopropyl)-1H-pyrazol-5-yl)-2-(2,2,3,3-tetrafluorocyclobutyl)acetamide | 4.2 | 436 |
| 153 | 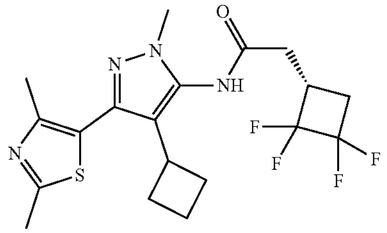 [SMILES: Cc1nc(C)c(-c2nn(C)c(NC(=O)C[C@@H]3CC(F)(F)C3(F)F)c2C2CCC2)s1] | (R)-N-(4-cyclobutyl-3-(2,4-dimethylthiazol-5-yl)-1-methyl-1H-pyrazol-5-yl)-2-(2,2,3,3-tetrafluorocyclobutyl)acetamide | 3.6 | 431 |
| 154 | 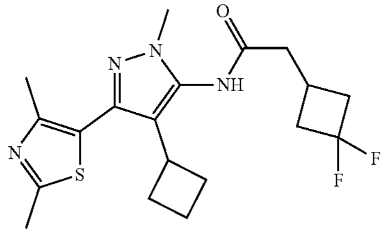 [SMILES: Cc1nc(C)c(-c2nn(C)c(NC(=O)CC3CC(F)(F)C3)c2C2CCC2)s1] | N-(4-cyclobutyl-3-(2,4-dimethylthiazol-5-yl)-1-methyl-1H-pyrazol-5-yl)-2-(3,3-difluorocyclobutyl)acetamide | 3.4 | 395 |
| 155 | 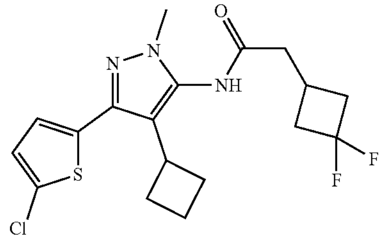 [SMILES: Cn1nc(-c2ccc(Cl)s2)c(C2CCC2)c1NC(=O)CC1CC(F)(F)C1] | N-(3-(5-chlorothiophen-2-yl)-4-cyclobutyl-1-methyl-1H-pyrazol-5-yl)-2-(3,3-difluorocyclobutyl)acetamide | 4.3 | 400 |
| 156 | 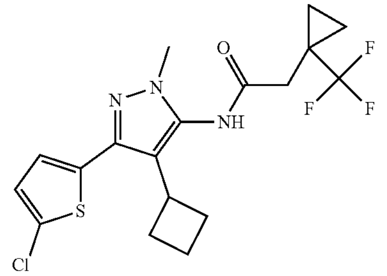 [SMILES: Cn1nc(-c2ccc(Cl)s2)c(C2CCC2)c1NC(=O)CC1(C(F)(F)F)CC1] | N-(3-(5-chlorothiophen-2-yl)-4-cyclobutyl-1-methyl-1H-pyrazol-5-yl)-2-(1-(trifluoromethyl)cyclopropyl)acetamide | 4.4 | 418 |
| 157 | 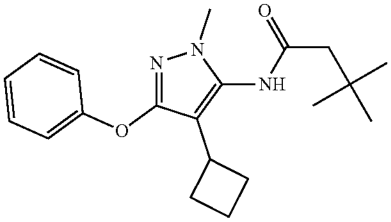 [SMILES: Cn1nc(Oc2ccccc2)c(C2CCC2)c1NC(=O)CC(C)(C)C] | N-(4-cyclobutyl-1-methyl-3-phenoxy-1H-pyrazol-5-yl)-3,3-dimethylbutanamide | 3.6 | 342 |

TABLE 1-continued

| Cmpd # | Structure | Name | LCMS RT (min)* | m/z (M + H)$^+$ |
|---|---|---|---|---|
| List of Compounds and Characterization Data | | | | |
| 158 | 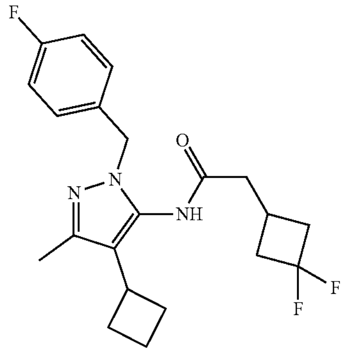 [SMILES: Cc1nn(Cc2ccc(F)cc2)c(NC(=O)CC2CC(F)(F)C2)c1C1CCC1] | N-(4-cyclobutyl-1-(4-fluorobenzyl)-3-methyl-1H-pyrazol-5-yl)-2-(3,3-difluorocyclobutyl)acetamide | 3.9 | 392 |
| 159 | 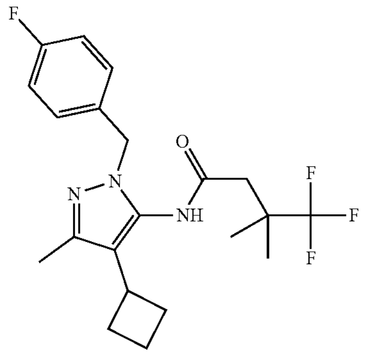 [SMILES: Cc1nn(Cc2ccc(F)cc2)c(NC(=O)CC(C)(C)C(F)(F)F)c1C1CCC1] | N-(4-cyclobutyl-1-(4-fluorobenzyl)-3-methyl-1H-pyrazol-5-yl)-4,4,4-trifluoro-3,3-dimethylbutanamide | 4.3 | 412 |
| 160 | 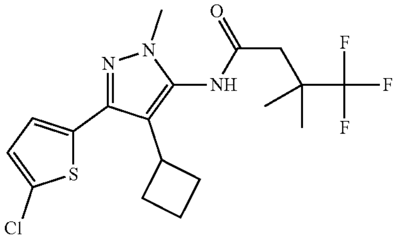 [SMILES: Cn1nc(-c2ccc(Cl)s2)c(C2CCC2)c1NC(=O)CC(C)(C)C(F)(F)F] | N-(3-(5-chlorothiophen-2-yl)-4-cyclobutyl-1-methyl-1H-pyrazol-5-yl)-4,4,4-trifluoro-3,3-dimethylbutanamide | 4.7 | 420 |
| 161 | 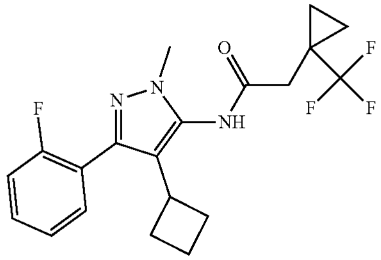 [SMILES: Cn1nc(-c2ccccc2F)c(C2CCC2)c1NC(=O)CC1(C(F)(F)F)CC1] | N-(4-cyclobutyl-3-(2-fluorophenyl)-1-methyl-1H-pyrazol-5-yl)-2-(1-(trifluoromethyl)cyclopropyl)acetamide | 4 | 396 |
| 162 | 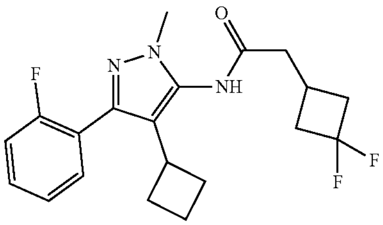 [SMILES: Cn1nc(-c2ccccc2F)c(C2CCC2)c1NC(=O)CC1CC(F)(F)C1] | N-(4-cyclobutyl-3-(2-fluorophenyl)-1-methyl-1H-pyrazol-5-yl)-2-(3,3-difluorocyclobutyl)acetamide | 3.8 | 378 |

TABLE 1-continued

List of Compounds and Characterization Data

| Cmpd # | Structure | Name | LCMS RT (min)* | m/z (M + H)+ |
|---|---|---|---|---|
| 163 | 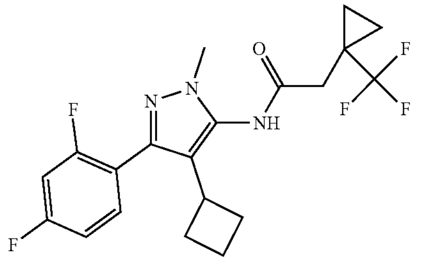 [SMILES: Cn1nc(-c2ccc(F)cc2F)c(C2CCC2)c1NC(=O)CC1(C(F)(F)F)CC1] | N-(4-cyclobutyl-3-(2,4-difluorophenyl)-1-methyl-1H-pyrazol-5-yl)-2-(1-(trifluoromethyl)cyclopropyl)acetamide | 4 | 414 |
| 164 | 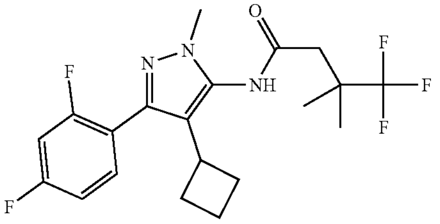 [SMILES: Cn1nc(-c2ccc(F)cc2F)c(C2CCC2)c1NC(=O)CC(C)(C)C(F)(F)F] | N-(4-cyclobutyl-3-(2,4-difluorophenyl)-1-methyl-1H-pyrazol-5-yl)-4,4,4-trifluoro-3,3-dimethylbutanamide | 4.2 | 416 |
| 165 | 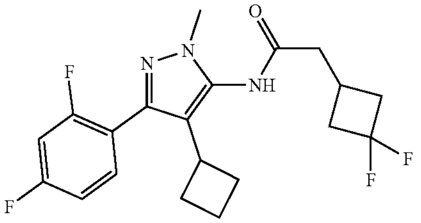 [SMILES: Cn1nc(-c2ccc(F)cc2F)c(C2CCC2)c1NC(=O)CC1CC(F)(F)C1] | N-(4-cyclobutyl-3-(2,4-difluorophenyl)-1-methyl-1H-pyrazol-5-yl)-2-(3,3-difluorocyclobutyl)acetamide | 3.9 | 396 |
| 166 | 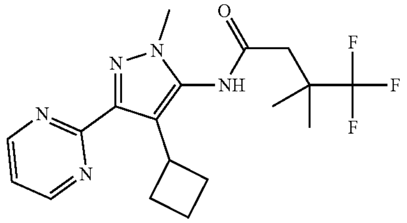 [SMILES: Cn1nc(-c2ncccn2)c(C2CCC2)c1NC(=O)CC(C)(C)C(F)(F)F] | N-(4-cyclobutyl-1-methyl-3-(pyrimidin-2-yl)-1H-pyrazol-5-yl)-4,4,4-trifluoro-3,3-dimethylbutanamide | 3.5 | 382 |
| 167 | 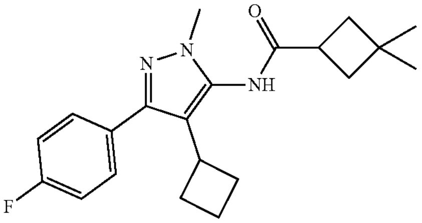 [SMILES: Cn1nc(-c2ccc(F)cc2)c(C2CCC2)c1NC(=O)C1CC(C)(C)C1] | N-(4-cyclobutyl-3-(4-fluorophenyl)-1-methyl-1H-pyrazol-5-yl)-3,3-dimethylcyclobutane-1-carboxamide | 4.3 | 356 |
| 168 | 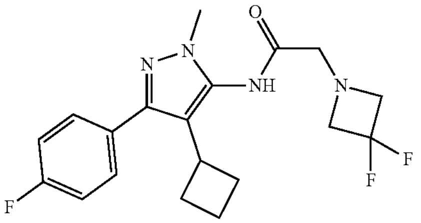 [SMILES: Cn1nc(-c2ccc(F)cc2)c(C2CCC2)c1NC(=O)CN1CC(F)(F)C1] | N-(4-cyclobutyl-3-(4-fluorophenyl)-1-methyl-1H-pyrazol-5-yl)-2-(3,3-difluoroazetidin-1-yl)acetamide | 3.6 | 379 |

TABLE 1-continued

List of Compounds and Characterization Data

| Cmpd # | Structure | Name | LCMS RT (min)* | m/z (M + H)+ |
|---|---|---|---|---|
| 169 | 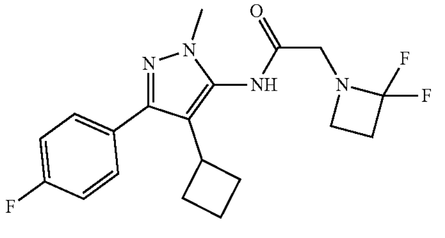 [SMILES: Cn1nc(-c2ccc(F)cc2)c(C2CCC2)c1NC(=O)CN1CCC1(F)F] Stereoisomer 1 | N-(4-cyclobutyl-3-(4-fluorophenyl)-1-methyl-1H-pyrazol-5-yl)-2-(2,2-difluorocyclobutyl)acetamide | 4 | 378 |
| 170 | 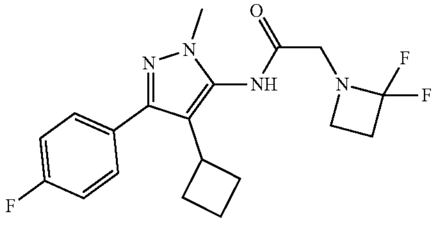 [SMILES: Cn1nc(-c2ccc(F)cc2)c(C2CCC2)c1NC(=O)CN1CCC1(F)F] Stereoisomer 2 | N-(4-cyclobutyl-3-(4-fluorophenyl)-1-methyl-1H-pyrazol-5-yl)-2-(2,2-difluorocyclobutyl)acetamide | 4 | 378 |
| 171 | 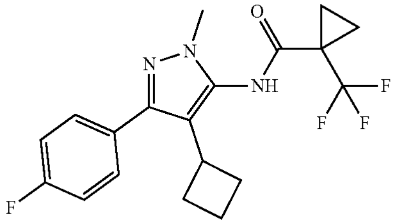 [SMILES: Cn1nc(-c2ccc(F)cc2)c(C2CCC2)c1NC(=O)C1(C(F)(F)F)CC1] | N-(4-cyclobutyl-3-(4-fluorophenyl)-1-methyl-1H-pyrazol-5-yl)-1-(trifluoromethyl)cyclopropane-1-carboxamide | 4.2 | 382 |
| 172 | 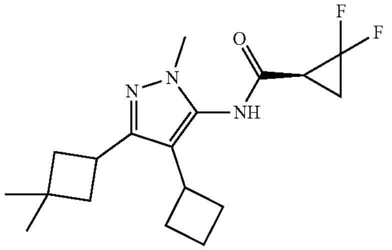 [SMILES: Cn1nc(C2CC(C)(C)C2)c(C2CCC2)c1NC(=O)[C@@H]1CC1(F)F] | (S)-N-(4-cyclobutyl-3-(3,3-dimethylcyclobutyl)-1-methyl-1H-pyrazol-5-yl)-2,2-difluorocyclopropane-1-carboxamide | 4.2 | 338 |
| 173 | 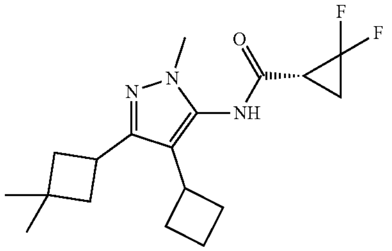 [SMILES: Cn1nc(C2CC(C)(C)C2)c(C2CCC2)c1NC(=O)[C@H]1CC1(F)F] | (R)-N-(4-cyclobutyl-3-(3,3-dimethylcyclobutyl)-1-methyl-1H-pyrazol-5-yl)-2,2-difluorocyclopropane-1-carboxamide | 4.2 | 338 |
| 174 | 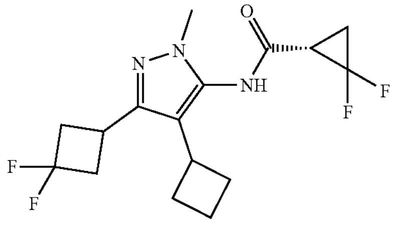 [SMILES: Cn1nc(C2CC(F)(F)C2)c(C2CCC2)c1NC(=O)[C@@H]1CC1(F)F] | (S)-N-(4-cyclobutyl-3-(3,3-difluorocyclobutyl)-1-methyl-1H-pyrazol-5-yl)-2,2-difluorocyclopropane-1-carboxamide | 3.8 | 346 |

TABLE 1-continued

| List of Compounds and Characterization Data | | | | |
|---|---|---|---|---|
| Cmpd # | Structure | Name | LCMS RT (min)* | m/z (M + H)+ |
| 175 | 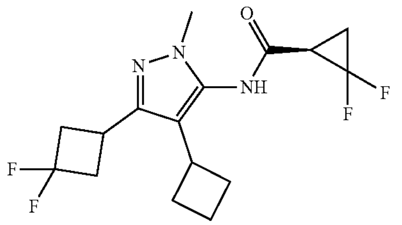 [SMILES: Cn1nc(C2CC(F)(F)C2)c(C2CCC2)c1NC(=O)[C@H]1CC1(F)F] | (R)-N-(4-cyclobutyl-3-(3,3-difluorocyclobutyl)-1-methyl-1H-pyrazol-5-yl)-2,2-difluorocyclopropane-1-carboxamide | 3.8 | 346 |
| 176 | 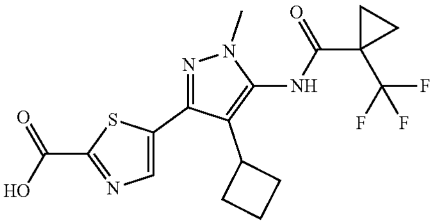 [SMILES: Cn1nc(-c2cnc(C(=O)O)s2)c(C2CCC2)c1NC(=O)C1(C(F)(F)F)CC1] | 5-(4-cyclobutyl-1-methyl-5-(1-(trifluoromethyl)cyclopropane-1-carboxamido)-1H-pyrazol-3-yl)thiazole-2-carboxylic acid | 3.8 | 415 |
| 177 | 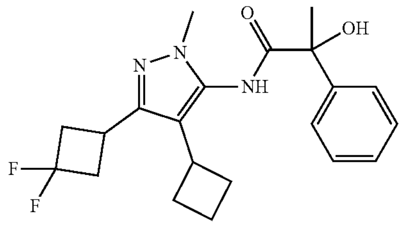 [SMILES: Cn1nc(C2CC(F)(F)C2)c(C2CCC2)c1NC(=O)C(C)(O)c1ccccc1] | (R)-N-(4-cyclobutyl-3-(3,3-difluorocyclobutyl)-1-methyl-1H-pyrazol-5-yl)-2-hydroxy-2-phenylpropanamide | 3.9 | 390 |
| 178 | 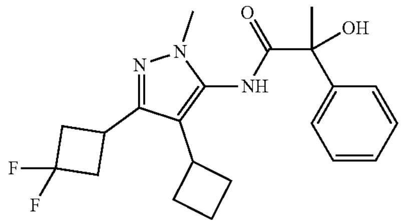 [SMILES: Cn1nc(C2CC(F)(F)C2)c(C2CCC2)c1NC(=O)C(C)(O)c1ccccc1] | (S)-N-(4-cyclobutyl-3-(3,3-difluorocyclobutyl)-1-methyl-1H-pyrazol-5-yl)-2-hydroxy-2-phenylpropanamide | 3.9 | 390 |
| 179 | 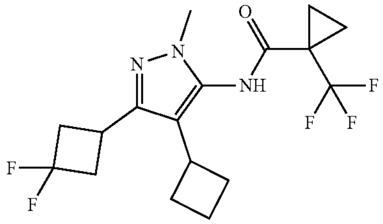 [SMILES: Cn1nc(C2CC(F)(F)C2)c(C2CCC2)c1NC(=O)C1(C(F)(F)F)CC1] | N-(4-cyclobutyl-3-(3,3-difluorocyclobutyl)-1-methyl-1H-pyrazol-5-yl)-1-(trifluoromethyl)cyclopropane-1-carboxamide | 4 | 378 |
| 180 | 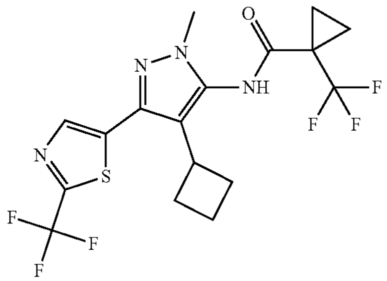 [SMILES: Cn1nc(-c2cnc(C(F)(F)F)s2)c(C2CCC2)c1NC(=O)C1(C(F)(F)F)CC1] | N-(4-cyclobutyl-1-methyl-3-(2-(trifluoromethyl)thiazol-5-yl)-1H-pyrazol-5-yl)-1-(trifluoromethyl)cyclopropane-1-carboxamide | 4.2 | 439 |

TABLE 1-continued

List of Compounds and Characterization Data

| Cmpd # | Structure | Name | LCMS RT (min)* | m/z (M + H)$^+$ |
|---|---|---|---|---|
| 181 | 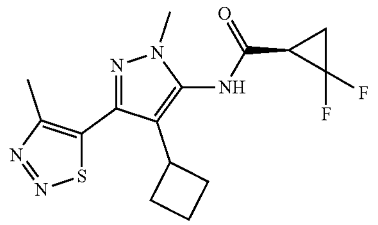 [SMILES: Cc1nnsc1-c1nn(C)c(NC(=O)[C@H]2CC2(F)F)c1C1CCC1] | (R)-N-(4-cyclobutyl-1-methyl-3-(4-methyl-1,2,3-thiadiazol-5-yl)-1H-pyrazol-5-yl)-2,2-difluorocyclopropane-1-carboxamide | 3.5 | 354 |
| 182 | 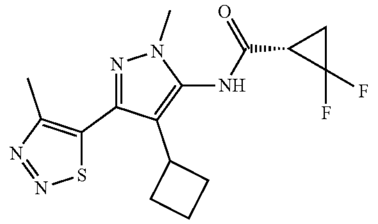 [SMILES: Cc1nnsc1-c1nn(C)c(NC(=O)[C@@H]2CC2(F)F)c1C1CCC1] | (S)-N-(4-cyclobutyl-1-methyl-3-(4-methyl-1,2,3-thiadiazol-5-yl)-1H-pyrazol-5-yl)-2,2-difluorocyclopropane-1-carboxamide | 3.5 | 354 |
| 183 | 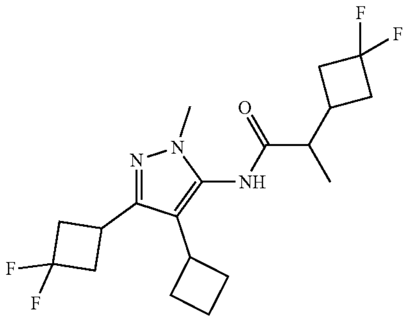 [SMILES: CC(C(=O)Nc1c(C2CCC2)c(C2CC(F)(F)C2)nn1C)C1CC(F)(F)C1] Stereoisomer 1 | N-(4-cyclobutyl-3-(3,3-difluorocyclobutyl)-1-methyl-1H-pyrazol-5-yl)-2-(3,3-difluorocyclobutyl)propanamide | 3.9 | 388 |
| 184 | 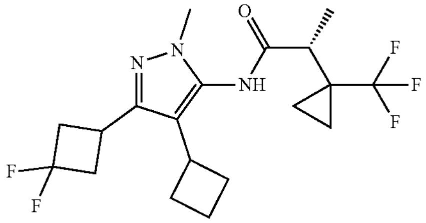 [SMILES: C[C@@H](C(=O)Nc1c(C2CCC2)c(C2CC(F)(F)C2)nn1C)C1(C(F)(F)F)CC1] | (R)-N-(4-cyclobutyl-3-(3,3-difluorocyclobutyl)-1-methyl-1H-pyrazol-5-yl)-2-(1-(trifluoromethyl)cyclopropyl)propanamide | 4.2 | 406 |
| 185 | 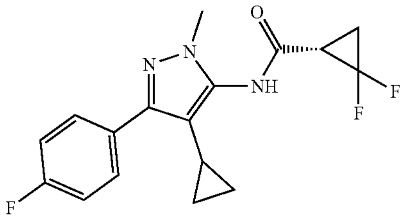 [SMILES: Cn1nc(-c2ccc(F)cc2)c(C2CC2)c1NC(=O)[C@@H]1CC1(F)F] | (S)-N-(4-cyclopropyl-3-(4-fluorophenyl)-1-methyl-1H-pyrazol-5-yl)-2,2-difluorocyclopropane-1-carboxamide | 3.7 | 336 |
| 186 | 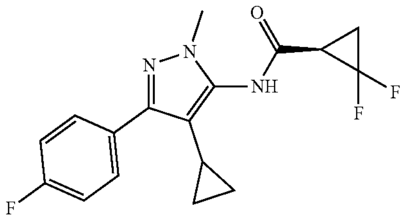 [SMILES: Cn1nc(-c2ccc(F)cc2)c(C2CC2)c1NC(=O)[C@H]1CC1(F)F] | (R)-N-(4-cyclopropyl-3-(4-fluorophenyl)-1-methyl-1H-pyrazol-5-yl)-2,2-difluorocyclopropane-1-carboxamide | 3.7 | 336 |

TABLE 1-continued

List of Compounds and Characterization Data

| Cmpd # | Structure | Name | LCMS RT (min)* | m/z (M + H)+ |
|---|---|---|---|---|
| 187 | 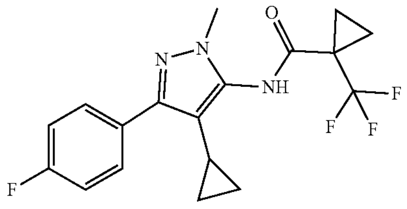 [SMILES: Cn1nc(-c2ccc(F)cc2)c(C2CC2)c1NC(=O)C1(C(F)(F)F)CC1] | N-(4-cyclopropyl-3-(4-fluorophenyl)-1-methyl-1H-pyrazol-5-yl)-1-(trifluoromethyl)cyclopropane-1-carboxamide | 3.9 | 368 |
| 188 | 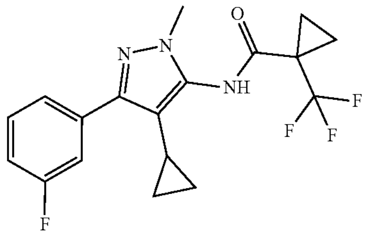 [SMILES: Cn1nc(-c2cccc(F)c2)c(C2CC2)c1NC(=O)C1(C(F)(F)F)CC1] | N-(4-cyclobutyl-3-(3-fluorophenyl)-1-methyl-1H-pyrazol-5-yl)-1-(trifluoromethyl)cyclopropane-1-carboxamide | 4.1 | 382 |
| 189 | 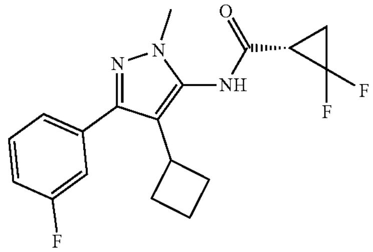 [SMILES: Cn1nc(-c2cccc(F)c2)c(C2CCC2)c1NC(=O)[C@@H]1CC1(F)F] | (S)-N-(4-cyclobutyl-3-(3-fluorophenyl)-1-methyl-1H-pyrazol-5-yl)-2,2-difluorocyclopropane-1-carboxamide | 3.9 | 350 |
| 190 | 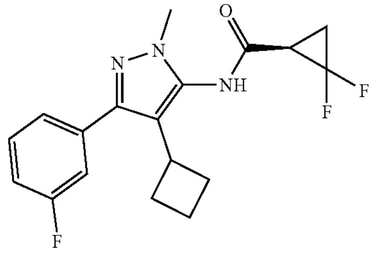 [SMILES: Cn1nc(-c2cccc(F)c2)c(C2CCC2)c1NC(=O)[C@H]1CC1(F)F] | (R)-N-(4-cyclobutyl-3-(3-fluorophenyl)-1-methyl-1H-pyrazol-5-yl)-2,2-difluorocyclopropane-1-carboxamide | 3.8 | 350 |
| 191 | 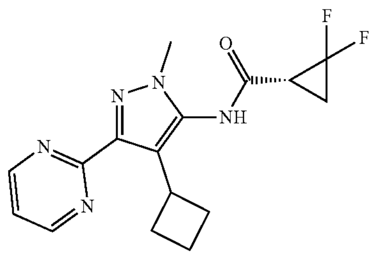 [SMILES: Cn1nc(-c2ncccn2)c(C2CCC2)c1NC(=O)[C@H]1CC1(F)F] | (R)-N-(4-cyclobutyl-1-methyl-3-(pyrimidin-2-yl)-1H-pyrazol-5-yl)-2,2-difluorocyclopropane-1-carboxamide | 3.1 | 334 |
| 192 | 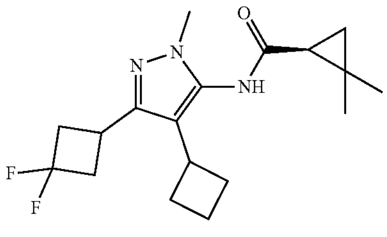 [SMILES: Cn1nc(C2CC(F)(F)C2)c(C2CCC2)c1NC(=O)[C@H]1CC1(C)C] | (S)-N-(4-cyclobutyl-3-(3,3-difluorocyclobutyl)-1-methyl-1H-pyrazol-5-yl)-2,2-dimethylcyclopropane-1-carboxamide | 4 | 338 |

TABLE 1-continued

List of Compounds and Characterization Data

| Cmpd # | Structure | Name | LCMS RT (min)* | m/z $(M+H)^+$ |
| --- | --- | --- | --- | --- |
| 193 | 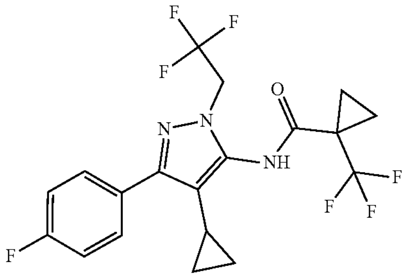 [SMILES: O=C(Nc1c(C2CC2)c(-c2ccc(F)cc2)nn1CC(F)(F)F)C1(C(F)(F)F)CC1] | N-(4-cyclobutyl-3-(4-fluorophenyl)-1-(2,2,2-trifluoroethyl)-1H-pyrazol-5-yl)-1-(trifluoromethyl)cyclopropane-1-carboxamide | 4.4 | 450 |
| 194 | 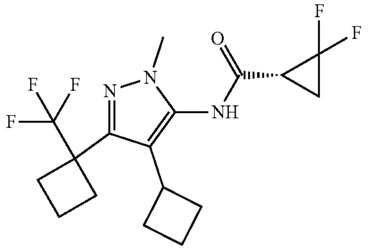 [SMILES: Cn1nc(C2(C(F)(F)F)CCC2)c(C2CCC2)c1NC(=O)[C@H]1CC1(F)F] | (R)-N-(4-cyclobutyl-1-methyl-3-(1-(trifluoromethyl)cyclobutyl)-1H-pyrazol-5-yl)-2,2-difluorocyclopropane-1-carboxamide | 4.1 | 378 |
| 195 | 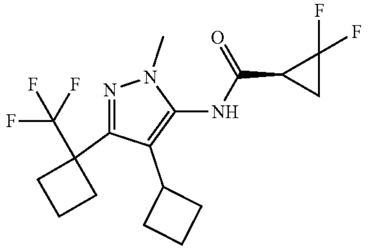 [SMILES: Cn1nc(C2(C(F)(F)F)CCC2)c(C2CCC2)c1NC(=O)[C@@H]1CC1(F)F] | (S)-N-(4-cyclobutyl-1-methyl-3-(1-(trifluoromethyl)cyclobutyl)-1H-pyrazol-5-yl)-2,2-difluorocyclopropane-1-carboxamide | 4.1 | 378 |
| 196 | 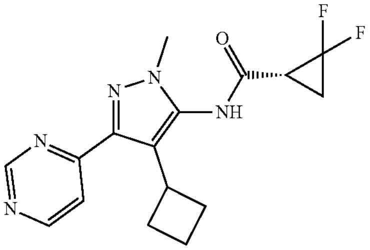 [SMILES: Cn1nc(-c2ccncn2)c(C2CCC2)c1NC(=O)[C@H]1CC1(F)F] | (R)-N-(4-cyclobutyl-1-methyl-3-(pyrimidin-4-yl)-1H-pyrazol-5-yl)-2,2-difluorocyclopropane-1-carboxamide | 3.2 | 334 |
| 197 | 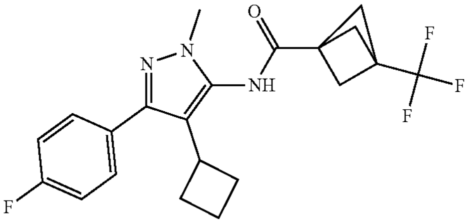 [SMILES: Cn1nc(-c2ccc(F)cc2)c(C2CCC2)c1NC(=O)C12CC(C(F)(F)F)(C1)C2] | N-(4-cyclobutyl-3-(4-fluorophenyl)-1-methyl-1H-pyrazol-5-yl)-3-(trifluoromethyl)bicyclo[1.1.1]pentane-1-carboxamide | 4.1 | 408 |

TABLE 1-continued

| List of Compounds and Characterization Data | | | | |
|---|---|---|---|---|
| Cmpd # | Structure | Name | LCMS RT (min)* | m/z (M + H)$^+$ |
| 198 | 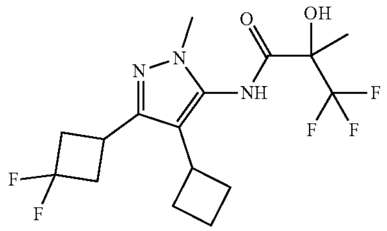 [SMILES: Cn1nc(C2CC(F)(F)C2)c(C2CCC2)c1NC(=O)C(C)(O)C(F)(F)F] Stereoisomer 1 | N-(4-cyclobutyl-3-(3,3-difluorocyclobutyl)-1-methyl-1H-pyrazol-5-yl)-3,3,3-trifluoro-2-hydroxy-2-methylpropanamide | 3.7 | 382 |
| 199 | 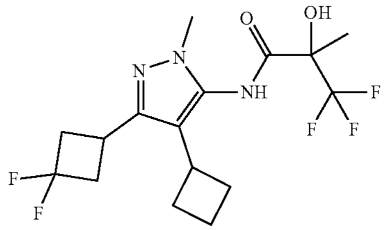 [SMILES: Cn1nc(C2CC(F)(F)C2)c(C2CCC2)c1NC(=O)C(C)(O)C(F)(F)F] Stereoisomer 2 | N-(4-cyclobutyl-3-(3,3-difluorocyclobutyl)-1-methyl-1H-pyrazol-5-yl)-3,3,3-trifluoro-2-hydroxy-2-methylpropanamide | 3.7 | 382 |
| 200 | 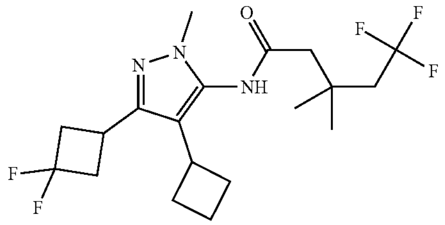 [SMILES: Cn1nc(C2CC(F)(F)C2)c(C2CCC2)c1NC(=O)CC(C)(C)CC(F)(F)F] | N-(4-cyclobutyl-3-(3,3-difluorocyclobutyl)-1-methyl-1H-pyrazol-5-yl)-5,5,5-trifluoro-3,3-dimethylpentanamide | 4.3 | 408 |
| 201 | 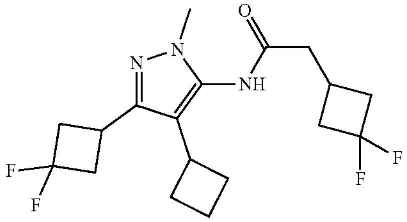 [SMILES: Cn1nc(C2CC(F)(F)C2)c(C2CCC2)c1NC(=O)CC1CC(F)(F)C1] | N-(4-cyclobutyl-3-(3,3-difluorocyclobutyl)-1-methyl-1H-pyrazol-5-yl)-2-(3,3-difluorocyclobutyl)acetamide | 3.8 | 374 |
| 202 | 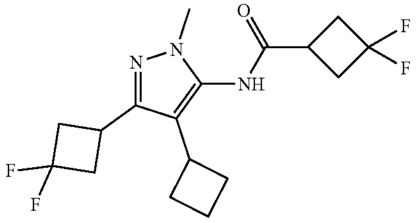 [SMILES: Cn1nc(C2CC(F)(F)C2)c(C2CCC2)c1NC(=O)C1CC(F)(F)C1] | N-(4-cyclobutyl-3-(3,3-difluorocyclobutyl)-1-methyl-1H-pyrazol-5-yl)-3,3-difluorocyclobutane-1-carboxamide | 3.8 | 360 |
| 203 | 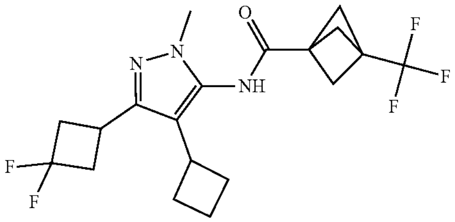 [SMILES: Cn1nc(C2CC(F)(F)C2)c(C2CCC2)c1NC(=O)C12CC(C(F)(F)F)(C1)C2] | N-(4-cyclobutyl-3-(3,3-difluorocyclobutyl)-1-methyl-1H-pyrazol-5-yl)-3-(trifluoromethyl)bicyclo[1.1.1]pentane-1-carboxamide | 4.1 | 404 |

TABLE 1-continued

| List of Compounds and Characterization Data | | | | |
|---|---|---|---|---|
| Cmpd # | Structure | Name | LCMS RT (min)* | m/z (M + H)+ |
| 204 | 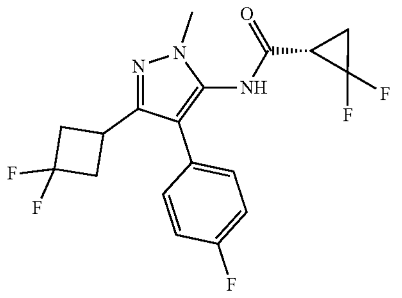 [SMILES: Cn1nc(C2CC(F)(F)C2)c(-c2ccc(F)cc2)c1NC(=O)[C@@H]1CC1(F)F] | (S)-N-(3-(3,3-difluorocyclobutyl)-4-(4-fluorophenyl)-1-methyl-1H-pyrazol-5-yl)-2,2-difluorocyclopropane-1-carboxamide | 3.8 | 386 |
| 205 | 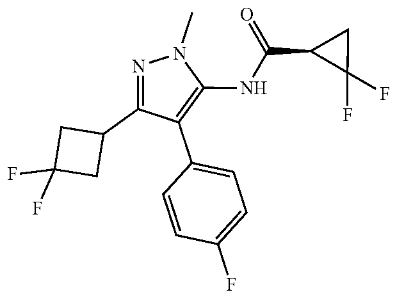 [SMILES: Cn1nc(C2CC(F)(F)C2)c(-c2ccc(F)cc2)c1NC(=O)[C@H]1CC1(F)F] | (R)-N-(3-(3,3-difluorocyclobutyl)-4-(4-fluorophenyl)-1-methyl-1H-pyrazol-5-yl)-2,2-difluorocyclopropane-1-carboxamide | 3.8 | 386 |
| 206 | 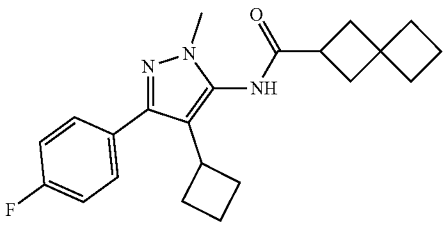 [SMILES: Cn1nc(-c2ccc(F)cc2)c(C2CCC2)c1NC(=O)C1CC2(CCC2)C1] | N-(4-cyclobutyl-3-(4-fluorophenyl)-1-methyl-1H-pyrazol-5-yl)spiro[3.3]heptane-2-carboxamide | 4.4 | 368 |
| 207 | 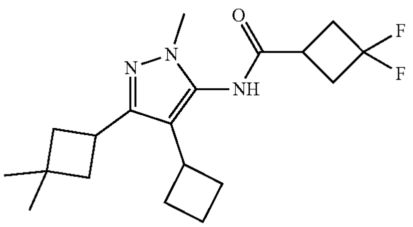 [SMILES: Cn1nc(C2CC(C)(C)C2)c(C2CCC2)c1NC(=O)C1CC(F)(F)C1] | N-(4-cyclobutyl-3-(3,3-dimethylcyclobutyl)-1-methyl-1H-pyrazol-5-yl)-3,3-difluorocyclobutane-1-carboxamide | 4.3 | 352 |
| 208 | 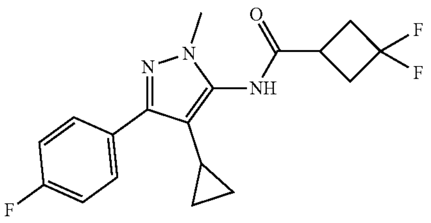 [SMILES: Cn1nc(-c2ccc(F)cc2)c(C2CC2)c1NC(=O)C1CC(F)(F)C1] | N-(4-cyclopropyl-3-(4-fluorophenyl)-1-methyl-1H-pyrazol-5-yl)-3,3-difluorocyclobutane-1-carboxamide | 3.8 | 350 |

TABLE 1-continued

List of Compounds and Characterization Data

| Cmpd # | Structure | Name | LCMS RT (min)* | m/z (M + H)+ |
| --- | --- | --- | --- | --- |
| 209 | 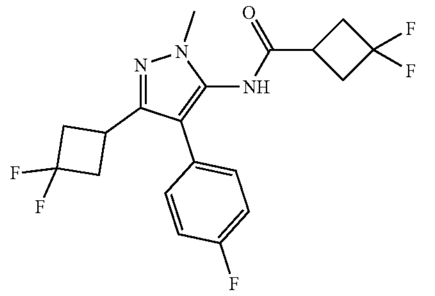 [SMILES: Cn1nc(C2CC(F)(F)C2)c(-c2ccc(F)cc2)c1NC(=O)C1CC(F)(F)C1] | N-(3-(3,3-difluorocyclobutyl)-4-(4-fluorophenyl)-1-methyl-1H-pyrazol-5-yl)-3,3-difluorocyclobutane-1-carboxamide | 3.9 | 400 |
| 210 | 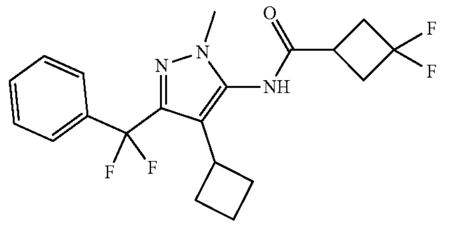 [SMILES: Cn1nc(C(F)(F)c2ccccc2)c(C2CCC2)c1NC(=O)C1CC(F)(F)C1] | N-(4-cyclobutyl-3-(difluoro(phenyl)methyl)-1-methyl-1H-pyrazol-5-yl)-3,3-difluorocyclobutane-1-carboxamide | 4.2 | 396 |
| 211 | 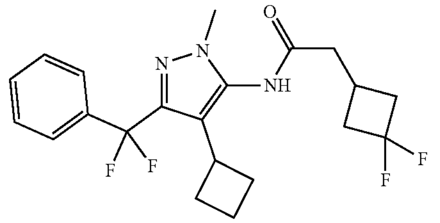 [SMILES: Cn1nc(C(F)(F)c2ccccc2)c(C2CCC2)c1NC(=O)CC1CC(F)(F)C1] | N-(4-cyclobutyl-3-(difluoro(phenyl)methyl)-1-methyl-1H-pyrazol-5-yl)-2-(3,3-difluorocyclobutyl)acetamide | 4.2 | 410 |
| 212 | 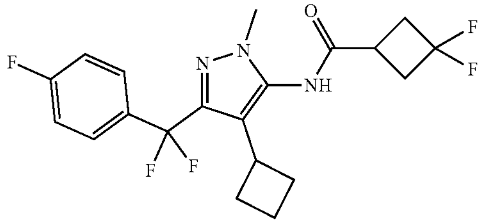 [SMILES: Cn1nc(C(F)(F)c2ccc(F)cc2)c(C2CCC2)c1NC(=O)C1CC(F)(F)C1] | N-(4-cyclobutyl-3-(difluoro(4-fluorophenyl)methyl)-1-methyl-1H-pyrazol-5-yl)-3,3-difluorocyclobutane-1-carboxamide | 4.2 | 414 |
| 213 | 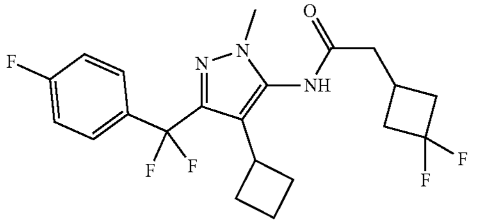 [SMILES: Cn1nc(C(F)(F)c2ccc(F)cc2)c(C2CCC2)c1NC(=O)CC1CC(F)(F)C1] | N-(4-cyclobutyl-3-(difluoro(4-fluorophenyl)methyl)-1-methyl-1H-pyrazol-5-yl)-2-(3,3-difluorocyclobutyl)acetamide | 4.2 | 428 |
| 214 | 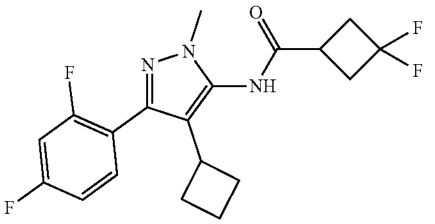 [SMILES: Cn1nc(-c2ccc(F)cc2F)c(C2CCC2)c1NC(=O)C1CC(F)(F)C1] | N-(4-cyclobutyl-3-(2,4-difluorophenyl)-1-methyl-1H-pyrazol-5-yl)-3,3-difluorocyclobutane-1-carboxamide | 3.9 | 382 |

TABLE 1-continued

List of Compounds and Characterization Data

| Cmpd # | Structure | Name | LCMS RT (min)* | m/z (M + H)+ |
|---|---|---|---|---|
| 215 | 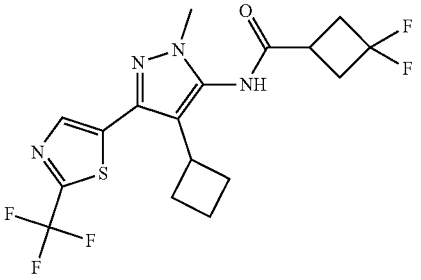 [SMILES: Cn1nc(-c2cnc(C(F)(F)F)s2)c(C2CCC2)c1NC(=O)C1CC(F)(F)C1] | N-(4-cyclobutyl-1-methyl-3-(2-(trifluoromethyl)thiazol-5-yl)-1H-pyrazol-5-yl)-3,3-difluorocyclobutane-1-carboxamide | 4.1 | 421 |
| 216 | 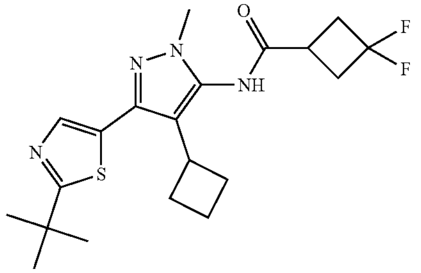 [SMILES: Cn1nc(-c2cnc(C(C)(C)C)s2)c(C2CCC2)c1NC(=O)C1CC(F)(F)C1] | N-(3-(2-(tert-butyl)thiazol-5-yl)-4-cyclobutyl-1-methyl-1H-pyrazol-5-yl)-3,3-difluorocyclobutane-1-carboxamide | 4.3 | 409 |
| 217 | 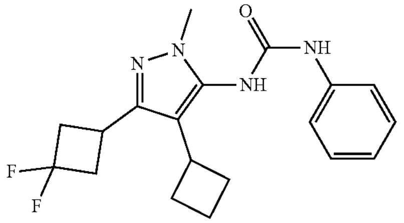 [SMILES: Cn1nc(C2CC(F)(F)C2)c(C2CCC2)c1NC(=O)Nc1ccccc1] | 1-(4-cyclobutyl-3-(3,3-difluorocyclobutyl)-1-methyl-1H-pyrazol-5-yl)-3-phenylurea | 3.9 | 361 |
| 218 | 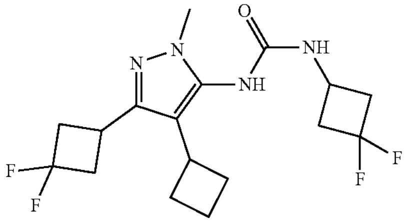 [SMILES: Cn1nc(C2CC(F)(F)C2)c(C2CCC2)c1NC(=O)NC1CC(F)(F)C1] | 1-(4-cyclobutyl-3-(3,3-difluorocyclobutyl)-1-methyl-1H-pyrazol-5-yl)-3-(3,3-difluorocyclobutyl)urea | 3.6 | 375 |
| 219 | 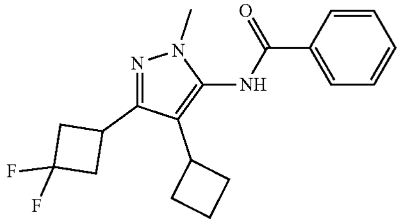 [SMILES: Cn1nc(C2CC(F)(F)C2)c(C2CCC2)c1NC(=O)c1ccccc1] | N-(4-cyclobutyl-3-(3,3-difluorocyclobutyl)-1-methyl-1H-pyrazol-5-yl)benzamide | 3.9 | 346 |
| 220 | 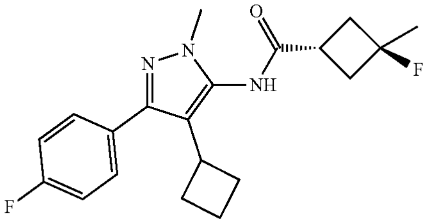 [SMILES: Cn1nc(-c2ccc(F)cc2)c(C2CCC2)c1NC(=O)[C@H]1C[C@](C)(F)C1] | trans-N-(4-cyclobutyl-3-(4-fluorophenyl)-1-methyl-1H-pyrazol-5-yl)-3-fluoro-3-methylcyclobutane-1-carboxamide | 4 | 360 |

TABLE 1-continued

List of Compounds and Characterization Data

| Cmpd # | Structure | Name | LCMS RT (min)* | m/z (M + H)+ |
|---|---|---|---|---|
| 221 | 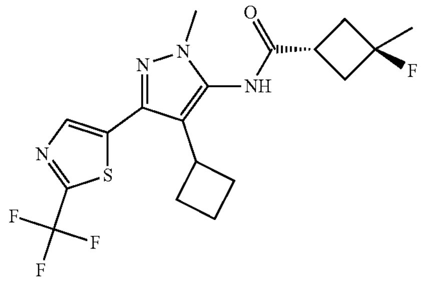 [SMILES: Cn1nc(-c2cnc(C(F)(F)F)s2)c(C2CCC2)c1NC(=O)[C@H]1C[C@](C)(F)C1] | trans-N-(4-cyclobutyl-1-methyl-3-(2-(trifluoromethyl)thiazol-5-yl)-1H-pyrazol-5-yl)-3-fluoro-3-methylcyclobutane-1-carboxamide | 4.2 | 417 |
| 222 | 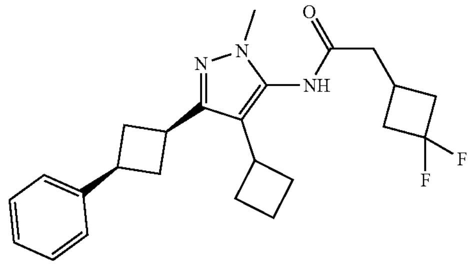 [SMILES: Cn1nc([C@H]2C[C@@H](c3ccccc3)C2)c(C2CCC2)c1NC(=O)CC1CC(F)(F)C1] | N-(4-cyclobutyl-1-methyl-3-(cis)-(3-phenylcyclobutyl)-1H-pyrazol-5-yl)-2-(3,3-difluorocyclobutyl)acetamide | 4.4 | 414 |
| 223 | 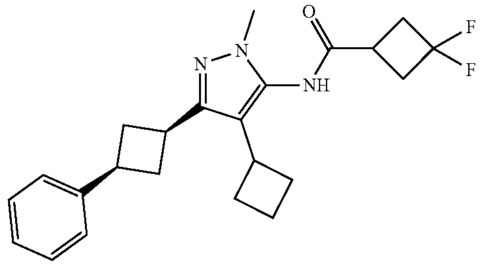 [SMILES: Cn1nc([C@H]2C[C@@H](c3ccccc3)C2)c(C2CCC2)c1NC(=O)C1CC(F)(F)C1] | N-(4-cyclobutyl-1-methyl-3-(cis)-(3-phenylcyclobutyl)-1H-pyrazol-5-yl)-3,3-difluorocyclobutane-1-carboxamide | 4.4 | 400 |
| 224 | 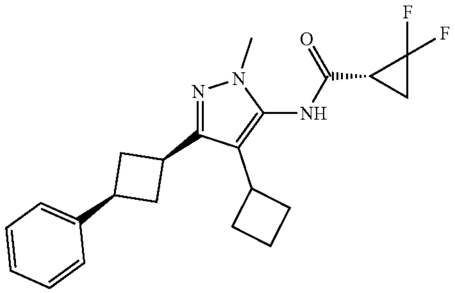 [SMILES: Cn1nc([C@H]2C[C@@H](c3ccccc3)C2)c(C2CCC2)c1NC(=O)[C@H]1CC1(F)F] | (R)-N-(4-cyclobutyl-1-methyl-3-(3-phenylcyclobutyl)-1H-pyrazol-5-yl)-2,2-difluorocyclopropane-1-carboxamide | 4.4 | 386 |
| 225 | 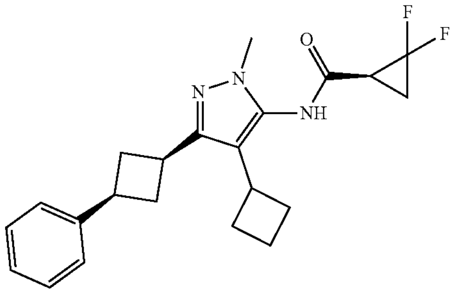 [SMILES: Cn1nc([C@H]2C[C@@H](c3ccccc3)C2)c(C2CCC2)c1NC(=O)[C@@H]1CC1(F)F] | (S)-N-(4-cyclobutyl-1-methyl-3-(3-phenylcyclobutyl)-1H-pyrazol-5-yl)-2,2-difluorocyclopropane-1-carboxamide | 4.4 | 386 |

TABLE 1-continued

| List of Compounds and Characterization Data | | | | |
|---|---|---|---|---|
| Cmpd # | Structure | Name | LCMS RT (min)* | m/z (M + H)+ |
| 226 | 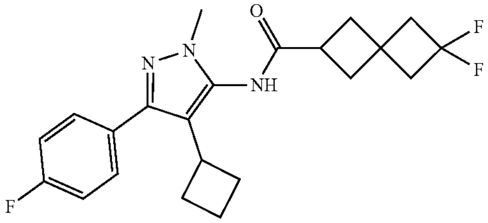 [SMILES: Cn1nc(-c2ccc(F)cc2)c(C2CCC2)c1NC(=O)C1CC2(C1)CC(F)(F)C2] | N-(4-cyclobutyl-3-(4-fluorophenyl)-1-methyl-1H-pyrazol-5-yl)-6,6-difluorospiro[3.3]heptane-2-carboxamide | 4.1 | 404 |
| 227 | 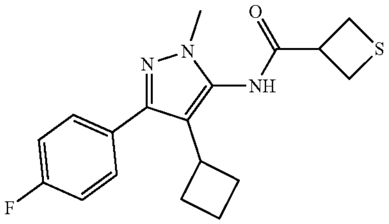 [SMILES: Cn1nc(-c2ccc(F)cc2)c(C2CCC2)c1NC(=O)C1CSC1] | N-(4-cyclobutyl-3-(4-fluorophenyl)-1-methyl-1H-pyrazol-5-yl)thietane-3-carboxamide | 3.8 | 346 |
| 228 | 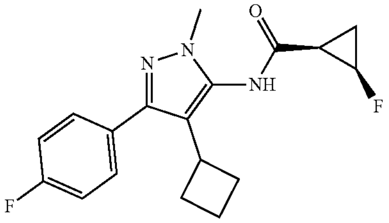 [SMILES: Cn1nc(-c2ccc(F)cc2)c(C2CCC2)c1NC(=O)[C@H]1C[C@H]1F] | (1R,2R)-N-(4-cyclobutyl-3-(4-fluorophenyl)-1-methyl-1H-pyrazol-5-yl)-2-fluorocyclopropane-1-carboxamide | 3.6 | 332 |
| 229 | 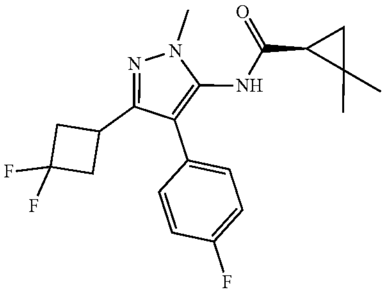 [SMILES: Cn1nc(C2CC(F)(F)C2)c(-c2ccc(F)cc2)c1NC(=O)[C@H]1CC1(C)C] | (S)-N-(3-(3,3-difluorocyclobutyl)-4-(4-fluorophenyl)-1-methyl-1H-pyrazol-5-yl)-2,2-dimethylcyclopropane-1-carboxamide | 4 | 378 |
| 230 | 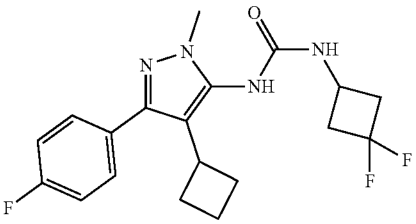 [SMILES: Cn1nc(-c2ccc(F)cc2)c(C2CCC2)c1NC(=O)NC1CC(F)(F)C1] | 1-(4-cyclobutyl-3-(4-fluorophenyl)-1-methyl-1H-pyrazol-5-yl)-3-(3,3-difluorocyclobutyl)urea | 3.7 | 379 |
| 231 | 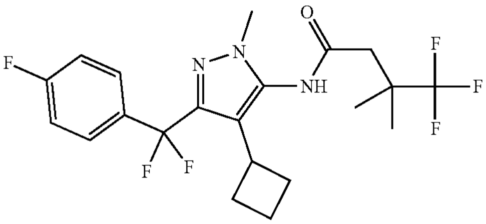 [SMILES: Cn1nc(C(F)(F)c2ccc(F)cc2)c(C2CCC2)c1NC(=O)CC(C)(C)C(F)(F)F] | N-(4-cyclobutyl-3-(difluoro(4-fluorophenyl)methyl)-1-methyl-1H-pyrazol-5-yl)-4,4,4-trifluoro-3,3-dimethylbutanamide | 4.6 | 448 |

TABLE 1-continued

| List of Compounds and Characterization Data | | | | |
|---|---|---|---|---|
| Cmpd # | Structure | Name | LCMS RT (min)* | m/z (M + H)+ |
| 232 | 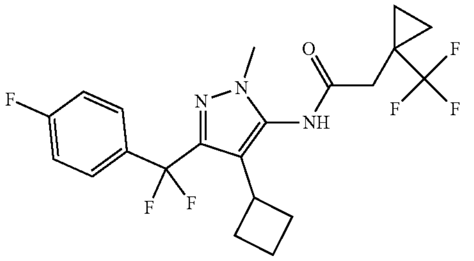 [SMILES: Cn1nc(C(F)(F)c2ccc(F)cc2)c(C2CCC2)c1NC(=O)CC1(C(F)(F)F)CC1] | N-(4-cyclobutyl-3-(difluoro(4-fluorophenyl)methyl)-1-methyl-1H-pyrazol-5-yl)-2-(1-(trifluoromethyl)cyclo-propyl)acetamide | 4.3 | 446 |
| 233 | 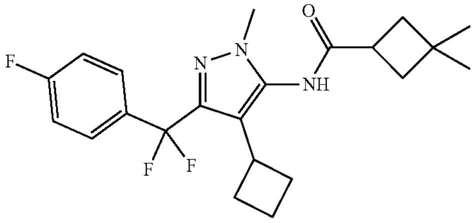 [SMILES: Cn1nc(C(F)(F)c2ccc(F)cc2)c(C2CCC2)c1NC(=O)C1CC(C)(C)C1] | N-(4-cyclobutyl-3-(difluoro(4-fluorophenyl)methyl)-1-methyl-1H-pyrazol-5-yl)-3,3-dimethylcyclobutane-1-carboxamide | 4.6 | 406 |
| 234 | 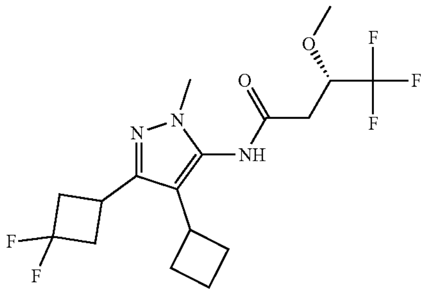 [SMILES: CO[C@@H](CC(=O)Nc1c(C2CCC2)c(C2CC(F)(F)C2)nn1C)C(F)(F)F] | (S)-N-(4-cyclobutyl-3-(3,3-difluorocyclobutyl)-1-methyl-1H-pyrazol-5-yl)-4,4,4-trifluoro-3-methoxybutanamide | 3.9 | 396 |
| 235 | 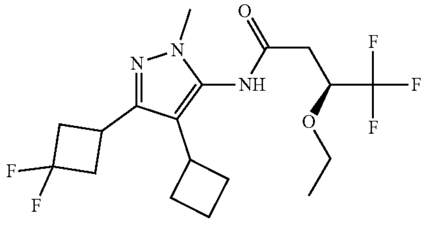 [SMILES: CCO[C@@H](CC(=O)Nc1c(C2CCC2)c(C2CC(F)(F)C2)nn1C)C(F)(F)F] | (S)-N-(4-cyclobutyl-3-(3,3-difluorocyclobutyl)-1-methyl-1H-pyrazol-5-yl)-3-ethoxy-4,4,4-trifluorobutanamide | 4.1 | 410 |
| 236 | 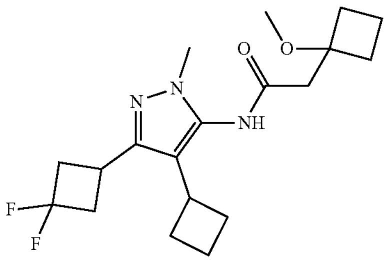 [SMILES: COC1(CC(=O)Nc2c(C3CCC3)c(C3CC(F)(F)C3)nn2C)CCC1] | N-(4-cyclobutyl-3-(3,3-difluorocyclobutyl)-1-methyl-1H-pyrazol-5-yl)-2-(1-methoxycyclobutyl)acetamide | 3.9 | 368 |
| 237 | 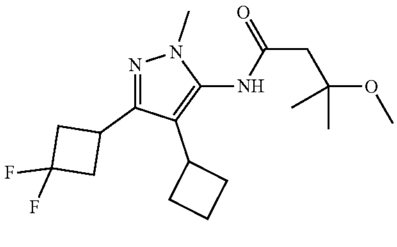 [SMILES: COC(C)(C)CC(=O)Nc1c(C2CCC2)c(C2CC(F)(F)C2)nn1C] | N-(4-cyclobutyl-3-(3,3-difluorocyclobutyl)-1-methyl-1H-pyrazol-5-yl)-3-methoxy-3-methylbutanamide | 3.8 | 356 |

TABLE 1-continued

List of Compounds and Characterization Data

| Cmpd # | Structure | Name | LCMS RT (min)* | m/z $(M + H)^+$ |
|---|---|---|---|---|
| 238 | 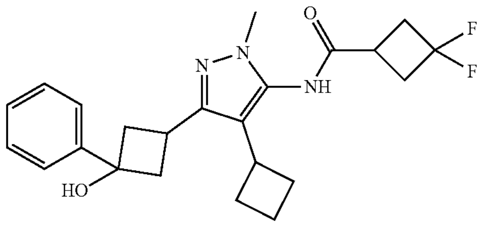 [SMILES: Cn1nc(C2CC(O)(c3ccccc3)C2)c(C2CCC2)c1NC(=O)C1CC(F)(F)C1] | N-(4-cyclobutyl-3-(3-hydroxy-3-phenylcyclobutyl)-1-methyl-1H-pyrazol-5-yl)-3,3-difluorocyclobutane-1-carboxamide | 3.7 | 416 |
| 239 | 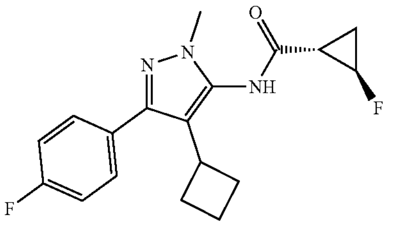 [SMILES: Cn1nc(-c2ccc(F)cc2)c(C2CCC2)c1NC(=O)[C@@H]1C[C@H]1F] | (1S,2R)-N-(4-cyclobutyl-3-(4-fluorophenyl)-1-methyl-1H-pyrazol-5-yl)-2-fluorocyclopropane-1-carboxamide | 3.8 | 332 |
| 240 | 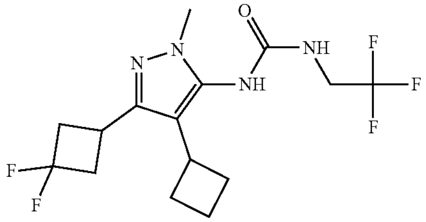 [SMILES: Cn1nc(C2CC(F)(F)C2)c(C2CCC2)c1NC(=O)NCC(F)(F)F] | 1-(4-cyclobutyl-3-(3,3-difluorocyclobutyl)-1-methyl-1H-pyrazol-5-yl)-3-(2,2,2-trifluoroethyl)urea | 3.6 | 367 |
| 241 | 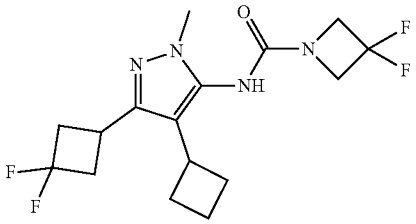 [SMILES: Cn1nc(C2CC(F)(F)C2)c(C2CCC2)c1NC(=O)N1CC(F)(F)C1] | N-(4-cyclobutyl-3-(3,3-difluorocyclobutyl)-1-methyl-1H-pyrazol-5-yl)-3,3-difluoroazetidine-1-carboxamide | 3.6 | 361 |
| 242 | 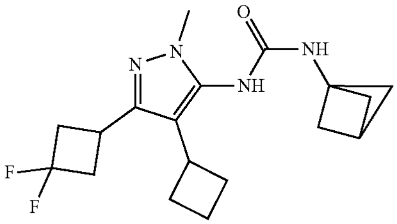 [SMILES: Cn1nc(C2CC(F)(F)C2)c(C2CCC2)c1NC(=O)NC12CC(C1)C2] | 1-(bicyclo[1.1.1]pentan-1-yl)-3-(4-cyclobutyl-3-(3,3-difluorocyclobutyl)-1-methyl-1H-pyrazol-5-yl)urea | 3.7 | 351 |
| 243 | 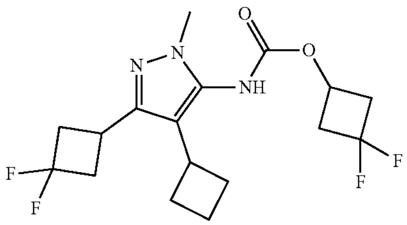 [SMILES: Cn1nc(C2CC(F)(F)C2)c(C2CCC2)c1NC(=O)OC1CC(F)(F)C1] | 3,3-difluorocyclobutyl (4-cyclobutyl-3-(3,3-difluorocyclobutyl)-1-methyl-1H-pyrazol-5-yl)carbamate | 4 | 376 |

TABLE 1-continued

List of Compounds and Characterization Data

| Cmpd # | Structure | Name | LCMS RT (min)* | m/z (M + H)+ |
|---|---|---|---|---|
| 244 | 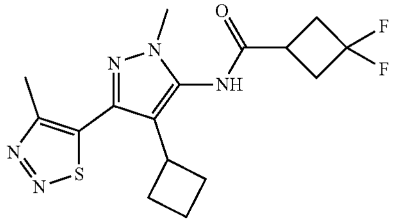 [SMILES: Cc1nnsc1-c1nn(C)c(NC(=O)C2CC(F)(F)C2)c1C1CCC1] | N-(4-cyclobutyl-1-methyl-3-(4-methyl-1,2,3-thiadiazol-5-yl)-1H-pyrazol-5-yl)-3,3-difluorocyclobutane-1-carboxamide | 3.6 | 368 |
| 245 | 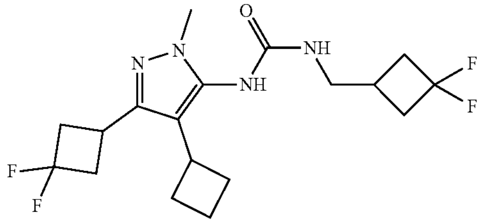 [SMILES: Cn1nc(C2CC(F)(F)C2)c(C2CCC2)c1NC(=O)NCC1CC(F)(F)C1] | 1-(4-cyclobutyl-3-(3,3-difluorocyclobutyl)-1-methyl-1H-pyrazol-5-yl)-3-((3,3-difluorocyclobutyl)methyl)urea | 3.7 | 389 |
| 246 | 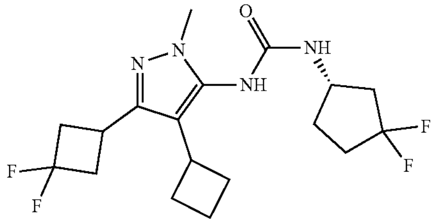 [SMILES: Cn1nc(C2CC(F)(F)C2)c(C2CCC2)c1NC(=O)N[C@H]1CCC(F)(F)C1] | (S)-1-(4-cyclobutyl-3-(3,3-difluorocyclobutyl)-1-methyl-1H-pyrazol-5-yl)-3-(3,3-difluorocyclopentyl)urea | 3.7 | 389 |
| 247 | 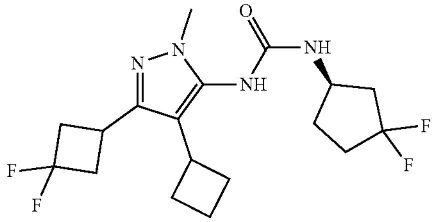 [SMILES: Cn1nc(C2CC(F)(F)C2)c(C2CCC2)c1NC(=O)N[C@@H]1CCC(F)(F)C1] | (R)-1-(4-cyclobutyl-3-(3,3-difluorocyclobutyl)-1-methyl-1H-pyrazol-5-yl)-3-(3,3-difluorocyclopentyl)urea | 3.7 | 389 |
| 248 | 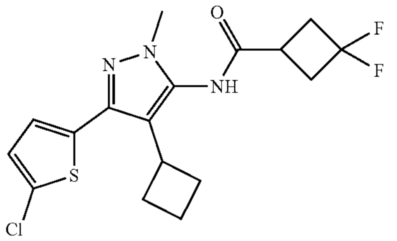 [SMILES: Cn1nc(-c2ccc(Cl)s2)c(C2CCC2)c1NC(=O)C1CC(F)(F)C1] | N-(3-(5-chlorothiophen-2-yl)-4-cyclobutyl-1-methyl-1H-pyrazol-5-yl)-3,3-difluorocyclobutane-1-carboxamide | 4.2 | 386 |
| 249 | 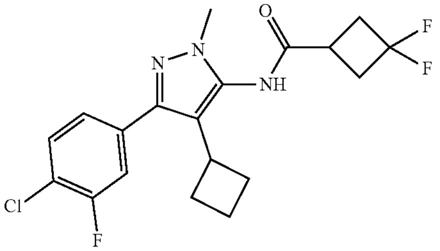 [SMILES: Cn1nc(-c2ccc(Cl)c(F)c2)c(C2CCC2)c1NC(=O)C1CC(F)(F)C1] | N-(3-(4-chloro-3-fluorophenyl)-4-cyclobutyl-1-methyl-1H-pyrazol-5-yl)-3,3-difluorocyclobutane-1-carboxamide | 4.2 | 412 |

TABLE 1-continued

| List of Compounds and Characterization Data | | | | |
|---|---|---|---|---|
| Cmpd # | Structure | Name | LCMS RT (min)* | m/z (M + H)$^+$ |
| 250 | 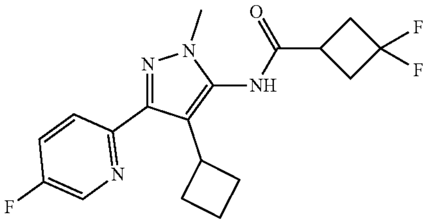 [SMILES: Cn1nc(-c2ccc(F)cn2)c(C2CCC2)c1NC(=O)C1CC(F)(F)C1] | N-(4-cyclobutyl-3-(5-fluoropyridin-2-yl)-1-methyl-1H-pyrazol-5-yl)-3,3-difluorocyclobutane-1-carboxamide | 3.7 | 379 |
| 251 | 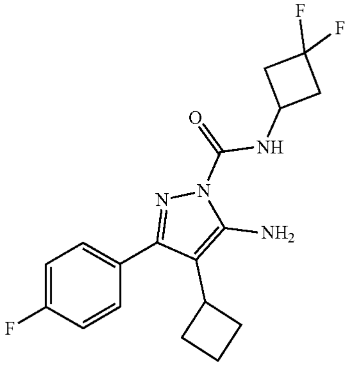 [SMILES: Nc1c(C2CCC2)c(-c2ccc(F)cc2)nn1C(=O)NC1CC(F)(F)C1] | 5-amino-4-cyclobutyl-N-(3,3-difluorocyclobutyl)-3-(4-fluorophenyl)-1H-pyrazole-1-carboxamide | 4.5 | 365 |
| 252 | 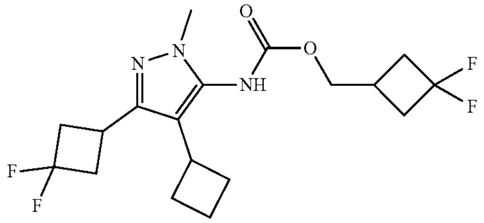 [SMILES: Cn1nc(C2CC(F)(F)C2)c(C2CCC2)c1NC(=O)OCC1CC(F)(F)C1] | (3,3-difluorocyclobutyl)methyl (4-cyclobutyl-3-(3,3-difluorocyclobutyl)-1-methyl-1H-pyrazol-5-yl)carbamate | 4 | 390 |
| 253 | 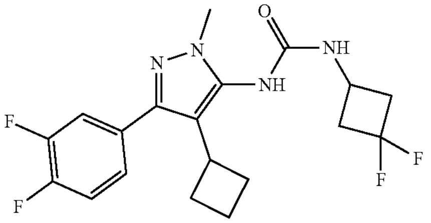 [SMILES: Cn1nc(-c2ccc(F)c(F)c2)c(C2CCC2)c1NC(=O)NC1CC(F)(F)C1] | 1-(4-cyclobutyl-3-(3,4-difluorophenyl)-1-methyl-1H-pyrazol-5-yl)-3-(3,3-difluorocyclobutyl)urea | 3.8 | 397 |
| 254 | 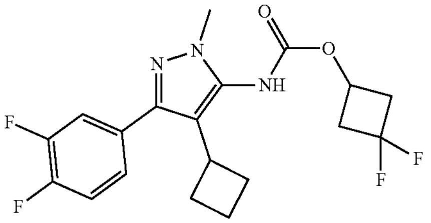 [SMILES: Cn1nc(-c2ccc(F)c(F)c2)c(C2CCC2)c1NC(=O)OC1CC(F)(F)C1] | 3,3-difluorocyclobutyl (4-cyclobutyl-3-(3,4-difluorophenyl)-1-methyl-1H-pyrazol-5-yl)carbamate | 4.1 | 398 |
| 255 | 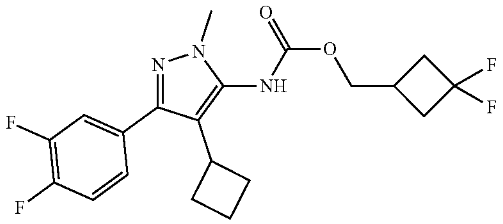 [SMILES: Cn1nc(-c2ccc(F)c(F)c2)c(C2CCC2)c1NC(=O)OCC1CC(F)(F)C1] | (3,3-difluorocyclobutyl)methyl (4-cyclobutyl-3-(3,4-difluorophenyl)-1-methyl-1H-pyrazol-5-yl)carbamate | 4.2 | 412 |

TABLE 1-continued

List of Compounds and Characterization Data

| Cmpd # | Structure | Name | LCMS RT (min)* | m/z (M + H)+ |
|---|---|---|---|---|
| 256 | 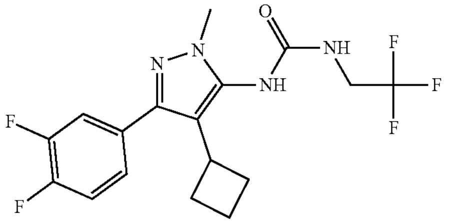 [SMILES: Cn1nc(-c2ccc(F)c(F)c2)c(C2CCC2)c1NC(=O)NCC(F)(F)F] | 1-(4-cyclobutyl-3-(3,4-difluorophenyl)-1-methyl-1H-pyrazol-5-yl)-3-(2,2,2-trifluoroethyl)urea | 3.8 | 389 |
| 257 | 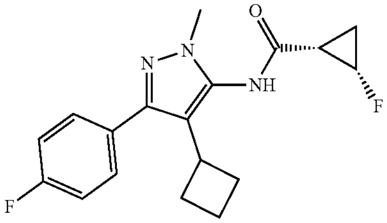 [SMILES: Cn1nc(-c2ccc(F)cc2)c(C2CCC2)c1NC(=O)[C@@H]1C[C@@H]1F] | (1S,2S)-N-(4-cyclobutyl-3-(4-fluorophenyl)-1-methyl-1H-pyrazol-5-yl)-2-fluorocyclopropane-1-carboxamide | 3.6 | 332 |
| 258 | 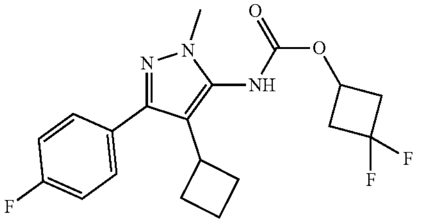 | 3,3-difluorocyclobutyl (4-cyclobutyl-3-(4-fluorophenyl)-1-methyl-1H-pyrazol-5-yl)carbamate | 4 | 378 |
| 259 | 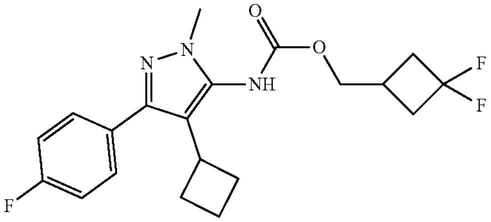 [SMILES: Cn1nc(-c2ccc(F)cc2)c(C2CCC2)c1NC(=O)OCC1CC(F)(F)C1] | (3,3-difluorocyclobutyl)methyl (4-cyclobutyl-3-(4-fluorophenyl)-1-methyl-1H-pyrazol-5-yl)carbamate | 4.1 | 394 |
| 260 | 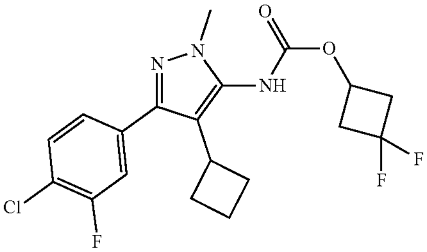 [SMILES: Cn1nc(-c2ccc(Cl)c(F)c2)c(C2CCC2)c1NC(=O)OC1CC(F)(F)C1] | 3,3-difluorocyclobutyl (3-(4-chloro-3-fluorophenyl)-4-cyclobutyl-1-methyl-1H-pyrazol-5-yl)carbamate | 4.4 | 414 |
| 261 | 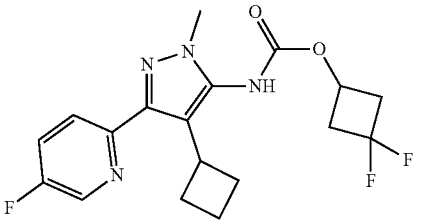 [SMILES: Cn1nc(-c2ccc(F)cn2)c(C2CCC2)c1NC(=O)OC1CC(F)(F)C1] | 3,3-difluorocyclobutyl (4-cyclobutyl-3-(5-fluoropyridin-2-yl)-1-methyl-1H-pyrazol-5-yl)carbamate | 3.9 | 381 |

TABLE 1-continued

| List of Compounds and Characterization Data | | | | |
|---|---|---|---|---|
| Cmpd # | Structure | Name | LCMS RT (min)* | m/z $(M + H)^+$ |
| 262 | 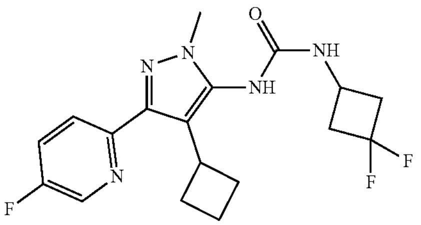 [SMILES: Cn1nc(-c2ccc(F)cn2)c(C2CCC2)c1NC(=O)NC1CC(F)(F)C1] | 1-(4-cyclobutyl-3-(5-fluoropyridin-2-yl)-1-methyl-1H-pyrazol-5-yl)-3-(3,3-difluorocyclobutyl)urea | 3.4 | 380 |
| 263 | 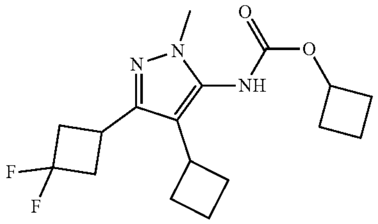 [SMILES: Cn1nc(C2CC(F)(F)C2)c(C2CCC2)c1NC(=O)OC1CCC1] | cyclobutyl (4-cyclobutyl-3-(3,3-difluorocyclobutyl)-1-methyl-1H-pyrazol-5-yl)carbamate | 4.1 | 340 |
| 264 | 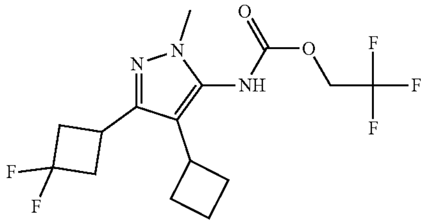 | 2,2,2-trifluoroethyl (4-cyclobutyl-3-(3,3-difluorocyclobutyl)-1-methyl-1H-pyrazol-5-yl)carbamate | 4 | 368 |
| 265 | 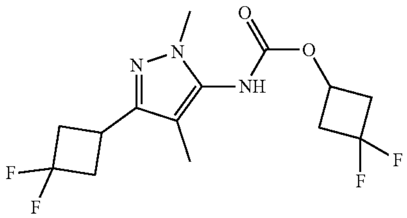 [SMILES: Cc1c(C2CC(F)(F)C2)nn(C)c1NC(=O)OC1CC(F)(F)C1] | 3,3-difluorocyclobutyl (3-(3,3-difluorocyclobutyl)-1,4-dimethyl-1H-pyrazol-5-yl)carbamate | 3.7 | 336 |
| 266 | 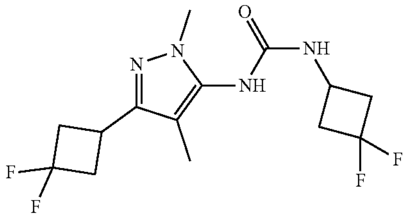 [SMILES: Cc1c(C2CC(F)(F)C2)nn(C)c1NC(=O)NC1CC(F)(F)C1] | 1-(3,3-difluorocyclobutyl)-3-(3-(3,3-difluorocyclobutyl)-1,4-dimethyl-1H-pyrazol-5-yl)urea | 3.3 | 335 |
| 267 | 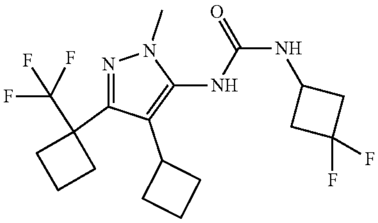 [SMILES: Cn1nc(C2(C(F)(F)F)CCC2)c(C2CCC2)c1NC(=O)NC1CC(F)(F)C1] | 1-(4-cyclobutyl-1-methyl-3-(1-(trifluoromethyl)cyclobutyl)-1H-pyrazol-5-yl)-3-(3,3-difluorocyclobutyl)urea | 3.9 | 407 |

TABLE 1-continued

List of Compounds and Characterization Data

| Cmpd # | Structure | Name | LCMS RT (min)* | m/z (M + H)+ |
|---|---|---|---|---|
| 268 | 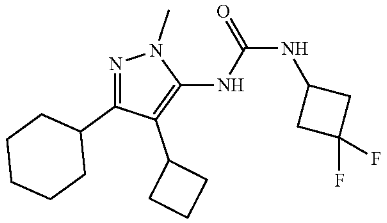 | 1-(4-cyclobutyl-3-cyclohexyl-1-methyl-1H-pyrazol-5-yl)-3-(3,3-difluorocyclobutyl)urea | 3.9 | 367 |
| 269 | 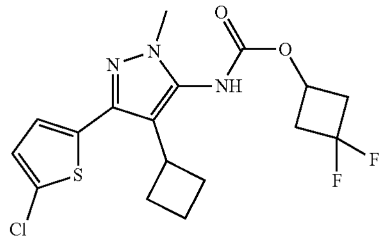 | 3,3-difluorocyclobutyl (3-(5-chlorothiophen-2-yl)-4-cyclobutyl-1-methyl-1H-pyrazol-5-yl)carbamate | 4.4 | 402 |
| 270 | 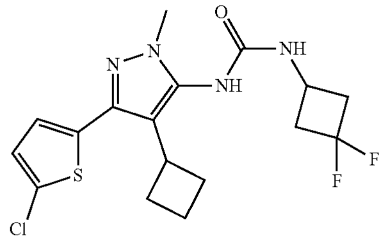 [SMILES: Cn1nc(-c2ccc(Cl)s2)c(C2CCC2)c1NC(=O)NC1CC(F)(F)C1] | 1-(3-(5-chlorothiophen-2-yl)-4-cyclobutyl-1-methyl-1H-pyrazol-5-yl)-3-(3,3-difluorocyclobutyl)urea | 4.0 | 401 |
| 271 | 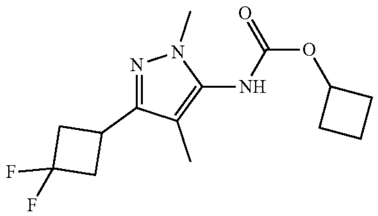 [SMILES: Cc1c(C2CC(F)(F)C2)nn(C)c1NC(=O)OC1CCC1] | cyclobutyl (3-(3,3-difluorocyclobutyl)-1,4-dimethyl-1H-pyrazol-5-yl)carbamate | 3.7 | 300 |
| 272 | 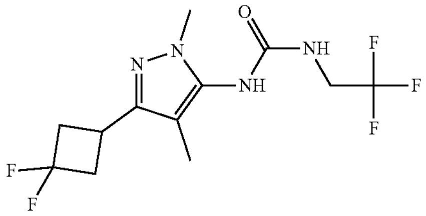 | 1-(3-(3,3-difluorocyclobutyl)-1,4-dimethyl-1H-pyrazol-5-yl)-3-(2,2,2-trifluoroethyl)urea | 3.3 | 327 |
| 273 | 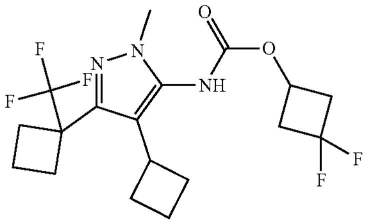 [SMILES: Cn1nc(C2(C(F)(F)F)CCC2)c(C2CCC2)c1NC(=O)OC1CC(F)(F)C1] | 3,3-difluorocyclobutyl (4-cyclobutyl-1-methyl-3-(1-(trifluoromethyl)cyclobutyl)-1H-pyrazol-5-yl)carbamate | 4.3 | 408 |

TABLE 1-continued

List of Compounds and Characterization Data

| Cmpd # | Structure | Name | LCMS RT (min)* | m/z (M + H)$^+$ |
|---|---|---|---|---|
| 274 | 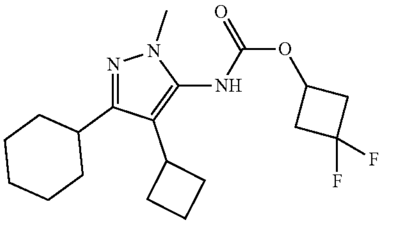 [SMILES: Cn1nc(C2CCCCC2)c(C2CCC2)c1NC(=O)OC1CC(F)(F)C1] | 3,3-difluorocyclobutyl (4-cyclobutyl-3-cyclohexyl-1-methyl-1H-pyrazol-5-yl)carbamate | 4.4 | 368 |
| 275 | 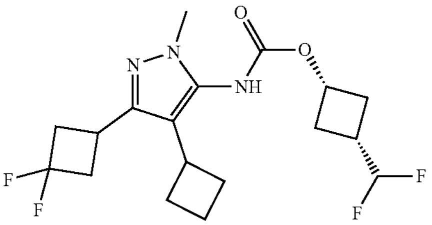 [SMILES: Cn1nc(C2CC(F)(F)C2)c(C2CCC2)c1NC(=O)O[C@H]1C[C@@H](C(F)F)C1] | (1s,3s)-3-(difluoromethyl)cyclobutyl (4-cyclobutyl-3-(3,3-difluorocyclobutyl)-1-methyl-1H-pyrazol-5-yl)carbamate | 4.0 | 390 |
| 276 | 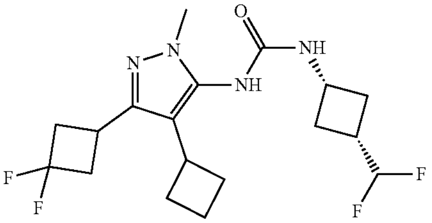 [SMILES: Cn1nc(C2CC(F)(F)C2)c(C2CCC2)c1NC(=O)N[C@H]1C[C@@H](C(F)F)C1] | 1-(4-cyclobutyl-3-(3,3-difluorocyclobutyl)-1-methyl-1H-pyrazol-5-yl)-3-((1s,3s)-3-(difluoromethyl)cyclobutyl)urea | 3.6 | 389 |
| 277 | 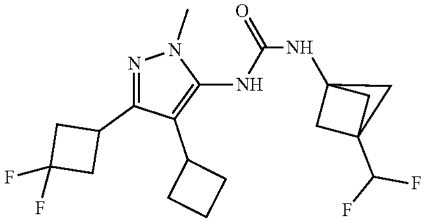 [SMILES: Cn1nc(C2CC(F)(F)C2)c(C2CCC2)c1NC(=O)NC12CC(C(F)F)(C1)C2] | 1-(4-cyclobutyl-3-(3,3-difluorocyclobutyl)-1-methyl-1H-pyrazol-5-yl)-3-(3-(difluoromethyl)bi-cyclo[1.1.1]pentan-1-yl)urea | 3.8 | 401 |
| 278 | 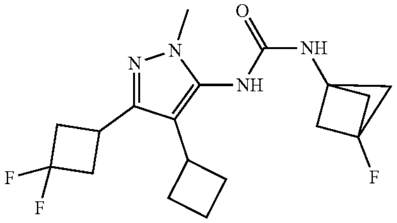 [SMILES: Cn1nc(C2CC(F)(F)C2)c(C2CCC2)c1NC(=O)NC12CC(F)(C1)C2] | 1-(4-cyclobutyl-3-(3,3-difluorocyclobutyl)-1-methyl-1H-pyrazol-5-yl)-3-(3-fluorobicyclo[1.1.1]pentan-1-yl)urea | 3.7 | 369 |
| 279 | 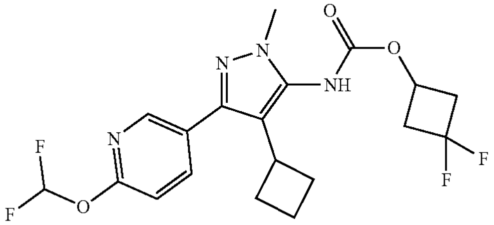 [SMILES: Cn1nc(-c2ccc(OC(F)F)nc2)c(C2CCC2)c1NC(=O)OC1CC(F)(F)C1] | 3,3-difluorocyclobutyl (4-cyclobutyl-3-(6-(difluoromethoxy)pyridin-3-yl)-1-methyl-1H-pyrazol-5-yl)carbamate | 4.0 | 429 |

TABLE 1-continued

List of Compounds and Characterization Data

| Cmpd # | Structure | Name | LCMS RT (min)* | m/z (M + H)+ |
|---|---|---|---|---|
| 280 | 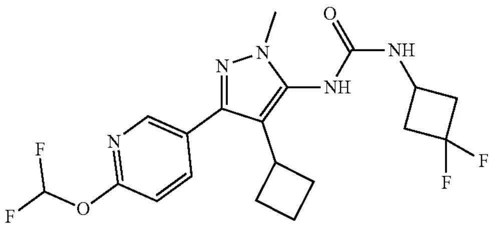 [SMILES: Cn1nc(-c2ccc(OC(F)F)nc2)c(C2CCC2)c1NC(=O)NC1CC(F)(F)C1] | 1-(4-cyclobutyl-3-(6-(difluoromethoxy)pyridin-3-yl)-1-methyl-1H-pyrazol-5-yl)-3-(3,3-difluorocyclobutyl)urea | 3.7 | 428 |
| 281 | 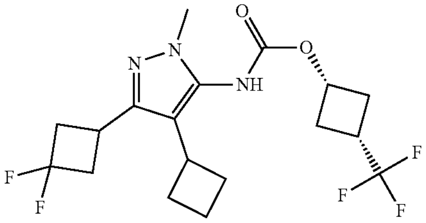 [SMILES: Cn1nc(C2CC(F)(F)C2)c(C2CCC2)c1NC(=O)O[C@H]1C[C@@H](C(F)(F)F)C1] | (1s,3s)-3-(trifluoromethyl)cyclobutyl (4-cyclobutyl-3-(3,3-difluorocyclobutyl)-1-methyl-1H-pyrazol-5-yl)carbamate | 4.2 | 408 |
| 282 | 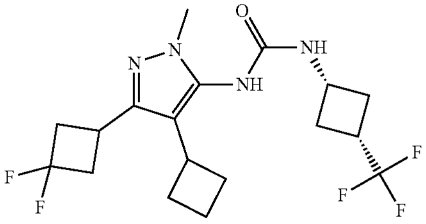 [SMILES: Cn1nc(C2CC(F)(F)C2)c(C2CCC2)c1NC(=O)N[C@H]1C[C@@H](C(F)(F)F)C1] | 1-(4-cyclobutyl-3-(3,3-difluorocyclobutyl)-1-methyl-1H-pyrazol-5-yl)-3-((1s,3s)-3-(trifluoromethyl)cyclobutyl)urea | 3.8 | 407 |
| 283 | 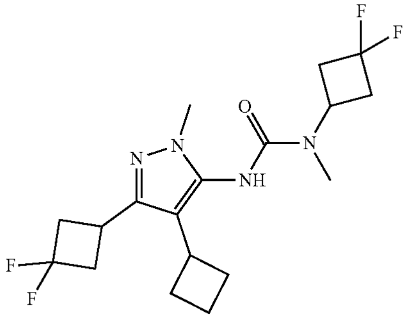 [SMILES: CN(C(=O)Nc1c(C2CCC2)c(C2CC(F)(F)C2)nn1C)C1CC(F)(F)C1] | 3-(4-cyclobutyl-3-(3,3-difluorocyclobutyl)-1-methyl-1H-pyrazol-5-yl)-1-(3,3-difluorocyclobutyl)-1-methylurea | 3.8 | 389 |
| 284 | 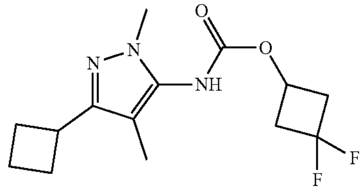 [SMILES: Cc1c(C2CCC2)nn(C)c1NC(=O)OC1CC(F)(F)C1] | 3,3-difluorocyclobutyl (3-cyclobutyl-1,4-dimethyl-1H-pyrazol-5-yl)carbamate | 3.6 | 300 |
| 285 | 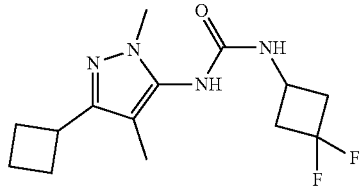 [SMILES: Cc1c(C2CCC2)nn(C)c1NC(=O)NC1CC(F)(F)C1] | 1-(3-cyclobutyl-1,4-dimethyl-1H-pyrazol-5-yl)-3-(3,3-difluorocyclobutyl)urea | 3.2 | 299 |

TABLE 1-continued

| List of Compounds and Characterization Data | | | | |
|---|---|---|---|---|
| Cmpd # | Structure | Name | LCMS RT (min)* | m/z (M + H)+ |
| 286 | 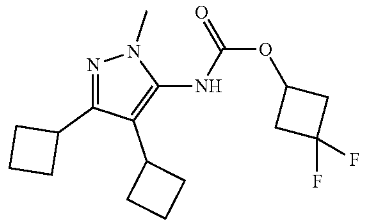 [SMILES: Cn1nc(C2CCC2)c(C2CCC2)c1NC(=O)OC1CC(F)(F)C1] | 3,3-difluorocyclobutyl (3,4-dicyclobutyl-1-methyl-1H-pyrazol-5-yl)carbamate | 4.0 | 340 |
| 287 | 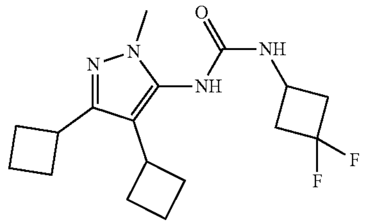 [SMILES: Cn1nc(C2CCC2)c(C2CCC2)c1NC(=O)NC1CC(F)(F)C1] | 1-(3,4-dicyclobutyl-1-methyl-1H-pyrazol-5-yl)-3-(3,3-difluorocyclobutyl)urea | 3.6 | 339 |
| 288 | 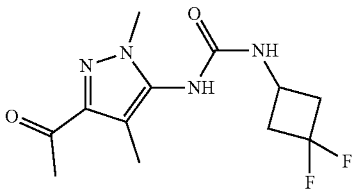 [SMILES: CC(=O)c1nn(C)c(NC(=O)NC2CC(F)(F)C2)c1C] | 1-(3-acetyl-1,4-dimethyl-1H-pyrazol-5-yl)-3-(3,3-difluorocyclobutyl)urea | 2.9 | 287 |
| 289 | 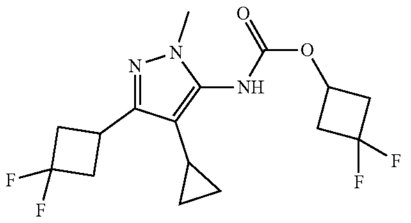 [SMILES: Cn1nc(C2CC(F)(F)C2)c(C2CC2)c1NC(=O)OC1CC(F)(F)C1] | 3,3-difluorocyclobutyl (4-cyclopropyl-3-(3,3-difluorocyclobutyl)-1-methyl-1H-pyrazol-5-yl)carbamate | 3.8 | 362 |
| 290 | 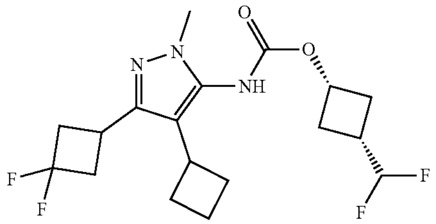 [SMILES: Cn1nc(C2CC(F)(F)C2)c(C2CCC2)c1NC(=O)O[C@H]1C[C@@H](C(F)F)C1] | (1s,3s)-3-(difluoromethyl)cyclobutyl (4-cyclopropyl-3-(3,3-difluorocyclobutyl)-1-methyl-1H-pyrazol-5-yl)carbamate | 3.8 | 376 |
| 291 | 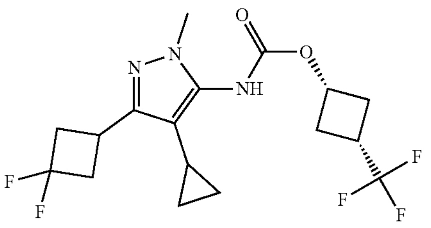 [SMILES: Cn1nc(C2CC(F)(F)C2)c(C2CC2)c1NC(=O)O[C@H]1C[C@@H](C(F)(F)F)C1] | (1s,3s)-3-(trifluoromethyl)cyclobutyl (4-cyclopropyl-3-(3,3-difluorocyclobutyl)-1-methyl-1H-pyrazol-5-yl)carbamate | 4.0 | 394 |

TABLE 1-continued

| List of Compounds and Characterization Data | | | | |
|---|---|---|---|---|
| Cmpd # | Structure | Name | LCMS RT (min)* | m/z (M + H)+ |
| 292 | 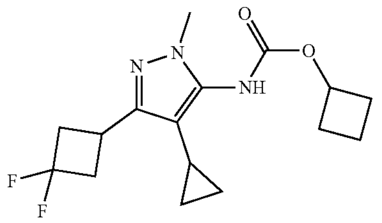 [SMILES: Cn1nc(C2CC(F)(F)C2)c(C2CC2)c1NC(=O)OC1CCC1] | cyclobutyl (4-cyclopropyl-3-(3,3-difluorocyclobutyl)-1-methyl-1H-pyrazol-5-yl)carbamate | 3.9 | 326 |
| 293 | 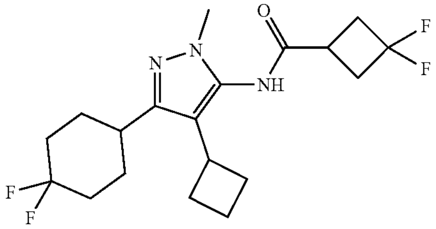 [SMILES: Cn1nc(C2CCC(F)(F)CC2)c(C2CCC2)c1NC(=O)C1CC(F)(F)C1] | N-(4-cyclobutyl-3-(4,4-difluorocyclohexyl)-1-methyl-1H-pyrazol-5-yl)-3,3-difluorocyclobutane-1-carboxamide | 3.9 | 388 |
| 294 | 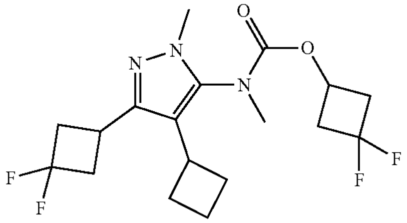 [SMILES: CN(C(=O)OC1CC(F)(F)C1)c1c(C2CCC2)c(C2CC(F)(F)C2)nn1C] | 3,3-difluorocyclobutyl (4-cyclobutyl-3-(3,3-difluorocyclobutyl)-1-methyl-1H-pyrazol-5-yl)(methyl)carbamate | 4.3 | 390 |
| 295 | 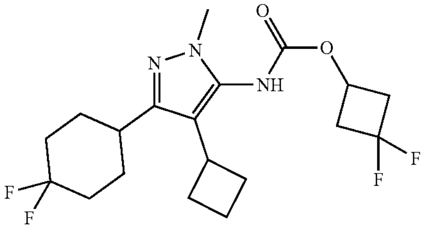 [SMILES: Cn1nc(C2CCC(F)(F)CC2)c(C2CCC2)c1NC(=O)OC1CC(F)(F)C1] | 3,3-difluorocyclobutyl (4-cyclobutyl-3-(4,4-difluorocyclohexyl)-1-methyl-1H-pyrazol-5-yl)carbamate | 4.0 | 404 |
| 296 | 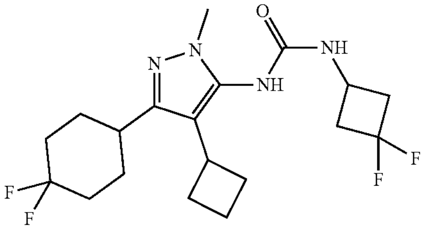 [SMILES: Cn1nc(C2CCC(F)(F)CC2)c(C2CCC2)c1NC(=O)NC1CC(F)(F)C1] | 1-(4-cyclobutyl-3-(4,4-difluorocyclohexyl)-1-methyl-1H-pyrazol-5-yl)-3-(3,3-difluorocyclobutyl)urea | 3.6 | 403 |
| 297 | 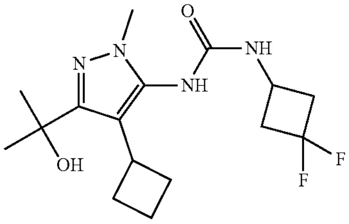 [SMILES: Cn1nc(C(C)(C)O)c(C2CCC2)c1NC(=O)NC1CC(F)(F)C1] | 1-(4-cyclobutyl-3-(2-hydroxypropan-2-yl)-1-methyl-1H-pyrazol-5-yl)-3-(3,3-difluorocyclobutyl)urea | 3.2 | 341** |

TABLE 1-continued

| Cmpd # | Structure | Name | LCMS RT (min)* | m/z (M + H)+ |
|---|---|---|---|---|
| List of Compounds and Characterization Data | | | | |
| 298 | 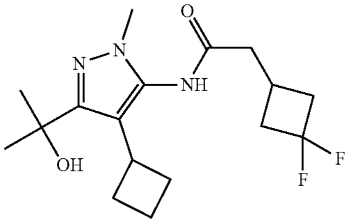 [SMILES: Cn1nc(C(C)(C)O)c(C2CCC2)c1NC(=O)CC1CC(F)(F)C1] | N-(4-cyclobutyl-3-(2-hydroxypropan-2-yl)-1-methyl-1H-pyrazol-5-yl)-2-(3,3-difluorocyclobutyl)acetamide | 3.2 | 340** |
| 299 | 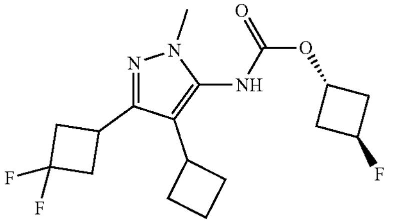 [SMILES: Cn1nc(C2CC(F)(F)C2)c(C2CCC2)c1NC(=O)O[C@H]1C[C@H](F)C1] | (1r,3r)-3-fluorocyclobutyl (4-cyclobutyl-3-(3,3-difluorocyclobutyl)-1-methyl-1H-pyrazol-5-yl)carbamate | 3.9 | 358 |
| 300 | 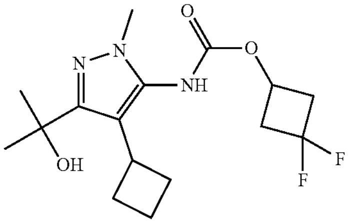 [SMILES: Cn1nc(C(C)(C)O)c(C2CCC2)c1NC(=O)OC1CC(F)(F)C1] | 3,3-difluorocyclobutyl (4-cyclobutyl-3-(2-hydroxypropan-2-yl)-1-methyl-1H-pyrazol-5-yl)carbamate | 3.3 | 344 |
| 301 | 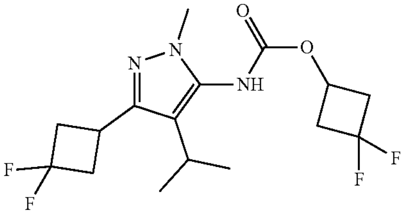 [SMILES: CC(C)c1c(C2CC(F)(F)C2)nn(C)c1NC(=O)OC1CC(F)(F)C1] | 3,3-difluorocyclobutyl (3-(3,3-difluorocyclobutyl)-4-isopropyl-1-methyl-1H-pyrazol-5-yl)carbamate | 4.0 | 364 |
| 302 | 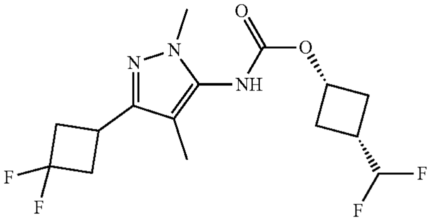 [SMILES: Cc1c(C2CC(F)(F)C2)nn(C)c1NC(=O)O[C@H]1C[C@@H](C(F)F)C1] | (1s,3s)-3-(difluoromethyl)cyclobutyl (3-(3,3-difluorocyclobutyl)-1,4-dimethyl-1H-pyrazol-5-yl)carbamate | 3.6 | 350 |
| 303 | 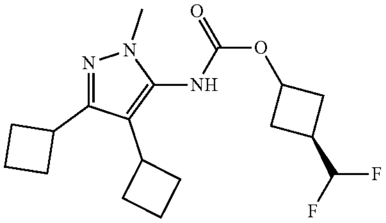 | (1s,3s)-3-(difluoromethyl)cyclobutyl (3,4-dicyclobutyl-1-methyl-1H-pyrazol-5-yl)carbamate | 4.1 | 354 |

TABLE 1-continued

List of Compounds and Characterization Data

| Cmpd # | Structure | Name | LCMS RT (min)* | m/z $(M + H)^+$ |
|---|---|---|---|---|
| 304 | 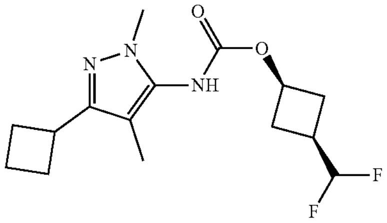 [SMILES: Cc1c(C2CCC2)nn(C)c1NC(=O)O[C@H]1C[C@@H](C(F)F)C1] | (1s,3s)-3-(difluoromethyl)cyclobutyl (3-cyclobutyl-1,4-dimethyl-1H-pyrazol-5-yl)carbamate | 3.6 | 314 |
| 305 | 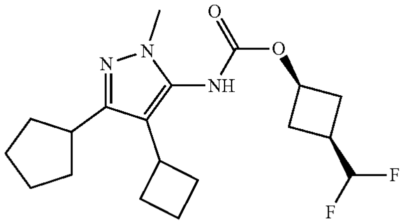 [SMILES: Cn1nc(C2CCCC2)c(C2CCC2)c1NC(=O)O[C@H]1C[C@@H](C(F)F)C1] | (1s,3s)-3-(difluoromethyl)cyclobutyl (4-cyclobutyl-3-cyclopentyl-1-methyl-1H-pyrazol-5-yl)carbamate | 4.2 | 368 |
| 306 | 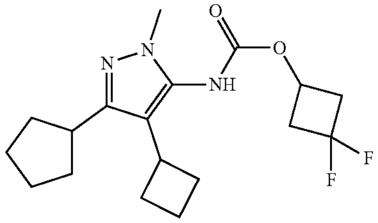 [SMILES: Cn1nc(C2CCCC2)c(C2CCC2)c1NC(=O)OC1CC(F)(F)C1] | 3,3-difluorocyclobutyl (4-cyclobutyl-3-cyclopentyl-1-methyl-1H-pyrazol-5-yl)carbamate | 4.2 | 354 |
| 307 | 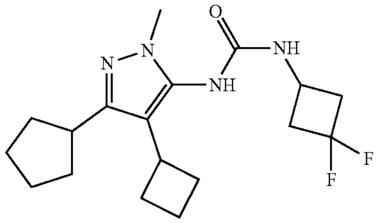 [SMILES: Cn1nc(C2CCCC2)c(C2CCC2)c1NC(=O)NC1CC(F)(F)C1] | 1-(4-cyclobutyl-3-cyclopentyl-1-methyl-1H-pyrazol-5-yl)-3-(3,3-difluorocyclobutyl)urea | 3.7 | 353 |
| 308 | 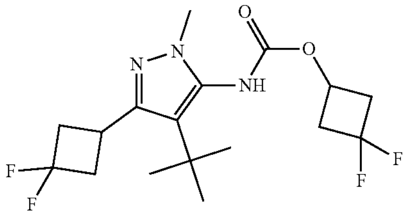 [SMILES: Cn1nc(C2CC(F)(F)C2)c(C(C)(C)C)c1NC(=O)OC1CC(F)(F)C1] | 3,3-difluorocyclobutyl (4-(tert-butyl)-3-(3,3-difluorocyclobutyl)-1-methyl-1H-pyrazol-5-yl)carbamate | 4.78 | 376 |
| 309 | 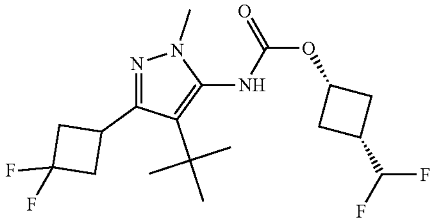 [SMILES: Cn1nc(C2CC(F)(F)C2)c(C(C)(C)C)c1NC(=O)O[C@H]1C[C@@H](C(F)F)C1] | (1s,3s)-3-(difluoromethyl)cyclobutyl (4-(tert-butyl)-3-(3,3-difluorocyclobutyl)-1-methyl-1H-pyrazol-5-yl)carbamate | 4.1 | 392 |

TABLE 1-continued

List of Compounds and Characterization Data

| Cmpd # | Structure | Name | LCMS RT (min)* | m/z $(M + H)^+$ |
|---|---|---|---|---|
| 310 | 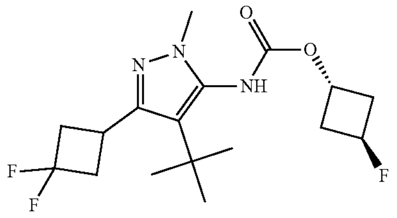 [SMILES: Cn1nc(C2CC(F)(F)C2)c(C(C)(C)C)c1NC(=O)O[C@H]1C[C@H](F)C1] | (1r,3r)-3-fluorocyclobutyl (4-(tert-butyl)-3-(3,3-difluorocyclobutyl)-1-methyl-1H-pyrazol-5-yl)carbamate | 4.0 | 360 |
| 311 | 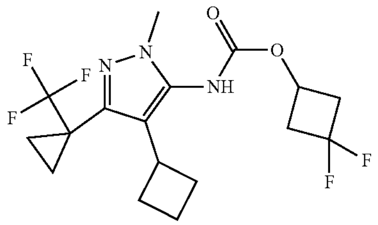 [SMILES: Cn1nc(C2(C(F)(F)F)CC2)c(C2CCC2)c1NC(=O)OC1CC(F)(F)C1] | 3,3-difluorocyclobutyl (4-cyclobutyl-1-methyl-3-(1-(trifluoromethyl)cyclopropyl)-1H-pyrazol-5-yl)carbamate | 4.0 | 394 |
| 312 | 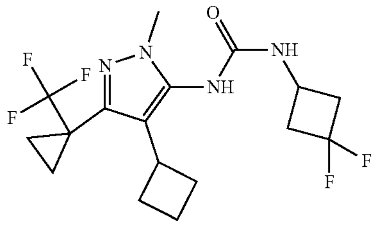 [SMILES: Cn1nc(C2(C(F)(F)F)CC2)c(C2CCC2)c1NC(=O)NC1CC(F)(F)C1] | 1-(4-cyclobutyl-1-methyl-3-(1-(trifluoromethyl)cyclopropyl)-1H-pyrazol-5-yl)-3-(3,3-difluorocyclobutyl)urea | 3.6 | 393 |
| 313 | 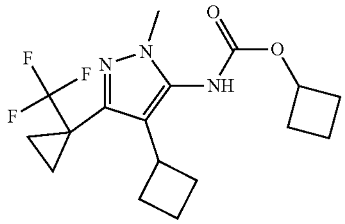 [SMILES: Cn1nc(C2(C(F)(F)F)CC2)c(C2CCC2)c1NC(=O)OC1CCC1] | cyclobutyl (4-cyclobutyl-1-methyl-3-(1-(trifluoromethyl)cyclopropyl)-1H-pyrazol-5-yl)carbamate | 4.1 | 358 |
| 314 | 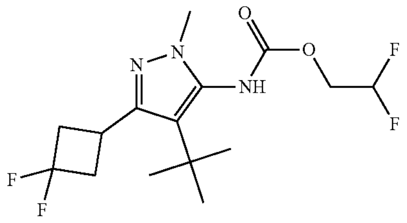 [SMILES: Cn1nc(C2CC(F)(F)C2)c(C(C)(C)C)c1NC(=O)OCC(F)F] | 2,2-difluoroethyl (4-(tert-butyl)-3-(3,3-difluorocyclobutyl)-1-methyl-1H-pyrazol-5-yl)carbamate | 3.9 | 352 |
| 315 | 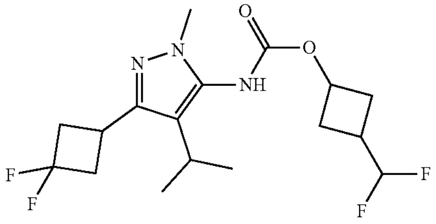 [SMILES: CC(C)c1c(C2CC(F)(F)C2)nn(C)c1NC(=O)OC1CC(C(F)F)C1] | 3-(difluoromethyl)cyclobutyl (3-(3,3-difluorocyclobutyl)-4-isopropyl-1-methyl-1H-pyrazol-5-yl)carbamate | 3.9 | 378 |

TABLE 1-continued

| List of Compounds and Characterization Data | | | | |
|---|---|---|---|---|
| Cmpd # | Structure | Name | LCMS RT (min)* | m/z (M + H)+ |
| 316 | 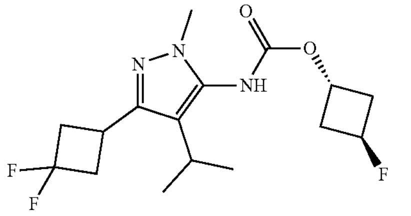 [SMILES: CC(C)c1c(C2CC(F)(F)C2)nn(C)c1NC(=O)O[C@H]1C[C@H](F)C1] | (1r,3r)-3-fluorocyclobutyl (3-(3,3-difluorocyclobutyl)-4-isopropyl-1-methyl-1H-pyrazol-5-yl)carbamate | 3.8 | 346 |
| 317 | 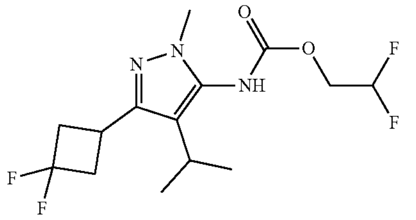 [SMILES: CC(C)c1c(C2CC(F)(F)C2)nn(C)c1NC(=O)OCC(F)F] | 2,2-difluoroethyl (3-(3,3-difluorocyclobutyl)-4-isopropyl-1-methyl-1H-pyrazol-5-yl)carbamate | 3.7 | 338 |
| 318 | 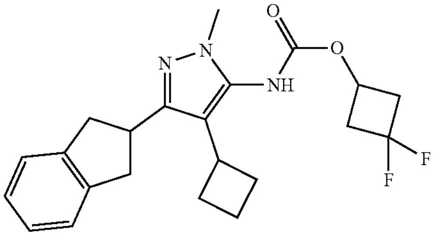 [SMILES: Cn1nc(C2Cc3ccccc3C2)c(C2CCC2)c1NC(=O)OC1CC(F)(F)C1] | 3,3-difluorocyclobutyl (4-cyclobutyl-3-(2,3-dihydro-1H-inden-2-yl)-1-methyl-1H-pyrazol-5-yl)carbamate | 4.4 | 402 |
| 319 | 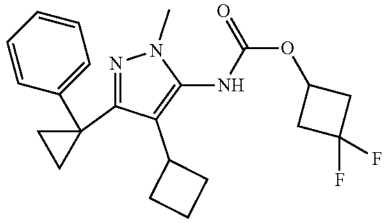 [SMILES: Cn1nc(C2(c3ccccc3)CC2)c(C2CCC2)c1NC(=O)OC1CC(F)(F)C1] | 3,3-difluorocyclobutyl (4-cyclobutyl-1-methyl-3-(1-phenylcyclopropyl)-1H-pyrazol-5-yl)carbamate | 4.2 | 402 |
| 320 | 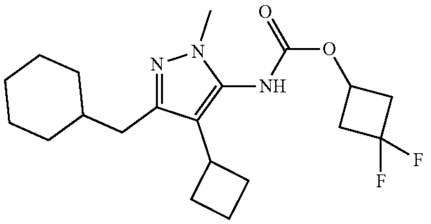 [SMILES: Cn1nc(CC2CCCCC2)c(C2CCC2)c1NC(=O)OC1CC(F)(F)C1] | 3,3-difluorocyclobutyl (4-cyclobutyl-3-(cyclohexylmethyl)-1-methyl-1H-pyrazol-5-yl)carbamate | 4.6 | 382 |
| 321 | 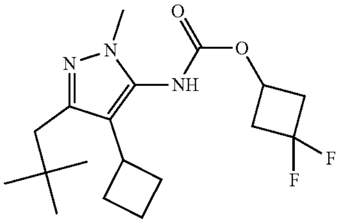 [SMILES: Cn1nc(CC(C)(C)C)c(C2CCC2)c1NC(=O)OC1CC(F)(F)C1] | 3,3-difluorocyclobutyl (4-cyclobutyl-1-methyl-3-neopentyl-1H-pyrazol-5-yl)carbamate | 4.3 | 356 |

TABLE 1-continued

List of Compounds and Characterization Data

| Cmpd # | Structure | Name | LCMS RT (min)* | m/z (M + H)+ |
|---|---|---|---|---|
| 322 | 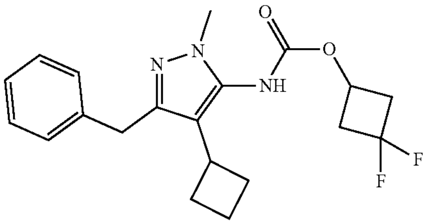 [SMILES: Cn1nc(Cc2ccccc2)c(C2CCC2)c1NC(=O)OC1CC(F)(F)C1] | 3,3-difluorocyclobutyl (3-benzyl-4-cyclobutyl-1-methyl-1H-pyrazol-5-yl)carbamate | 4.0 | 376 |
| 323 | 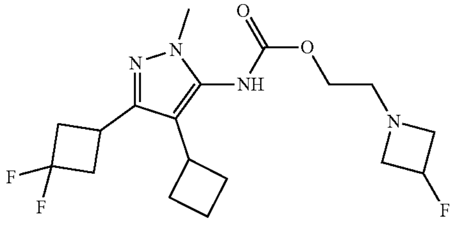 [SMILES: Cn1nc(C2CC(F)(F)C2)c(C2CCC2)c1NC(=O)OCCN1CC(F)C1] | 2-(3-fluoroazetidin-1-yl)ethyl (4-cyclobutyl-3-(3,3-difluorocyclobutyl)-1-methyl-1H-pyrazol-5-yl)carbamate | 2.7 | 387 |
| 324 | 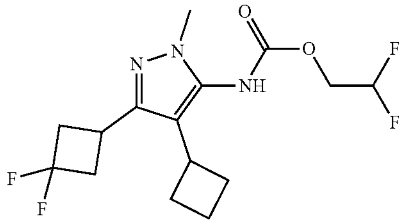 [SMILES: Cn1nc(C2CC(F)(F)C2)c(C2CCC2)c1NC(=O)OCC(F)F] | 2,2-difluoroethyl (4-cyclobutyl-3-(3,3-difluorocyclobutyl)-1-methyl-1H-pyrazol-5-yl)carbamate | 3.8 | 350 |
| 325 | 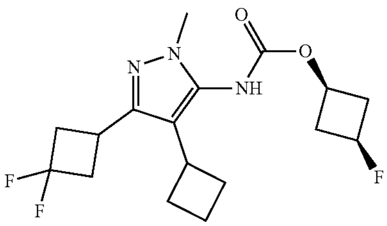 [SMILES: Cn1nc(C2CC(F)(F)C2)c(C2CCC2)c1NC(=O)O[C@H]1C[C@@H](F)C1] | (1s,3s)-3-fluorocyclobutyl (4-cyclobutyl-3-(3,3-difluorocyclobutyl)-1-methyl-1H-pyrazol-5-yl)carbamate | 3.9 | 358 |
| 326 | 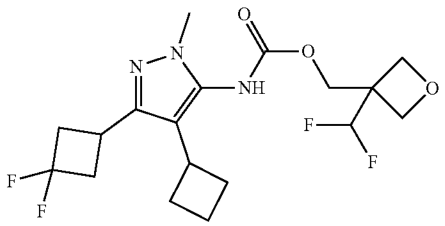 [SMILES: Cn1nc(C2CC(F)(F)C2)c(C2CCC2)c1NC(=O)OCC1(C(F)F)COC1] | (3-(difluoromethyl)oxetan-3-yl)methyl (4-cyclobutyl-3-(3,3-difluorocyclobutyl)-1-methyl-1H-pyrazol-5-yl)carbamate | 3.7 | 406 |
| 327 | 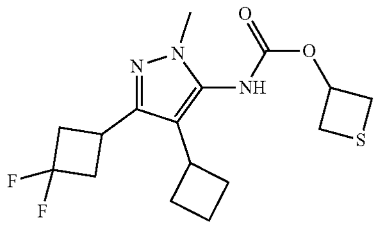 [SMILES: Cn1nc(C2CC(F)(F)C2)c(C2CCC2)c1NC(=O)OC1CSC1] | thietan-3-yl (4-cyclobutyl-3-(3,3-difluorocyclobutyl)-1-methyl-1H-pyrazol-5-yl)carbamate | 4.0 | 358 |

TABLE 1-continued

| List of Compounds and Characterization Data | | | | |
|---|---|---|---|---|
| Cmpd # | Structure | Name | LCMS RT (min)* | m/z (M + H)+ |
| 328 | 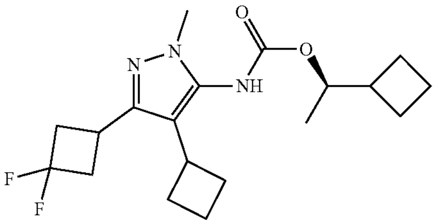 [SMILES: C[C@@H](OC(=O)Nc1c(C2CCC2)c(C2CC(F)(F)C2)nn1C)C1CCC1] | (R)-1-cyclobutylethyl (4-cyclobutyl-3-(3,3-difluorocyclobutyl)-1-methyl-1H-pyrazol-5-yl)carbamate | 4.5 | 368 |
| 329 | 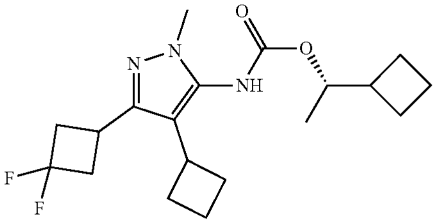 [SMILES: C[C@H](OC(=O)Nc1c(C2CCC2)c(C2CC(F)(F)C2)nn1C)C1CCC1] | (S)-1-cyclobutylethyl (4-cyclobutyl-3-(3,3-difluorocyclobutyl)-1-methyl-1H-pyrazol-5-yl)carbamate | 4.5 | 368 |
| 330 | 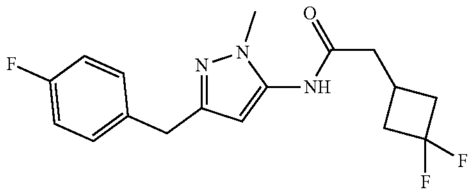 [SMILES: Cn1nc(Cc2ccc(F)cc2)cc1NC(=O)CC1CC(F)(F)C1] | 2-(3,3-difluorocyclobutyl)-N-(3-(4-fluorobenzyl)-1-methyl-1H-pyrazol-5-yl)acetamide | 3.6 | 338 |
| 331 | 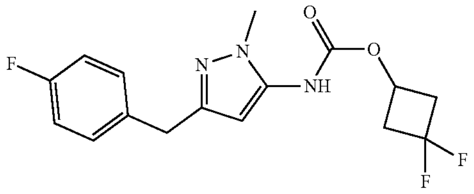 [SMILES: Cn1nc(Cc2ccc(F)cc2)cc1NC(=O)OC1CC(F)(F)C1] | 3,3-difluorocyclobutyl (3-(4-fluorobenzyl)-1-methyl-1H-pyrazol-5-yl)carbamate | 3.7 | 340 |
| 332 | 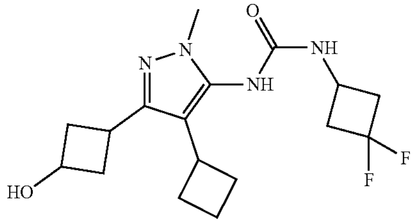 [SMILES: Cn1nc(C2CC(O)C2)c(C2CCC2)c1NC(=O)NC1CC(F)(F)C1] | 1-(4-cyclobutyl-3-(3-hydroxycyclobutyl)-1-methyl-1H-pyrazol-5-yl)-3-(3,3-difluorocyclobutyl)urea | 2.9 | 355 |
| 333 | 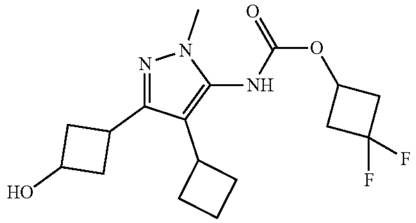 [SMILES: Cn1nc(C2CC(O)C2)c(C2CCC2)c1NC(=O)OC1CC(F)(F)C1] | 3,3-difluorocyclobutyl (4-cyclobutyl-3-(3-hydroxycyclobutyl)-1-methyl-1H-pyrazol-5-yl)carbamate | 3.2 | 356 |

TABLE 1-continued

List of Compounds and Characterization Data

| Cmpd # | Structure | Name | LCMS RT (min)* | m/z (M + H)$^+$ |
|---|---|---|---|---|
| 334 | 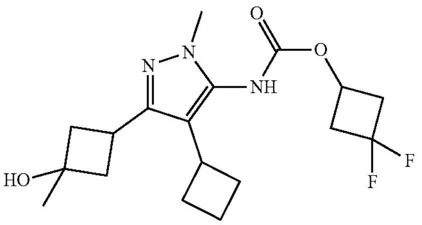 [SMILES: Cn1nc(C2CC(C)(O)C2)c(C2CCC2)c1NC(=O)OC1CC(F)(F)C1] | 3,3-difluorocyclobutyl (4-cyclobutyl-3-(3-hydroxy-3-methylcyclobutyl)-1-methyl-1H-pyrazol-5-yl)carbamate | 3.4 | 370 |
| 335 | 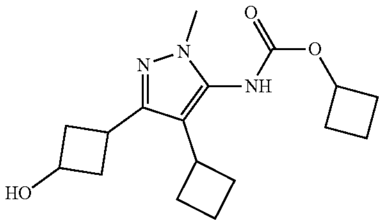 [SMILES: Cn1nc(C2CC(O)C2)c(C2CCC2)c1NC(=O)OC1CCC1] | cyclobutyl (4-cyclobutyl-3-(3-hydroxycyclobutyl)-1-methyl-1H-pyrazol-5-yl)carbamate | 3.2 | 320 |
| 336 | 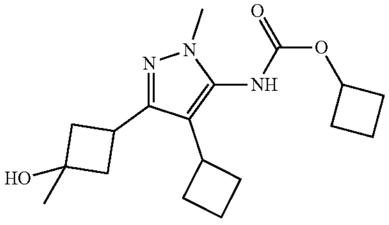 [SMILES: Cn1nc(C2CC(C)(O)C2)c(C2CCC2)c1NC(=O)OC1CCC1] | cyclobutyl (4-cyclobutyl-3-(3-hydroxy-3-methylcyclobutyl)-1-methyl-1H-pyrazol-5-yl)carbamate | 3.4 | 334 |
| 337 | 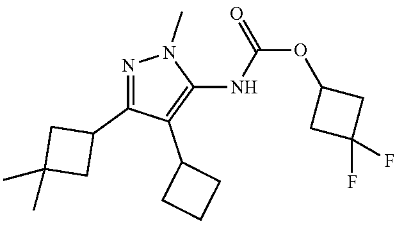 [SMILES: Cn1nc(C2CC(C)(C)C2)c(C2CCC2)c1NC(=O)OC1CC(F)(F)C1] | 3,3-difluorocyclobutyl (4-cyclobutyl-3-(3,3-dimethylcyclobutyl)-1-methyl-1H-pyrazol-5-yl)carbamate | 4.4 | 368 |
| 338 | 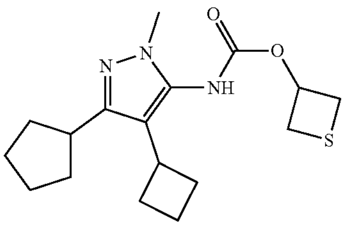 [SMILES: Cn1nc(C2CCCC2)c(C2CCC2)c1NC(=O)OC1CSC1] | thietan-3-yl (4-cyclobutyl-3-cyclopentyl-1-methyl-1H-pyrazol-5-yl)carbamate | 4.2 | 336 |
| 339 | 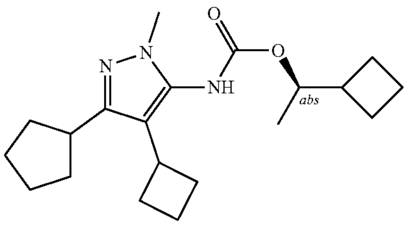 [SMILES: C[C@@H](OC(=O)Nc1c(C2CCC2)c(C2CCCC2)nn1C)C1CCC1] | (R)-1-cyclobutylethyl (4-cyclobutyl-3-cyclopentyl-1-methyl-1H-pyrazol-5-yl)carbamate | 4.8 | 346 |

TABLE 1-continued

| List of Compounds and Characterization Data | | | | |
|---|---|---|---|---|
| Cmpd # | Structure | Name | LCMS RT (min)* | m/z (M + H)$^+$ |
| 340 | 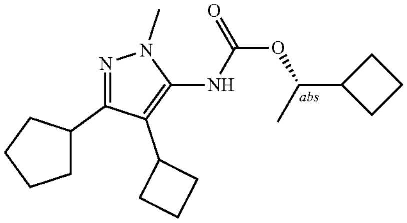 [SMILES: C[C@H](OC(=O)Nc1c(C2CCC2)c(C2CCCC2)nn1C)C1CCC1] | (S)-1-cyclobutylethyl (4-cyclobutyl-3-cyclopentyl-1-methyl-1H-pyrazol-5-yl)carbamate | 4.8 | 346 |
| 341 | 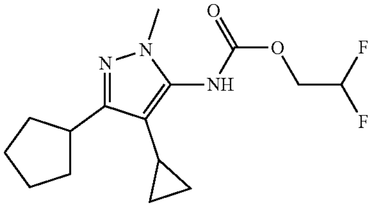 [SMILES: Cn1nc(C2CCCC2)c(C2CC2)c1NC(=O)OCC(F)F] | 2,2-difluoroethyl (4-cyclobutyl-3-cyclopentyl-1-methyl-1H-pyrazol-5-yl)carbamate | 4.0 | 328 |
| 342 | 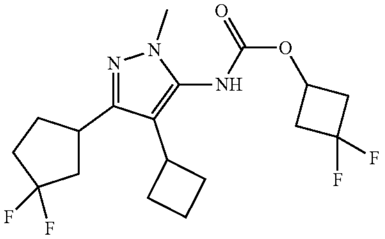 [SMILES: Cn1nc(C2CCC(F)(F)C2)c(C2CCC2)c1NC(=O)OC1CC(F)(F)C1] | 3,3-difluorocyclobutyl (4-cyclobutyl-3-(3,3-difluorocyclopentyl)-1-methyl-1H-pyrazol-5-yl)carbamate | 4.1 | 390 |
| 343 | 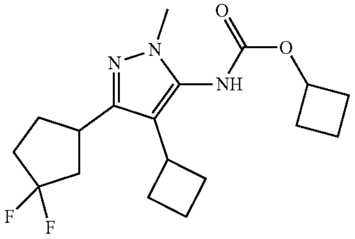 [SMILES: Cn1nc(C2CCC(F)(F)C2)c(C2CCC2)c1NC(=O)OC1CCC1] | cyclobutyl (4-cyclobutyl-3-(3,3-difluorocyclopentyl)-1-methyl-1H-pyrazol-5-yl)carbamate | 4.1 | 354 |
| 344 | 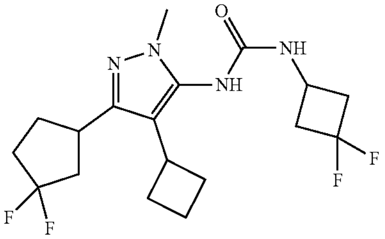 [SMILES: Cn1nc(C2CCC(F)(F)C2)c(C2CCC2)c1NC(=O)NC1CC(F)(F)C1] | 1-(4-cyclobutyl-3-(3,3-difluorocyclopentyl)-1-methyl-1H-pyrazol-5-yl)-3-(3,3-difluorocyclobutyl)urea | 3.6 | 389 |
| 345 | 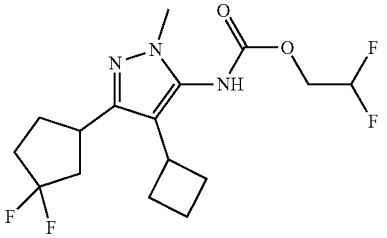 [SMILES: Cn1nc(C2CCC(F)(F)C2)c(C2CCC2)c1NC(=O)OCC(F)F] | 2,2-difluoroethyl (4-cyclobutyl-3-(3,3-difluorocyclopentyl)-1-methyl-1H-pyrazol-5-yl)carbamate | 3.8 | 364 |

TABLE 1-continued

List of Compounds and Characterization Data

| Cmpd # | Structure | Name | LCMS RT (min)* | m/z (M + H)+ |
|---|---|---|---|---|
| 346 | 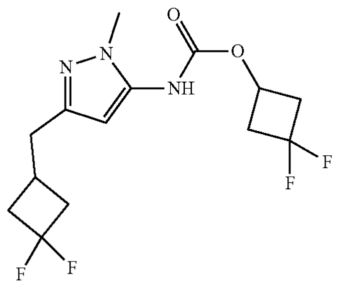 [SMILES: Cn1nc(CC2CC(F)(F)C2)cc1NC(=O)OC1CC(F)(F)C1] | 3,3-difluorocyclobutyl (3-((3,3-difluorocyclobutyl)methyl)-1-methyl-1H-pyrazol-5-yl)carbamate | 3.7 | 336 |
| 347 | 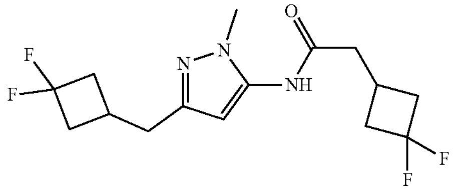 [SMILES: Cn1nc(CC2CC(F)(F)C2)cc1NC(=O)CC1CC(F)(F)C1] | 2-(3,3-difluorocyclobutyl)-N-(3-((3,3-difluorocyclobutyl)methyl)-1-methyl-1H-pyrazol-5-yl)acetamide | 3.6 | 334 |
| 348 | 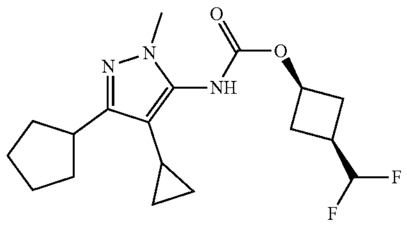 [SMILES: Cn1nc(C2CCCC2)c(C2CC2)c1NC(=O)O[C@H]1C[C@@H](C(F)F)C1] | (1s,3s)-3-(difluoromethyl)cyclobutyl (3-cyclopentyl-4-cyclopropyl-1-methyl-1H-pyrazol-5-yl)carbamate | 4.1 | 354 |
| 349 | 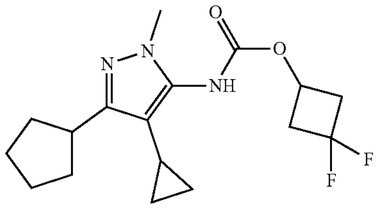 [SMILES: Cn1nc(C2CCCC2)c(C2CC2)c1NC(=O)OC1CC(F)(F)C1] | 3,3-difluorocyclobutyl (3-cyclopentyl-4-cyclopropyl-1-methyl-1H-pyrazol-5-yl)carbamate | 4.0 | 340 |
| 350 | 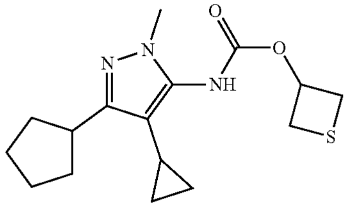 [SMILES: Cn1nc(C2CCCC2)c(C2CC2)c1NC(=O)OC1CSC1] | thietan-3-yl (3-cyclopentyl-4-cyclopropyl-1-methyl-1H-pyrazol-5-yl)carbamate | 4.0 | 322 |
| 351 | 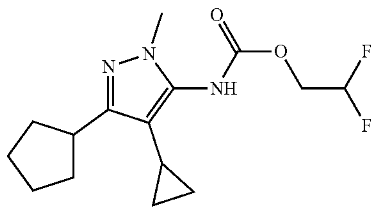 [SMILES: Cn1nc(C2CCCC2)c(C2CC2)c1NC(=O)OCC(F)F] | 2,2-difluoroethyl (3-cyclopentyl-4-cyclopropyl-1-methyl-1H-pyrazol-5-yl)carbamate | 3.9 | 314 |

TABLE 1-continued

| List of Compounds and Characterization Data | | | | |
|---|---|---|---|---|
| Cmpd # | Structure | Name | LCMS RT (min)* | m/z $(M + H)^+$ |
| 352 | 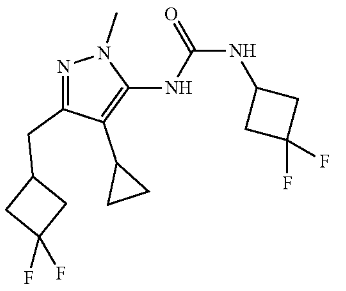 [SMILES: Cn1nc(CC2CC(F)(F)C2)c(C2CC2)c1NC(=O)NC1CC(F)(F)C1] | 1-(4-cyclopropyl-3-((3,3-difluorocyclobutyl)methyl)-1-methyl-1H-pyrazol-5-yl)-3-(3,3-difluorocyclobutyl)urea | 3.6 | 375 |
| 353 | 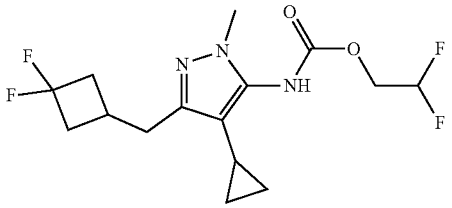 [SMILES: Cn1nc(CC2CC(F)(F)C2)c(C2CC2)c1NC(=O)OCC(F)F] | 2,2-difluoroethyl (4-cyclopropyl-3-((3,3-difluorocyclobutyl)methyl)-1-methyl-1H-pyrazol-5-yl)carbamate | 3.7 | 350 |
| 354 | 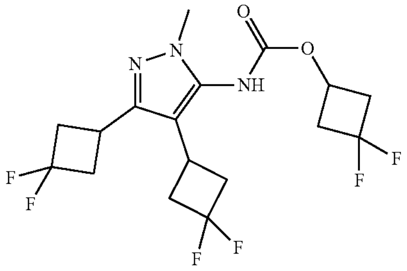 [SMILES: Cn1nc(C2CC(F)(F)C2)c(C2CC(F)(F)C2)c1NC(=O)OC1CC(F)(F)C1] | 3,3-difluorocyclobutyl (3,4-bis(3,3-difluorocyclobutyl)-1-methyl-1H-pyrazol-5-yl)carbamate | 4.0 | 412 |
| 355 | 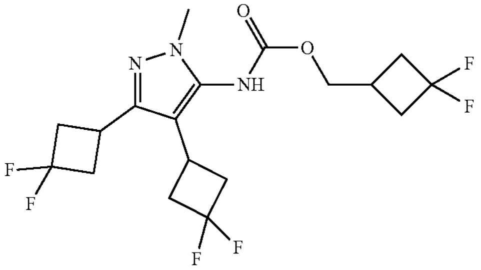 [SMILES: Cn1nc(C2CC(F)(F)C2)c(C2CC(F)(F)C2)c1NC(=O)OCC1CC(F)(F)C1] | (3,3-difluorocyclobutyl)methyl (3,4-bis(3,3-difluorocyclobutyl)-1-methyl-1H-pyrazol-5-yl)carbamate | 4.0 | 426 |
| 356 | 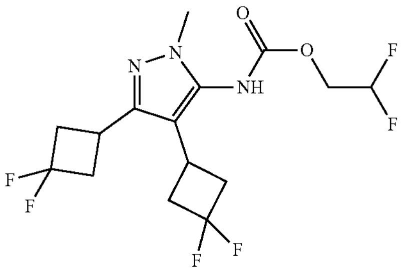 [SMILES: Cn1nc(C2CC(F)(F)C2)c(C2CC(F)(F)C2)c1NC(=O)OCC(F)F] | 2,2-difluoroethyl (3,4-bis(3,3-difluorocyclobutyl)-1-methyl-1H-pyrazol-5-yl)carbamate | 3.8 | 386 |

TABLE 1-continued

| Cmpd # | Structure | Name | LCMS RT (min)* | m/z (M + H)+ |
| --- | --- | --- | --- | --- |
| | | List of Compounds and Characterization Data | | |
| 357 | 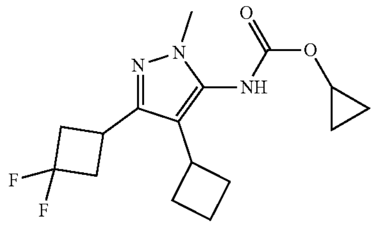 [SMILES: Cn1nc(C2CC(F)(F)C2)c(C2CCC2)c1NC(=O)OC1CC1] | cyclopropyl (4-cyclobutyl-3-(3,3-difluorocyclobutyl)-1-methyl-1H-pyrazol-5-yl)carbamate | 3.9 | 326 |
| 358 | 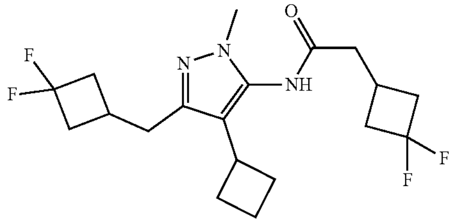 | N-(4-cyclobutyl-3-((3,3-difluorocyclobutyl)methyl)-1-methyl-1H-pyrazol-5-yl)-2-(3,3-difluorocyclobutyl)acetamide | 4.0 | 388 |
| 359 | 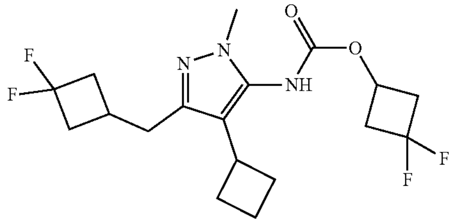 [SMILES: Cn1nc(CC2CC(F)(F)C2)c(C2CCC2)c1NC(=O)OC1CC(F)(F)C1] | 3,3-difluorocyclobutyl (4-cyclobutyl-3-((3,3-difluorocyclobutyl)methyl)-1-methyl-1H-pyrazol-5-yl)carbamate | 4.1 | 390 |
| 360 | 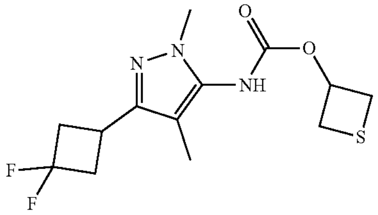 [SMILES: Cc1c(C2CC(F)(F)C2)nn(C)c1NC(=O)OC1CSC1] | thietan-3-yl (3-(3,3-difluorocyclobutyl)-1,4-dimethyl-1H-pyrazol-5-yl)carbamate | 3.6 | 318 |
| 361 | 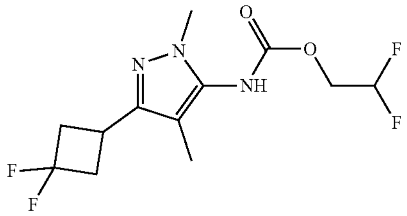 [SMILES: Cc1c(C2CC(F)(F)C2)nn(C)c1NC(=O)OCC(F)F] | 2,2-difluoroethyl (3-(3,3-difluorocyclobutyl)-1,4-dimethyl-1H-pyrazol-5-yl)carbamate | 3.5 | 310 |
| 362 | 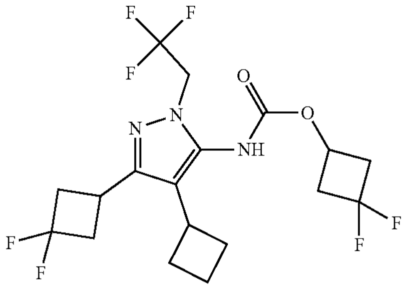 [SMILES: O=C(Nc1c(C2CCC2)c(C2CC(F)(F)C2)nn1CC(F)(F)F)OC1CC(F)(F)C1] | 3,3-difluorocyclobutyl (4-cyclobutyl-3-(3,3-difluorocyclobutyl)-1-(2,2,2-trifluoroethyl)-1H-pyrazol-5-yl)carbamate | 4.3 | 444 |

TABLE 1-continued

| List of Compounds and Characterization Data | | | | |
|---|---|---|---|---|
| Cmpd # | Structure | Name | LCMS RT (min)* | m/z (M + H)$^+$ |
| 363 | 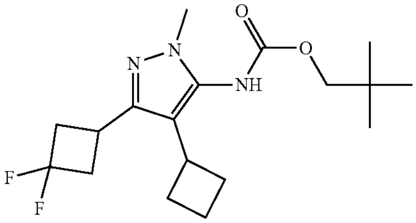 [SMILES: Cn1nc(C2CC(F)(F)C2)c(C2CCC2)c1NC(=O)OCC(C)(C)C] | neopentyl (4-cyclobutyl-3-(3,3-difluorocyclobutyl)-1-methyl-1H-pyrazol-5-yl)carbamate | 4.4 | 356 |
| 364 | 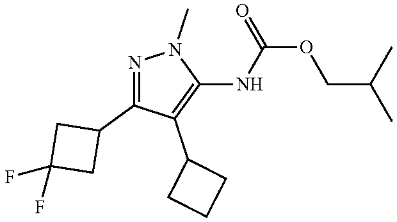 [SMILES: CC(C)COC(=O)Nc1c(C2CCC2)c(C2CC(F)(F)C2)nn1C] | isobutyl (4-cyclobutyl-3-(3,3-difluorocyclobutyl)-1-methyl-1H-pyrazol-5-yl)carbamate | 4.3 | 342 |
| 365 | 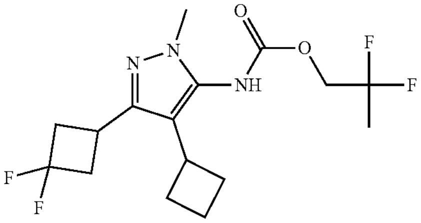 [SMILES: Cn1nc(C2CC(F)(F)C2)c(C2CCC2)c1NC(=O)OCC(C)(F)F] | 2,2-difluoropropyl (4-cyclobutyl-3-(3,3-difluorocyclobutyl)-1-methyl-1H-pyrazol-5-yl)carbamate | 4.0 | 364 |
| 366 | 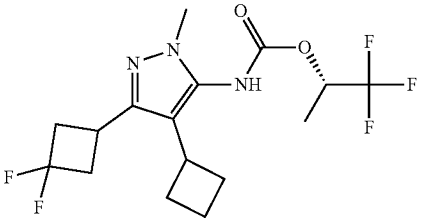 [SMILES: C[C@H](OC(=O)Nc1c(C2CCC2)c(C2CC(F)(F)C2)nn1C)C(F)(F)F] | (S)-1,1,1-trifluoropropan-2-yl (4-cyclobutyl-3-(3,3-difluorocyclobutyl)-1-methyl-1H-pyrazol-5-yl)carbamate | 4.3 | 382 |
| 367 | 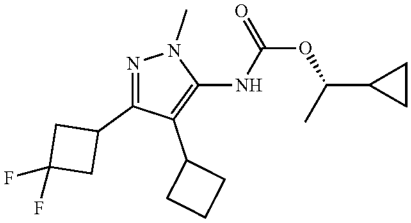 [SMILES: C[C@H](OC(=O)Nc1c(C2CCC2)c(C2CC(F)(F)C2)nn1C)C1CC1] | (S)-1-cyclopropylethyl (4-cyclobutyl-3-(3,3-difluorocyclobutyl)-1-methyl-1H-pyrazol-5-yl)carbamate | 4.3 | 354 |
| 368 | 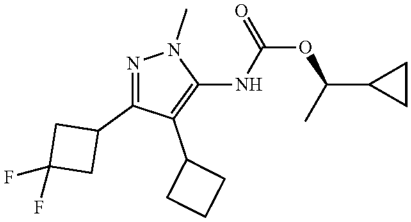 [SMILES: C[C@@H](OC(=O)Nc1c(C2CCC2)c(C2CC(F)(F)C2)nn1C)C1CC1] | (R)-1-cyclopropylethyl (4-cyclobutyl-3-(3,3-difluorocyclobutyl)-1-methyl-1H-pyrazol-5-yl)carbamate | 4.3 | 354 |

TABLE 1-continued

| List of Compounds and Characterization Data | | | | |
|---|---|---|---|---|
| Cmpd # | Structure | Name | LCMS RT (min)* | m/z (M + H)+ |
| 369 | 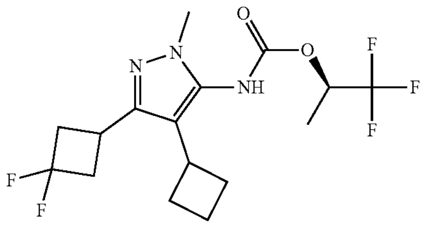 [SMILES: C[C@@H](OC(=O)Nc1c(C2CCC2)c(C2CC(F)(F)C2)nn1C)C(F)(F)F] | (R)-1,1,1-trifluoropropan-2-yl (4-cyclobutyl-3-(3,3-difluorocyclobutyl)-1-methyl-1H-pyrazol-5-yl)carbamate | 4.2 | 382 |
| 370 | 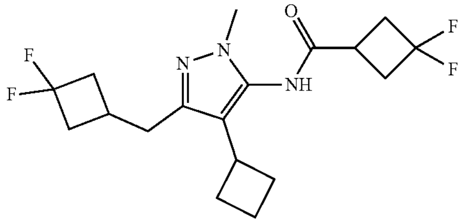 [SMILES: Cn1nc(CC2CC(F)(F)C2)c(C2CCC2)c1NC(=O)C1CC(F)(F)C1] | N-(4-cyclobutyl-3-((3,3-difluorocyclobutyl)methyl)-1-methyl-1H-pyrazol-5-yl)-3,3-difluorocyclobutane-1-carboxamide | 3.9 | 374 |
| 371 | 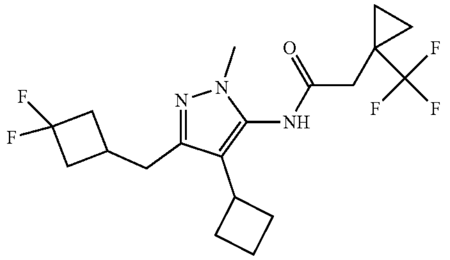 [SMILES: Cn1nc(CC2CC(F)(F)C2)c(C2CCC2)c1NC(=O)CC1(C(F)(F)F)CC1] | N-(4-cyclobutyl-3-((3,3-difluorocyclobutyl)methyl)-1-methyl-1H-pyrazol-5-yl)-2-(1-(trifluoromethyl)cyclopropyl)acetamide | 4.0 | 406 |
| 372 | 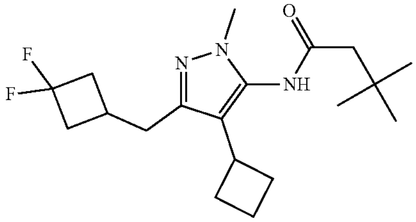 [SMILES: Cn1nc(CC2CC(F)(F)C2)c(C2CCC2)c1NC(=O)CC(C)(C)C] | N-(4-cyclobutyl-3-((3,3-difluorocyclobutyl)methyl)-1-methyl-1H-pyrazol-5-yl)-3,3-dimethylbutanamide | 4.2 | 354 |
| 373 | 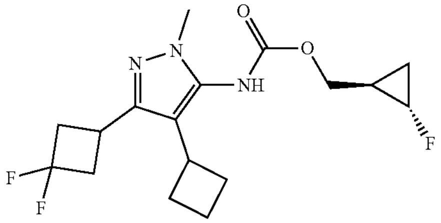 [SMILES: Cn1nc(C2CC(F)(F)C2)c(C2CCC2)c1NC(=O)OC[C@H]1C[C@@H]1F] | ((1R,2S)-2-fluorocyclopropyl)methyl (4-cyclobutyl-3-(3,3-difluorocyclobutyl)-1-methyl-1H-pyrazol-5-yl)carbamate | 4.0 | 358 |
| 374 | 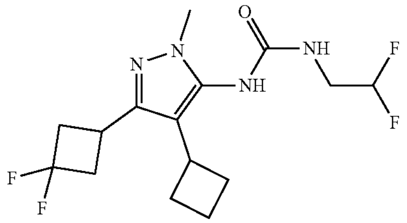 [SMILES: Cn1nc(C2CC(F)(F)C2)c(C2CCC2)c1NC(=O)NCC(F)F] | 1-(4-cyclobutyl-3-(3,3-difluorocyclobutyl)-1-methyl-1H-pyrazol-5-yl)-3-(2,2-difluoroethyl)urea | 3.5 | 349 |

TABLE 1-continued

| List of Compounds and Characterization Data | | | | |
|---|---|---|---|---|
| Cmpd # | Structure | Name | LCMS RT (min)* | m/z (M + H)+ |
| 375 | 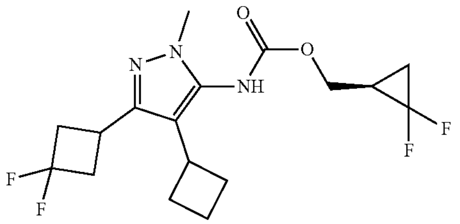 [SMILES: Cn1nc(C2CC(F)(F)C2)c(C2CCC2)c1NC(=O)OC[C@H]1CC1(F)F] | (R)-(2,2-difluorocyclopropyl)methyl (4-cyclobutyl-3-(3,3-difluorocyclobutyl)-1-methyl-1H-pyrazol-5-yl)carbamate | 4.0 | 376 |
| 376 | 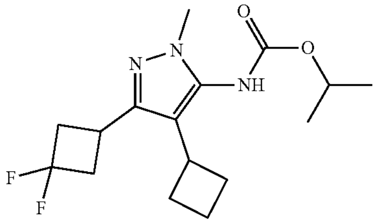 [SMILES: CC(C)OC(=O)Nc1c(C2CCC2)c(C2CC(F)(F)C2)nn1C] | isopropyl (4-cyclobutyl-3-(3,3-difluorocyclobutyl)-1-methyl-1H-pyrazol-5-yl)carbamate | 4.0 | 328 |
| 377 | 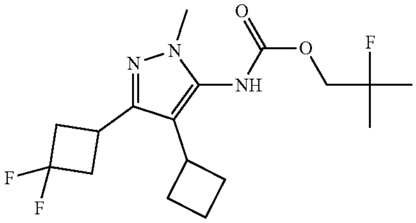 [SMILES: Cn1nc(C2CC(F)(F)C2)c(C2CCC2)c1NC(=O)OCC(C)(C)F] | 2-fluoro-2-methylpropyl (4-cyclobutyl-3-(3,3-difluorocyclobutyl)-1-methyl-1H-pyrazol-5-yl)carbamate | 4.0 | 360 |
| 378 | 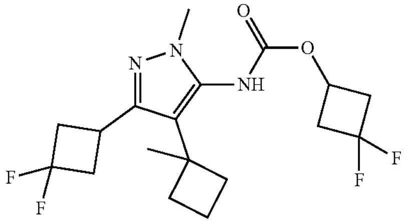 [SMILES: Cn1nc(C2CC(F)(F)C2)c(C2(C)CCC2)c1NC(=O)OC1CC(F)(F)C1] | 3,3-difluorocyclobutyl (3-(3,3-difluorocyclobutyl)-1-methyl-4-(1-methylcyclobutyl)-1H-pyrazol-5-yl)carbamate | 5.3 | 390 |
| 379 | 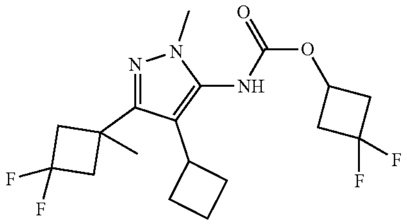 [SMILES: Cn1nc(C2(C)CC(F)(F)C2)c(C2CCC2)c1NC(=O)OC1CC(F)(F)C1] | 3,3-difluorocyclobutyl (4-cyclobutyl-3-(3,3-difluoro-1-methylcyclobutyl)-1-methyl-1H-pyrazol-5-yl)carbamate | 4.1 | 390 |
| 380 | 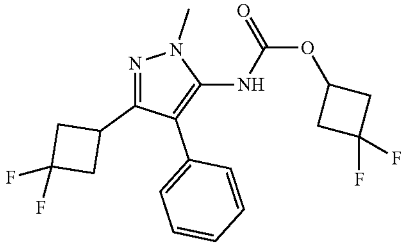 [SMILES: Cn1nc(C2CC(F)(F)C2)c(-c2ccccc2)c1NC(=O)OC1CC(F)(F)C1] | 3,3-difluorocyclobutyl (3-(3,3-difluorocyclobutyl)-1-methyl-4-phenyl-1H-pyrazol-5-yl)carbamate | 4.0 | 398 |

TABLE 1-continued

List of Compounds and Characterization Data

| Cmpd # | Structure | Name | LCMS RT (min)* | m/z (M + H)+ |
|---|---|---|---|---|
| 381 | 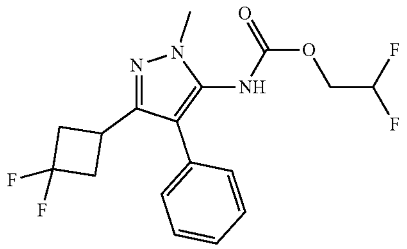 [SMILES: Cn1nc(C2CC(F)(F)C2)c(-c2ccccc2)c1NC(=O)OCC(F)F] | 2,2-difluoroethyl (3-(3,3-difluorocyclobutyl)-1-methyl-4-phenyl-1H-pyrazol-5-yl)carbamate | 3.9 | 372 |
| 382 | 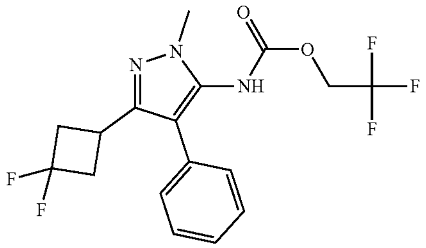 [SMILES: Cn1nc(C2CC(F)(F)C2)c(-c2ccccc2)c1NC(=O)OCC(F)(F)F] | 2,2,2-trifluoroethyl (3-(3,3-difluorocyclobutyl)-1-methyl-4-phenyl-1H-pyrazol-5-yl)carbamate | 4.1 | 390 |
| 383 | 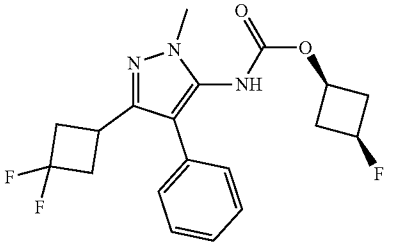 [SMILES: Cn1nc(C2CC(F)(F)C2)c(-c2ccccc2)c1NC(=O)O[C@H]1C[C@@H](F)C1] | (1s,3s)-3-fluorocyclobutyl (3-(3,3-difluorocyclobutyl)-1-methyl-4-phenyl-1H-pyrazol-5-yl)carbamate | 3.9 | 380 |
| 384 | 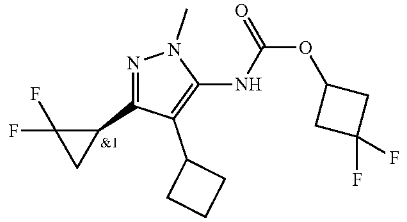 [SMILES: Cn1nc([C@H]2CC2(F)F)c(C2CCC2)c1NC(=O)OC1CC(F)(F)C1] | rac-3,3-difluorocyclobutyl (R)-(4-cyclobutyl-3-(2,2-difluorocyclopropyl)-1-methyl-1H-pyrazol-5-yl)carbamate | 4.0 | 362 |
| 385 | 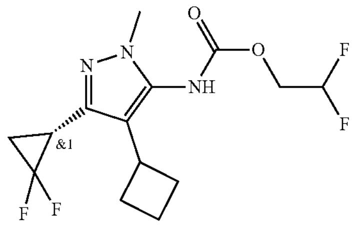 [SMILES: Cn1nc([C@H]2CC2(F)F)c(C2CCC2)c1NC(=O)OCC(F)F] | rac-2,2-difluoroethyl (R)-(4-cyclobutyl-3-(2,2-difluorocyclopropyl)-1-methyl-1H-pyrazol-5-yl)carbamate | 3.7 | 336 |
| 386 | 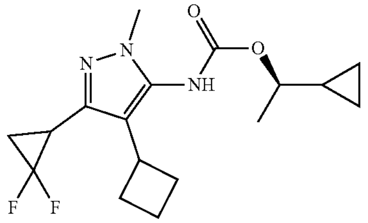 [SMILES: C[C@@H](OC(=O)Nc1c(C2CCC2)c(C2CC2(F)F)nn1C)C1CC1] | (R)-1-cyclopropylethyl (4-cyclobutyl-3-(2,2-difluorocyclopropyl)-1-methyl-1H-pyrazol-5-yl)carbamate | 4.1 | 340 |

TABLE 1-continued

| List of Compounds and Characterization Data | | | | |
|---|---|---|---|---|
| Cmpd # | Structure | Name | LCMS RT (min)* | m/z (M + H)$^+$ |
| 387 | 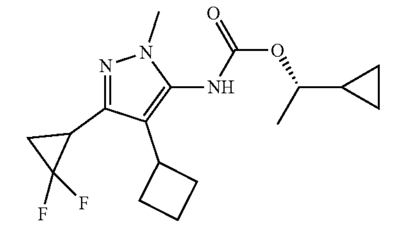 [SMILES: C[C@H](OC(=O)Nc1c(C2CCC2)c(C2CC2(F)F)nn1C)C1CC1] | (S)-1-cyclopropylethyl (4-cyclobutyl-3-(2,2-difluorocyclopropyl)-1-methyl-1H-pyrazol-5-yl)carbamate | 4.1 | 340 |
| 388 | 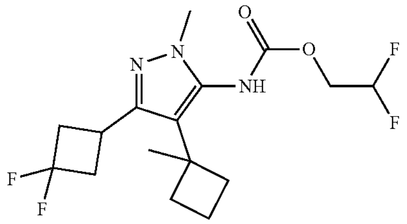 [SMILES: Cn1nc(C2CC(F)(F)C2)c(C2(C)CCC2)c1NC(=O)OCC(F)F] | 2,2-difluoroethyl (3-(3,3-difluorocyclobutyl)-1-methyl-4-(1-methylcyclobutyl)-1H-pyrazol-5-yl)carbamate | 4.0 | 364 |
| 389 | 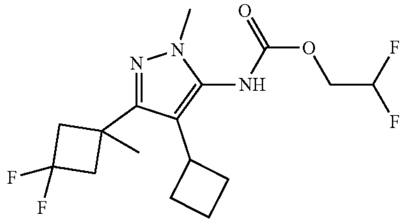 [SMILES: Cn1nc(C2(C)CC(F)(F)C2)c(C2CCC2)c1NC(=O)OCC(F)F] | 2,2-difluoroethyl (4-cyclobutyl-3-(3,3-difluoro-1-methylcyclobutyl)-1-methyl-1H-pyrazol-5-yl)carbamate | 4.0 | 364 |
| 390 | 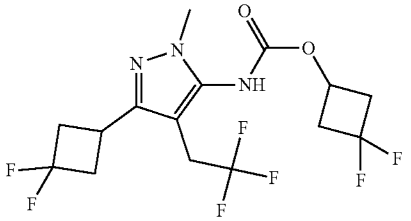 [SMILES: Cn1nc(C2CC(F)(F)C2)c(CC(F)(F)F)c1NC(=O)OC1CC(F)(F)C1] | 3,3-difluorocyclobutyl (3-(3,3-difluorocyclobutyl)-1-methyl-4-(2,2,2-trifluoroethyl)-1H-pyrazol-5-yl)carbamate | 3.9 | 404 |
| 391 | 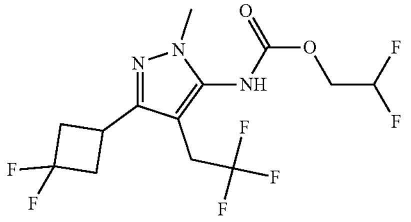 [SMILES: Cn1nc(C2CC(F)(F)C2)c(CC(F)(F)F)c1NC(=O)OCC(F)F] | 2,2-difluoroethyl (3-(3,3-difluorocyclobutyl)-1-methyl-4-(2,2,2-trifluoroethyl)-1H-pyrazol-5-yl)carbamate | 3.8 | 378 |
| 392 | 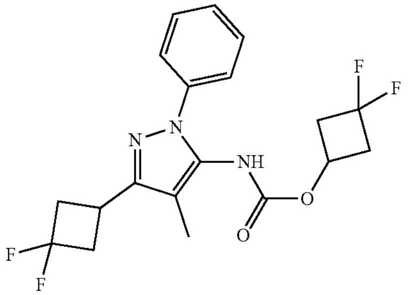 [SMILES: Cc1c(C2CC(F)(F)C2)nn(-c2ccccc2)c1NC(=O)OC1CC(F)(F)C1] | 3,3-difluorocyclobutyl (3-(3,3-difluorocyclobutyl)-4-methyl-1-phenyl-1H-pyrazol-5-yl)carbamate | 4.1 | 398 |

TABLE 1-continued

| Cmpd # | Structure | Name | LCMS RT (min)* | m/z $(M + H)^+$ |
|---|---|---|---|---|
| List of Compounds and Characterization Data | | | | |
| 393 | 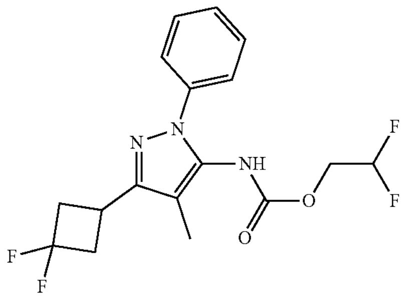 [SMILES: Cc1c(C2CC(F)(F)C2)nn(-c2ccccc2)c1NC(=O)OCC(F)F] | 2,2-difluoroethyl (3-(3,3-difluorocyclobutyl)-4-methyl-1-phenyl-1H-pyrazol-5-yl)carbamate | 4.0 | 372 |
| 394 | 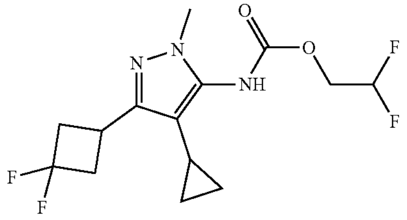 [SMILES: Cn1nc(C2CC(F)(F)C2)c(C2CC2)c1NC(=O)OCC(F)F] | 2,2-difluoroethyl (4-cyclopropyl-3-(3,3-difluorocyclobutyl)-1-methyl-1H-pyrazol-5-yl)carbamate | 3.7 | 336 |
| 395 | 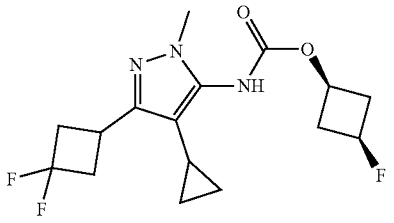 [SMILES: Cn1nc(C2CC(F)(F)C2)c(C2CC2)c1NC(=O)O[C@H]1C[C@@H](F)C1] | (1s,3s)-3-fluorocyclobutyl (4-cyclopropyl-3-(3,3-difluorocyclobutyl)-1-methyl-1H-pyrazol-5-yl)carbamate | 3.7 | 344 |
| 396 | 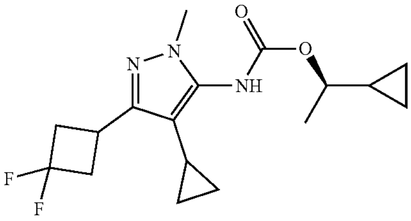 [SMILES: C[C@@H](OC(=O)Nc1c(C2CC2)c(C2CC(F)(F)C2)nn1C)C1CC1] | (R)-1-cyclopropylethyl (4-cyclopropyl-3-(3,3-difluorocyclobutyl)-1-methyl-1H-pyrazol-5-yl)carbamate | 4.1 | 340 |
| 397 | 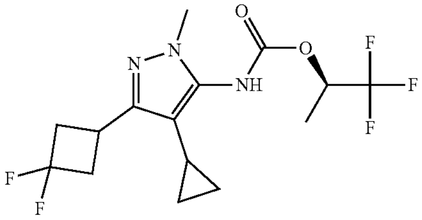 [SMILES: C[C@@H](OC(=O)Nc1c(C2CC2)c(C2CC(F)(F)C2)nn1C)C(F)(F)F] | (R)-1,1,1-trifluoropropan-2-yl (4-cyclopropyl-3-(3,3-difluorocyclobutyl)-1-methyl-1H-pyrazol-5-yl)carbamate | 4.1 | 368 |
| 398 | 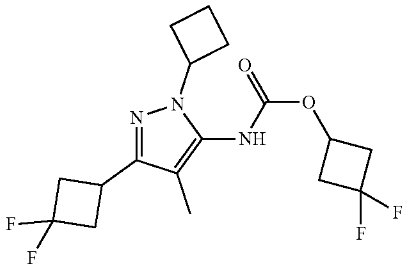 [SMILES: Cc1c(C2CC(F)(F)C2)nn(C2CCC2)c1NC(=O)OC1CC(F)(F)C1] | 3,3-difluorocyclobutyl (1-cyclobutyl-3-(3,3-difluorocyclobutyl)-4-methyl-1H-pyrazol-5-yl)carbamate | 3.2 | 376 |

TABLE 1-continued

| List of Compounds and Characterization Data | | | | |
|---|---|---|---|---|
| Cmpd # | Structure | Name | LCMS RT (min)* | m/z (M + H)$^+$ |
| 399 | 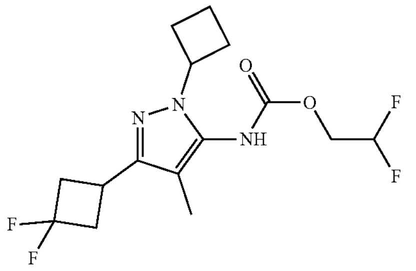 [SMILES: Cc1c(C2CC(F)(F)C2)nn(C2CCC2)c1NC(=O)OCC(F)F] | 2,2-difluoroethyl (1-cyclobutyl-3-(3,3-difluorocyclobutyl)-4-methyl-1H-pyrazol-5-yl)carbamate | 4.1 | 350 |
| 400 | 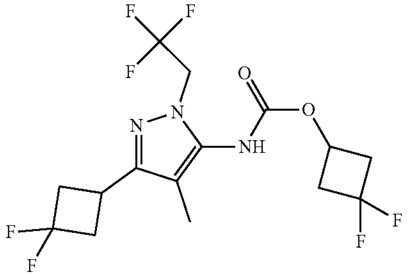 [SMILES: Cc1c(C2CC(F)(F)C2)nn(CC(F)(F)F)c1NC(=O)OC1CC(F)(F)C1] | 3,3-difluorocyclobutyl (3-(3,3-difluorocyclobutyl)-4-methyl-1-(2,2,2-trifluoroethyl)-1H-pyrazol-5-yl)carbamate | 4.0 | 404 |
| 401 | 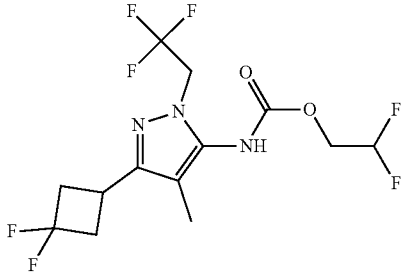 [SMILES: Cc1c(C2CC(F)(F)C2)nn(CC(F)(F)F)c1NC(=O)OCC(F)F] | 2,2-difluoroethyl (3-(3,3-difluorocyclobutyl)-4-methyl-1-(2,2,2-trifluoroethyl)-1H-pyrazol-5-yl)carbamate | 3.9 | 378 |
| 402 | 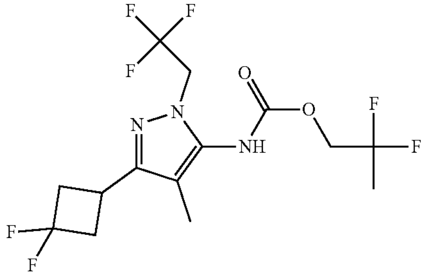 [SMILES: Cc1c(C2CC(F)(F)C2)nn(CC(F)(F)F)c1NC(=O)OCC(C)(F)F] | 2,2-difluoropropyl (3-(3,3-difluorocyclobutyl)-4-methyl-1-(2,2,2-trifluoroethyl)-1H-pyrazol-5-yl)carbamate | 4.0 | 392 |
| 403 | 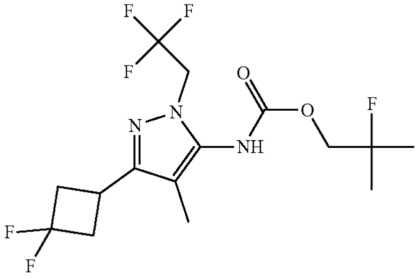 [SMILES: Cc1c(C2CC(F)(F)C2)nn(CC(F)(F)F)c1NC(=O)OCC(C)(C)F] | 2-fluoro-2-methylpropyl (3-(3,3-difluorocyclobutyl)-4-methyl-1-(2,2,2-trifluoroethyl)-1H-pyrazol-5-yl)carbamate | 4.1 | 388 |

TABLE 1-continued

List of Compounds and Characterization Data

| Cmpd # | Structure | Name | LCMS RT (min)* | m/z (M + H)+ |
|---|---|---|---|---|
| 404 | 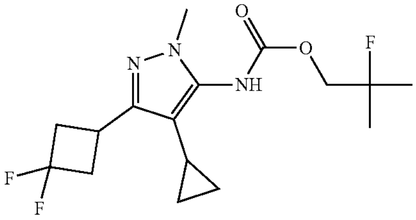 [SMILES: Cn1nc(C2CC(F)(F)C2)c(C2CC2)c1NC(=O)OCC(C)(C)F] | 2-fluoro-2-methylpropyl (4-cyclopropyl-3-(3,3-difluorocyclobutyl)-1-methyl-1H-pyrazol-5-yl)carbamate | 3.8 | 346 |
| 405 | 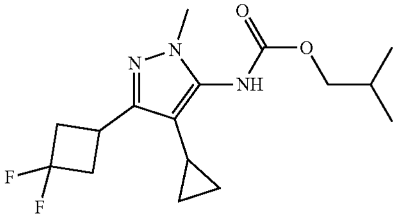 [SMILES: CC(C)COC(=O)Nc1c(C2CC2)c(C2CC(F)(F)C2)nn1C] | isobutyl (4-cyclopropyl-3-(3,3-difluorocyclobutyl)-1-methyl-1H-pyrazol-5-yl)carbamate | 4.0 | 328 |
| 406 | 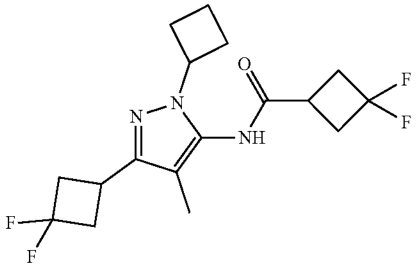 [SMILES: Cc1c(C2CC(F)(F)C2)nn(C2CCC2)c1NC(=O)C1CC(F)(F)C1] | N-(1-cyclobutyl-3-(3,3-difluorocyclobutyl)-4-methyl-1H-pyrazol-5-yl)-3,3-difluorocyclobutane-1-carboxamide | 4 | 360 |
| 407 | 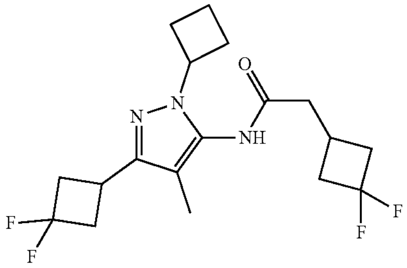 | N-(1-cyclobutyl-3-(3,3-difluorocyclobutyl)-4-methyl-1H-pyrazol-5-yl)-2-(3,3-difluorocyclobutyl)acetamide | 4.1 | 374 |
| 408 | 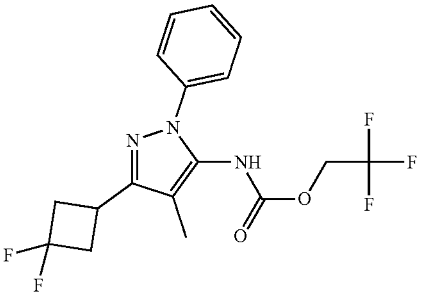 | 2,2,2-trifluoroethyl (3-(3,3-difluorocyclobutyl)-4-methyl-1-phenyl-1H-pyrazol-5-yl)carbamate | 4.1 | 390 |

TABLE 1-continued

| List of Compounds and Characterization Data | | | | |
|---|---|---|---|---|
| Cmpd # | Structure | Name | LCMS RT (min)* | m/z $(M + H)^+$ |
| 409 | 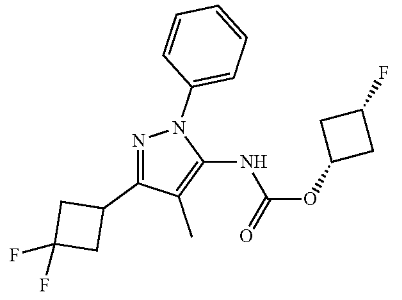 [SMILES: Cc1c(C2CC(F)(F)C2)nn(-c2ccccc2)c1NC(=O)O[C@H]1C[C@@H](F)C1] | (1s,3s)-3-fluorocyclobutyl (3-(3,3-difluorocyclobutyl)-4-methyl-1-phenyl-1H-pyrazol-5-yl)carbamate | 4.0 | 380 |
| 410 | 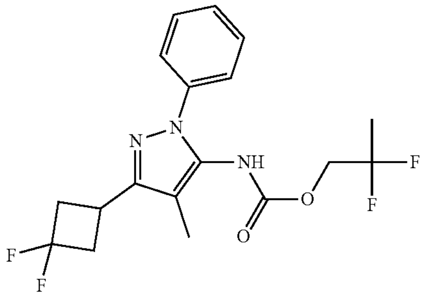 [SMILES: Cc1c(C2CC(F)(F)C2)nn(-c2ccccc2)c1NC(=O)OCC(C)(F)F] | 2,2-difluoropropyl (3-(3,3-difluorocyclobutyl)-4-methyl-1-phenyl-1H-pyrazol-5-yl)carbamate | 4.1 | 386 |
| 411 | 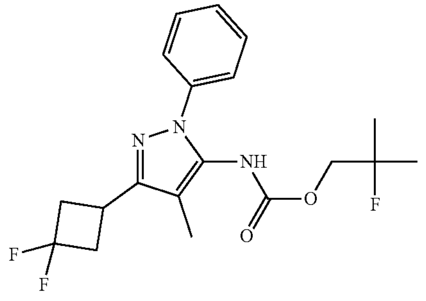 [SMILES: Cc1c(C2CC(F)(F)C2)nn(-c2ccccc2)c1NC(=O)OCC(C)(C)F] | 2-fluoro-2-methylpropyl (3-(3,3-difluorocyclobutyl)-4-methyl-1-phenyl-1H-pyrazol-5-yl)carbamate | 4.1 | 382 |
| 412 | 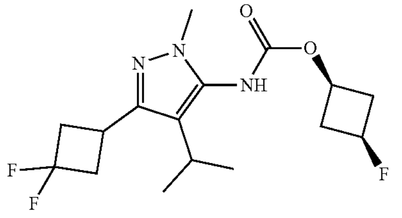 [SMILES: CC(C)c1c(C2CC(F)(F)C2)nn(C)c1NC(=O)O[C@H]1C[C@@H](F)C1] | (1s,3s)-3-fluorocyclobutyl (3-(3,3-difluorocyclobutyl)-4-isopropyl-1-methyl-1H-pyrazol-5-yl)carbamate | 3.9 | 346 |
| 413 | 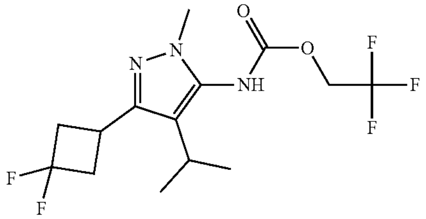 [SMILES: CC(C)c1c(C2CC(F)(F)C2)nn(C)c1NC(=O)OCC(F)(F)F] | 2,2,2-trifluoroethyl (3-(3,3-difluorocyclobutyl)-4-isopropyl-1-methyl-1H-pyrazol-5-yl)carbamate | 4.0 | 356 |

TABLE 1-continued

List of Compounds and Characterization Data

| Cmpd # | Structure | Name | LCMS RT (min)* | m/z (M + H)+ |
|---|---|---|---|---|
| 414 | 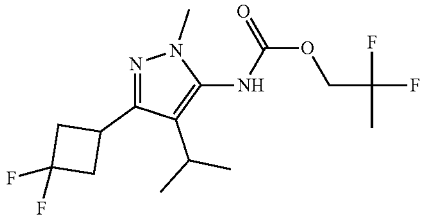 [SMILES: CC(C)c1c(C2CC(F)(F)C2)nn(C)c1NC(=O)OCC(C)(F)F] | 2,2-difluoropropyl (3-(3,3-difluorocyclobutyl)-4-isopropyl-1-methyl-1H-pyrazol-5-yl)carbamate | 3.9 | 352 |
| 415 | 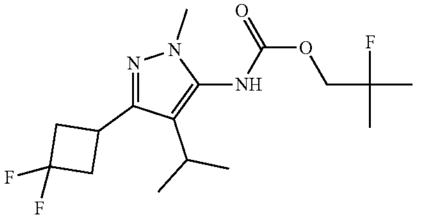 [SMILES: CC(C)c1c(C2CC(F)(F)C2)nn(C)c1NC(=O)OCC(C)(C)F] | 2-fluoro-2-methylpropyl (3-(3,3-difluorocyclobutyl)-4-isopropyl-1-methyl-1H-pyrazol-5-yl)carbamate | 4.0 | 348 |
| 416 | 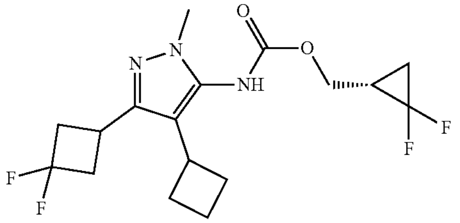 [SMILES: Cn1nc(C2CC(F)(F)C2)c(C2CCC2)c1NC(=O)OC[C@@H]1CC1(F)F] | (S)-(2,2-difluorocyclopropyl)methyl (4-cyclobutyl-3-(3,3-difluorocyclobutyl)-1-methyl-1H-pyrazol-5-yl)carbamate | 4.0 | 376 |
| 417 | 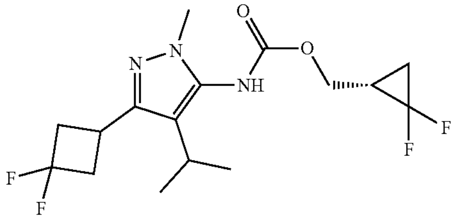 [SMILES: CC(C)c1c(C2CC(F)(F)C2)nn(C)c1NC(=O)OC[C@@H]1CC1(F)F] | (S)-(2,2-difluorocyclopropyl)methyl (3-(3,3-difluorocyclobutyl)-4-isopropyl-1-methyl-1H-pyrazol-5-yl)carbamate | 4.0 | 364 |
| 418 | 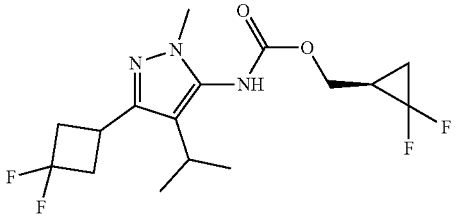 [SMILES: CC(C)c1c(C2CC(F)(F)C2)nn(C)c1NC(=O)OC[C@H]1CC1(F)F] | (R)-(2,2-difluorocyclopropyl)methyl (3-(3,3-difluorocyclobutyl)-4-isopropyl-1-methyl-1H-pyrazol-5-yl)carbamate | 4.0 | 364 |
| 419 | 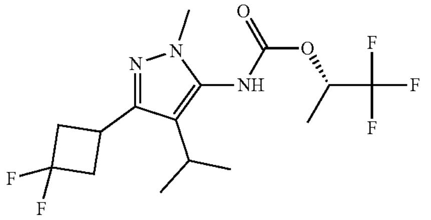 [SMILES: CC(C)c1c(C2CC(F)(F)C2)nn(C)c1NC(=O)O[C@@H](C)C(F)(F)F] | (S)-1,1,1-trifluoropropan-2-yl (3-(3,3-difluorocyclobutyl)-4-isopropyl-1-methyl-1H-pyrazol-5-yl)carbamate | 4.2 | 370 |

TABLE 1-continued

| List of Compounds and Characterization Data | | | | |
|---|---|---|---|---|
| Cmpd # | Structure | Name | LCMS RT (min)* | m/z (M + H)+ |
| 420 | 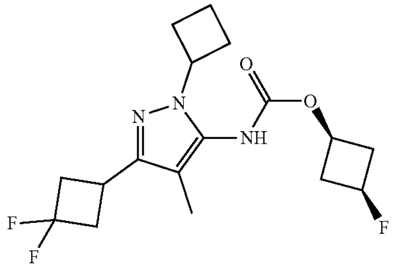 [SMILES: Cc1c(C2CC(F)(F)C2)nn(C2CCC2)c1NC(=O)O[C@H]1C[C@@H](F)C1] | (1s,3s)-3-fluorocyclobutyl (1-cyclobutyl-3-(3,3-difluorocyclobutyl)-4-methyl-1H-pyrazol-5-yl)carbamate | 4.1 | 358 |
| 421 | 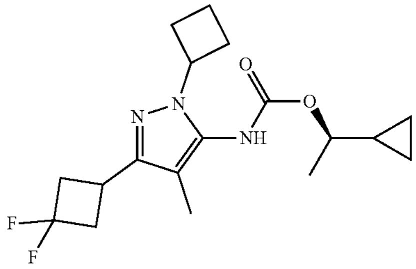 [SMILES: Cc1c(C2CC(F)(F)C2)nn(C2CCC2)c1NC(=O)O[C@H](C)C1CC1] | (R)-1-cyclopropylethyl (1-cyclobutyl-3-(3,3-difluorocyclobutyl)-4-methyl-1H-pyrazol-5-yl)carbamate | 4.4 | 354 |
| 422 | 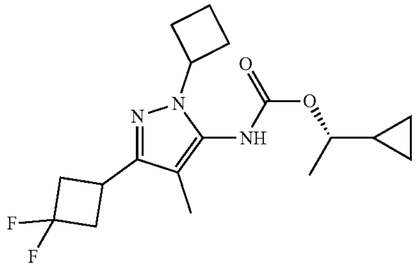 [SMILES: Cc1c(C2CC(F)(F)C2)nn(C2CCC2)c1NC(=O)O[C@@H](C)C1CC1] | (S)-1-cyclopropylethyl (1-cyclobutyl-3-(3,3-difluorocyclobutyl)-4-methyl-1H-pyrazol-5-yl)carbamate | 4.4 | 354 |
| 423 | 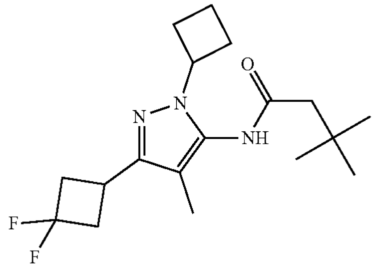 [SMILES: Cc1c(C2CC(F)(F)C2)nn(C2CCC2)c1NC(=O)CC(C)(C)C] | N-(1-cyclobutyl-3-(3,3-difluorocyclobutyl)-4-methyl-1H-pyrazol-5-yl)-3,3-dimethylbutanamide | 4.2 | 340 |
| 424 | 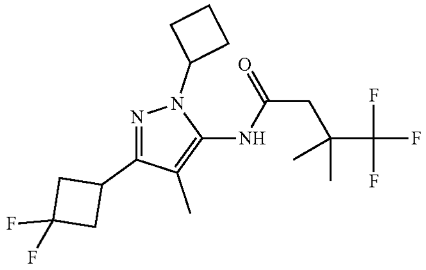 [SMILES: Cc1c(C2CC(F)(F)C2)nn(C2CCC2)c1NC(=O)CC(C)(C)C(F)(F)F] | N-(1-cyclobutyl-3-(3,3-difluorocyclobutyl)-4-methyl-1H-pyrazol-5-yl)-4,4,4-trifluoro-3,3-dimethylbutanamide | 4.4 | 394 |

TABLE 1-continued

List of Compounds and Characterization Data

| Cmpd # | Structure | Name | LCMS RT (min)* | m/z (M + H)+ |
|---|---|---|---|---|
| 425 | 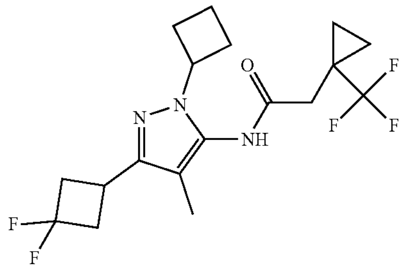 [SMILES: Cc1c(C2CC(F)(F)C2)nn(C2CCC2)c1NC(=O)CC1(C(F)(F)F)CC1] | N-(1-cyclobutyl-3-(3,3-difluorocyclobutyl)-4-methyl-1H-pyrazol-5-yl)-2-(1-(trifluoromethyl)cyclopropyl)acetamide | 4.2 | 392 |
| 426 | 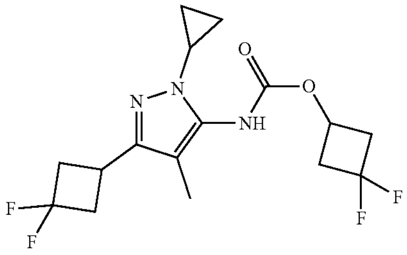 [SMILES: Cc1c(C2CC(F)(F)C2)nn(C2CC2)c1NC(=O)OC1CC(F)(F)C1] | 3,3-difluorocyclobutyl (1-cyclopropyl-3-(3,3-difluorocyclobutyl)-4-methyl-1H-pyrazol-5-yl)carbamate | 3.9 | 362 |
| 427 | 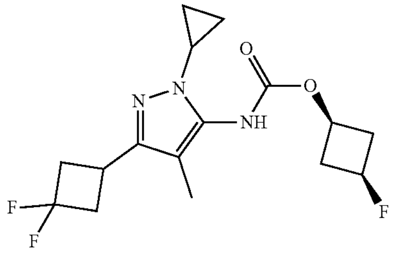 [SMILES: Cc1c(C2CC(F)(F)C2)nn(C2CC2)c1NC(=O)O[C@H]1C[C@@H](F)C1] | (1s,3s)-3-fluorocyclobutyl (1-cyclopropyl-3-(3,3-difluorocyclobutyl)-4-methyl-1H-pyrazol-5-yl)carbamate | 3.8 | 344 |
| 428 | 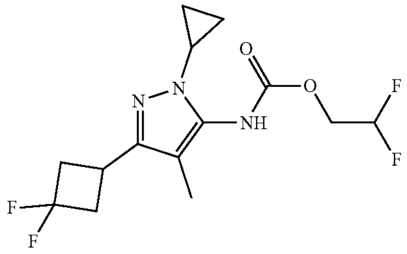 [SMILES: Cc1c(C2CC(F)(F)C2)nn(C2CC2)c1NC(=O)OCC(F)F] | 2,2-difluoroethyl (1-cyclopropyl-3-(3,3-difluorocyclobutyl)-4-methyl-1H-pyrazol-5-yl)carbamate | 3.7 | 336 |
| 429 | 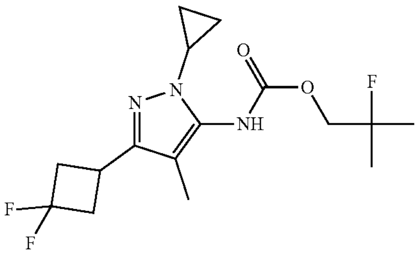 [SMILES: Cc1c(C2CC(F)(F)C2)nn(C2CC2)c1NC(=O)OCC(C)(C)F] | 2-fluoro-2-methylpropyl (1-cyclopropyl-3-(3,3-difluorocyclobutyl)-4-methyl-1H-pyrazol-5-yl)carbamate | 3.9 | 346 |

TABLE 1-continued

List of Compounds and Characterization Data

| Cmpd # | Structure | Name | LCMS RT (min)* | m/z (M + H)+ |
|---|---|---|---|---|
| 430 | 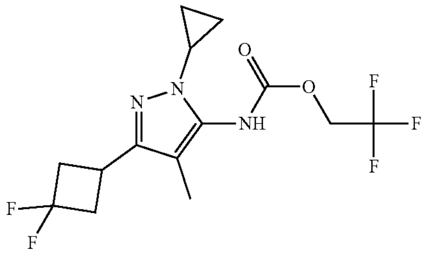 [SMILES: Cc1c(C2CC(F)(F)C2)nn(C2CC2)c1NC(=O)OCC(F)(F)F] | 2,2,2-trifluoroethyl (1-cyclopropyl-3-(3,3-difluorocyclobutyl)-4-methyl-1H-pyrazol-5-yl)carbamate | 3.9 | 354 |
| 431 | 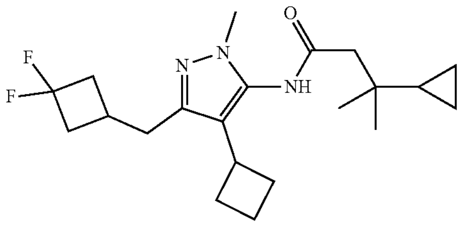 [SMILES: Cn1nc(CC2CC(F)(F)C2)c(C2CCC2)c1NC(=O)CC(C)(C)C1CC1] | N-(4-cyclobutyl-3-((3,3-difluorocyclobutyl)methyl)-1-methyl-1H-pyrazol-5-yl)-3-cyclopropyl-3-methylbutanamide | 4.4 | 380 |
| 432 | 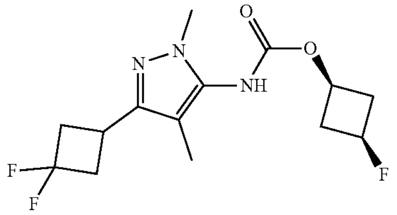 [SMILES: Cc1c(C2CC(F)(F)C2)nn(C)c1NC(=O)O[C@H]1C[C@@H](F)C1] | (1s,3s)-3-fluorocyclobutyl (3-(3,3-difluorocyclobutyl)-1,4-dimethyl-1H-pyrazol-5-yl)carbamate | 3.5 | 318 |
| 433 | 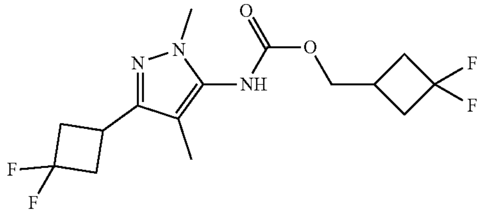 [SMILES: Cc1c(C2CC(F)(F)C2)nn(C)c1NC(=O)OCC1CC(F)(F)C1] | (3,3-difluorocyclobutyl)methyl (3-(3,3-difluorocyclobutyl)-1,4-dimethyl-1H-pyrazol-5-yl)carbamate | 3.8 | 350 |
| 434 | 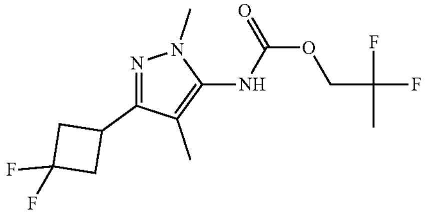 | 2,2-difluoropropyl (3-(3,3-difluorocyclobutyl)-1,4-dimethyl-1H-pyrazol-5-yl)carbamate | 3.6 | 324 |
| 435 | 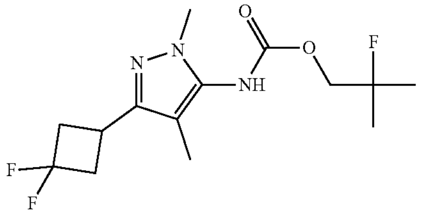 [SMILES: Cc1c(C2CC(F)(F)C2)nn(C)c1NC(=O)OCC(C)(C)F] | 2-fluoro-2-methylpropyl (3-(3,3-difluorocyclobutyl)-1,4-dimethyl-1H-pyrazol-5-yl)carbamate | 3.7 | 320 |

TABLE 1-continued

| List of Compounds and Characterization Data | | | | |
|---|---|---|---|---|
| Cmpd # | Structure | Name | LCMS RT (min)* | m/z $(M + H)^+$ |
| 436 | 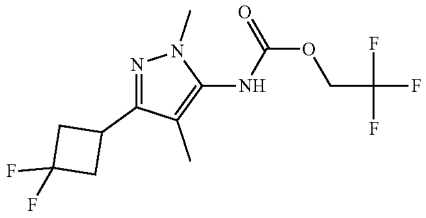 [SMILES: Cc1c(C2CC(F)(F)C2)nn(C)c1NC(=O)OCC(F)(F)F] | 2,2,2-trifluoroethyl (3-(3,3-difluorocyclobutyl)-1,4-dimethyl-1H-pyrazol-5-yl)carbamate | 3.7 | 328 |
| 437 | 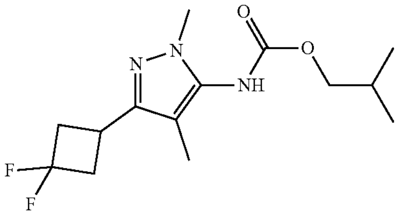 [SMILES: Cc1c(C2CC(F)(F)C2)nn(C)c1NC(=O)OCC(C)C] | isobutyl (3-(3,3-difluorocyclobutyl)-1,4-dimethyl-1H-pyrazol-5-yl)carbamate | 3.8 | 302 |
| 438 | 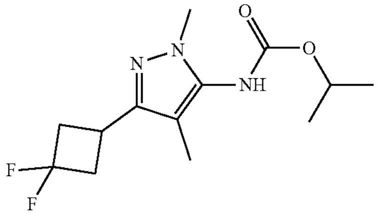 [SMILES: Cc1c(C2CC(F)(F)C2)nn(C)c1NC(=O)OC(C)C] | isopropyl (3-(3,3-difluorocyclobutyl)-1,4-dimethyl-1H-pyrazol-5-yl)carbamate | 3.6 | 288 |
| 439 | 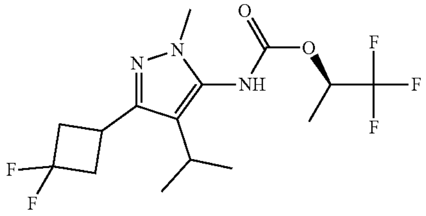 [SMILES: CC(C)c1c(C2CC(F)(F)C2)nn(C)c1NC(=O)O[C@H](C)C(F)(F)F] | (R)-1,1,1-trifluoropropan-2-yl (3-(3,3-difluorocyclobutyl)-4-isopropyl-1-methyl-1H-pyrazol-5-yl)carbamate | 4.2 | 370 |
| 440 | 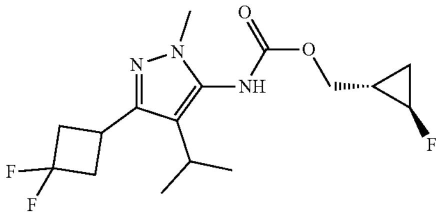 [SMILES: CC(C)c1c(C2CC(F)(F)C2)nn(C)c1NC(=O)OC[C@@H]1C[C@H]1F] | ((1S,2R)-2-fluorocyclopropyl)methyl (3-(3,3-difluorocyclobutyl)-4-isopropyl-1-methyl-1H-pyrazol-5-yl)carbamate | 3.9 | 346 |
| 441 | 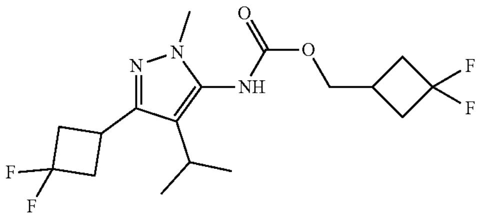 [SMILES: CC(C)c1c(C2CC(F)(F)C2)nn(C)c1NC(=O)OCC1CC(F)(F)C1] | (3,3-difluorocyclobutyl)methyl (3-(3,3-difluorocyclobutyl)-4-isopropyl-1-methyl-1H-pyrazol-5-yl)carbamate | 4.0 | 378 |

TABLE 1-continued

| List of Compounds and Characterization Data | | | | |
|---|---|---|---|---|
| Cmpd # | Structure | Name | LCMS RT (min)* | m/z $(M + H)^+$ |
| 442 | 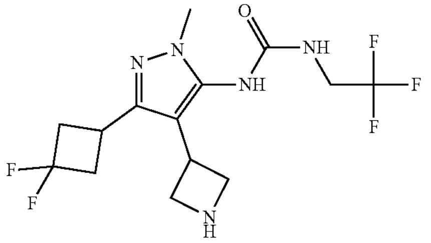 [SMILES: Cn1nc(C2CC(F)(F)C2)c(C2CNC2)c1NC(=O)NCC(F)(F)F] | 1-(4-(azetidin-3-yl)-3-(3,3-difluorocyclobutyl)-1-methyl-1H-pyrazol-5-yl)-3-(2,2,2-trifluoroethyl)urea | 2.3 | 368 |
| 443 | 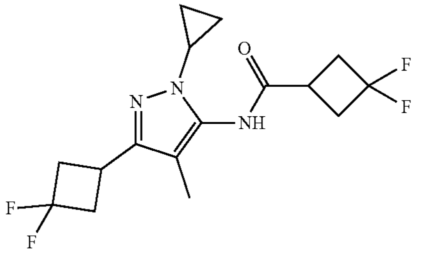 [SMILES: Cc1c(C2CC(F)(F)C2)nn(C2CC2)c1NC(=O)C1CC(F)(F)C1] | N-(1-cyclopropyl-3-(3,3-difluorocyclobutyl)-4-methyl-1H-pyrazol-5-yl)-3,3-difluorocyclobutane-1-carboxamide | 3.7 | 346 |
| 444 | 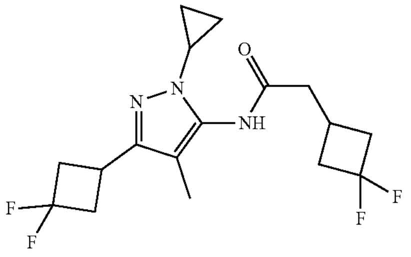 [SMILES: Cc1c(C2CC(F)(F)C2)nn(C2CC2)c1NC(=O)CC1CC(F)(F)C1] | N-(1-cyclopropyl-3-(3,3-difluorocyclobutyl)-4-methyl-1H-pyrazol-5-yl)-2-(3,3-difluorocyclobutyl)acetamide | 3.7 | 360 |
| 445 | 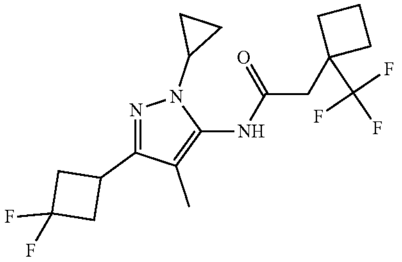 [SMILES: Cc1c(C2CC(F)(F)C2)nn(C2CC2)c1NC(=O)CC1(C(F)(F)F)CCC1] | N-(1-cyclopropyl-3-(3,3-difluorocyclobutyl)-4-methyl-1H-pyrazol-5-yl)-2-(1-(trifluoromethyl)cyclobutyl)acetamide | 4.1 | 392 |
| 446 | 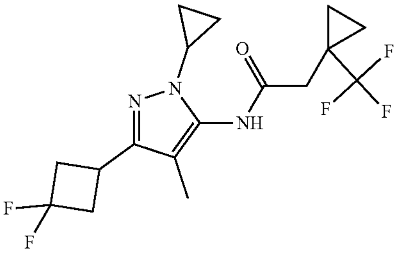 [SMILES: Cc1c(C2CC(F)(F)C2)nn(C2CC2)c1NC(=O)CC1(C(F)(F)F)CC1] | N-(1-cyclopropyl-3-(3,3-difluorocyclobutyl)-4-methyl-1H-pyrazol-5-yl)-2-(1-(trifluoromethyl)cyclopropyl)acetamide | 3.9 | 378 |

TABLE 1-continued

List of Compounds and Characterization Data

| Cmpd # | Structure | Name | LCMS RT (min)* | m/z (M + H)+ |
|---|---|---|---|---|
| 447 | 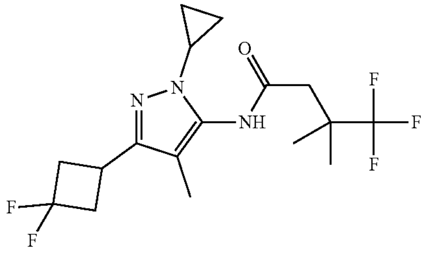 [SMILES: Cc1c(C2CC(F)(F)C2)nn(C2CC2)c1NC(=O)CC(C)(C)C(F)(F)F] | N-(1-cyclopropyl-3-(3,3-difluorocyclobutyl)-4-methyl-1H-pyrazol-5-yl)-4,4,4-trifluoro-3,3-dimethylbutanamide | 4.1 | 380 |
| 448 | 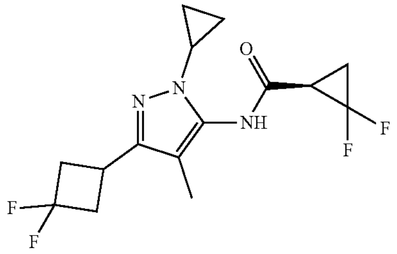 [SMILES: Cc1c(C2CC(F)(F)C2)nn(C2CC2)c1NC(=O)[C@H]1CC1(F)F] | (R)-N-(1-cyclopropyl-3-(3,3-difluorocyclobutyl)-4-methyl-1H-pyrazol-5-yl)-2,2-difluorocyclopropane-1-carboxamide | 3.6 | 332 |
| 449 | 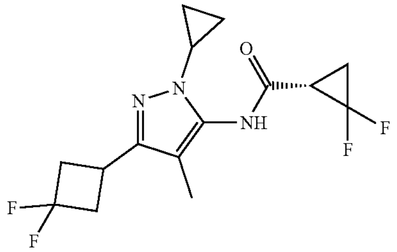 [SMILES: Cc1c(C2CC(F)(F)C2)nn(C2CC2)c1NC(=O)[C@@H]1CC1(F)F] | (S)-N-(1-cyclopropyl-3-(3,3-difluorocyclobutyl)-4-methyl-1H-pyrazol-5-yl)-2,2-difluorocyclopropane-1-carboxamide | 3.6 | 332 |
| 450 | 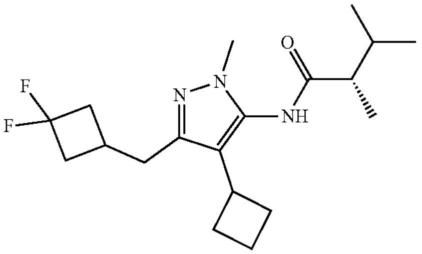 [SMILES: CC(C)[C@H](C)C(=O)Nc1c(C2CCC2)c(CC2CC(F)(F)C2)nn1C] | (S)-N-(4-cyclobutyl-3-((3,3-difluorocyclobutyl)methyl)-1-methyl-1H-pyrazol-5-yl)-2,3-dimethylbutanamide | 4.1 | 354 |
| 451 | 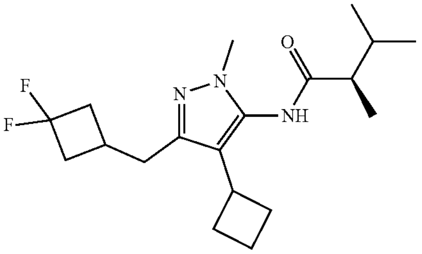 [SMILES: CC(C)[C@@H](C)C(=O)Nc1c(C2CCC2)c(CC2CC(F)(F)C2)nn1C] | (R)-N-(4-cyclobutyl-3-((3,3-difluorocyclobutyl)methyl)-1-methyl-1H-pyrazol-5-yl)-2,3-dimethylbutanamide | 4.1 | 354 |
| 452 | 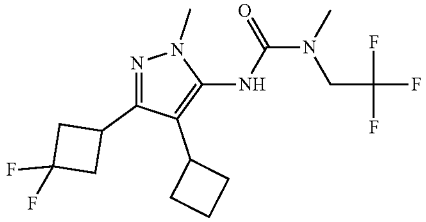 [SMILES: CN(CC(F)(F)F)C(=O)Nc1c(C2CCC2)c(C2CC(F)(F)C2)nn1C] | 3-(4-cyclobutyl-3-(3,3-difluorocyclobutyl)-1-methyl-1H-pyrazol-5-yl)-1-methyl-1-(2,2,2-trifluoroethyl)urea | 3.8 | 381 |

TABLE 1-continued

| List of Compounds and Characterization Data | | | | |
|---|---|---|---|---|
| Cmpd # | Structure | Name | LCMS RT (min)* | m/z $(M + H)^+$ |
| 453 | 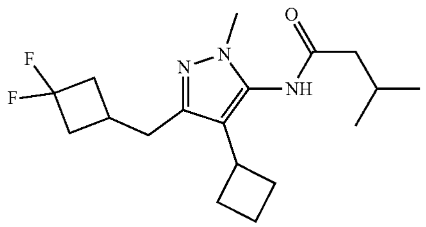 [SMILES: CC(C)CC(=O)Nc1c(C2CCC2)c(CC2CC(F)(F)C2)nn1C] | N-(4-cyclobutyl-3-((3,3-difluorocyclobutyl)methyl)-1-methyl-1H-pyrazol-5-yl)-3-methylbutanamide | 3.8 | 340 |
| 454 | 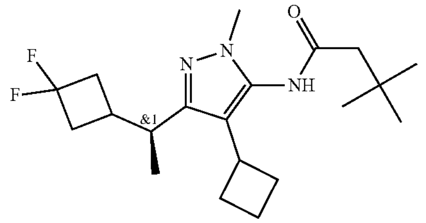 [SMILES: C[C@H](c1nn(C)c(NC(=O)CC(C)(C)C)c1C1CCC1)C1CC(F)(F)C1] | rac-(R)-N-(4-cyclobutyl-3-(1-(3,3-difluorocyclobutyl)ethyl)-1-methyl-1H-pyrazol-5-yl)-3,3-dimethylbutanamide | 4.3 | 368 |
| 455 | 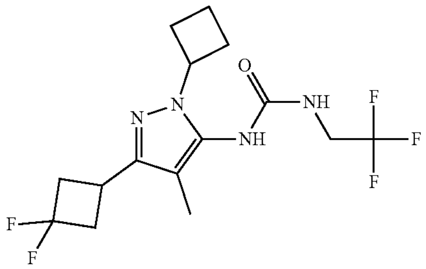 [SMILES: Cc1c(C2CC(F)(F)C2)nn(C2CCC2)c1NC(=O)NCC(F)(F)F] | 1-(1-cyclobutyl-3-(3,3-difluorocyclobutyl)-4-methyl-1H-pyrazol-5-yl)-3-(2,2,2-trifluoroethyl)urea | 3.8 | 367 |
| 456 | 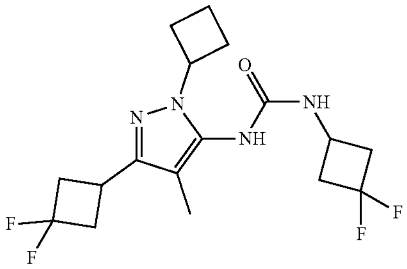 | 1-(1-cyclobutyl-3-(3,3-difluorocyclobutyl)-4-methyl-1H-pyrazol-5-yl)-3-(3,3-difluorocyclobutyl)urea | 3.8 | 375 |
| 457 | 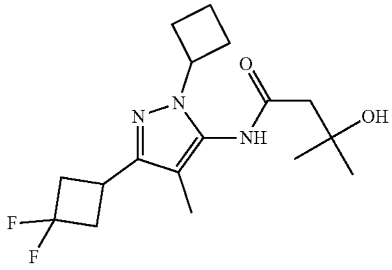 [SMILES: Cc1c(C2CC(F)(F)C2)nn(C2CCC2)c1NC(=O)CC(C)(C)O] | N-(1-cyclobutyl-3-(3,3-difluorocyclobutyl)-4-methyl-1H-pyrazol-5-yl)-3-hydroxy-3-methylbutanamide | 3.5 | 342 |

TABLE 1-continued

List of Compounds and Characterization Data

| Cmpd # | Structure | Name | LCMS RT (min)* | m/z (M + H)+ |
| --- | --- | --- | --- | --- |
| 458 | 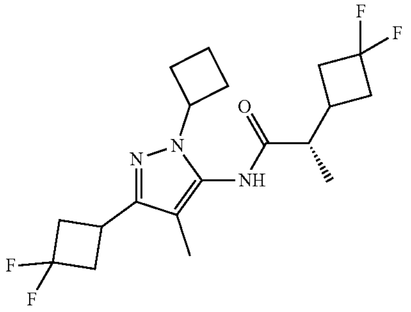 [SMILES: Cc1c(C2CC(F)(F)C2)nn(C2CCC2)c1NC(=O)[C@@H](C)C1CC(F)(F)C1] | (S)-N-(1-cyclobutyl-3-(3,3-difluorocyclobutyl)-4-methyl-1H-pyrazol-5-yl)-2-(3,3-difluorocyclobutyl)propenamide | 4.1 | 388 |
| 459 | 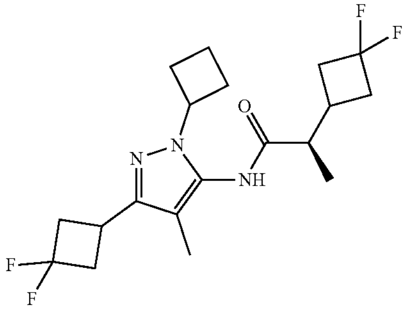 [SMILES: Cc1c(C2CC(F)(F)C2)nn(C2CCC2)c1NC(=O)[C@H](C)C1CC(F)(F)C1] | (R)-N-(1-cyclobutyl-3-(3,3-difluorocyclobutyl)-4-methyl-1H-pyrazol-5-yl)-2-(3,3-difluorocyclobutyl)propanamide | 4.1 | 388 |
| 460 | 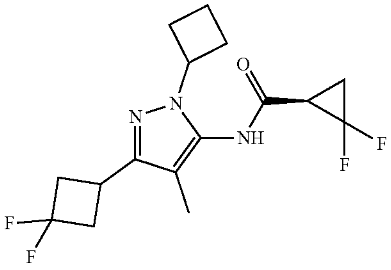 [SMILES: Cc1c(C2CC(F)(F)C2)nn(C2CCC2)c1NC(=O)[C@H]1CC1(F)F] | (R)-N-(1-cyclobutyl-3-(3,3-difluorocyclobutyl)-4-methyl-1H-pyrazol-5-yl)-2,2-difluorocyclopropane-1-carboxamide | 4.0 | 346 |
| 461 | 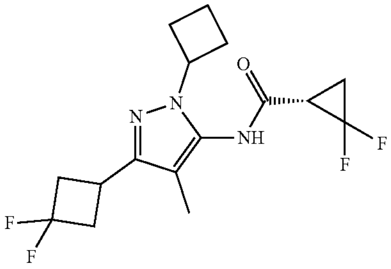 [SMILES: Cc1c(C2CC(F)(F)C2)nn(C2CCC2)c1NC(=O)[C@@H]1CC1(F)F] | (S)-N-(1-cyclobutyl-3-(3,3-difluorocyclobutyl)-4-methyl-1H-pyrazol-5-yl)-2,2-difluorocyclopropane-1-carboxamide | 4.0 | 346 |
| 462 | 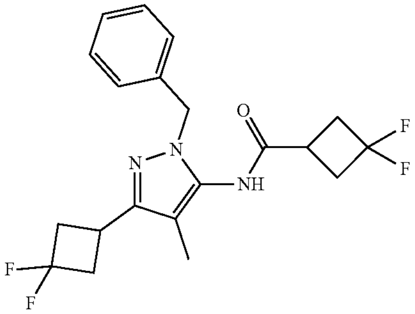 [SMILES: Cc1c(C2CC(F)(F)C2)nn(Cc2ccccc2)c1NC(=O)C1CC(F)(F)C1] | N-(1-benzyl-3-(3,3-difluorocyclobutyl)-4-methyl-1H-pyrazol-5-yl)-3,3-difluorocyclobutane-1-carboxamide | 4.0 | 396 |

TABLE 1-continued

| List of Compounds and Characterization Data | | | | |
|---|---|---|---|---|
| Cmpd # | Structure | Name | LCMS RT (min)* | m/z (M + H)+ |
| 463 | 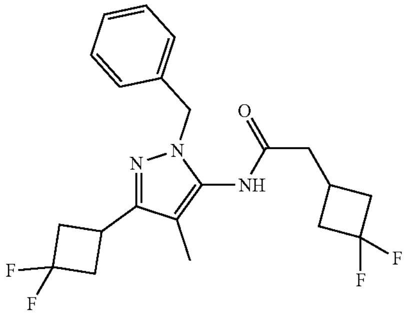 [SMILES: Cc1c(C2CC(F)(F)C2)nn(Cc2ccccc2)c1NC(=O)CC1CC(F)(F)C1] | N-(1-benzyl-3-(3,3-difluorocyclobutyl)-4-methyl-1H-pyrazol-5-yl)-2-(3,3-difluorocyclobutyl)acetamide | 4 | 410 |
| 464 | 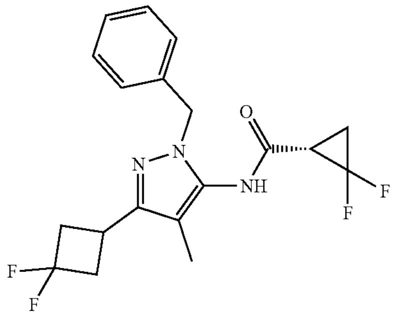 [SMILES: Cc1c(C2CC(F)(F)C2)nn(Cc2ccccc2)c1NC(=O)[C@@H]1CC1(F)F] | (S)-N-(1-benzyl-3-(3,3-difluorocyclobutyl)-4-methyl-1H-pyrazol-5-yl)-2,2-difluorocyclopropane-1-carboxamide | 3.9 | 382 |
| 465 | 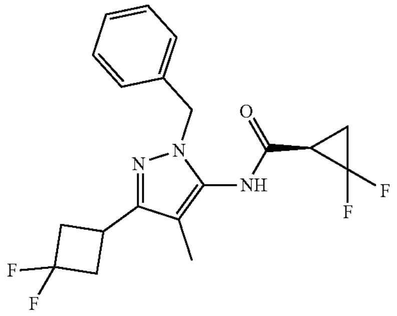 [SMILES: Cc1c(C2CC(F)(F)C2)nn(Cc2ccccc2)c1NC(=O)[C@H]1CC1(F)F] | (R)-N-(1-benzyl-3-(3,3-difluorocyclobutyl)-4-methyl-1H-pyrazol-5-yl)-2,2-difluorocyclopropane-1-carboxamide | 3.9 | 382 |
| 466 | 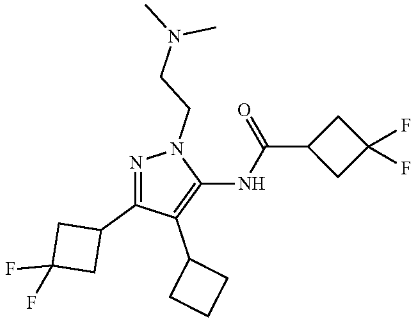 [SMILES: CN(C)CCn1nc(C2CC(F)(F)C2)c(C2CCC2)c1NC(=O)C1CC(F)(F)C1] | N-(4-cyclobutyl-3-(3,3-difluorocyclobutyl)-1-(2-(dimethylamino)ethyl)-1H-pyrazol-5-yl)-3,3-difluorocyclobutane-1-carboxamide | 2.9 | 417 |

TABLE 1-continued

| List of Compounds and Characterization Data | | | | |
|---|---|---|---|---|
| Cmpd # | Structure | Name | LCMS RT (min)* | m/z (M + H)+ |
| 467 | 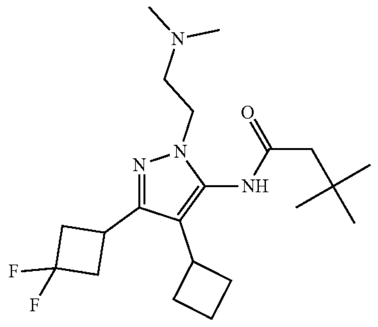 [SMILES: CN(C)CCn1nc(C2CC(F)(F)C2)c(C2CCC2)c1NC(=O)CC(C)(C)C] | N-(4-cyclobutyl-3-(3,3-difluorocyclobutyl)-1-(2-(dimethylamino)ethyl)-1H-pyrazol-5-yl)-3,3-dimethylbutanamide | 3.0 | 397 |
| 468 | 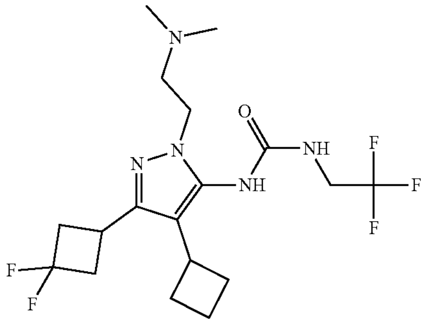 [SMILES: CN(C)CCn1nc(C2CC(F)(F)C2)c(C2CCC2)c1NC(=O)NCC(F)(F)F] | 1-(4-cyclobutyl-3-(3,3-difluorocyclobutyl)-1-(2-(dimethylamino)ethyl)-1H-pyrazol-5-yl)-3-(2,2,2-trifluoroethyl)urea | 2.8 | 424 |
| 469 | 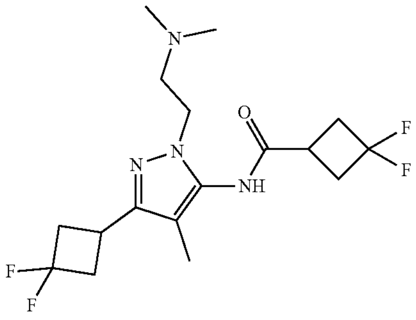 [SMILES: Cc1c(C2CC(F)(F)C2)nn(CCN(C)C)c1NC(=O)C1CC(F)(F)C1] | N-(3-(3,3-difluorocyclobutyl)-1-(2-(dimethylamino)ethyl)-4-methyl-1H-pyrazol-5-yl)-3,3-difluorocyclobutane-1-carboxamide | 2.7 | 377 |
| 470 | 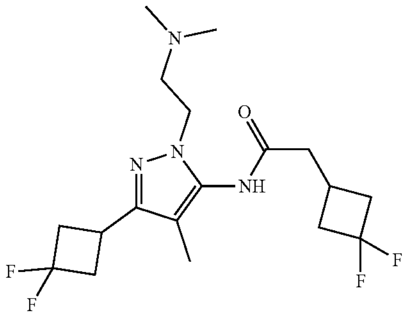 [SMILES: Cc1c(C2CC(F)(F)C2)nn(CCN(C)C)c1NC(=O)CC1CC(F)(F)C1] | 2-(3,3-difluorocyclobutyl)-N-(3-(3,3-difluorocyclobutyl)-1-(2-(dimethylamino)ethyl)-4-methyl-1H-pyrazol-5-yl)acetamide | 2.7 | 391 |

TABLE 1-continued

| List of Compounds and Characterization Data | | | | |
|---|---|---|---|---|
| Cmpd # | Structure | Name | LCMS RT (min)* | m/z (M + H)+ |
| 471 | 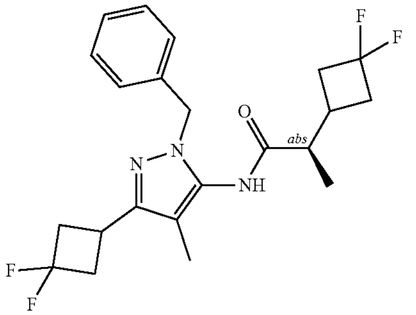 [SMILES: Cc1c(C2CC(F)(F)C2)nn(Cc2ccccc2)c1NC(=O)[C@H](C)C1CC(F)(F)C1] | (R)-N-(1-benzyl-3-(3,3-difluorocyclobutyl)-4-methyl-1H-pyrazol-5-yl)-2-(3,3-difluorocyclobutyl)propanamide | 4.1 | 424 |
| 472 | 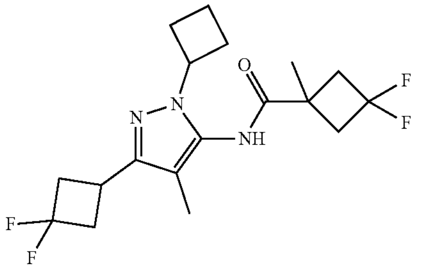 [SMILES: Cc1c(C2CC(F)(F)C2)nn(C2CCC2)c1NC(=O)C1(C)CC(F)(F)C1] | N-(1-cyclobutyl-3-(3,3-difluorocyclobutyl)-4-methyl-1H-pyrazol-5-yl)-3,3-difluoro-1-methylcyclobutane-1-carboxamide | 4.1 | 374 |
| 473 | 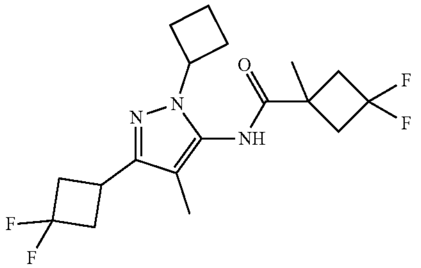 [SMILES: Cc1c(C2CC(F)(F)C2)nn(C2CCC2)c1NC(=O)C1(C)CC(F)(F)C1] | N-(3-(3,3-difluorocyclobutyl)-4-methyl-1-(1-methylcyclobutyl)-1H-pyrazol-5-yl)-3,3-difluorocyclobutane-1-carboxamide | 4.0 | 374 |
| 474 | 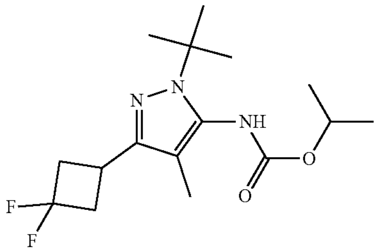 [SMILES: Cc1c(C2CC(F)(F)C2)nn(C(C)(C)C)c1NC(=O)OC(C)C] | isopropyl (1-(tert-butyl)-3-(3,3-difluorocyclobutyl)-4-methyl-1H-pyrazol-5-yl)carbamate | 16.5 | 328.8** |
| 475 | 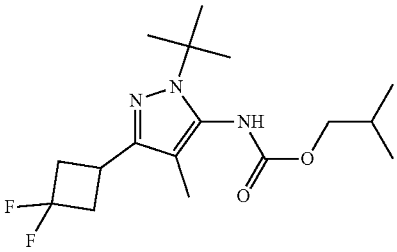 [SMILES: Cc1c(C2CC(F)(F)C2)nn(C(C)(C)C)c1NC(=O)OCC(C)C] | isobutyl (1-(tert-butyl)-3-(3,3-difluorocyclobutyl)-4-methyl-1H-pyrazol-5-yl)carbamate | 16.5 | 342.8** |

TABLE 1-continued

| List of Compounds and Characterization Data | | | | |
|---|---|---|---|---|
| Cmpd # | Structure | Name | LCMS RT (min)* | m/z (M + H)+ |
| 476 | 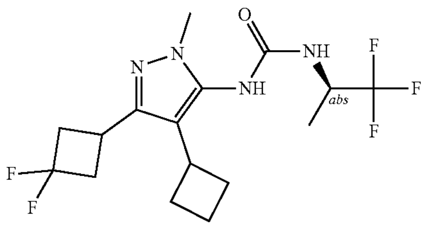 [SMILES: C[C@@H](NC(=O)Nc1c(C2CCC2)c(C2CC(F)(F)C2)nn1C)C(F)(F)F] | (R)-1-(4-cyclobutyl-3-(3,3-difluorocyclobutyl)-1-methyl-1H-pyrazol-5-yl)-3-(1, 1,1-trifluoropropan-2-yl)urea | 16 | 379.7** |
| 477 | 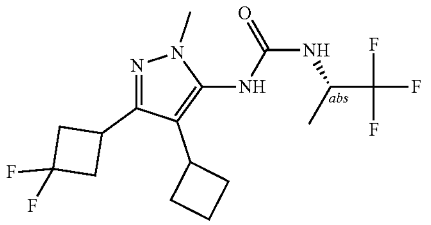 [SMILES: C[C@H](NC(=O)Nc1c(C2CCC2)c(C2CC(F)(F)C2)nn1C)C(F)(F)F] | (S)-1-(4-cyclobutyl-3-(3,3-difluorocyclobutyl)-1-methyl-1H-pyrazol-5-yl)-3-(1,1,1-trifluoropropan-2-yl)urea | 16 | 379.3** |
| 478 | 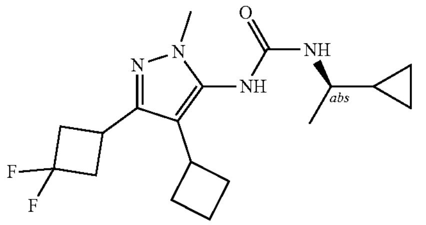 [SMILES: C[C@@H](NC(=O)Nc1c(C2CCC2)c(C2CC(F)(F)C2)nn1C)C1CC1] | (R)-1-(4-cyclobutyl-3-(3,3-difluorocyclobutyl)-1-methyl-1H-pyrazol-5-yl)-3-(1-cyclopropylethyl)urea | 16.2 | 351.2** |
| 479 | 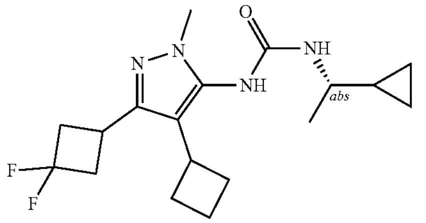 [SMILES: C[C@H](NC(=O)Nc1c(C2CCC2)c(C2CC(F)(F)C2)nn1C)C1CC1] | (S)-1-(4-cyclobutyl-3-(3,3-difluorocyclobutyl)-1-methyl-1H-pyrazol-5-yl)-3-(1-cyclopropylethyl)urea | 16.2 | 351.3** |
| 480 | 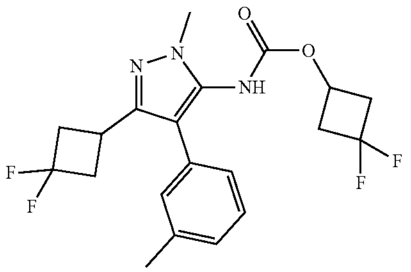 [SMILES: Cc1cccc(-c2c(C3CC(F)(F)C3)nn(C)c2NC(=O)OC2CC(F)(F)C2)c1] | 3,3-difluorocyclobutyl (3-(3,3-difluorocyclobutyl)-1-methyl-4-(m-tolyl)-1H-pyrazol-5-yl)carbamate | 4.14 | 412 |
| 481 | 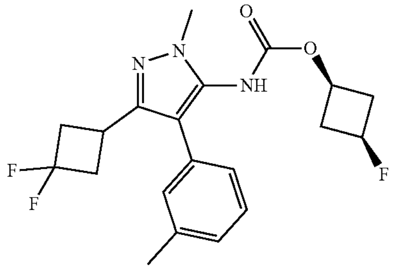 [SMILES: Cc1cccc(-c2c(C3CC(F)(F)C3)nn(C)c2NC(=O)O[C@H]2C[C@@H](F)C2)c1] | (1s,3s)-3-fluorocyclobutyl (3-(3,3-difluorocyclobutyl)-1-methyl-4-(m-tolyl)-1H-pyrazol-5-yl)carbamate | 4.04 | 394 |

TABLE 1-continued

List of Compounds and Characterization Data

| Cmpd # | Structure | Name | LCMS RT (min)* | m/z (M + H)+ |
|---|---|---|---|---|
| 482 | 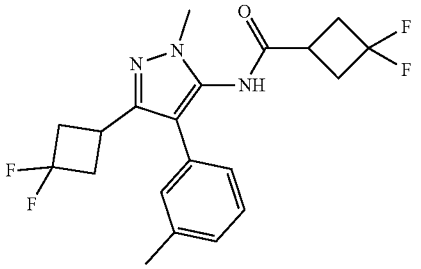 [SMILES: Cc1cccc(-c2c(C3CC(F)(F)C3)nn(C)c2NC(=O)C2CC(F)(F)C2)c1] | N-(3-(3,3-difluorocyclobutyl)-1-methyl-4-(m-tolyl)-1H-pyrazol-5-yl)-3,3-difluorocyclobutane-1-carboxamide | 4.01 | 396 |
| 483 | 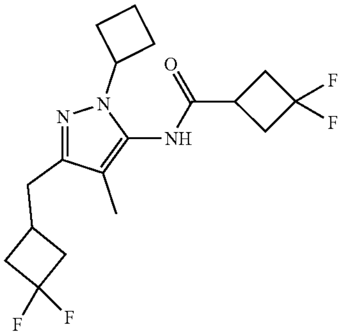 [SMILES: Cc1c(CC2CC(F)(F)C2)nn(C2CCC2)c1NC(=O)C1CC(F)(F)C1] | N-(1-cyclobutyl-3-((3,3-difluorocyclobutyl)methyl)-4-methyl-1H-pyrazol-5-yl)-3,3-difluorocyclobutane-1-carboxamide | 3.9 | 374 |
| 484 | 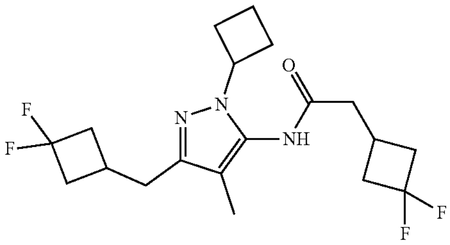 [SMILES: Cc1c(CC2CC(F)(F)C2)nn(C2CCC2)c1NC(=O)CC1CC(F)(F)C1] | N-(1-cyclobutyl-3-((3,3-difluorocyclobutyl)methyl)-4-methyl-1H-pyrazol-5-yl)-2-(3,3-difluorocyclobutyl)acetamide | 3.9 | 388 |
| 485 | 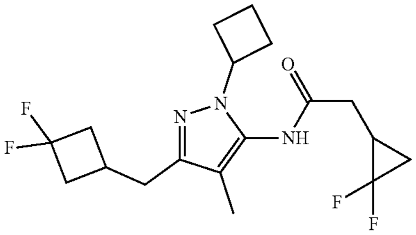 [SMILES: Cc1c(CC2CC(F)(F)C2)nn(C2CCC2)c1NC(=O)CC1CC1(F)F] | N-(1-cyclobutyl-3-((3,3-difluorocyclobutyl)methyl)-4-methyl-1H-pyrazol-5-yl)-2-(2,2-difluorocyclopropyl)acetamide | 3.9 | 374 |
| 486 | 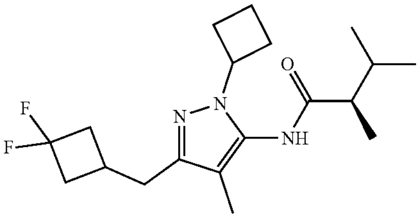 [SMILES: Cc1c(CC2CC(F)(F)C2)nn(C2CCC2)c1NC(=O)[C@H](C)C(C)C] | (R)-N-(1-cyclobutyl-3-((3,3-difluorocyclobutyl)methyl)-4-methyl-1H-pyrazol-5-yl)-2,3-dimethylbutanamide | 4.1 | 354 |

TABLE 1-continued

List of Compounds and Characterization Data

| Cmpd # | Structure | Name | LCMS RT (min)* | m/z (M + H)+ |
|---|---|---|---|---|
| 487 | 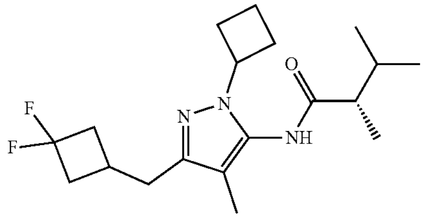 [SMILES: Cc1c(CC2CC(F)(F)C2)nn(C2CCC2)c1NC(=O)[C@@H](C)C(C)C] | (S)-N-(1-cyclobutyl-3-((3,3-difluorocyclobutyl)methyl)-4-methyl-1H-pyrazol-5-yl)-2,3-dimethylbutanamide | 4.1 | 354 |
| 488 | 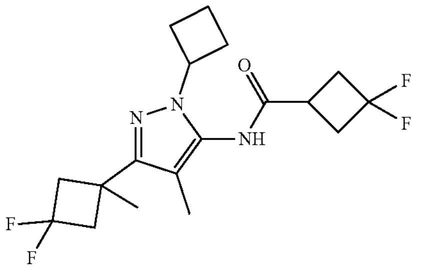 [SMILES: Cc1c(C2(C)CC(F)(F)C2)nn(C2CCC2)c1NC(=O)C1CC(F)(F)C1] | N-(1-cyclobutyl-3-(3,3-difluoro-1-methylcyclobutyl)-4-methyl-1H-pyrazol-5-yl)-3,3-difluorocyclobutane-1-carboxamide | 4.1<br>4.08 | 374.0 |
| 489 | 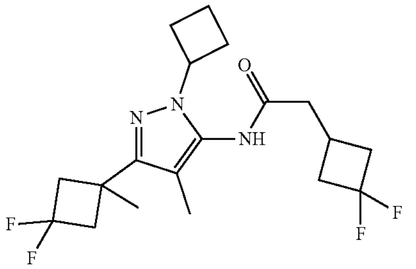 [SMILES: Cc1c(C2(C)CC(F)(F)C2)nn(C2CCC2)c1NC(=O)CC1CC(F)(F)C1] | N-(1-cyclobutyl-3-(3,3-difluoro-1-methylcyclobutyl)-4-methyl-1H-pyrazol-5-yl)-2-(3,3-difluorocyclobutyl)acetamide | 4.1 | 388 |
| 490 | 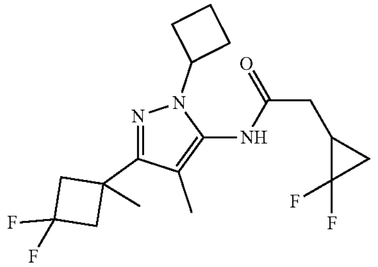 [SMILES: Cc1c(C2(C)CC(F)(F)C2)nn(C2CCC2)c1NC(=O)CC1CC1(F)F] | N-(1-cyclobutyl-3-(3,3-difluoro-1-methylcyclobutyl)-4-methyl-1H-pyrazol-5-yl)-2-(2,2-difluorocyclopropyl)acetamide | 4.03 | 374 |
| 491 | 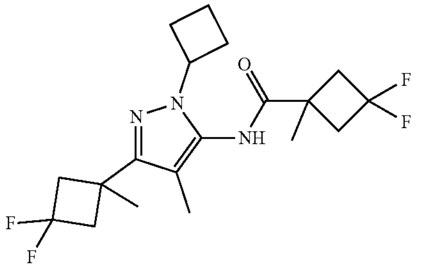 [SMILES: Cc1c(C2(C)CC(F)(F)C2)nn(C2CCC2)c1NC(=O)C1(C)CC(F)(F)C1] | N-(1-cyclobutyl-3-(3,3-difluoro-1-methylcyclobutyl)-4-methyl-1H-pyrazol-5-yl)-3,3-difluoro-1-methylcyclobutane-1-carboxamide | 4.2 | 388 |

TABLE 1-continued

List of Compounds and Characterization Data

| Cmpd # | Structure | Name | LCMS RT (min)* | m/z (M + H)+ |
| --- | --- | --- | --- | --- |
| 492 | 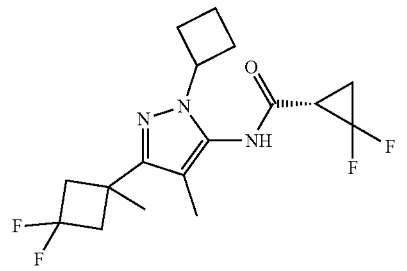 [SMILES: Cc1c(C2(C)CC(F)(F)C2)nn(C2CCC2)c1NC(=O)[C@@H]1CC1(F)F] | (S)-N-(1-cyclobutyl-3-(3,3-difluoro-1-methylcyclobutyl)-4-methyl-1H-pyrazol-5-yl)-2,2-difluorocyclopropane-1-carboxamide | 4 | 360 |
| 493 | 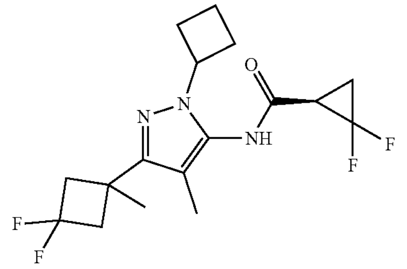 [SMILES: Cc1c(C2(C)CC(F)(F)C2)nn(C2CCC2)c1NC(=O)[C@H]1CC1(F)F] | (R)-N-(1-cyclobutyl-3-(3,3-difluoro-1-methylcyclobutyl)-4-methyl-1H-pyrazol-5-yl)-2,2-difluorocyclopropane-1-carboxamide | 4 | 360 |
| 494 | 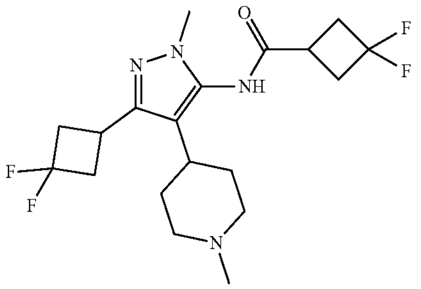 [SMILES: CN1CCC(c2c(C3CC(F)(F)C3)nn(C)c2NC(=O)C2CC(F)(F)C2)CC1] | N-(3-(3,3-difluorocyclobutyl)-1-methyl-4-(1-methylpiperidin-4-yl)-1H-pyrazol-5-yl)-3,3-difluorocyclobutane-1-carboxamide | 2.52 | 403 |
| 495 | 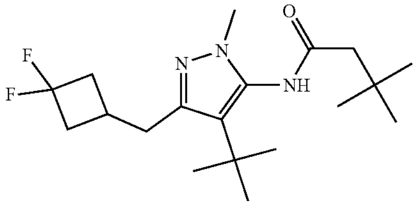 [SMILES: Cn1nc(CC2CC(F)(F)C2)c(C(C)(C)C)c1NC(=O)CC(C)(C)C] | N-(4-(tert-butyl)-3-((3,3-difluorocyclobutyl)methyl)-1-methyl-1H-pyrazol-5-yl)-3,3-dimethylbutanamide | 4.3 | 356 |
| 496 | 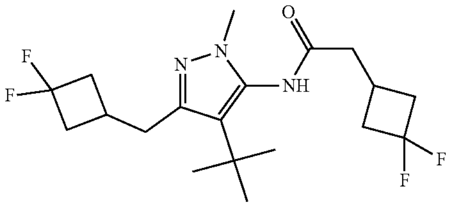 [SMILES: Cn1nc(CC2CC(F)(F)C2)c(C(C)(C)C)c1NC(=O)CC1CC(F)(F)C1] | N-(4-(tert-butyl)-3-((3,3-difluorocyclobutyl)methyl)-1-methyl-1H-pyrazol-5-yl)-2-(3,3-difluorocyclobutyl)acetamide | 4 | 389.4 |
| 498 | 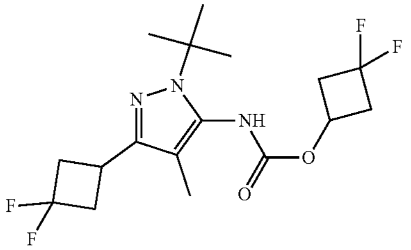 | 3,3-difluorocyclobutyl (1-(tert-butyl)-3-(3,3-difluorocyclobutyl)-4-methyl-1H-pyrazol-5-yl)carbamate | 4.88 | 376** |

TABLE 1-continued

List of Compounds and Characterization Data

| Cmpd # | Structure | Name | LCMS RT (min)* | m/z (M + H)+ |
|---|---|---|---|---|
| 499 | 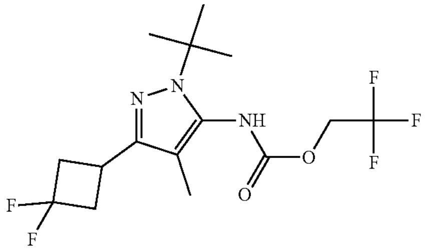 [SMILES: Cc1c(C2CC(F)(F)C2)nn(C(C)(C)C)c1NC(=O)OCC(F)(F)F] | 2,2,2-trifluoroethyl (1-(tert-butyl)-3-(3,3-difluorocyclobutyl)-4-methyl-1H-pyrazol-5-yl)carbamate | 5.07 | 368** |
| 500 | 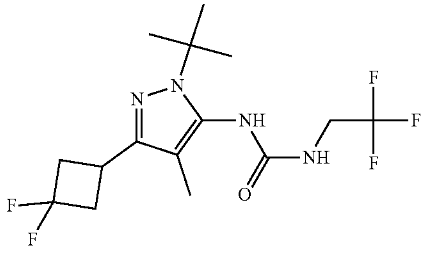 [SMILES: Cc1c(C2CC(F)(F)C2)nn(C(C)(C)C)c1NC(=O)NCC(F)(F)F] | 1-(1-(tert-butyl)-3-(3,3-difluorocyclobutyl)-4-methyl-1H-pyrazol-5-yl)-3-(2,2,2-trifluorethyl)urea | 4.48 | 367** |
| 501 | 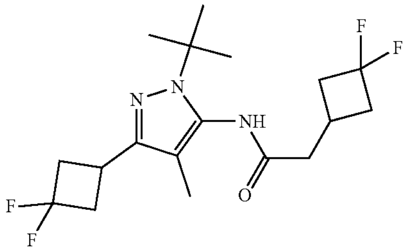 [SMILES: Cc1c(C2CC(F)(F)C2)nn(C(C)(C)C)c1NC(=O)CC1CC(F)(F)C1] | N-(1-(tert-butyl)-3-(3,3-difluorocyclobutyl)-4-methyl-1H-pyrazol-5-yl)-2-(3,3-difluorocyclobutyl)acetamide | 4.75 | 375** |
| 502 | 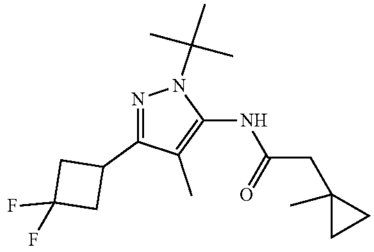 [SMILES: Cc1c(C2CC(F)(F)C2)nn(C(C)(C)C)c1NC(=O)CC1(C)CC1] | N-(1-(tert-butyl)-3-(3,3-difluorocyclobutyl)-4-methyl-1H-pyrazol-5-yl)-2-(1-methylcyclopropyl)acetamide | 4.87 | 338** |
| 503 | 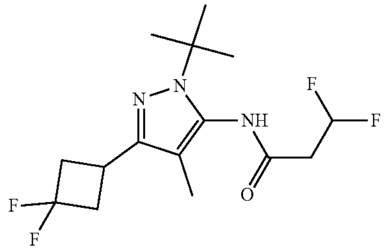 [SMILES: Cc1c(C2CC(F)(F)C2)nn(C(C)(C)C)c1NC(=O)CC(F)F] | N-(1-(tert-butyl)-3-(3,3-difluorocyclobutyl)-4-methyl-1H-pyrazol-5-yl)-3,3-difluoropropanamide | 4.5 | 335** |
| 504 | 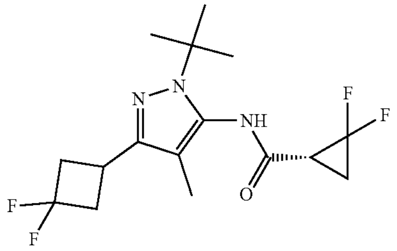 [SMILES: Cc1c(C2CC(F)(F)C2)nn(C(C)(C)C)c1NC(=O)[C@H]1CC1(F)F] | (R)-N-(1-(tert-butyl)-3-(3,3-difluorocyclobutyl)-4-methyl-1H-pyrazol-5-yl)-2,2-difluorocyclopropane-1-carboxamide | 4.62 | 346** |

TABLE 1-continued

List of Compounds and Characterization Data

| Cmpd # | Structure | Name | LCMS RT (min)* | m/z (M + H)+ |
|---|---|---|---|---|
| 505 | 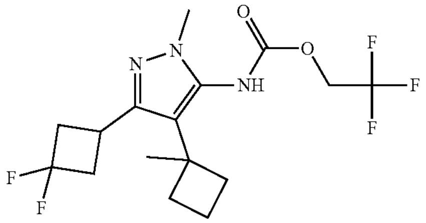 [SMILES: Cn1nc(C2CC(F)(F)C2)c(C2(C)CCC2)c1NC(=O)OCC(F)(F)F] | 2,2,2-trifluoroethyl (3-(3,3-difluorocyclobutyl)-1-methyl-4-(1-methylcyclobutyl)-1H-pyrazol-5-yl)carbamate | 4.82 | 380** |
| 506 | 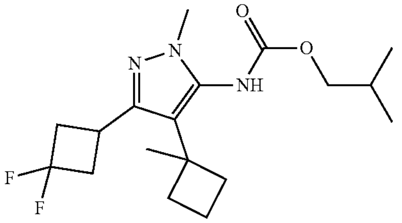 [SMILES: CC(C)COC(=O)Nc1c(C2(C)CCC2)c(C2CC(F)(F)C2)nn1C] | isobutyl (3-(3,3-difluorocyclobutyl)-1-methyl-4-(1-methylcyclobutyl)-1H-pyrazol-5-yl)carbamate | 5 | 354** |
| 507 | 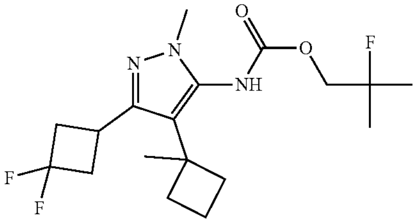 [SMILES: Cn1nc(C2CC(F)(F)C2)c(C2(C)CCC2)c1NC(=O)OCC(C)(C)F] | 2-fluoro-2-methylpropyl (3-(3,3-difluorocyclobutyl)-1-methyl-4-(1-methylcyclobutyl)-1H-pyrazol-5-yl)carbamate | 4.77 | 373** |
| 508 | 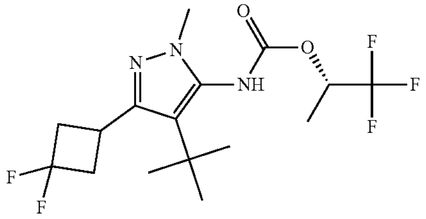 [SMILES: C[C@H](OC(=O)Nc1c(C(C)(C)C)c(C2CC(F)(F)C2)nn1C)C(F)(F)F] | (S)-1,1,1-trifluoropropan-2-yl (4-(tert-butyl)-3-(3,3-difluorocyclobutyl)-1-methyl-1H-pyrazol-5-yl)carbamate | 4.93 | 383** |
| 509 | 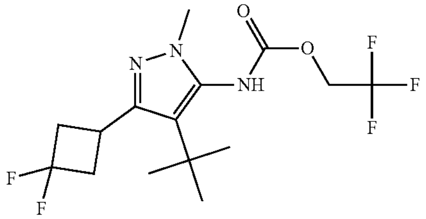 [SMILES: Cn1nc(C2CC(F)(F)C2)c(C(C)(C)C)c1NC(=O)OCC(F)(F)F] | 2,2,2-trifluoroethyl (4-(tert-butyl)-3-(3,3-difluorocyclobutyl)-1-methyl-1H-pyrazol-5-yl)carbamate | 4.77 | 368** |
| 510 | 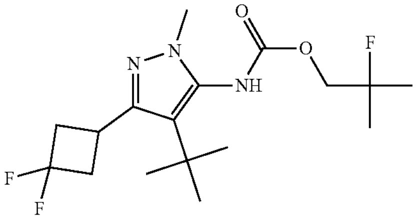 [SMILES: Cn1nc(C2CC(F)(F)C2)c(C(C)(C)C)c1NC(=O)OCC(C)(C)F] | 2-fluoro-2-methylpropyl (4-(tert-butyl)-3-(3,3-difluorocyclobutyl)-1-methyl-1H-pyrazol-5-yl)carbamate | 4.73 | 360** |

TABLE 1-continued

| Cmpd # | Structure | Name | LCMS RT (min)* | m/z (M + H)+ |
|---|---|---|---|---|
| List of Compounds and Characterization Data | | | | |
| 511 | 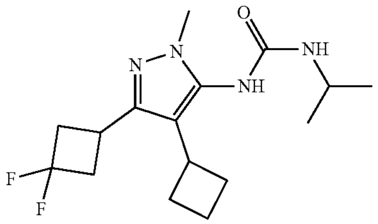 [SMILES: CC(C)NC(=O)Nc1c(C2CCC2)c(C2CC(F)(F)C2)nn1C] | 1-(4-cyclobutyl-3-(3,3-difluorocyclobutyl)-1-methyl-1H-pyrazol-5-yl)-3-isopropylurea | 4.1 | 326** |
| 512 | 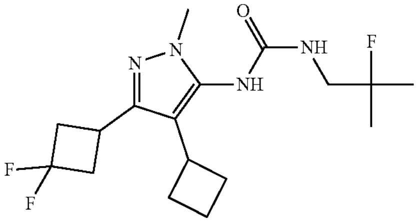 [SMILES: Cn1nc(C2CC(F)(F)C2)c(C2CCC2)c1NC(=O)NCC(C)(C)F] | 1-(4-cyclobutyl-3-(3,3-difluorocyclobutyl)-1-methyl-1H-pyrazol-5-yl)-3-(2-fluoro-2-methylpropyl)urea | 4.18 | 357** |
| 513 | 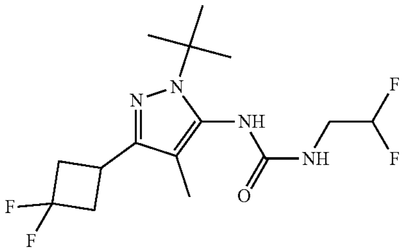 [SMILES: Cc1c(C2CC(F)(F)C2)nn(C(C)(C)C)c1NC(=O)NCC(F)F] | 1-(1-(tert-butyl)-3-(3,3-difluorocyclobutyl)-4-methyl-1H-pyrazol-5-yl)-3-(2,2-difluoroethyl)urea | 4.35 | 349** |
| 514 | 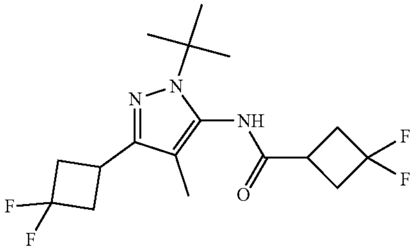 [SMILES: Cc1c(C2CC(F)(F)C2)nn(C(C)(C)C)c1NC(=O)C1CC(F)(F)C1] | N-(1-(tert-butyl)-3-(3,3-difluorocyclobutyl)-4-methyl-1H-pyrazol-5-yl)-3,3-difluorocyclobutane-1-carboxamide | 4.7 | 360** |
| 515 | 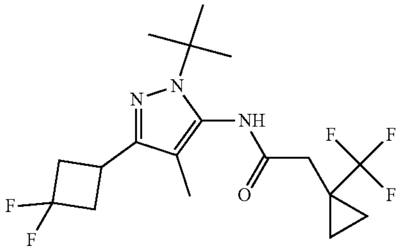 [SMILES: Cc1c(C2CC(F)(F)C2)nn(C(C)(C)C)c1NC(=O)CC1(C(F)(F)F)CC1] | N-(1-(tert-butyl)-3-(3,3-difluorocyclobutyl)-4-methyl-1H-pyrazol-5-yl)-2-(1-(trifluoromethyl)cyclopropyl)acetamide | 4.85 | 394 |
| 516 | 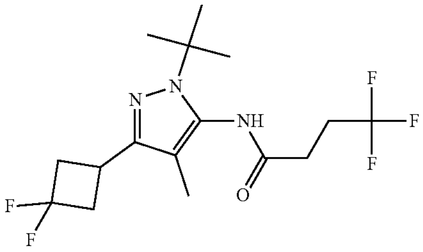 [SMILES: Cc1c(C2CC(F)(F)C2)nn(C(C)(C)C)c1NC(=O)CCC(F)(F)F] | N-(1-(tert-butyl)-3-(3,3-difluorocyclobutyl)-4-methyl-1H-pyrazol-5-yl)-4,4,4-trifluorobutanamide | 4.73 | 366** |

TABLE 1-continued

List of Compounds and Characterization Data

| Cmpd # | Structure | Name | LCMS RT (min)* | m/z (M + H)$^+$ |
|---|---|---|---|---|
| 517 | 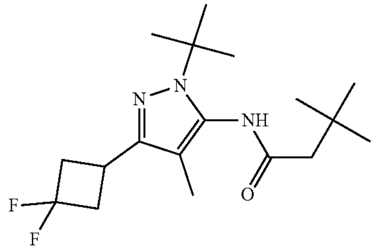 [SMILES: Cc1c(C2CC(F)(F)C2)nn(C(C)(C)C)c1NC(=O)CC(C)(C)C] | N-(1-(tert-butyl)-3-(3,3-difluorocyclobutyl)-4-methyl-1H-pyrazol-5-yl)-3,3-dimethylbutanamide | 4.95 | 340** |
| 518 | 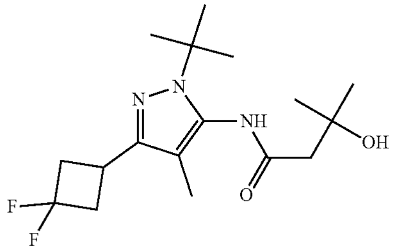 [SMILES: Cc1c(C2CC(F)(F)C2)nn(C(C)(C)C)c1NC(=O)CC(C)(C)O] | N-(1-(tert-butyl)-3-(3,3-difluorocyclobutyl)-4-methyl-1H-pyrazol-5-yl)-3-hydroxy-3-methylbutanamide | 4.23 | 342** |
| 519 | 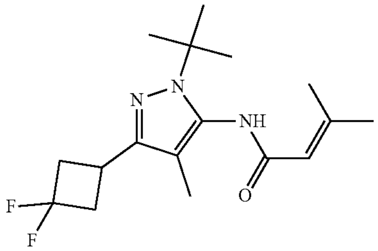 [SMILES: CC(C)=CC(=O)Nc1c(C)c(C2CC(F)(F)C2)nn1C(C)(C)C] | N-(1-(tert-butyl)-3-(3,3-difluorocyclobutyl)-4-methyl-1H-pyrazol-5-yl)-3-methylbut-2-enamide | 4.72 | 324** |
| 520 | 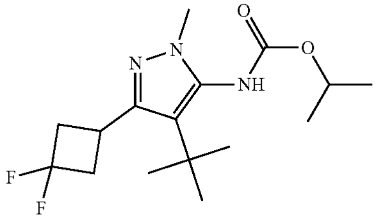 [SMILES: CC(C)OC(=O)Nc1c(C(C)(C)C)c(C2CC(F)(F)C2)nn1C] | isopropyl (4-(tert-butyl)-3-(3,3-difluorocyclobutyl)-1-methyl-1H-pyrazol-5-yl)carbamate | 4.33 | 328** |
| 521 | 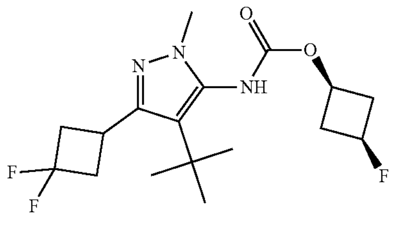 [SMILES: Cn1nc(C2CC(F)(F)C2)c(C(C)(C)C)c1NC(=O)O[C@H]1C[C@@H](F)C1] | (1s,3s)-3-fluorocyclobutyl (4-(tert-butyl)-3-(3,3-difluorocyclobutyl)-1-methyl-1H-pyrazol-5-yl)carbamate | 4.65 | 358** |
| 522 | 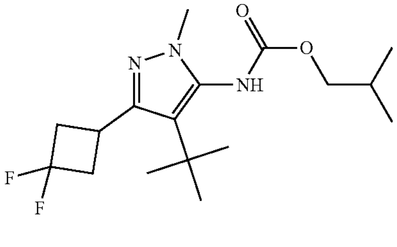 [SMILES: CC(C)COC(=O)Nc1c(C(C)(C)C)c(C2CC(F)(F)C2)nn1C] | isobutyl (4-(tert-butyl)-3-(3,3-difluorocyclobutyl)-1-methyl-1H-pyrazol-5-yl)carbamate | 4.95 | 345 |

TABLE 1-continued

| List of Compounds and Characterization Data | | | | |
|---|---|---|---|---|
| Cmpd # | Structure | Name | LCMS RT (min)* | m/z (M + H)+ |
| 523 | 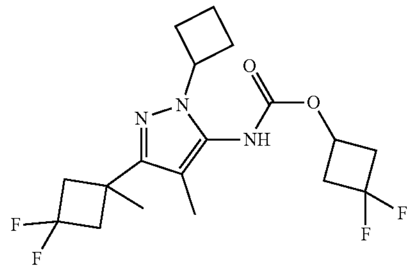 [SMILES: Cc1c(C2(C)CC(F)(F)C2)nn(C2CCC2)c1NC(=O)OC1CC(F)(F)C1] | 3,3-difluorocyclobutyl (1-cyclobutyl-3-(3,3-difluoro-1-methylcyclobutyl)-4-methyl-1H-pyrazol-5-yl)carbamate | 4.2 | 390 |
| 524 | 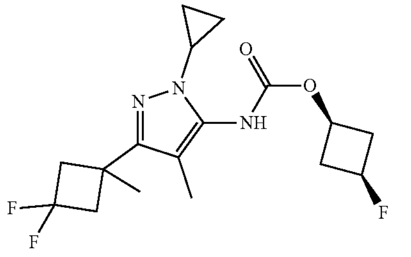 [SMILES: Cc1c(C2(C)CC(F)(F)C2)nn(C2CC2)c1NC(=O)O[C@H]1C[C@@H](F)C1] | (1s,3s)-3-fluorocyclobutyl (1-cyclobutyl-3-(3,3-difluoro-1-methylcyclobutyl)-4-methyl-1H-pyrazol-5-yl)carbamate | 4.2 | 372 |
| 525 | 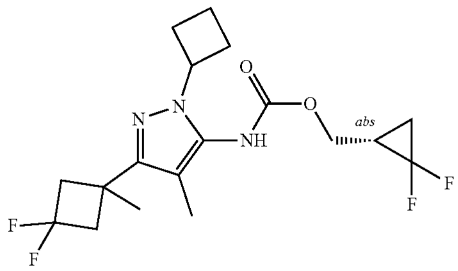 [SMILES: Cc1c(C2(C)CC(F)(F)C2)nn(C2CCC2)c1NC(=O)OC[C@@H]1CC1(F)F] | (S)-(2,2-difluorocyclopropyl)methyl (1-cyclobutyl-3-(3,3-difluoro-1-methylcyclobutyl)-4-methyl-1H-pyrazol-5-yl)carbamate | 4.2 | 390 |
| 526 | 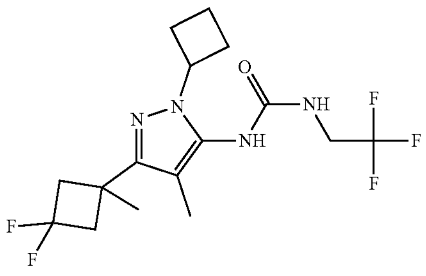 [SMILES: Cc1c(C2(C)CC(F)(F)C2)nn(C2CCC2)c1NC(=O)NCC(F)(F)F] | 1-(1-cyclobutyl-3-(3,3-difluoro-1-methylcyclobutyl)-4-methyl-1H-pyrazol-5-yl)-3-(2,2,2-trifluoroethyl)urea | 3.88 | 381 |
| 527 | 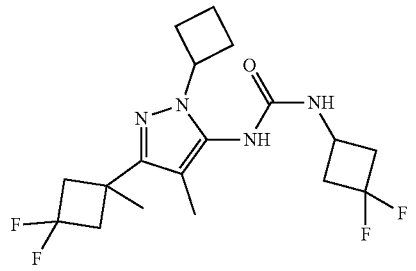 [SMILES: Cc1c(C2(C)CC(F)(F)C2)nn(C2CCC2)c1NC(=O)NC1CC(F)(F)C1] | 1-(1-cyclobutyl-3-(3,3-difluoro-1-methylcyclobutyl)-4-methyl-1H-pyrazol-5-yl)-3-(3,3-difluorocyclobutyl)urea | 3.88 | 389 |

TABLE 1-continued

| List of Compounds and Characterization Data | | | | |
|---|---|---|---|---|
| Cmpd # | Structure | Name | LCMS RT (min)* | m/z (M + H)+ |
| 528 | 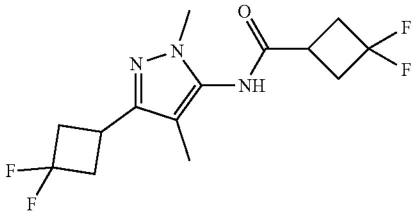 [SMILES: Cc1c(C2CC(F)(F)C2)nn(C)c1NC(=O)C1CC(F)(F)C1] | N-(3-(3,3-difluorocyclobutyl)-1,4-dimethyl-1H-pyrazol-5-yl)-3,3-difluorocyclobutane-1-carboxamide | 3.5 | 320 |
| 529 | 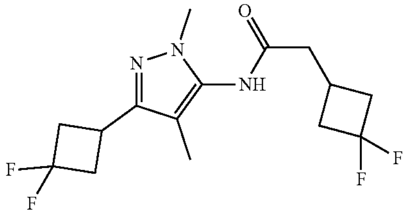 [SMILES: Cc1c(C2CC(F)(F)C2)nn(C)c1NC(=O)CC1CC(F)(F)C1] | 2-(3,3-difluorocyclobutyl)-N-(3-(3,3-difluorocyclobutyl)-1,4-dimethyl-1H-pyrazol-5-yl)acetamide | 3.52 | 334 |
| 530 | 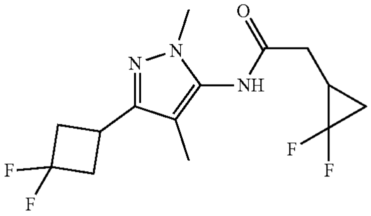 [SMILES: Cc1c(C2CC(F)(F)C2)nn(C)c1NC(=O)CC1CC1(F)F] | N-(3-(3,3-difluorocyclobutyl)-1,4-dimethyl-1H-pyrazol-5-yl)-2-(2,2-difluorocyclopropyl)acetamide | 3.44 | 320 |
| 531 | 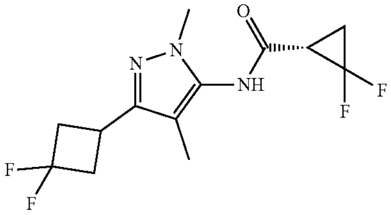 [SMILES: Cc1c(C2CC(F)(F)C2)nn(C)c1NC(=O)[C@@H]1CC1(F)F] | (S)-N-(3-(3,3-difluorocyclobutyl)-1,4-dimethyl-1H-pyrazol-5-yl)-2,2-difluorocyclopropane-1-carboxamide | 3.42 | 306 |
| 532 | 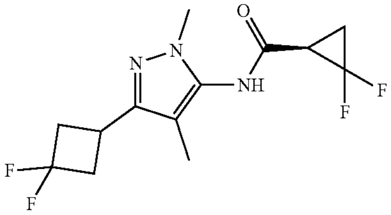 [SMILES: Cc1c(C2CC(F)(F)C2)nn(C)c1NC(=O)[C@H]1CC1(F)F] | (R)-N-(3-(3,3-difluorocyclobutyl)-1,4-dimethyl-1H-pyrazol-5-yl)-2,2-difluorocyclopropane-1-carboxamide | 3.43 | 306 |
| 533 | 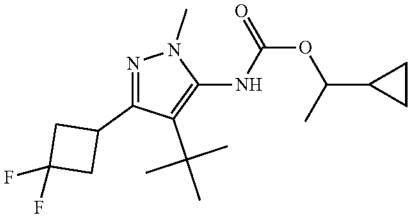 [SMILES: CC(OC(=O)Nc1c(C(C)(C)C)c(C2CC(F)(F)C2)nn1C)C1CC1] | 1-cyclopropylethyl (4-(tert-butyl)-3-(3,3-difluorocyclobutyl)-1-methyl-1H-pyrazol-5-yl)carbamate | 5.2 | 354** |

TABLE 1-continued

| List of Compounds and Characterization Data | | | | |
|---|---|---|---|---|
| Cmpd # | Structure | Name | LCMS RT (min)* | m/z (M + H)$^+$ |
| 534 | 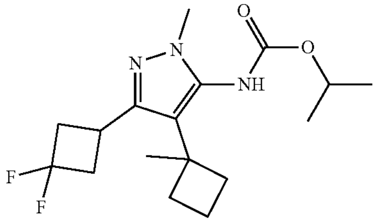 [SMILES: CC(C)OC(=O)Nc1c(C2(C)CCC2)c(C2CC(F)(F)C2)nn1C] | isopropyl (3-(3,3-difluorocyclobutyl)-1-methyl-4-(1-methylcyclobutyl)-1H-pyrazol-5-yl)carbamate | 4.8 | 340** |
| 535 | 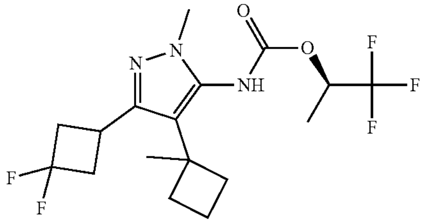 [SMILES: C[C@@H](OC(=O)Nc1c(C2(C)CCC2)c(C2CC(F)(F)C2)nn1C)C(F)(F)F] | (R)-1,1,1-trifluoropropan-2-yl (3-(3,3-difluorocyclobutyl)-1-methyl-4-(1-methylcyclobutyl)-1H-pyrazol-5-yl)carbamate | 4.97 | 394** |
| 536 | 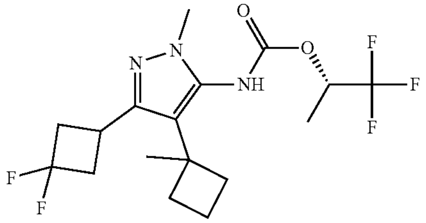 [SMILES: C[C@H](OC(=O)Nc1c(C2(C)CCC2)c(C2CC(F)(F)C2)nn1C)C(F)(F)F] | (S)-1,1,1-trifluoropropan-2-yl (3-(3,3-difluorocyclobutyl)-1-methyl-4-(1-methylcyclobutyl)-1H-pyrazol-5-yl)carbamate | 4.98 | 394** |
| 537 | 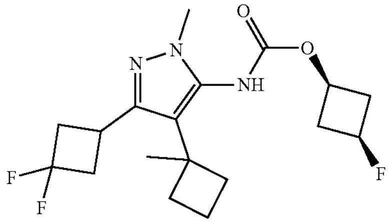 [SMILES: Cn1nc(C2CC(F)(F)C2)c(C2(C)CCC2)c1NC(=O)O[C@H]1C[C@@H](F)C1] | (1s,3s)-3-fluorocyclobutyl (3-(3,3-difluorocyclobutyl)-1-methyl-4-(1-methylcyclobutyl)-1H-pyrazol-5-yl)carbamate | 4.5 | 370** |
| 538 | 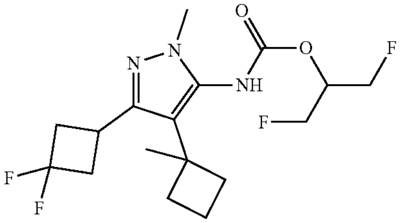 [SMILES: Cn1nc(C2CC(F)(F)C2)c(C2(C)CCC2)c1NC(=O)OC(CF)CF] | 1,3-difluoropropan-2-yl (3-(3,3-difluorocyclobutyl)-1-methyl-4-(1-methylcyclobutyl)-1H-pyrazol-5-yl)carbamate | 4.58 | 376** |
| 539 | 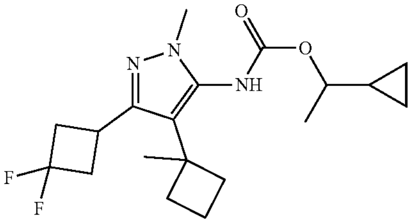 [SMILES: CC(OC(=O)Nc1c(C2(C)CCC2)c(C2CC(F)(F)C2)nn1C)C1CC1] | 1-cyclopropylethyl (3-(3,3-difluorocyclobutyl)-1-methyl-4-(1-methylcyclobutyl)-1H-pyrazol-5-yl)carbamate | 4.97 | 366** |

TABLE 1-continued

| Cmpd # | Structure | Name | LCMS RT (min)* | m/z (M + H)+ |
|---|---|---|---|---|
| List of Compounds and Characterization Data | | | | |
| 540 | 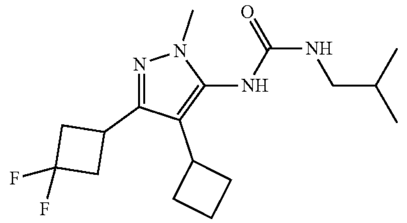 [SMILES: CC(C)CNC(=O)Nc1c(C2CCC2)c(C2CC(F)(F)C2)nn1C] | 1-(4-cyclobutyl-3-(3,3-difluorocyclobutyl)-1-methyl-1H-pyrazol-5-yl)-3-isobutylurea | 4.33 | 339** |
| 541 | 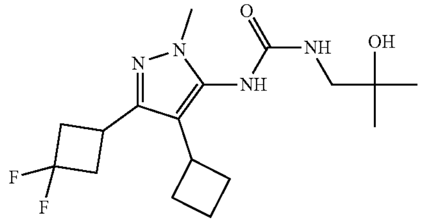 [SMILES: Cn1nc(C2CC(F)(F)C2)c(C2CCC2)c1NC(=O)NCC(C)(C)O] | 1-(4-cyclobutyl-3-(3,3-difluorocyclobutyl)-1-methyl-1H-pyrazol-5-yl)-3-(2-hydroxy-2-methylpropyl)urea | 3.72 | 355** |
| 542 | 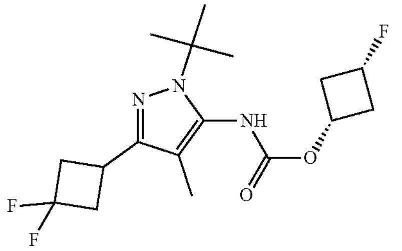 [SMILES: Cc1c(C2CC(F)(F)C2)nn(C(C)(C)C)c1NC(=O)O[C@H]1C[C@@H](F)C1] | (1s,3s)-3-fluorocyclobutyl (1-(tert-butyl)-3-(3,3-difluorocyclobutyl)-4-methyl-1H-pyrazol-5-yl)carbamate | 4.78 | 358** |
| 543 | 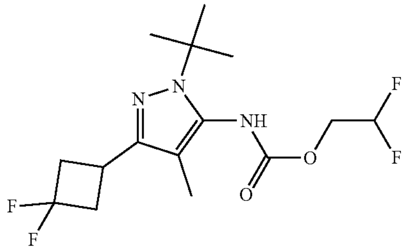 [SMILES: Cc1c(C2CC(F)(F)C2)nn(C(C)(C)C)c1NC(=O)OCC(F)F] | 2,2-difluoroethyl (1-(tert-butyl)-3-(3,3-difluorocyclobutyl)-4-methyl-1H-pyrazol-5-yl)carbamate | 4.73 | 350** |
| 544 | 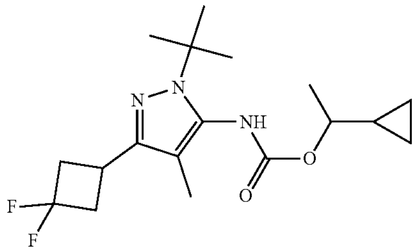 [SMILES: Cc1c(C2CC(F)(F)C2)nn(C(C)(C)C)c1NC(=O)OC(C)C1CC1] | 1-cyclopropylethyl (1-(tert-butyl)-3-(3,3-difluorocyclobutyl)-4-methyl-1H-pyrazol-5-yl)carbamate | 5.08 | 354** |
| 545 | 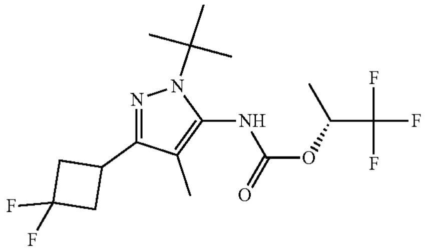 [SMILES: Cc1c(C2CC(F)(F)C2)nn(C(C)(C)C)c1NC(=O)O[C@H](C)C(F)(F)F] | (R)-1,1,1-trifluoropropan-2-yl (1-(tert-butyl)-3-(3,3-difluorocyclobutyl)-4-methyl-1H-pyrazol-5-yl)carbamate | 5.07 | 382** |

TABLE 1-continued

| List of Compounds and Characterization Data | | | | |
|---|---|---|---|---|
| Cmpd # | Structure | Name | LCMS RT (min)* | m/z (M + H)+ |
| 546 | 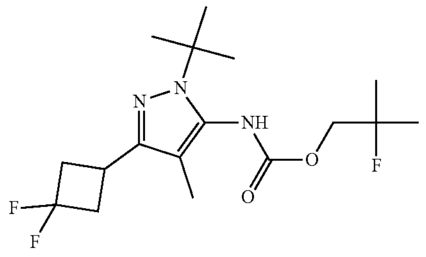 [SMILES: Cc1c(C2CC(F)(F)C2)nn(C(C)(C)C)c1NC(=O)OCC(C)(C)F] | 2-fluoro-2-methylpropyl (1-(tert-butyl)-3-(3,3-difluorocyclobutyl)-4-methyl-1H-pyrazol-5-yl)carbamate | 4.88 | 360** |
| 547 | 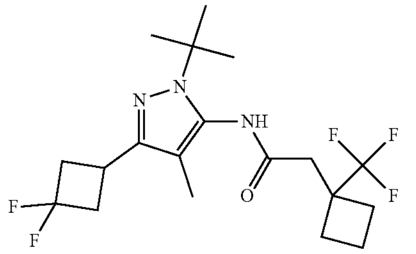 [SMILES: Cc1c(C2CC(F)(F)C2)nn(C(C)(C)C)c1NC(=O)CC1(C(F)(F)F)CCC1] | N-(1-(tert-butyl)-3-(3,3-difluorocyclobutyl)-4-methyl-1H-pyrazol-5-yl)-2-(1-(trifluoromethyl) cyclobutyl)acetamide | 5.1 | 406** |
| 548 | 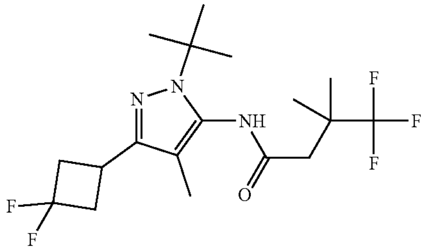 [SMILES: Cc1c(C2CC(F)(F)C2)nn(C(C)(C)C)c1NC(=O)CC(C)(C)C(F)(F)F] | N-(1-(tert-butyl)-3-(3,3-difluorocyclobutyl)-4-methyl-1H-pyrazol-5-yl)-4,4,4-trifluoro-3,3-dimethylbutanamide | 5.07 | 394** |
| 549 | 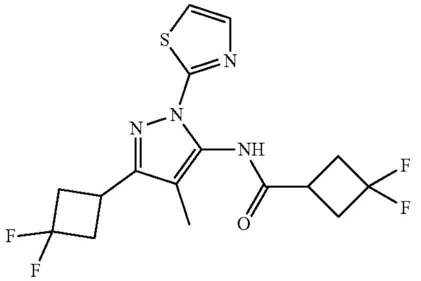 [SMILES: Cc1c(C2CC(F)(F)C2)nn(-c2nccs2)c1NC(=O)C1CC(F)(F)C1] | N-(3-(3,3-difluorocyclobutyl)-4-methyl-1-(thiazol-2-yl)-1H-pyrazol-5-yl)-3,3-difluorocyclobutane-1-carboxamide | 4.06 | 389 |
| 550 | 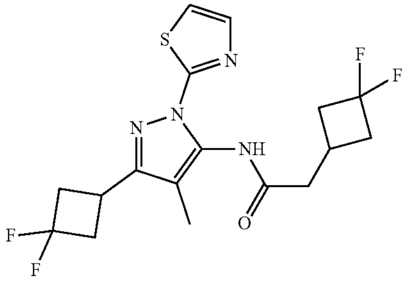 [SMILES: Cc1c(C2CC(F)(F)C2)nn(-c2nccs2)c1NC(=O)CC1CC(F)(F)C1] | 2-(3,3-difluorocyclobutyl)-N-(3-(3,3-difluorocyclobutyl)-4-methyl-1-(thiazol-2-yl)-1H-pyrazol-5-yl)acetamide | 4.07 | 401** |

TABLE 1-continued

List of Compounds and Characterization Data

| Cmpd # | Structure | Name | LCMS RT (min)* | m/z (M + H)+ |
| --- | --- | --- | --- | --- |
| 551 | 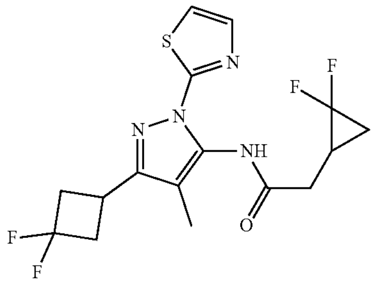 [SMILES: Cc1c(C2CC(F)(F)C2)nn(-c2nccs2)c1NC(=O)CC1CC1(F)F] | N-(3-(3,3-difluorocyclobutyl)-4-methyl-1-(thiazol-2-yl)-1H-pyrazol-5-yl)-2-(2,2-difluorocyclopropyl)acetamide | 4.06 | 389 |
| 552 | 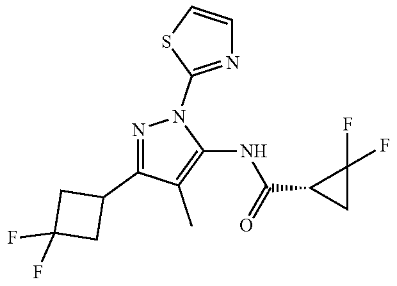 [SMILES: Cc1c(C2CC(F)(F)C2)nn(-c2nccs2)c1NC(=O)[C@H]1CC1(F)F] | (R)-N-(3-(3,3-difluorocyclobutyl)-4-methyl-1-(thiazol-2-yl)-1H-pyrazol-5-yl)-2,2-difluorocyclopropane-1-carboxamide | 4.07 | 375 |
| 553 | 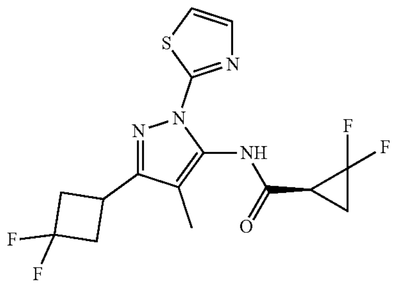 [SMILES: Cc1c(C2CC(F)(F)C2)nn(-c2nccs2)c1NC(=O)[C@@H]1CC1(F)F] | (S)-N-(3-(3,3-difluorocyclobutyl)-4-methyl-1-(thiazol-2-yl)-1H-pyrazol-5-yl)-2,2-difluorocyclopropane-1-carboxamide | 4.07 | 375 |
| 554 | 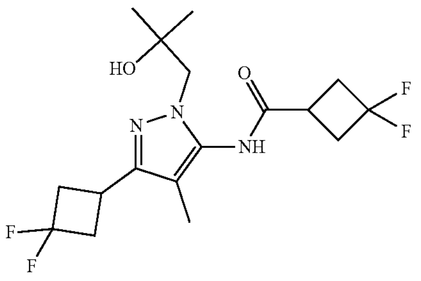 [SMILES: Cc1c(C2CC(F)(F)C2)nn(CC(C)(C)O)c1NC(=O)C1CC(F)(F)C1] | N-(3-(3,3-difluorocyclobutyl)-1-(2-hydroxy-2-methylpropyl)-4-methyl-1H-pyrazol-5-yl)-3,3-difluorocyclobutane-1-carboxamide | 3.57 | 378 |
| 555 | 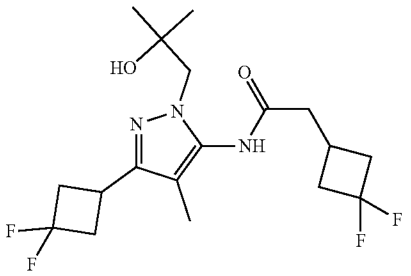 [SMILES: Cc1c(C2CC(F)(F)C2)nn(CC(C)(C)O)c1NC(=O)CC1CC(F)(F)C1] | 2-(3,3-difluorocyclobutyl)-N-(3-(3,3-difluorocyclobutyl)-1-(2-hydroxy-2-methylpropyl)-4-methyl-1H-pyrazol-5-yl)acetamide | 3.60 | 392 |

TABLE 1-continued

List of Compounds and Characterization Data

| Cmpd # | Structure | Name | LCMS RT (min)* | m/z (M + H)+ |
| --- | --- | --- | --- | --- |
| 556 | 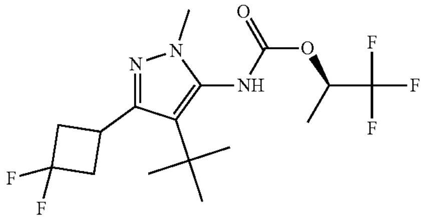 [SMILES: C[C@@H](OC(=O)Nc1c(C(C)(C)C)c(C2CC(F)(F)C2)nn1C)C(F)(F)F] | (R)-1,1,1-trifluoropropan-2-yl (4-(tert-butyl)-3-(3,3-difluorocyclobutyl)-1-methyl-1H-pyrazol-5-yl)carbamate | 5.03 | 384 |
| 557 | 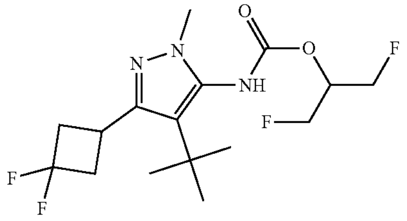 [SMILES: Cn1nc(C2CC(F)(F)C2)c(C(C)(C)C)c1NC(=O)OC(CF)CF] | 1,3-difluoropropan-2-yl (4-(tert-butyl)-3-(3,3-difluorocyclobutyl)-1-methyl-1H-pyrazol-5-yl)carbamate | 3.9 | 366 |
| 558 | 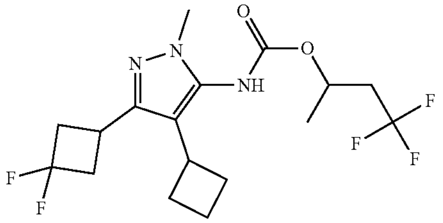 [SMILES: CC(CC(F)(F)F)OC(=O)Nc1c(C2CCC2)c(C2CC(F)(F)C2)nn1C] | 4,4,4-trifluorobutan-2-yl (4-cyclobutyl-3-(3,3-difluorocyclobutyl)-1-methyl-1H-pyrazol-5-yl)carbamate | 5.88 | 396 |
| 559 | 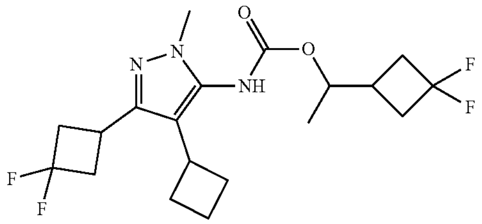 [SMILES: CC(OC(=O)Nc1c(C2CCC2)c(C2CC(F)(F)C2)nn1C)C1CC(F)(F)C1] | 1-(3,3-difluorocyclobutyl)ethyl (4-cyclobutyl-3-(3,3-difluorocyclobutyl)-1-methyl-1H-pyrazol-5-yl)carbamate | 5.95 | 404 |
| 560 | 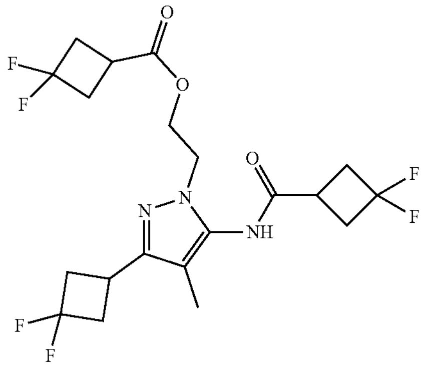 [SMILES: Cc1c(C2CC(F)(F)C2)nn(CCOC(=O)C2CC(F)(F)C2)c1NC(=O)C1CC(F)(F)C1] | 2-(5-(3,3-difluorocyclobutane-1-carboxamido)-3-(3,3-difluorocyclobutyl)-4-methyl-1H-pyrazol-1-yl)ethyl 3,3-difluorocyclobutane-1-carboxylate | 3.9 | 468 |

TABLE 1-continued

List of Compounds and Characterization Data

| Cmpd # | Structure | Name | LCMS RT (min)* | m/z (M + H)$^+$ |
|---|---|---|---|---|
| 561 | 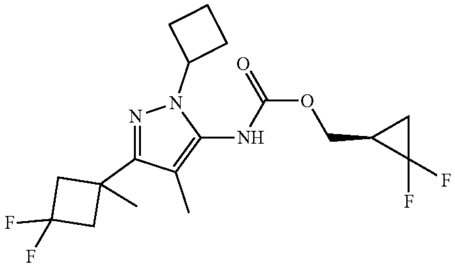 [SMILES: Cc1c(C2(C)CC(F)(F)C2)nn(C2CCC2)c1NC(=O)OC[C@H]1CC1(F)F] | (R)-(2,2-difluorocyclo-propyl)methyl (1-cyclobutyl-3-(3,3-difluoro-1-methylcyclobutyl)-4-methyl-1H-pyrazol-5-yl)carbamate | 4.2 | 390 |
| 562 | 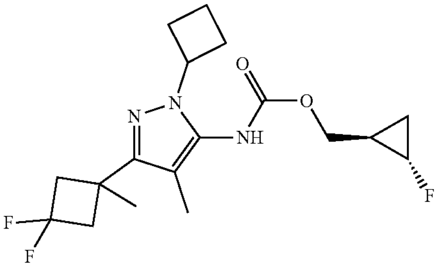 [SMILES: Cc1c(C2(C)CC(F)(F)C2)nn(C2CCC2)c1NC(=O)OC[C@H]1C[C@@H]1F] | ((1R,2S)-2-fluorocyclopropyl)methyl (1-cyclobutyl-3-(3,3-difluoro-1-methylcyclobutyl)-4-methyl-1H-pyrazol-5-yl)carbamate | 4.1 | 372 |
| 563 | 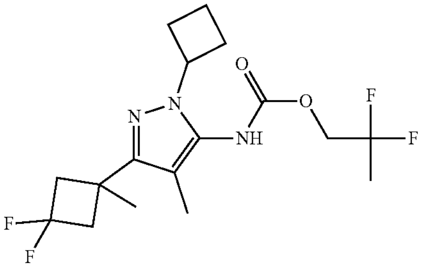 [SMILES: Cc1c(C2(C)CC(F)(F)C2)nn(C2CCC2)c1NC(=O)OCC(C)(F)F] | 2,2-difluoropropyl (1-cyclobutyl-3-(3,3-difluoro-1-methylcyclobutyl)-4-methyl-1H-pyrazol-5-yl)carbamate | 4.2 | 378 |
| 564 | 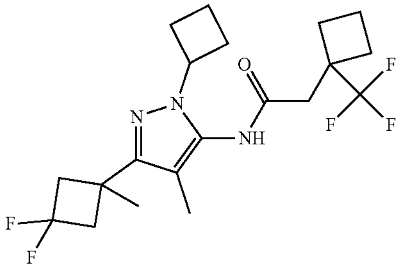 [SMILES: Cc1c(C2(C)CC(F)(F)C2)nn(C2CCC2)c1NC(=O)CC1(C(F)(F)F)CCC1] | N-(1-cyclobutyl-3-(3,3-difluoro-1-methylcyclobutyl)-4-methyl-1H-pyrazol-5-yl)-2-(1-(trifluoromethyl)cyclo-butyl)acetamide | 4.4 | 420 |
| 565 | 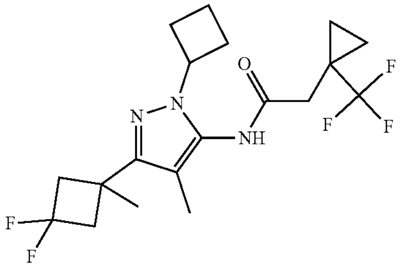 [SMILES: Cc1c(C2(C)CC(F)(F)C2)nn(C2CCC2)c1NC(=O)CC1(C(F)(F)F)CC1] | N-(1-cyclobutyl-3-(3,3-difluoro-1-methylcyclobutyl)-4-methyl-1H-pyrazol-5-yl)-2-(1-(trifluoromethyl)cyclo-propyl)acetamide | 4.2 | 406 |

TABLE 1-continued

| List of Compounds and Characterization Data | | | | |
|---|---|---|---|---|
| Cmpd # | Structure | Name | LCMS RT (min)* | m/z (M + H)$^+$ |
| 566 | 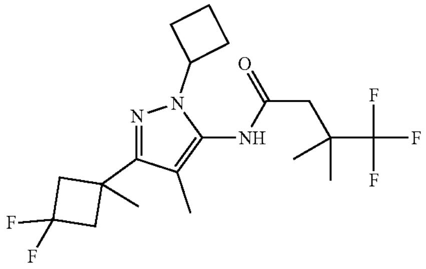 [SMILES: Cc1c(C2(C)CC(F)(F)C2)nn(C2CCC2)c1NC(=O)CC(C)(C)C(F)(F)F] | N-(1-cyclobutyl-3-(3,3-difluoro-1-methylcyclobutyl)-4-methyl-1H-pyrazol-5-yl)-4,4,4-trifluoro-3,3-dimethylbutanamide | 4.4 | 408 |
| 568 | 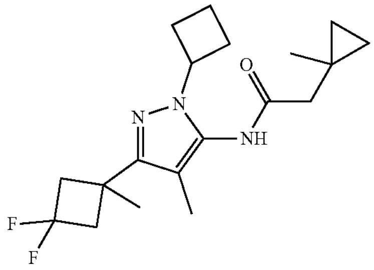 [SMILES: Cc1c(C2(C)CC(F)(F)C2)nn(C2CCC2)c1NC(=O)CC1(C)CC1] | N-(1-cyclobutyl-3-(3,3-difluoro-1-methylcyclobutyl)-4-methyl-1H-pyrazol-5-yl)-2-(1-methylcyclopropyl)acetamide | 4.17 | 352 |
| 569 | 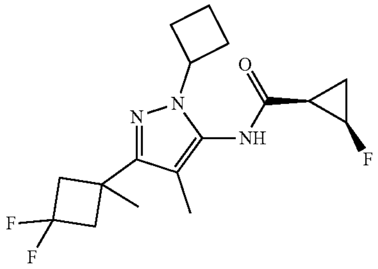 [SMILES: Cc1c(C2(C)CC(F)(F)C2)nn(C2CCC2)c1NC(=O)[C@H]1C[C@H]1F] | (1R,2R)-N-(1-cyclobutyl-3-(3,3-difluoro-1-methylcyclobutyl)-4-methyl-1H-pyrazol-5-yl)-2-fluorocyclopropane-1-carboxamide | 3.81 | 342 |
| 570 | 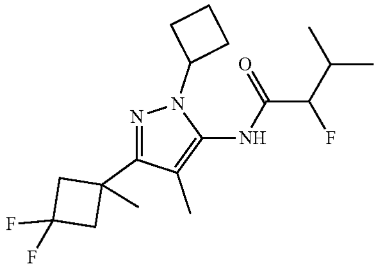 [SMILES: Cc1c(C2(C)CC(F)(F)C2)nn(C2CCC2)c1NC(=O)C(F)C(C)C] | N-(1-cyclobutyl-3-(3,3-difluoro-1-methylcyclobutyl)-4-methyl-1H-pyrazol-5-yl)-2-fluoro-3-methylbutanamide | 4.28 | 358 |
| 571 | 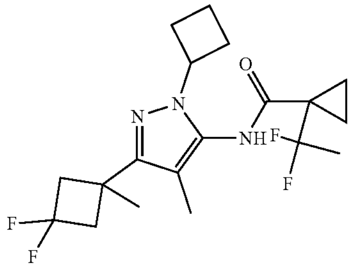 [SMILES: Cc1c(C2(C)CC(F)(F)C2)nn(C2CCC2)c1NC(=O)C1(C(C)(F)F)CC1] | N-(1-cyclobutyl-3-(3,3-difluoro-1-methylcyclobutyl)-4-methyl-1H-pyrazol-5-yl)-1-(1,1-difluoroethyl)cyclopropane-1-carboxamide | 4.24 | 388 |

TABLE 1-continued

List of Compounds and Characterization Data

| Cmpd # | Structure | Name | LCMS RT (min)* | m/z (M + H)+ |
|---|---|---|---|---|
| 572 | 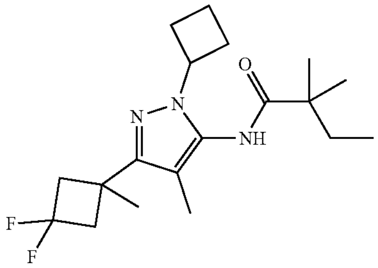 [SMILES: CCC(C)(C)C(=O)Nc1c(C)c(C2(C)CC(F)(F)C2)nn1C1CCC1] | N-(1-cyclobutyl-3-(3,3-difluoro-1-methylcyclobutyl)-4-methyl-1H-pyrazol-5-yl)-2,2-dimethylbutanamide | 4.33 | 354 |
| 573 | 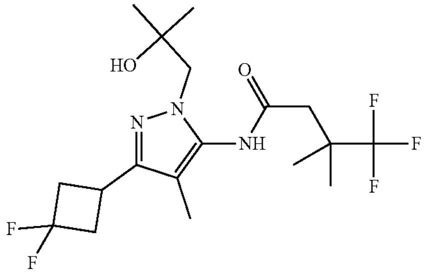 [SMILES: Cc1c(C2CC(F)(F)C2)nn(CC(C)(C)O)c1NC(=O)CC(C)(C)C(F)(F)F] | N-(3-(3,3-difluorocyclobutyl)-1-(2-hydroxy-2-methylpropyl)-4-methyl-1H-pyrazol-5-yl)-4,4,4-trifluoro-3,3-dimethylbutanamide | 3.91 | 412 |
| 574 | 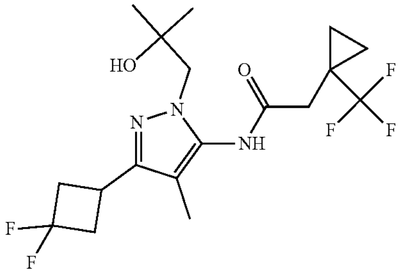 [SMILES: Cc1c(C2CC(F)(F)C2)nn(CC(C)(C)O)c1NC(=O)CC1(C(F)(F)F)CC1] | N-(3-(3,3-difluorocyclobutyl)-1-(2-hydroxy-2-methylpropyl)-4-methyl-1H-pyrazol-5-yl)-2-(1-(trifluoromethyl)cyclopropyl)acetamide | 3.71 | 410 |

*See Table 2 for the corresponding LCMS method.
**m/z value corresponds to $(M - H)^-$

TABLE 2

Analytical and Synthetic Methods for Compounds listed in Table 1

| Cmpd # | LCMS Method | Synthetic Method: β-ketonitriles | Synthetic Method: Alkyl Pyrazole | Synthetic Method: Amine functionalization, final step |
|---|---|---|---|---|
| 1 | A | C | J | O |
| 2 | A | C | J | O |
| 3 | A | C | J | O |
| 4 | A | C | J | O |
| 5 | A | C | J | O |
| 6 | A | C | J | O |
| 7 | A | C | J | O |
| 8 | A | C | J | O |
| 9 | A | C | J | O |
| 10 | A | C | J | O |
| 11 | A | C | J | O |
| 12 | A | A | E | K |
| 13 | A | A | E | P |
| 14 | A | A | E | O |
| 15 | A | A | E | K |
| 16 | A | A | E | K |
| 17 | A | A | E | K |
| 18 | A | A | E | K |
| 19 | A | A | E | K |
| 20 | A | A | E | K |

TABLE 2-continued

Analytical and Synthetic Methods for Compounds listed in Table 1

| Cmpd # | LCMS Method | Synthetic Method: β-ketonitriles | Synthetic Method: Alkyl Pyrazole | Synthetic Method: Amine functionalization, final step |
|---|---|---|---|---|
| 21 | A | A | E | K |
| 22 | A | A | E | O |
| 23 | A | A | E | K |
| 24 | A | A | E | K |
| 25 | A | A | E | K |
| 26 | A | A | E | K |
| 27 | A | A | E | K |
| 28 | A | A | E | K |
| 29 | A | A | E | K |
| 30 | A | A | E | K |
| 31 | A | A | E | K |
| 32 | A | A | E | K |
| 33 | A | A | E | K |
| 34 | A | A | E | K |
| 35 | A | A | E | K |
| 36 | A | A | E | K |
| 37 | A | A | E | K |
| 38 | A | A | E | K |
| 39 | A | A | E | K |
| 40 | A | A | E | K |

TABLE 2-continued

Analytical and Synthetic Methods for Compounds listed in Table 1

| Cmpd # | LCMS Method | Synthetic Method: β-ketonitriles | Synthetic Method: Alkyl Pyrazole | Synthetic Method: Amine functionalization, final step |
|---|---|---|---|---|
| 41 | A | A | E | K |
| 42 | A | A | E | K |
| 43 | A | A | E | K |
| 44 | A | A | E | K |
| 45 | A | A | E | K |
| 46 | A | A | E | K |
| 47 | A | A | E | K |
| 48 | A | A | E | K |
| 49 | A | B | E | O |
| 50 | A | B | E | K |
| 51 | A | B | E | K |
| 52 | A | A | E | K |
| 53 | A | A | E | K |
| 54 | A | A | E | K |
| 55 | A | A | E | K |
| 56 | A | A | E | K |
| 57 | A | A | E | K |
| 58 | A | B | E | K |
| 59 | A | A | E | K |
| 60 | A | A | E | K |
| 61 | A | A | E | K |
| 62 | A | B | H | O |
| 63 | A | B | H | K |
| 64 | A | A | E | K |
| 65 | A | A | E | K |
| 66 | A | A | E | K |
| 67 | A | A | E | K |
| 68 | A | | | K |
| 69 | A | A | E | K |
| 70 | A | A | E | K |
| 71 | A | A | E | K |
| 72 | A | A | E | K |
| 73 | A | | | K |
| 74 | A | | | K |
| 75 | A | A | E | K |
| 76 | A | A | E | K |
| 77 | A | B | E | O, Y |
| 78 | A | A | E | K |
| 79 | A | A | E | K |
| 80 | A | A | E | K |
| 81 | A | B | H | K |
| 82 | A | B | H | K |
| 83 | A | A | H | K |
| 84 | A | A | E | K |
| 85 | A | A | E | K |
| 86 | A | A | E | K |
| 87 | A | A | E | K |
| 88 | A | B | H | K |
| 89 | A | B | H | K |
| 90 | A | B | H | K |
| 91 | A | B | H | K |
| 92 | A | B | H | K |
| 93 | A | A | E | K |
| 94 | A | A | E | K |
| 95 | A | A | E | K |
| 96 | A | A | E | K |
| 97 | A | A | H | K |
| 98 | A | A | E | K |
| 99 | A | A | E | K |
| 100 | A | A | E | K |
| 101 | A | A | E | K |
| 102 | A | B | H | K, W |
| 103 | A | A | E | K |
| 104 | A | A | E | K |
| 105 | A | A | E | K |
| 106 | A | A | E | K |
| 107 | A | A | E | K |
| 108 | A | A | E | K |
| 109 | A | A | E | K |
| 110 | A | A | E | K |
| 111 | A | A | E | K |
| 112 | A | A | E | K |
| 113 | A | A | E | K |

TABLE 2-continued

Analytical and Synthetic Methods for Compounds listed in Table 1

| Cmpd # | LCMS Method | Synthetic Method: β-ketonitriles | Synthetic Method: Alkyl Pyrazole | Synthetic Method: Amine functionalization, final step |
|---|---|---|---|---|
| 114 | A | A | E | K |
| 115 | A | A | E | K |
| 116 | A | A | E | K |
| 117 | A | A | E | K |
| 118 | A | A | E | K |
| 119 | A | A | E | K |
| 120 | A | A | E | K |
| 121 | A | A | E | K |
| 122 | A | A | E | K |
| 123 | A | A | E | K |
| 124 | A | A | H | K |
| 125 | A | A | H | K |
| 126 | A | A | E | K |
| 127 | A | A | E | P |
| 128 | A | A | E | P |
| 129 | A | A | H | K, W |
| 130 | A | D | E | K |
| 131 | A | D | E | K |
| 132 | A | A | E | K |
| 133 | A | A | E | K |
| 134 | A | A | E | K |
| 135 | A | A | H | K, W |
| 136 | A | D | E | K |
| 137 | A | D | E | K |
| 138 | A | A | E | K |
| 139 | A | A | E | K |
| 140 | A | A | E | K |
| 141 | A | A | E | K |
| 142 | A | A | E | K |
| 143 | A | A | E | K |
| 144 | A | A | E | K |
| 145 | A | A | E | K |
| 146 | A | A | E | K |
| 147 | A | A | E | K |
| 148 | A | A | E | K |
| 149 | A | C, DD | E | O |
| 150 | A | A | E | K |
| 151 | A | C, DD | E | K |
| 152 | A | A | E | K |
| 153 | A | A | E | K |
| 154 | A | A | E | K |
| 155 | A | B | E | K |
| 156 | A | B | E | K |
| 157 | A | C | E, DD | O |
| 158 | A | A | H | K |
| 159 | A | A | H | K |
| 160 | A | B | H | K |
| 161 | A | A | H | K |
| 162 | A | A | H | K |
| 163 | A | A | H | K |
| 164 | A | A | H | K |
| 165 | A | A | H | K |
| 166 | A | B | E | K |
| 167 | A | B | H | K |
| 168 | A | B | H | K |
| 169 | A | B | H | K |
| 170 | A | B | H | K |
| 171 | A | A | E | K |
| 172 | A | A | E | K |
| 173 | A | A | E | K |
| 174 | A | A | E | K |
| 175 | A | A | E | K |
| 176 | A | A | E | |
| 177 | A | A | E | K |
| 178 | A | A | E | K |
| 179 | A | A | E | K |
| 180 | A | A | E | R |
| 181 | A | A | E | K |
| 182 | A | A | E | K |
| 183 | A | A | E | K |
| 184 | A | A | E | K |
| 185 | A | A | E | K |
| 186 | A | A | E | K |

TABLE 2-continued

Analytical and Synthetic Methods for Compounds listed in Table 1

| Cmpd # | LCMS Method | Synthetic Method: β-ketonitriles | Synthetic Method: Alkyl Pyrazole | Synthetic Method: Amine functionalization, final step |
|---|---|---|---|---|
| 187 | A | A | E | K |
| 188 | A | A | H | K |
| 189 | A | A | H | K |
| 190 | A | A | H | K |
| 191 | A | B | E | K |
| 192 | A | A | E | K |
| 193 | A | A | E | R |
| 194 | A | A | E | R |
| 195 | A | A | E | R |
| 196 | A | B | E | K |
| 197 | A | A | E | K |
| 198 | A | A | E | K |
| 199 | A | A | E | K |
| 200 | A | A | E | K |
| 201 | A | A | E | K |
| 202 | A | A | E | K |
| 203 | A | A | E | K |
| 204 | A | B | F | K |
| 205 | A | B | F | K |
| 206 | A | A | E | K |
| 207 | A | A | E | K |
| 208 | A | A | E | K |
| 209 | A | B | F | K |
| 210 | A | A | E | K |
| 211 | A | A | E | K |
| 212 | A | A | E | K |
| 213 | A | A | E | K |
| 214 | A | A | H | K |
| 215 | A | A | E | K |
| 216 | A | A | E | K |
| 217 | A | A | E | S |
| 218 | A | A | E | M |
| 219 | A | A | E | O |
| 220 | A | A | E | K |
| 221 | A | A | E | K |
| 222 | A | A | E | K |
| 223 | A | A | E | K |
| 224 | A | A | E | K |
| 225 | A | A | E | K |
| 226 | A | A | E | K |
| 227 | A | A | E | K |
| 228 | A | A | E | K |
| 229 | A | B | F | K |
| 230 | A | A | H | M |
| 231 | A | A | E | K |
| 232 | A | A | E | K |
| 233 | A | A | E | K |
| 234 | A | A | E | K |
| 235 | A | A | E | K |
| 236 | A | A | E | K |
| 237 | A | A | E | K |
| 238 | A | A | E | K, CC |
| 239 | A | A | E | K |
| 240 | A | A | E | M |
| 241 | A | A | E | M |
| 242 | A | A | E | M |
| 243 | A | A | E | L |
| 244 | A | A | E | K |
| 245 | A | A | E | M |
| 246 | A | A | E | M |
| 247 | A | A | E | M |
| 248 | A | B | H | K |
| 249 | A | A | T | K |
| 250 | A | A | T | K |
| 251 | A | A | H | AA |
| 252 | A | A | H | L |
| 253 | A | A | H | M |
| 254 | A | A | H | L |
| 255 | A | A | H | L |
| 256 | A | A | H | M |
| 257 | A | A | E | K |
| 258 | A | A | H | L |
| 259 | A | A | H | L |

TABLE 2-continued

Analytical and Synthetic Methods for Compounds listed in Table 1

| Cmpd # | LCMS Method | Synthetic Method: β-ketonitriles | Synthetic Method: Alkyl Pyrazole | Synthetic Method: Amine functionalization, final step |
|---|---|---|---|---|
| 260 | A | A | T | L |
| 261 | A | A | T | L |
| 262 | A | A | T | M |
| 263 | A | A | E | L |
| 264 | A | A | E | L |
| 265 | A | B | E | L |
| 266 | A | B | E | M |
| 267 | A | A | E | M |
| 268 | A | A | H | M |
| 269 | A | B | E | L |
| 270 | A | B | E | M |
| 271 | A | B | E | L |
| 272 | A | B | E | M |
| 273 | A | A | E | L |
| 274 | A | A | H | L |
| 275 | A | A | E | L |
| 276 | A | A | E | M |
| 277 | A | A | E | M |
| 278 | A | A | E | M |
| 279 | A | B | T | L |
| 280 | A | B | T | M |
| 281 | A | A | E | L |
| 282 | A | A | E | M |
| 283 | A | A | E | M |
| 284 | A | A | E | L |
| 285 | A | A | E | M |
| 286 | A | A | E | L |
| 287 | A | A | E | M |
| 288 | A | U | I | L |
| 289 | A | A | E | L |
| 290 | A | A | E | L |
| 291 | A | A | E | L |
| 292 | A | A | E | L |
| 293 | A | B | T | K |
| 294 | A | A | E | L, X |
| 295 | A | B | T | L |
| 296 | A | B | T | M |
| 297 | A | U | I | L |
| 298 | A | U | I | K |
| 299 | A | A | E | L |
| 300 | A | U | I | L |
| 301 | A | B | E | L |
| 302 | A | B | E | L |
| 303 | A | A | E | L |
| 304 | A | A | E | L |
| 305 | A | A | E | L |
| 306 | A | A | E | L |
| 307 | A | A | E | M |
| 308 | A | B | F | L |
| 309 | A | B | F | L |
| 310 | A | B | F | L |
| 311 | A | A | E | L |
| 312 | A | A | E | M |
| 313 | A | A | E | L |
| 314 | A | B | F | L |
| 315 | A | B | E | L |
| 316 | A | B | E | L |
| 317 | A | B | E | L |
| 318 | A | A | E | L |
| 319 | A | A | E | L |
| 320 | A | A | E | L |
| 321 | A | A | E | L |
| 322 | A | A | E | L |
| 323 | A | A | E | L |
| 324 | A | A | E | L |
| 325 | A | A | E | L |
| 326 | A | A | E | L |
| 327 | A | B | E | L |
| 328 | A | B | E | L |
| 329 | A | B | E | L |
| 330 | A | C | E | K |
| 331 | A | C | E | K |
| 332 | A | A | E | M, DD |

TABLE 2-continued

Analytical and Synthetic Methods for Compounds listed in Table 1

| Cmpd # | LCMS Method | Synthetic Method: β-ketonitriles | Synthetic Method: Alkyl Pyrazole | Synthetic Method: Amine functionalization, final step |
|---|---|---|---|---|
| 333 | A | A | E | L, DD |
| 334 | A | A | E | L, CC |
| 335 | A | A | E | L, DD |
| 336 | A | A | E | L, CC |
| 337 | A | A | E | L |
| 338 | A | A | E | L |
| 339 | A | A | E | L |
| 340 | A | A | E | L |
| 341 | A | A | E | L |
| 342 | A | A | E | L |
| 343 | A | A | E | L |
| 344 | A | A | E | M |
| 345 | A | A | E | L |
| 346 | A | C | J | K |
| 347 | A | C | J | K |
| 348 | A | A | E | L |
| 349 | A | A | E | L |
| 350 | A | A | E | L |
| 351 | A | A | E | L |
| 352 | A | A | E | M |
| 353 | A | A | E | L |
| 354 | A | A | E | L |
| 355 | A | A | E | L |
| 356 | A | A | E | L |
| 357 | A | B | E | L |
| 358 | A | A | J | K |
| 359 | A | A | J | L |
| 360 | A | B | E | L |
| 361 | A | B | E | L |
| 362 | A | A | E | L |
| 363 | A | A | E | L |
| 364 | A | A | E | L |
| 365 | A | A | E | L |
| 366 | A | B | E | L |
| 367 | A | B | E | L |
| 368 | A | B | E | L |
| 369 | A | B | E | L |
| 370 | A | A | J | K |
| 371 | A | A | J | K |
| 372 | A | A | J | O |
| 373 | A | A | E | L |
| 374 | A | A | E | M |
| 375 | A | A | E | L |
| 376 | A | A | E | L |
| 377 | A | A | E | L |
| 378 | A | B | E | L |
| 379 | A | B | E | L |
| 380 | A | B | F | L |
| 381 | A | B | F | L |
| 382 | A | B | F | L |
| 383 | A | B | F | L |
| 384 | A | A | E | L |
| 385 | A | A | E | L |
| 386 | A | A | E | L |
| 387 | A | A | E | L |
| 388 | A | B | E | L |
| 389 | A | B | E | L |
| 390 | A | A | E | L |
| 391 | A | A | E | L |
| 392 | A | B | E | L |
| 393 | A | B | E | L |
| 394 | A | A | E | L |
| 395 | A | A | E | L |
| 396 | A | B | E | L |
| 397 | A | B | E | L |
| 398 | A | B | V | L |
| 399 | A | B | V | L |
| 400 | A | B | E | L |
| 401 | A | B | E | L |
| 402 | A | B | E | L |
| 403 | A | B | E | L |
| 404 | A | A | E | L |
| 405 | A | A | E | L |

TABLE 2-continued

Analytical and Synthetic Methods for Compounds listed in Table 1

| Cmpd # | LCMS Method | Synthetic Method: β-ketonitriles | Synthetic Method: Alkyl Pyrazole | Synthetic Method: Amine functionalization, final step |
|---|---|---|---|---|
| 406 | A | B | V | K |
| 407 | A | B | V | K |
| 408 | A | B | E | L |
| 409 | A | B | E | L |
| 410 | A | B | E | L |
| 411 | A | B | E | L |
| 412 | A | B | E | L |
| 413 | A | B | E | L |
| 414 | A | B | E | L |
| 415 | A | B | E | L |
| 416 | A | A | E | L |
| 417 | A | B | E | L |
| 418 | A | B | E | L |
| 419 | A | B | E | L |
| 420 | A | B | V | L |
| 421 | A | B | V | L |
| 422 | A | B | V | L |
| 423 | A | B | V | K |
| 424 | A | B | V | K |
| 425 | A | B | V | K |
| 426 | A | B | E | L |
| 427 | A | B | E | L |
| 428 | A | B | E | L |
| 429 | A | B | E | L |
| 430 | A | B | E | L |
| 431 | A | A | J | K |
| 432 | A | B | E | L |
| 433 | A | B | E | L |
| 434 | A | B | E | L |
| 435 | A | B | E | L |
| 436 | A | B | E | L |
| 437 | A | B | E | L |
| 438 | A | B | E | L |
| 439 | A | B | E | L |
| 440 | A | B | E | L |
| 441 | A | B | E | L |
| 442 | A | A | E | M, Z |
| 443 | A | B | E | K |
| 444 | A | B | E | K |
| 445 | A | B | E | K |
| 446 | A | B | E | K |
| 447 | A | B | E | K |
| 448 | A | B | E | K |
| 449 | A | B | E | K |
| 450 | A | A | J | N |
| 451 | A | A | J | N |
| 452 | A | A | E | M |
| 453 | A | A | J | O |
| 454 | A | A | J | O |
| 455 | A | B | V | M |
| 456 | A | B | V | M |
| 457 | A | B | V | K |
| 458 | A | B | V | K |
| 459 | A | B | V | K |
| 460 | A | B | V | K |
| 461 | A | B | V | K |
| 462 | A | B | E | K |
| 463 | A | B | E | K |
| 464 | A | B | E | K |
| 465 | A | B | E | K |
| 466 | A | A | E | K |
| 467 | A | A | E | K |
| 468 | A | A | E | M |
| 469 | A | B | E | K |
| 470 | A | B | E | K |
| 471 | A | B | E | K |
| 472 | A | B | V | K |
| 473 | A | B | V | K |
| 474 | B | A | G | P |
| 475 | B | A | G | P |
| 476 | B | A | E | M |
| 477 | B | A | E | M |
| 478 | B | A | E | M |

TABLE 2-continued

Analytical and Synthetic Methods for Compounds listed in Table 1

| Cmpd # | LCMS Method | Synthetic Method: β-ketonitriles | Synthetic Method: Alkyl Pyrazole | Synthetic Method: Amine functionalization, final step |
|---|---|---|---|---|
| 479 | B | A | E | M |
| 480 | A | B | F | L |
| 481 | A | B | F | L |
| 482 | A | B | F | K |
| 483 | A | B | E | N |
| 484 | A | B | E | N |
| 485 | A | B | E | N |
| 486 | A | B | E | N |
| 487 | A | B | E | N |
| 488 | A | B | E | K |
| 489 | A | B | E | K |
| 490 | A | B | E | K |
| 491 | A | B | E | K |
| 492 | A | B | E | K |
| 493 | A | B | E | K |
| 494 | A | A | E | K |
| 495 | A | A | F | O |
| 496 | A | A | F | K |
| 498 | B | A | G | Q |
| 499 | B | A | G | Q |
| 500 | B | A | G | M |
| 501 | B | A | G | N |
| 502 | B | A | G | N |
| 503 | B | A | G | N |
| 504 | B | A | G | N |
| 505 | B | B | F | L |
| 506 | B | B | F | L |
| 507 | B | B | F | L |
| 508 | B | B | F | L |
| 509 | B | B | F | Q |
| 510 | B | B | F | Q |
| 511 | B | A | E | M |
| 512 | B | A | E | M |
| 513 | B | A | G | M |
| 514 | B | A | G | N |
| 515 | B | A | G | N |
| 516 | B | A | G | N |
| 517 | B | A | G | N |
| 518 | B | A | G | N |
| 519 | B | A | G | N |
| 520 | B | B | F | Q |
| 521 | B | B | F | Q |
| 522 | B | B | F | P |
| 523 | A | B | E | L |
| 524 | A | B | E | L |
| 525 | A | B | E | L |
| 526 | A | B | E | M |
| 527 | A | B | E | M |
| 528 | A | B | E | K |
| 529 | A | B | E | K |
| 530 | A | B | E | K |
| 531 | A | B | E | K |
| 532 | A | B | E | K |
| 533 | B | B | F | Q |
| 534 | B | B | F | Q |
| 535 | B | B | F | Q |
| 536 | B | B | F | Q |
| 537 | B | B | F | Q |
| 538 | B | B | F | Q |
| 539 | B | B | F | Q |
| 540 | B | A | E | M |
| 541 | B | A | E | M |
| 542 | B | A | G | Q |
| 543 | B | A | G | Q |
| 544 | B | A | G | Q |
| 545 | B | A | G | Q |
| 546 | B | A | G | Q |
| 547 | B | A | G | N |
| 548 | B | A | G | N |
| 549 | A | B | E | K |
| 550 | A | B | E | K |
| 551 | A | B | E | K |
| 552 | A | B | E | K |
| 553 | A | B | E | K |
| 554 | A | B | V | K, BB |
| 555 | A | B | V | K, BB |
| 556 | B | B | F | L |
| 557 | B | B | F | L |
| 558 | B | A | E | L |
| 559 | B | A | E | L |
| 560 | A | A | E | K |
| 561 | A | B | E | L |
| 562 | A | B | E | L |
| 563 | A | B | E | L |
| 564 | A | B | E | K |
| 565 | A | B | E | K |
| 566 | A | B | E | K |
| 568 | A | B | E | K |
| 569 | A | B | E | K |
| 570 | A | B | E | K |
| 571 | A | B | E | K |
| 572 | A | B | E | K |
| 573 | A | B | V | K, BB |
| 574 | A | B | V | K, BB |

Biological Assay Methods

Kv7.2/7.3 Activation Assay

The Thallium Flux Assay is used as a surrogate indicator of potassium channel activity.

The experimental protocol was adapted from the FluxOR™ II Green Potassium Ion Channel Assay User Guide (Pub. No. MAN0016084, Invitrogen). Conditions were optimized for the Kv7.2/7.3 cell line.

Cell Line: The hKV7.2/7.3 cell line was obtained from Chantest (Cleveland, Ohio 44128) cat. #CT6147.

Cell Culture: Kv7.2/7.3 cells were maintained in a media containing DMEM/F12; 50/50 (Fisher 11-330), 10% Fetal Bovine Serum (FBS) (Fisher 26-140), 100 units/mL Penicillin-Streptomycin (Fisher 15-140), 0.005 mg/ml Blasticidin (InvivoGen ant-bl-1), 0.5 mg/mL Geneticin (InvivoGen ant-gn-5), and 0.1 mg/mL Zeocin (Fisher R25001). One day prior to experimentation, cells were plated in 96 well clear bottom plates (Corning cat. #353219) in a media without Blasticidin, Geneticin, or Zeocin. Channel expression was induced by adding tetracycline (Sigma T7660) at a final concentration of 10 ng/mL.

Compound Plates: The test compound is diluted in a mixture of 0.1% DMSO/extracellular solution at a single concentration of 10 μM. Dilutions were made on a Biomek NXP (BECKMAN COULTER).

Measurement and data analysis: A plate reader (Enspire, Perkin Elmer) is used to characterize the ion-channel modulating properties of novel compounds using an excitation wavelength of 475 nm and an emission wavelength of 530 nm. After a 15 sec baseline measurement, the stimulus buffer containing thallium and potassium is injected. A final end-point measure is taken after 90 sec. Responses are normalized to the positive control (retigabine, 30 μM).

Data of the 7.2/7.3 Thallium Flux Assay is summarized in Table 2

TABLE 2

| Kv7.2/7.3 Thallium Flux Assay Results. | |
|---|---|
| Compound | Kv7.2/7.3 Activity[a] |
| 1 | − |
| 2 | + |
| 3 | − |
| 4 | + |
| 5 | + |
| 6 | − |
| 7 | − |
| 8 | + |
| 9 | − |
| 10 | − |
| 11 | − |
| 12 | + |
| 13 | − |
| 14 | ++ |
| 15 | + |
| 16 | ++ |
| 17 | + |
| 18 | ++ |
| 19 | + |
| 20 | + |
| 21 | + |
| 22 | ++ |
| 23 | + |
| 24 | ++ |
| 25 | ++ |
| 26 | ++ |
| 27 | ++ |
| 28 | ++ |
| 29 | ++ |
| 30 | ++ |
| 31 | ++ |
| 32 | ++ |
| 33 | ++ |
| 34 | ++ |
| 35 | ++ |
| 36 | ++ |
| 37 | ++ |
| 38 | + |
| 39 | + |
| 40 | + |
| 41 | ++ |
| 42 | ++ |
| 43 | ++ |
| 44 | + |
| 45 | ++ |
| 46 | ++ |
| 47 | ++ |
| 48 | ++ |
| 49 | + |
| 50 | ++ |
| 51 | ++ |
| 52 | + |
| 53 | + |
| 54 | + |
| 55 | ++ |
| 56 | + |
| 57 | ++ |
| 58 | ++ |
| 59 | + |
| 60 | + |
| 61 | + |
| 62 | ++ |
| 63 | ++ |
| 64 | ++ |
| 65 | + |
| 66 | + |
| 67 | − |
| 68 | − |
| 69 | − |
| 70 | + |
| 71 | ++ |
| 72 | ++ |
| 73 | ++ |
| 74 | + |
| 75 | ++ |
| 76 | ++ |

TABLE 2-continued

| Kv7.2/7.3 Thallium Flux Assay Results. | |
|---|---|
| Compound | Kv7.2/7.3 Activity[a] |
| 77 | + |
| 78 | ++ |
| 79 | ++ |
| 80 | ++ |
| 81 | ++ |
| 82 | + |
| 83 | + |
| 84 | ++ |
| 85 | ++ |
| 86 | ++ |
| 87 | + |
| 88 | − |
| 89 | − |
| 90 | + |
| 91 | + |
| 92 | + |
| 93 | + |
| 94 | ++ |
| 95 | ++ |
| 96 | − |
| 97 | ++ |
| 98 | ++ |
| 99 | + |
| 100 | ++ |
| 101 | ++ |
| 102 | + |
| 103 | ++ |
| 104 | + |
| 105 | ++ |
| 106 | + |
| 107 | + |
| 108 | + |
| 109 | + |
| 110 | ++ |
| 111 | ++ |
| 112 | + |
| 113 | ++ |
| 114 | + |
| 115 | ++ |
| 116 | + |
| 117 | + |
| 118 | − |
| 119 | − |
| 120 | ++ |
| 121 | ++ |
| 122 | ++ |
| 123 | ++ |
| 124 | ++ |
| 125 | ++ |
| 126 | ++ |
| 127 | + |
| 128 | + |
| 129 | ++ |
| 130 | ++ |
| 131 | ++ |
| 132 | ++ |
| 133 | ++ |
| 134 | + |
| 135 | + |
| 136 | + |
| 137 | ++ |
| 138 | ++ |
| 139 | ++ |
| 140 | ++ |
| 141 | ++ |
| 142 | + |
| 143 | + |
| 144 | + |
| 145 | − |
| 146 | − |
| 147 | ++ |
| 148 | + |
| 149 | − |
| 150 | − |
| 151 | − |
| 152 | ++ |

TABLE 2-continued

Kv7.2/7.3 Thallium Flux Assay Results.

| Compound | Kv7.2/7.3 Activity[a] |
|---|---|
| 153 | + |
| 154 | − |
| 155 | − |
| 156 | − |
| 157 | − |
| 158 | − |
| 159 | + |
| 160 | + |
| 161 | − |
| 162 | + |
| 163 | ++ |
| 164 | ++ |
| 165 | + |
| 166 | − |
| 167 | + |
| 168 | − |
| 169 | + |
| 170 | + |
| 171 | − |
| 172 | − |
| 173 | + |
| 174 | ++ |
| 175 | ++ |
| 176 | − |
| 177 | ++ |
| 178 | + |
| 179 | + |
| 180 | − |
| 181 | + |
| 182 | + |
| 183 | ++ |
| 184 | ++ |
| 185 | + |
| 186 | + |
| 187 | + |
| 188 | − |
| 189 | + |
| 190 | ++ |
| 191 | − |
| 192 | ++ |
| 193 | + |
| 194 | + |
| 195 | + |
| 196 | − |
| 197 | + |
| 198 | ++ |
| 199 | + |
| 200 | ++ |
| 201 | ++ |
| 202 | ++ |
| 203 | ++ |
| 204 | ++ |
| 205 | ++ |
| 206 | ++ |
| 207 | ++ |
| 208 | + |
| 209 | ++ |
| 210 | ++ |
| 211 | ++ |
| 212 | ++ |
| 213 | ++ |
| 214 | ++ |
| 215 | − |
| 216 | + |
| 217 | + |
| 218 | ++ |
| 219 | + |
| 220 | ++ |
| 221 | − |
| 222 | ++ |
| 223 | + |
| 224 | + |
| 225 | + |
| 226 | + |
| 227 | + |
| 228 | − |

TABLE 2-continued

Kv7.2/7.3 Thallium Flux Assay Results.

| Compound | Kv7.2/7.3 Activity[a] |
|---|---|
| 229 | ++ |
| 230 | + |
| 231 | + |
| 232 | + |
| 233 | + |
| 234 | ++ |
| 235 | + |
| 236 | + |
| 237 | ++ |
| 238 | − |
| 239 | − |
| 240 | ++ |
| 241 | + |
| 242 | ++ |
| 243 | ++ |
| 244 | ++ |
| 245 | ++ |
| 246 | ++ |
| 247 | ++ |
| 248 | + |
| 249 | + |
| 250 | + |
| 251 | − |
| 252 | ++ |
| 253 | ++ |
| 254 | ++ |
| 255 | + |
| 256 | ++ |
| 257 | − |
| 258 | ++ |
| 259 | + |
| 260 | + |
| 261 | + |
| 262 | + |
| 263 | ++ |
| 264 | ++ |
| 265 | ++ |
| 266 | ++ |
| 267 | − |
| 268 | − |
| 269 | + |
| 270 | + |
| 271 | ++ |
| 272 | + |
| 273 | + |
| 274 | ++ |
| 275 | ++ |
| 276 | ++ |
| 277 | + |
| 278 | ++ |
| 279 | + |
| 280 | + |
| 281 | ++ |
| 282 | ++ |
| 283 | − |
| 284 | + |
| 285 | + |
| 286 | ++ |
| 287 | ++ |
| 288 | − |
| 289 | ++ |
| 290 | ++ |
| 291 | ++ |
| 292 | ++ |
| 293 | ++ |
| 294 | − |
| 295 | ++ |
| 296 | ++ |
| 297 | − |
| 298 | − |
| 299 | ++ |
| 300 | − |
| 301 | ++ |
| 302 | + |
| 303 | ++ |
| 304 | + |

TABLE 2-continued

Kv7.2/7.3 Thallium Flux Assay Results.

| Compound | Kv7.2/7.3 Activity[a] |
|---|---|
| 305 | ++ |
| 306 | ++ |
| 307 | ++ |
| 308 | ++ |
| 309 | ++ |
| 310 | ++ |
| 311 | ++ |
| 312 | ++ |
| 313 | ++ |
| 314 | ++ |
| 315 | ++ |
| 316 | ++ |
| 317 | ++ |
| 318 | ++ |
| 319 | ++ |
| 320 | ++ |
| 321 | ++ |
| 322 | ++ |
| 323 | − |
| 324 | ++ |
| 325 | ++ |
| 326 | ++ |
| 327 | ++ |
| 328 | ++ |
| 329 | ++ |
| 330 | |
| 331 | |
| 332 | − |
| 333 | + |
| 334 | + |
| 335 | − |
| 336 | − |
| 337 | ++ |
| 338 | ++ |
| 339 | + |
| 340 | ++ |
| 341 | ++ |
| 342 | ++ |
| 343 | ++ |
| 344 | ++ |
| 345 | ++ |
| 346 | |
| 347 | |
| 348 | ++ |
| 349 | ++ |
| 350 | ++ |
| 351 | + |
| 352 | ++ |
| 353 | + |
| 354 | ++ |
| 355 | ++ |
| 356 | ++ |
| 357 | ++ |
| 358 | ++ |
| 359 | ++ |
| 360 | + |
| 361 | − |
| 362 | ++ |
| 363 | ++ |
| 364 | ++ |
| 365 | ++ |
| 366 | + |
| 367 | + |
| 368 | ++ |
| 369 | ++ |
| 370 | ++ |
| 371 | ++ |
| 372 | ++ |
| 373 | ++ |
| 374 | ++ |
| 375 | ++ |
| 376 | ++ |
| 377 | ++ |
| 378 | ++ |
| 379 | ++ |
| 380 | ++ |

TABLE 2-continued

Kv7.2/7.3 Thallium Flux Assay Results.

| Compound | Kv7.2/7.3 Activity[a] |
|---|---|
| 381 | ++ |
| 382 | ++ |
| 383 | ++ |
| 384 | + |
| 385 | − |
| 386 | − |
| 387 | + |
| 388 | ++ |
| 389 | ++ |
| 390 | ++ |
| 391 | + |
| 392 | ++ |
| 393 | ++ |
| 394 | + |
| 395 | ++ |
| 396 | + |
| 397 | ++ |
| 398 | ++ |
| 399 | ++ |
| 400 | ++ |
| 401 | + |
| 402 | ++ |
| 403 | ++ |
| 404 | ++ |
| 405 | ++ |
| 406 | ++ |
| 407 | ++ |
| 408 | + |
| 409 | ++ |
| 410 | ++ |
| 411 | ++ |
| 412 | ++ |
| 413 | ++ |
| 414 | + |
| 415 | + |
| 416 | ++ |
| 417 | ++ |
| 418 | ++ |
| 419 | + |
| 420 | ++ |
| 421 | ++ |
| 422 | + |
| 423 | ++ |
| 424 | ++ |
| 425 | ++ |
| 426 | ++ |
| 427 | ++ |
| 428 | − |
| 429 | ++ |
| 430 | + |
| 431 | ++ |
| 432 | ++ |
| 433 | ++ |
| 434 | + |
| 435 | + |
| 436 | ++ |
| 437 | + |
| 438 | + |
| 439 | ++ |
| 440 | ++ |
| 441 | ++ |
| 442 | − |
| 443 | + |
| 444 | ++ |
| 445 | ++ |
| 446 | ++ |
| 447 | ++ |
| 448 | + |
| 449 | + |
| 450 | ++ |
| 451 | + |
| 452 | + |
| 453 | ++ |
| 454 | ++ |
| 455 | ++ |
| 456 | ++ |

TABLE 2-continued

Kv7.2/7.3 Thallium Flux Assay Results.

| Compound | Kv7.2/7.3 Activity[a] |
|---|---|
| 457 | + |
| 458 | ++ |
| 459 | + |
| 460 | ++ |
| 461 | ++ |
| 462 | ++ |
| 463 | ++ |
| 464 | + |
| 465 | ++ |
| 466 | ++ |
| 467 | ++ |
| 468 | ++ |
| 469 | + |
| 470 | − |
| 471 | + |
| 472 | |
| 473 | ++ |
| 474 | + |
| 475 | + |
| 476 | ++ |
| 477 | + |
| 478 | ++ |
| 479 | + |
| 480 | ++ |
| 481 | ++ |
| 482 | ++ |
| 483 | ++ |
| 484 | ++ |
| 485 | ++ |
| 486 | + |
| 487 | + |
| 488 | ++ |
| 489 | ++ |
| 490 | ++ |
| 491 | + |
| 492 | ++ |
| 493 | ++ |
| 494 | − |
| 495 | ++ |
| 496 | ++ |
| 498 | ++ |
| 499 | ++ |
| 500 | ++ |
| 501 | ++ |
| 502 | ++ |
| 503 | + |
| 504 | ++ |
| 505 | ++ |
| 506 | ++ |
| 507 | ++ |
| 508 | + |
| 509 | ++ |
| 510 | ++ |
| 511 | + |
| 512 | ++ |
| 513 | ++ |
| 514 | ++ |
| 515 | ++ |
| 516 | ++ |
| 517 | ++ |
| 518 | − |
| 519 | ++ |
| 520 | + |
| 521 | ++ |
| 522 | ++ |
| 523 | ++ |
| 524 | ++ |
| 525 | ++ |
| 526 | ++ |
| 527 | ++ |
| 528 | + |
| 529 | + |
| 530 | + |
| 531 | + |
| 532 | + |
| 533 | ++ |

TABLE 2-continued

Kv7.2/7.3 Thallium Flux Assay Results.

| Compound | Kv7.2/7.3 Activity[a] |
|---|---|
| 534 | ++ |
| 535 | ++ |
| 536 | ++ |
| 537 | ++ |
| 538 | ++ |
| 539 | ++ |
| 540 | ++ |
| 541 | + |
| 542 | ++ |
| 543 | ++ |
| 544 | + |
| 545 | ++ |
| 546 | + |
| 547 | ++ |
| 548 | ++ |
| 549 | ++ |
| 550 | ++ |
| 551 | ++ |
| 552 | ++ |
| 553 | + |
| 554 | + |
| 555 | ++ |
| 556 | − |
| 557 | + |
| 558 | + |
| 559 | + |

[a]Measured Kv7.2/Kv7.3 activation using thallium flux assay as described in Biological Assay Methods section, described as a range from "−" No Activity <0.15, "+" Moderate Activity 0.15-0.7, and "++" High Activity ≥0.7.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A compound represented by Formula 1, or a pharmaceutically acceptable salt thereof, Formula 1

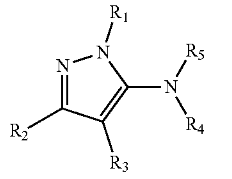

wherein:

$R_1$ is optionally substituted $C_{1-4}$ alkyl, optionally substituted $C_{3-8}$ cycloalkyl, optionally substituted $C_{5-10}$ aryl, optionally substituted $C_{2-8}$ heteroaryl, optionally substituted $C_{2-8}$ heterocyclyl, wherein each optional substituent is independently selected from the group consisting of halogen, OH, CN, —C(O)$NH_2$, —N($C_{1-4}$ alkyl)$_2$, or $C_{1-4}$ alkyl;

$R_2$ is optionally substituted $C_{1-8}$ alkyl, optionally substituted $C_{1-8}$ haloalkyl, optionally substituted —$OC_{1-8}$ alkyl, optionally substituted $C_{3-6}$ cycloalkyl, wherein each optional substituent is independently selected from the group consisting of halogen, OH, CN, $C_{1-4}$ alkyl, $C_{1-4}$ hydroxyalkyl, $C_{1-4}$ haloalkyl, —$OC_{1-4}$ alkyl, —$OC_{1-4}$ haloalkyl, $C_{3-8}$ cycloalkyl, $C_{3-8}$ halocycloalkyl;

$R_3$ is halogen, optionally substituted $C_{1-6}$ alkyl, optionally substituted $C_{3-8}$ cycloalkyl, optionally substituted $C_{2-8}$ heterocyclyl, or optionally substituted $C_{5-10}$ aryl, wherein each optional substituent is independently selected from the group consisting of halogen, OH, CN, $C_{1-4}$ alkyl, $C_{1-4}$ hydroxyalkyl, and $C_{1-4}$ haloalkyl;

$R_4$ is H or $C_{1-3}$ alkyl;

$R_5$ is

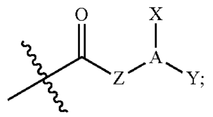

A is $C_{3-8}$ cycloalkyl, $C_{5-10}$ bicycloalkyl, $C_{2-5}$ heterocyclyl, $C_{5-10}$ aryl, or $C_{2-8}$ heteroaryl;

X and Y are each independently H, F, Cl, optionally substituted $C_{1-6}$ alkyl, optionally substituted $C_{3-8}$ cycloalkyl, or optionally substituted —$OC_{1-6}$ alkyl, wherein each optional substituent is independently selected from the group consisting of halogen, OH, $C_{1-3}$ alkyl, $C_{1-3}$ haloalkyl, —$OC_{1-3}$ alkyl, and CN;

Z is a bond, $C(R_6)_2$, $NR_6$, and O;

$R_6$ is H, $C_{1-3}$ alkyl, or $C_{1-4}$ hydroxyalkyl;

wherein the compound comprises at least one F; and provided that $R_1$ is optionally substituted $C_{3-8}$ cycloalkyl; $R_2$ is optionally substituted $C_{3-6}$ cycloalkyl; $R_3$ is optionally substituted $C_{3-8}$ cycloalkyl; or A is $C_{3-8}$ cycloalkyl.

2. The compound of claim 1, wherein $R_1$ is optionally substituted $C_{1-4}$ alkyl or optionally substituted $C_{3-8}$ cycloalkyl, and $R_3$ is optionally substituted $C_{1-6}$ alkyl or optionally substituted $C_{3-8}$ cycloalkyl.

3. The compound of claim 1, wherein at least one of $R_1$ and $R_3$ comprises at least 3 carbons.

4. The compound of claim 1, wherein at least one of $R_1$, $R_2$, $R_3$, and $R_5$ comprises an optionally substituted cyclobutyl, or an optionally substituted cyclopropyl, or one of $R_1$-$R_5$ comprises an optionally substituted cyclobutyl and another of $R_1$, $R_2$, $R_3$, and $R_5$ comprises an optionally substituted cyclopropyl.

5. The compound of claim 1, wherein at least one of $R_1$, $R_2$, $R_3$, and $R_5$ comprises a perfluorinated methyl, a perfluorinated methylene, or a combination thereof.

6. The compound of claim 1, wherein:

at least one of $R_1$, $R_2$, $R_3$, and $R_5$ comprises an optionally substituted cyclobutyl, or an optionally substituted cyclopropyl, or one of $R_1$, $R_2$, $R_3$, and $R_5$ comprises an optionally substituted cyclobutyl and another of $R_1$-$R_5$ comprises an optionally substituted cyclopropyl; and at least one of $R_1$, $R_2$, $R_3$, and $R_5$ comprises a perfluorinated methyl, a perfluorinated methylene, or a combination thereof.

7. The compound of claim 1, wherein:

at least one of $R_1$ and $R_3$ comprises at least 3 carbons;

at least one of $R_1$, $R_2$, $R_3$, and $R_5$ comprises an optionally substituted cyclobutyl, or an optionally substituted cyclopropyl, or one of $R_1$, $R_2$, $R_3$, and $R_5$ comprises an optionally substituted cyclobutyl and another of $R_1$, $R_2$, $R_3$, and $R_5$ comprises an optionally substituted cyclopropyl; and at least one of $R_1$, $R_2$, $R_3$, and $R_5$ comprises a perfluorinated methyl, a perfluorinated methylene, or a combination thereof.

8. The compound of claim 1, wherein at least one of $R_1$, $R_2$, $R_3$, and $R_5$ comprises an optionally substituted cyclobutyl, or an optionally substituted cyclopropyl, or one of $R_1$, $R_2$, $R_3$, and $R_5$ comprises an optionally substituted cyclobutyl and another of $R_1$, $R_2$, $R_3$, and $R_5$ comprises an optionally substituted cyclopropyl;

at least one of $R_1$, $R_2$, $R_3$, and $R_5$ comprises a perfluorinated methyl, a perfluorinated methylene, or a combination thereof;

$R_1$ and $R_3$ are each independently optionally substituted $C_{1-4}$ alkyl or optionally substituted $C_{3-8}$ cycloalkyl and at least one of $R_1$ and $R_3$ comprises at least 3 carbons;

X is H, F, optionally substituted $C_{1-6}$ alkyl or optionally substituted $C_{3-8}$ cycloalkyl, Y is H or halogen; and Z is a bond, $C(R_6)_2$, $NR_6$, and O.

9. A compound of the following table, or a pharmaceutically acceptable salt thereof

| Cmpd # | Structure | Name |
|---|---|---|
| 73 | 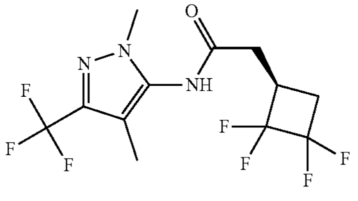 [SMILES: Cc1c(C(F)(F)F)nn(C)c1NC(=O)C[C@H]1CC(F)(F)C1(F)F] | (S)-N-(1,4-dimethyl-3-(trifluoromethyl)-1H-pyrazol-5-yl)-2-(2,2,3,3-tetrafluorocyclobutyl)acetamide |

-continued

| Cmpd # | Structure | Name |
| --- | --- | --- |
| 100 | 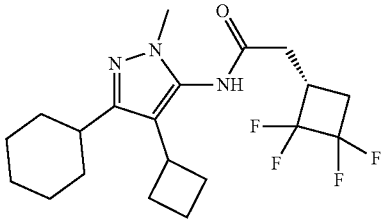 [SMILES: Cn1nc(C2CCCCC2)c(C2CCC2)c1NC(=O)C[C@@H]1CC(F)(F)C1(F)F] | (R)-N-(4-cyclobutyl-3-cyclohexyl-1-methyl-1H-pyrazol-5-yl)-2-(2,2,3,3-tetrafluorocyclobutyl)acetamide |
| 101 | 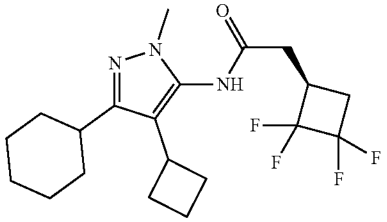 [SMILES: Cn1nc(C2CCCCC2)c(C2CCC2)c1NC(=O)C[C@H]1CC(F)(F)C1(F)F] | (S)-N-(4-cyclobutyl-3-cyclohexyl-1-methyl-1H-pyrazol-5-yl)-2-(2,2,3,3-tetrafluorocyclobutyl)acetamide |
| 113 | 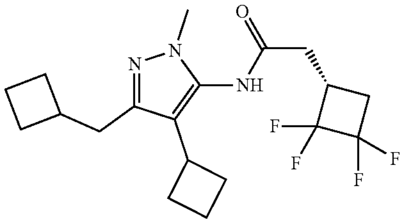 [SMILES: Cn1nc(CC2CCC2)c(C2CCC2)c1NC(=O)C[C@@H]1CC(F)(F)C1(F)F] | (R)-N-(4-cyclobutyl-3-(cyclobutylmethyl)-1-methyl-1H-pyrazol-5-yl)-2-(2,2,3,3-tetrafluorocyclobutyl)acetamide |
| 114 | 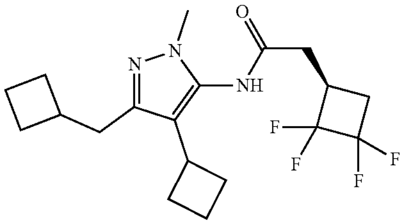 [SMILES: Cn1nc(CC2CCC2)c(C2CCC2)c1NC(=O)C[C@H]1CC(F)(F)C1(F)F] | (S)-N-(4-cyclobutyl-3-(cyclobutylmethyl)-1-methyl-1H-pyrazol-5-yl)-2-(2,2,3,3-tetrafluorocyclobutyl)acetamide |
| 115 | 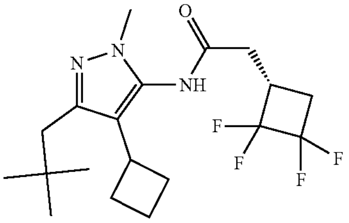 [SMILES: Cn1nc(CC(C)(C)C)c(C2CCC2)c1NC(=O)C[C@@H]1CC(F)(F)C1(F)F] | (R)-N-(4-cyclobutyl-1-methyl-3-neopentyl-1H-pyrazol-5-yl)-2-(2,2,3,3-tetrafluorocyclobutyl)acetamide |
| 116 | 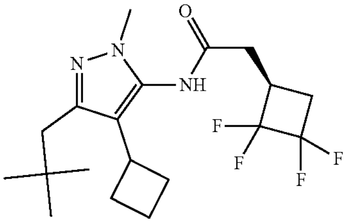 [SMILES: Cn1nc(CC(C)(C)C)c(C2CCC2)c1NC(=O)C[C@H]1CC(F)(F)C1(F)F] | (S)-N-(4-cyclobutyl-1-methyl-3-neopentyl-1H-pyrazol-5-yl)-2-(2,2,3,3-tetrafluorocyclobutyl)acetamide |

-continued

| Cmpd # | Structure | Name |
|---|---|---|
| 120 | 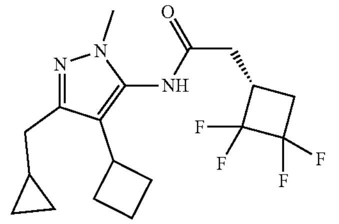 [SMILES: Cn1nc(CC2CC2)c(C2CCC2)c1NC(=O)C[C@@H]1CC(F)(F)C1(F)F] | (R)-N-(4-cyclobutyl-3-(cyclopropylmethyl)-1-methyl-1H-pyrazol-5-yl)-2-(2,2,3,3-tetrafluorocyclobutyl)acetamide |
| 121 | 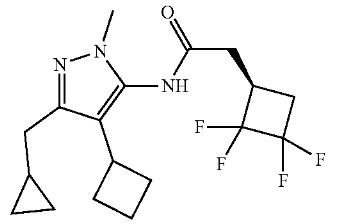 [SMILES: Cn1nc(CC2CC2)c(C2CCC2)c1NC(=O)C[C@H]1CC(F)(F)C1(F)F] | (S)-N-(4-cyclobutyl-3-(cyclopropylmethyl)-1-methyl-1H-pyrazol-5-yl)-2-(2,2,3,3-tetrafluorocyclobutyl)acetamide |
| 123 | 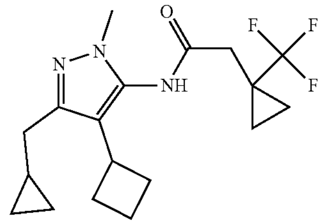 [SMILES: Cn1nc(CC2CC2)c(C2CCC2)c1NC(=O)CC1(C(F)(F)F)CC1] | N-(4-cyclobutyl-3-(cyclopropylmethyl)-1-methyl-1H-pyrazol-5-yl)-2-(1-(trifluoromethyl)cyclopropyl)acetamide |
| 126 | 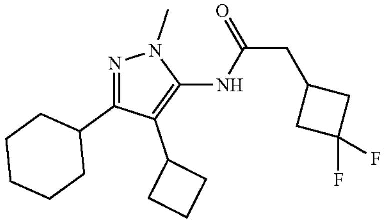 | N-(4-cyclobutyl-3-cyclohexyl-1-methyl-1H-pyrazol-5-yl)-2-(3,3-difluorocyclobutyl)acetamide |
| 132 | 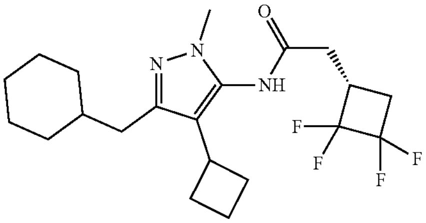 [SMILES: Cn1nc(CC2CCCCC2)c(C2CCC2)c1NC(=O)C[C@@H]1CC(F)(F)C1(F)F] | (R)-N-(4-cyclobutyl-3-(cyclohexylmethyl)-1-methyl-1H-pyrazol-5-yl)-2-(2,2,3,3-tetrafluorocyclobutyl)acetamide |
| 133 | 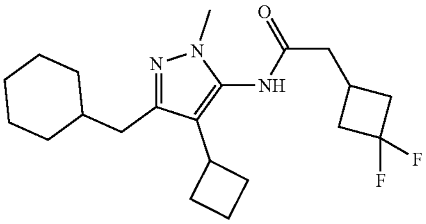 | N-(4-cyclobutyl-3-(cyclohexylmethyl)-1-methyl-1H-pyrazol-5-yl)-2-(3,3-difluorocyclobutyl)acetamide |

-continued

| Cmpd # | Structure | Name |
| --- | --- | --- |
| 134 | 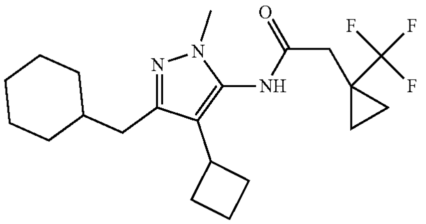 [SMILES: Cn1nc(CC2CCCCC2)c(C2CCC2)c1NC(=O)CC1(C(F)(F)F)CC1] | N-(4-cyclobutyl-3-(cyclohexyl-methyl)-1-methyl-1H-pyrazol-5-yl)-2-(1-(trifluoromethyl)cyclo-propyl)acetamide |
| 136 | 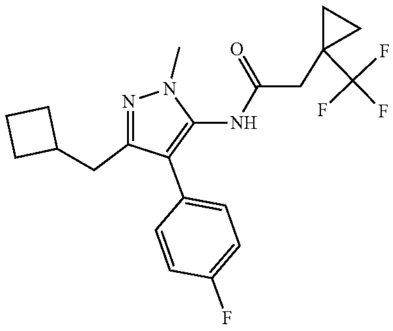 [SMILES: Cn1nc(CC2CCC2)c(-c2ccc(F)cc2)c1NC(=O)CC1(C(F)(F)F)CC1] | N-(3-(cyclobutylmethyl)-4-(4-fluorophenyl)-1-methyl-1H-pyrazol-5-yl)-2-(1-(trifluoro-methyl)cyclopropyl)acetamide |
| 137 | 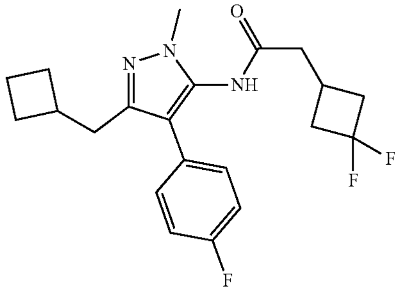 [SMILES: Cn1nc(CC2CCC2)c(-c2ccc(F)cc2)c1NC(=O)CC1CC(F)(F)C1] | N-(3-(cyclobutylmethyl)-4-(4-fluorophenyl)-1-methyl-1H-pyrazol-5-yl)-2-(3,3-difluoro-cyclobutyl)acetamide |
| 150 | | N-(4-cyclobutyl-1-methyl-3-(1-(trifluoromethyl)cyclobutyl)-1H-pyrazol-5-yl)-2-(1-(trifluoro-methyl)cyclopropyl)acetamide |
| 172 | 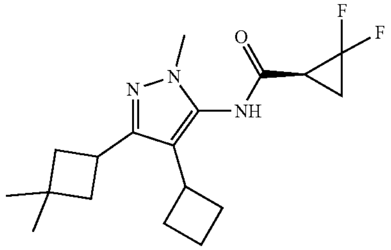 [SMILES: Cn1nc(C2CC(C)(C)C2)c(C2CCC2)c1NC(=O)[C@@H]1CC1(F)F] | (S)-N-(4-cyclobutyl-3-(3,3-dimethylcyclobutyl)-1-methyl-1H-pyrazol-5-yl)-2,2-difluoro-cyclopropane-1-carboxamide |
| 173 | 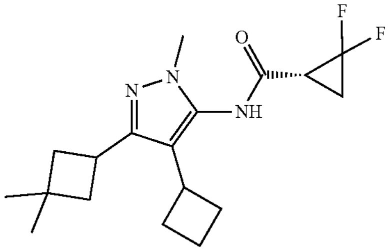 [SMILES: Cn1nc(C2CC(C)(C)C2)c(C2CCC2)c1NC(=O)[C@H]1CC1(F)F] | (R)-N-(4-cyclobutyl-3-(3,3-dimethylcyclobutyl)-1-methyl-1H-pyrazol-5-yl)-2,2-difluoro-cyclopropane-1-carboxamide |

-continued

| Cmpd # | Structure | Name |
|---|---|---|
| 174 | 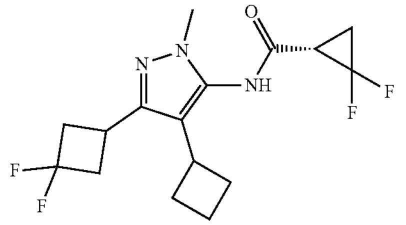 [SMILES: Cn1nc(C2CC(F)(F)C2)c(C2CCC2)c1NC(=O)[C@@H]1CC1(F)F] | (S)-N-(4-cyclobutyl-3-(3,3-difluorocyclobutyl)-1-methyl-1H-pyrazol-5-yl)-2,2-difluoro-cyclopropane-1-carboxamide |
| 175 | 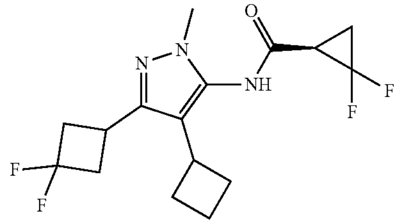 [SMILES: Cn1nc(C2CC(F)(F)C2)c(C2CCC2)c1NC(=O)[C@H]1CC1(F)F] | (R)-N-(4-cyclobutyl-3-(3,3-difluorocyclobutyl)-1-methyl-1H-pyrazol-5-yl)-2,2-difluoro-cyclopropane-1-carboxamide |
| 179 | 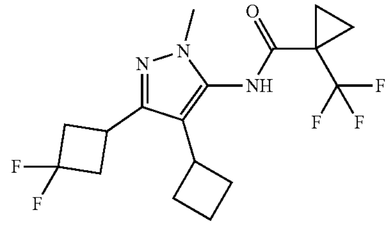 [SMILES: Cn1nc(C2CC(F)(F)C2)c(C2CCC2)c1NC(=O)C1(C(F)(F)F)CC1] | N-(4-cyclobutyl-3-(3,3-difluoro-cyclobutyl)-1-methyl-1H-pyrazol-5-yl)-1-(trifluoro-methyl)-cyclopropane-1-carboxamide |
| 183 | 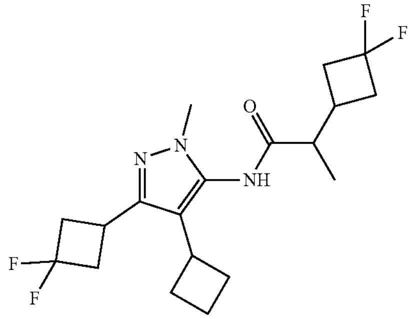 Stereoisomer 1 | N-(4-cyclobutyl-3-(3,3-difluoro-cyclobutyl)-1-methyl-1H-pyrazol-5-yl)-2-(3,3-difluoro-cyclobutyl)propanamide |
| 184 | 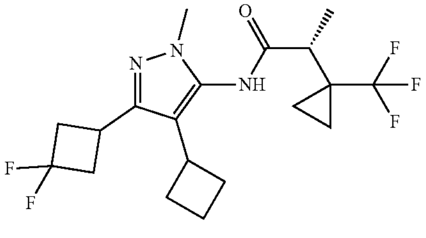 [SMILES: C[C@@H](C(=O)Nc1c(C2CCC2)c(C2CC(F)(F)C2)nn1C)C1(C(F)(F)F)CC1] | (R)-N-(4-cyclobutyl-3-(3,3-difluorocyclobutyl)-1-methyl-1H-pyrazol-5-yl)-2-(1-(trifluoro-methyl)cyclopropyl)propanamide |
| 192 | 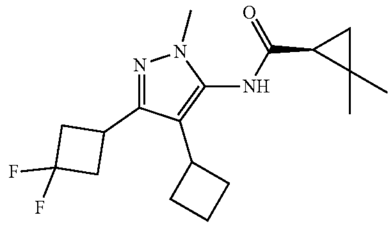 [SMILES: Cn1nc(C2CC(F)(F)C2)c(C2CCC2)c1NC(=O)[C@H]1CC1(C)C] | (S)-N-(4-cyclobutyl-3-(3,3-difluorocyclobutyl)-1-methyl-1H-pyrazol-5-yl)-2,2-dimethyl-cyclopropane-1-carboxamide |

-continued

| Cmpd # | Structure | Name |
|---|---|---|
| 194 | 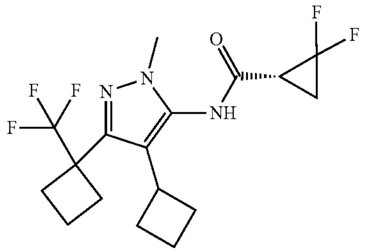 [SMILES: Cn1nc(C2(C(F)(F)F)CCC2)c(C2CCC2)c1NC(=O)[C@H]1CC1(F)F] | (R)-N-(4-cyclobutyl-1-methyl-3-(1-(trifluoromethyl)cyclobutyl)-1H-pyrazol-5-yl)-2,2-difluoro-cyclopropane-1-carboxamide |
| 195 | 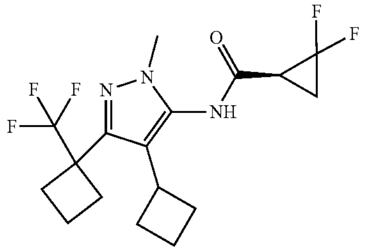 [SMILES: Cn1nc(C2(C(F)(F)F)CCC2)c(C2CCC2)c1NC(=O)[C@@H]1CC1(F)F] | (S)-N-(4-cyclobutyl-1-methyl-3-(1-(trifluoromethyl)cyclobutyl)-1H-pyrazol-5-yl)-2,2-difluoro-cyclopropane-1-carboxamide |
| 201 | 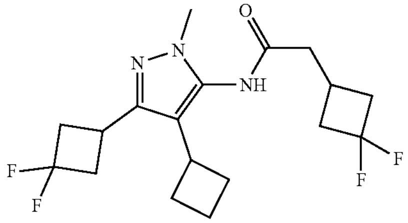 [SMILES: Cn1nc(C2CC(F)(F)C2)c(C2CCC2)c1NC(=O)CC1CC(F)(F)C1] | N-(4-cyclobutyl-3-(3,3-difluoro-cyclobutyl)-1-methyl-1H-pyrazol-5-yl)-2-(3,3-difluoro-cyclobutyl)acetamide |
| 202 | 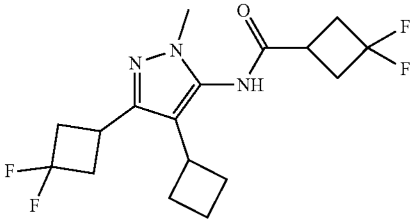 | N-(4-cyclobutyl-3-(3,3-difluoro-cyclobutyl)-1-methyl-1H-pyrazol-5-yl)-3,3-difluoro-cyclobutane-1-carboxamide |
| 203 | 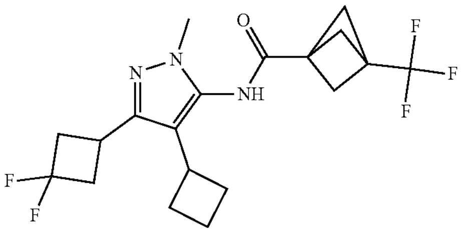 [SMILES: Cn1nc(C2CC(F)(F)C2)c(C2CCC2)c1NC(=O)C12CC(C(F)(F)F)(C1)C2] | N-(4-cyclobutyl-3-(3,3-difluoro-cyclobutyl)-1-methyl-1H-pyrazol-5-yl)-3-(trifluoro-methyl)bicyclo[1.1.1]pentane-1-carboxamide |
| 204 | 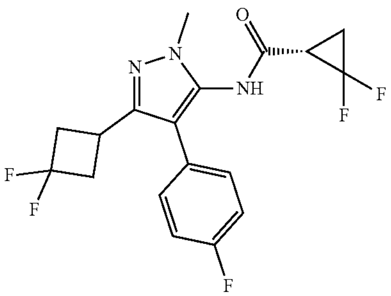 [SMILES: Cn1nc(C2CC(F)(F)C2)c(-c2ccc(F)cc2)c1NC(=O)[C@@H]1CC1(F)F] | (S)-N-(3-(3,3-difluoroyclobutyl)-4-(4-fluorophenyl)-1-methyl-1H-pyrazol-5-yl)-2,2-difluorocyclo-propane-1-carboxamide |

-continued

| Cmpd # | Structure | Name |
|---|---|---|
| 205 | 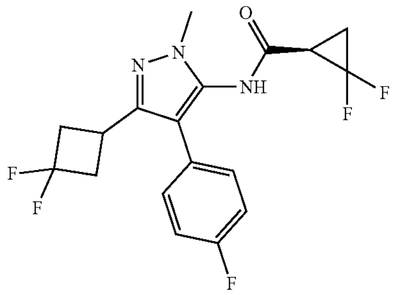 [SMILES: Cn1nc(C2CC(F)(F)C2)c(-c2ccc(F)cc2)c1NC(=O)[C@H]1CC1(F)F] | (R)-N-(3-(3,3-difluorocycloutyl)-4-(4-fluorophenyl)-1-methyl-1H-pyrazol-5-yl)-2,2-difluorocyclo-propane-1-carboxamide |
| 207 | 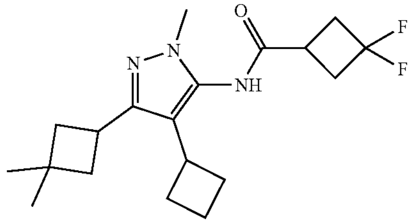 [SMILES: Cn1nc(C2CC(C)(C)C2)c(C2CCC2)c1NC(=O)C1CC(F)(F)C1] | N-(4-cyclobutyl-3-(3,3-dimeth-ylcyclobutyl)-1-methyl-1H-pyrazol-5-yl)-3,3-difluorocyclo-butane-1-carboxamide |
| 209 | 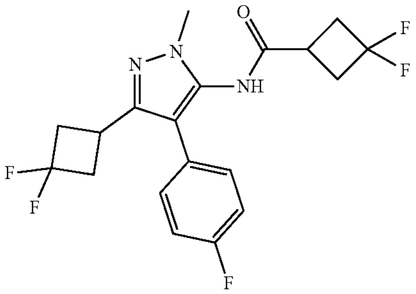 [SMILES: Cn1nc(C2CC(F)(F)C2)c(-c2ccc(F)cc2)c1NC(=O)C1CC(F)(F)C1] | N-(3-(3,3-difluorocyclobutyl)-4-(4-fluorophenyl)-1-methyl-1H-pyrazol-5-yl)-3,3-difluorocyclo-butane-1-carboxamide |
| 217 | 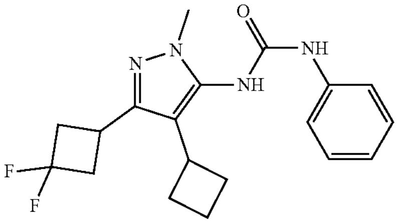 [SMILES: Cn1nc(C2CC(F)(F)C2)c(C2CCC2)c1NC(=O)Nc1ccccc1] | 1-(4-cyclobutyl-3-(3,3-difluoro-cyclobutyl)-1-methyl-1H-pyrazol-5-yl)-3-phenylurea |
| 218 | 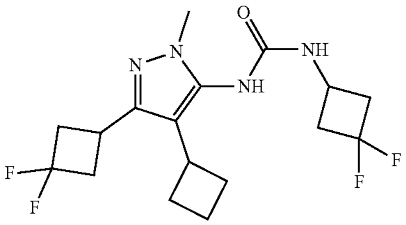 [SMILES: Cn1nc(C2CC(F)(F)C2)c(C2CCC2)c1NC(=O)NC1CC(F)(F)C1] | 1-(4-cyclobutyl-3-(3,3-difluoro-cyclobutyl)-1-methyl-1H-pyrazol-5-yl)-3-(3,3-difluoro-cyclobutyl)urea |
| 219 | 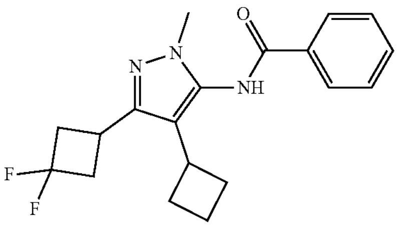 [SMILES: Cn1nc(C2CC(F)(F)C2)c(C2CCC2)c1NC(=O)c1ccccc1] | N-(4-cyclobutyl-3-(3,3-difluoro-cyclobutyl)-1-methyl-1H-pyrazol-5-yl)benzamide |

-continued

| Cmpd # | Structure | Name |
| --- | --- | --- |
| 229 | 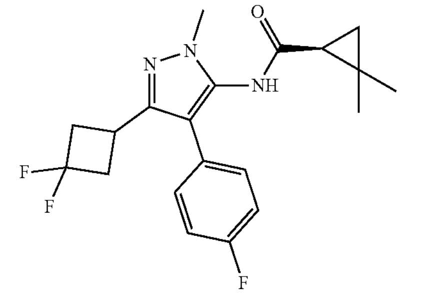 [SMILES: Cn1nc(C2CC(F)(F)C2)c(-c2ccc(F)cc2)c1NC(=O)[C@H]1CC1(C)C] | (S)-N-(3-(3,3-difluorocyclobutyl)-4-(4-fluorophenyl)-1-methyl-1H-pyrazol-5-yl)-2,2-dimethylcyclopropane-1-carboxamide |
| 236 | 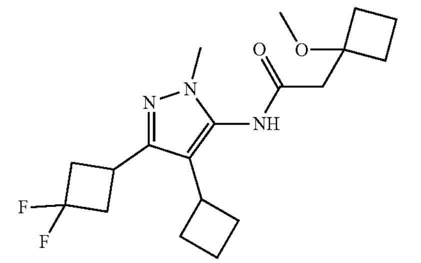 [SMILES: COC1(CC(=O)Nc2c(C3CCC3)c(C3CC(F)(F)C3)nn2C)CCC1] | N-(4-cyclobutyl-3-(3,3-difluorocyclobutyl)-1-methyl-1H-pyrazol-5-yl)-2-(1-methoxycyclobutyl)acetamide |
| 241 | 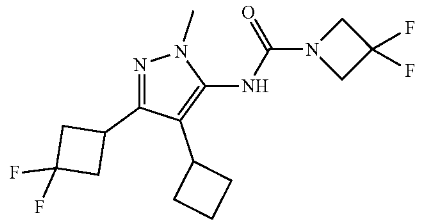 | N-(4-cyclobutyl-3-(3,3-difluorocyclobutyl)-1-methyl-1H-pyrazol-5-yl)-3,3-difluoroazetidine-1-carboxamide |
| 242 | 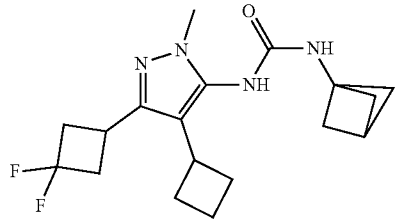 [SMILES: Cn1nc(C2CC(F)(F)C2)c(C2CCC2)c1NC(=O)NC12CC(C1)C2] | 1-(bicyclo[1.1.1]pentan-1-yl)-3-(4-cyclobutyl-3-(3,3-difluorocyclobutyl)-1-methyl-1H-pyrazol-5-yl)urea |
| 243 | 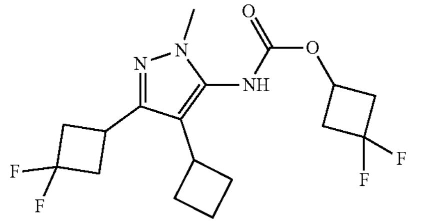 | 3,3-difluorocyclobutyl (4-cyclobutyl-3-(3,3-difluorocyclobutyl)-1-methyl-1H-pyrazol-5-yl)carbamate |
| 245 | 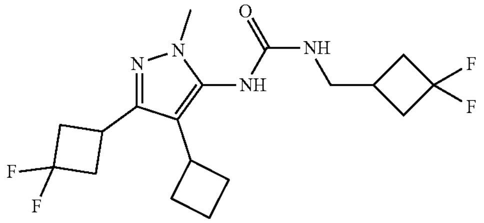 | 1-(4-cyclobutyl-3-(3,3-difluorocyclobutyl)-1-methyl-1H-pyrazol-5-yl)-3-((3,3-difluorocyclobutyl)methyl)urea |

-continued

| Cmpd # | Structure | Name |
|---|---|---|
| 246 | 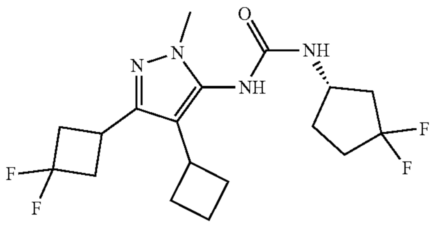 [SMILES: Cn1nc(C2CC(F)(F)C2)c(C2CCC2)c1NC(=O)N[C@H]1CCC(F)(F)C1] | (S)-1-(4-cyclobutyl-3-(3,3-difluorocyclobutyl)-1-methyl-1H-pyrazol-5-yl)-3-(3,3-difluorocyclopentyl)urea |
| 247 | 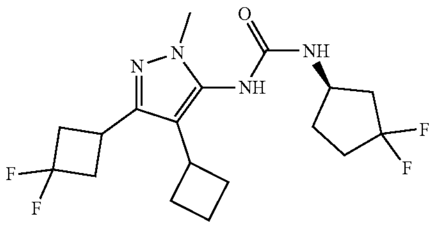 [SMILES: Cn1nc(C2CC(F)(F)C2)c(C2CCC2)c1NC(=O)N[C@@H]1CCC(F)(F)C1] | (R)-1-(4-cyclobutyl-3-(3,3-difluorocyclobutyl)-1-methyl-1H-pyrazol-5-yl)-3-(3,3-difluorocyclopentyl)urea |
| 252 | 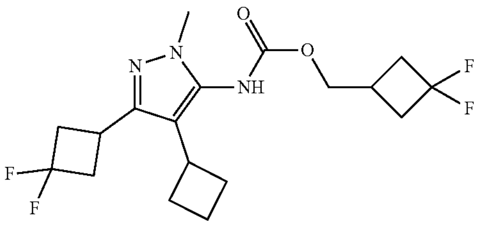 [SMILES: Cn1nc(C2CC(F)(F)C2)c(C2CCC2)c1NC(=O)OCC1CC(F)(F)C1] | (3,3-difluorocyclobutyl)methyl (4-cyclobutyl-3-(3,3-difluorocyclobutyl)-1-methyl-1H-pyrazol-5-yl)carbamate |
| 262 | 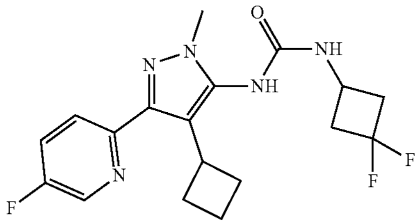 | 1-(4-cyclobutyl-3-(5-fluoropyridin-2-yl)-1-methyl-1H-pyrazol-5-yl)-3-(3,3-difluorocyclobutyl)urea |
| 263 | 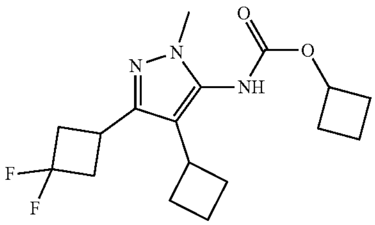 [SMILES: Cn1nc(C2CC(F)(F)C2)c(C2CCC2)c1NC(=O)OC1CCC1] | cyclobutyl (4-cyclobutyl-3-(3,3-difluorocyclobutyl)-1-methyl-1H-pyrazol-5-yl)carbamate |
| 265 | 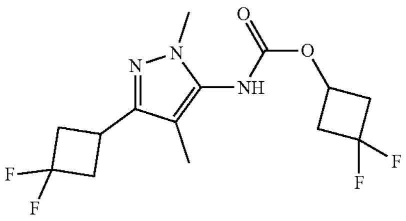 [SMILES: Cc1c(C2CC(F)(F)C2)nn(C)c1NC(=O)OC1CC(F)(F)C1] | 3,3-difluorocyclobutyl (3-(3,3-difluorocyclobutyl)-1,4-dimethyl-1H-pyrazol-5-yl)carbamate |

-continued

| Cmpd # | Structure | Name |
|---|---|---|
| 266 | 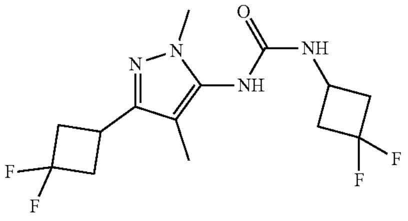 [SMILES: Cc1c(C2CC(F)(F)C2)nn(C)c1NC(=O)NC1CC(F)(F)C1] | 1-(3,3-difluorocyclobutyl)-3-(3-(3,3-difluorocyclobutyl)-1,4-dimethyl-1H-pyrazol-5-yl)urea |
| 267 | | 1-(4-cyclobutyl-1-methyl-3-(1-(trifluoromethyl)cyclobutyl)-1H-pyrazol-5-yl)-3-(3,3-difluoro-cyclobutyl)urea |
| 268 | 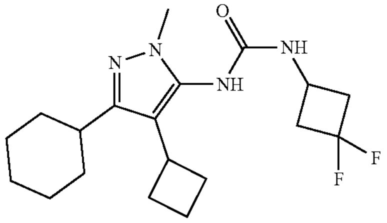 [SMILES: Cn1nc(C2CCCCC2)c(C2CCC2)c1NC(=O)NC1CC(F)(F)C1] | 1-(4-cyclobutyl-3-cyclohexyl-1-methyl-1H-pyrazol-5-yl)-3-(3,3-difluorocyclobutyl)urea |
| 271 | 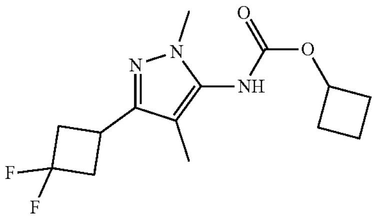 [SMILES: Cc1c(C2CC(F)(F)C2)nn(C)c1NC(=O)OC1CCC1] | cyclobutyl (3-(3,3-difluorocyclo-butyl)-1,4-dimethyl-1H-pyrazol-5-yl)carbamate |
| 273 | 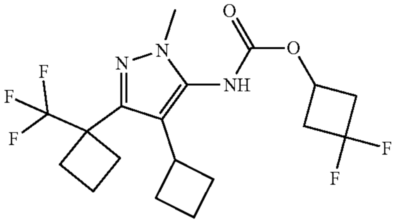 [SMILES: Cn1nc(C2(C(F)(F)F)CCC2)c(C2CCC2)c1NC(=O)OC1CC(F)(F)C1] | 3,3-difluorocyclobutyl (4-cyclo-butyl-1-methyl-3-(1-(trifluoro-methyl)cyclobutyl)-1H-pyrazol-5-yl)carbamate |
| 274 | 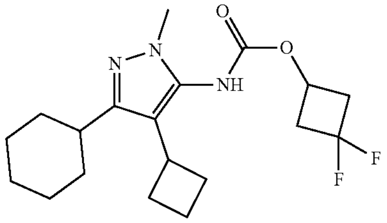 [SMILES: Cn1nc(C2CCCCC2)c(C2CCC2)c1NC(=O)OC1CC(F)(F)C1] | 3,3-difluorocyclobutyl (4-cyclo-butyl-3-cyclohexyl-1-methyl-1H-pyrazol-5-yl)carbamate |
| 275 | 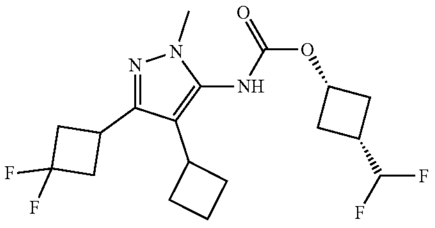 [SMILES: Cn1nc(C2CC(F)(F)C2)c(C2CCC2)c1NC(=O)O[C@H]1C[C@@H](C(F)F)C1] | (1s,3s)-3-(difluoromethyl)cyclo-butyl (4-cyclobutyl-3-(3,3-difluorocyclobutyl)-1-methyl-1H-pyrazol-5-yl)carbamate |

-continued

| Cmpd # | Structure | Name |
| --- | --- | --- |
| 276 | 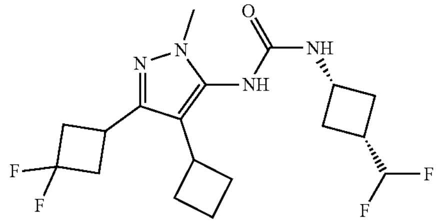 [SMILES: Cn1nc(C2CC(F)(F)C2)c(C2CCC2)c1NC(=O)N[C@H]1C[C@@H](C(F)F)C1] | 1-(4-cyclobutyl-3-(3,3-difluoro-cyclobutyl)-1-methyl-1H-pyrazol-5-yl)-3-((1s,3s)-3-(difluoromethyl)cyclobutyl)urea |
| 277 | 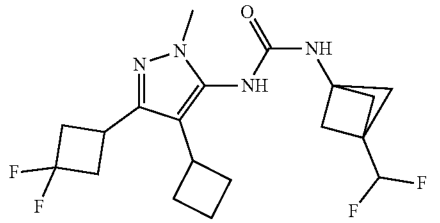 [SMILES: Cn1nc(C2CC(F)(F)C2)c(C2CCC2)c1NC(=O)NC12CC(C(F)F)(C1)C2] | 1-(4-cyclobutyl-3-(3,3-difluoro-cyclobutyl)-1-methyl-1H-pyrazol-5-yl)-3-(3-(difluorometh-yl)bicyclo[1.1.1]pentan-1-yl)urea |
| 278 | 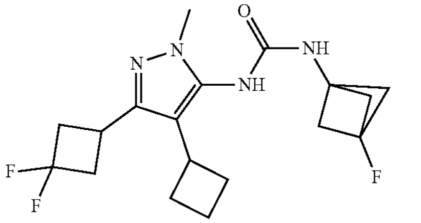 [SMILES: Cn1nc(C2CC(F)(F)C2)c(C2CCC2)c1NC(=O)NC12CC(F)(C1)C2] | 1-(4-cyclobutyl-3-(3,3-difluoro-cyclobutyl)-1-methyl-1H-pyrazol-5-yl)-3-(3-fluoro-bicyclo[1.1.1]pentan-1-yl)urea |
| 281 | 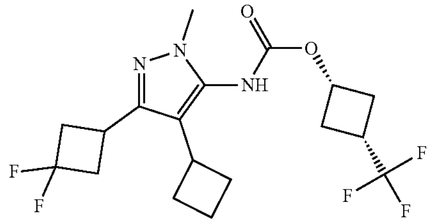 [SMILES: Cn1nc(C2CC(F)(F)C2)c(C2CCC2)c1NC(=O)O[C@H]1C[C@@H](C(F)(F)F)C1] | (1s,3s)-3-(trifluoromethyl)cyclo-butyl (4-cyclobutyl-3-(3,3-di-fluorocyclobutyl)-1-methyl-1H-pyrazol-5-yl)carbamate |
| 282 | 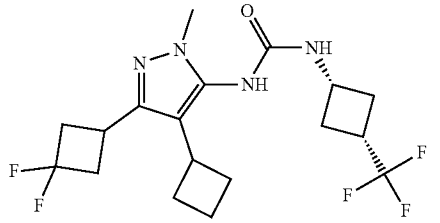 [SMILES: Cn1nc(C2CC(F)(F)C2)c(C2CCC2)c1NC(=O)N[C@H]1C[C@@H](C(F)(F)F)C1] | 1-(4-cyclobutyl-3-(3,3-difluoro-cyclobutyl)-1-methyl-1H-pyrazol-5-yl)-3-((1s,3s)-3-(tri-fluoromethyl)cyclobutyl)urea |
| 283 | 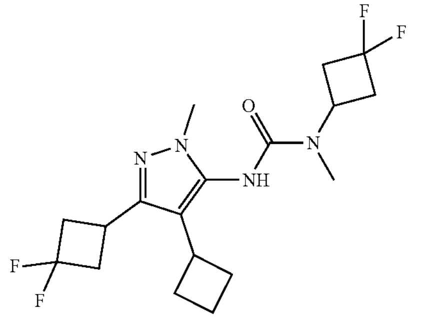 [SMILES: CN(C(=O)Nc1c(C2CCC2)c(C2CC(F)(F)C2)nn1C)C1CC(F)(F)C1] | 3-(4-cyclobutyl-3-(3,3-difluoro-cyclobutyl)-1-methyl-1H-pyrazol-5-yl)-1-(3,3-difluoro-cyclobutyl)-1-methylurea |

-continued

| Cmpd # | Structure | Name |
| --- | --- | --- |
| 284 | 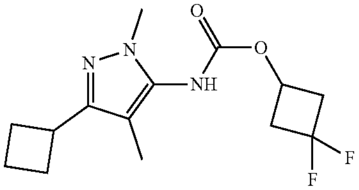 [SMILES: Cc1c(C2CCC2)nn(C)c1NC(=O)OC1CC(F)(F)C1] | 3,3-difluorocyclobutyl (3-cyclobutyl-1,4-dimethyl-1H-pyrazol-5-yl)carbamate |
| 285 | 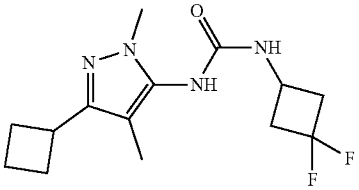 [SMILES: Cc1c(C2CCC2)nn(C)c1NC(=O)NC1CC(F)(F)C1] | 1-(3-cyclobutyl-1,4-dimethyl-1H-pyrazol-5-yl)-3-(3,3-difluorocyclobutyl)urea |
| 286 | 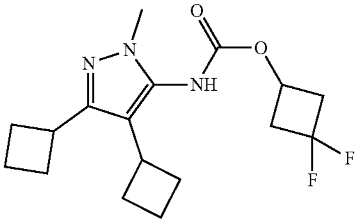 [SMILES: Cn1nc(C2CCC2)c(C2CCC2)c1NC(=O)OC1CC(F)(F)C1] | 3,3-difluorocyclobutyl (3,4-dicyclobutyl-1-methyl-1H-pyrazol-5-yl)carbamate |
| 287 | 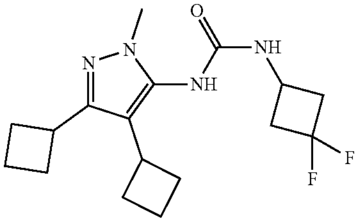 [SMILES: Cn1nc(C2CCC2)c(C2CCC2)c1NC(=O)NC1CC(F)(F)C1] | 1-(3,4-dicyclobutyl-1-methyl-1H-pyrazol-5-yl)-3-(3,3-difluorocyclobutyl)urea |
| 289 | 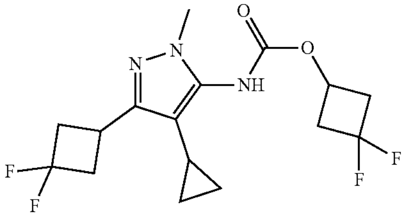 [SMILES: Cn1nc(C2CC(F)(F)C2)c(C2CC2)c1NC(=O)OC1CC(F)(F)C1] | 3,3-difluorocyclobutyl (4-cyclopropyl-3-(3,3-difluorocyclobutyl)-1-methyl-1H-pyrazol-5-yl)-carbamate |
| 290 | 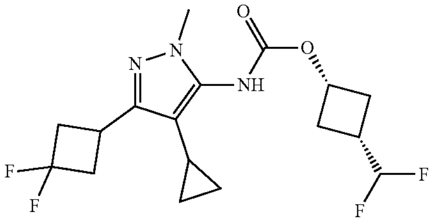 [SMILES: Cn1nc(C2CC(F)(F)C2)c(C2CC2)c1NC(=O)O[C@H]1C[C@@H](C(F)F)C1] | (1s,3s)-3-(difluoromethyl)cyclobutyl (4-cyclopropyl-3-(3,3-difluorocyclobutyl)-1-methyl-1H-pyrazol-5-yl)carbamate |
| 291 | 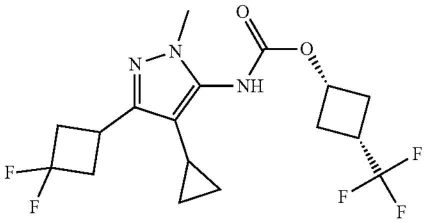 [SMILES: Cn1nc(C2CC(F)(F)C2)c(C2CC2)c1NC(=O)O[C@H]1C[C@@H](C(F)(F)F)C1] | (1s,3s)-3-(trifluoromethyl)cyclobutyl (4-cyclopropyl-3-(3,3-difluorocyclobutyl)-1-methyl-1H-pyrazol-5-yl)carbamate |

-continued

| Cmpd # | Structure | Name |
|---|---|---|
| 292 | 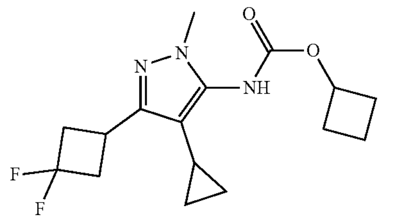 [SMILES: Cn1nc(C2CC(F)(F)C2)c(C2CC2)c1NC(=O)OC1CCC1] | cyclobutyl (4-cyclopropyl-3-(3,3-difluorocyclobutyl)-1-methyl-1H-pyrazol-5-yl)carbamate |
| 293 | 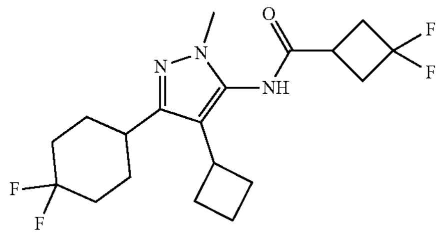 [SMILES: Cn1nc(C2CCC(F)(F)CC2)c(C2CCC2)c1NC(=O)C1CC(F)(F)C1] | N-(4-cyclobutyl-3-(4,4-difluoro-cyclohexyl)-1-methyl-1H-pyrazol-5-yl)-3,3-difluoro-cyclobutane-1-carboxamide |
| 294 | 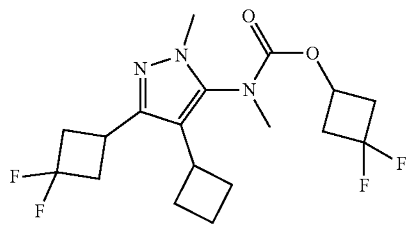 [SMILES: CN(C(=O)OC1CC(F)(F)C1)c1c(C2CCC2)c(C2CC(F)(F)C2)nn1C] | 3,3-difluorocyclobutyl (4-cyclo-butyl-3-(3,3-difluorocyclobutyl)-1-methyl-1H-pyrazol-5-yl)(meth-yl)carbamate |
| 295 | 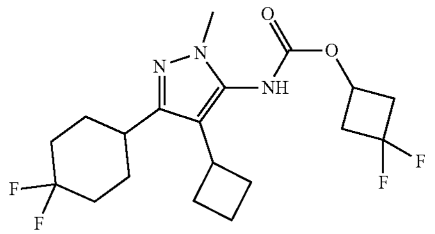 [SMILES: Cn1nc(C2CCC(F)(F)CC2)c(C2CCC2)c1NC(=O)OC1CC(F)(F)C1] | 3,3-difluorocyclobutyl (4-cyclo-butyl-3-(4,4-difluorocyclohex-yl)-1-methyl-1H-pyrazol-5-yl)-carbamate |
| 296 | 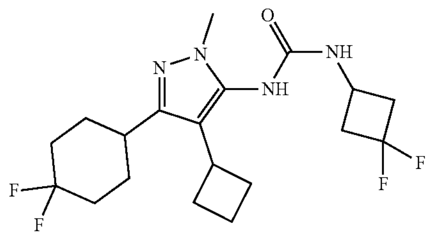 [SMILES: Cn1nc(C2CCC(F)(F)CC2)c(C2CCC2)c1NC(=O)NC1CC(F)(F)C1] | 1-(4-cyclobutyl-3-(4,4-difluoro-cyclohexyl)-1-methyl-1H-pyrazol-5-yl)-3-(3,3-difluoro-cyclobutyl)urea |
| 299 | 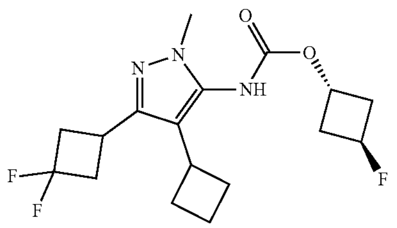 [SMILES: Cn1nc(C2CC(F)(F)C2)c(C2CCC2)c1NC(=O)O[C@H]1C[C@H](F)C1] | (1r,3r)-3-fluorocyclobutyl (4-cyclobutyl-3-(3,3-difluorocyclo-butyl)-1-methyl-1H-pyrazol-5-yl)carbamate |

-continued

| Cmpd # | Structure | Name |
|---|---|---|
| 300 | 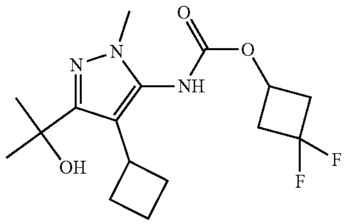 [SMILES: Cn1nc(C(C)(C)O)c(C2CCC2)c1NC(=O)OC1CC(F)(F)C1] | 3,3-difluorocyclobutyl (4-cyclobutyl-3-(2-hydroxypropan-2-yl)-1-methyl-1H-pyrazol-5-yl)carbamate |
| 301 | 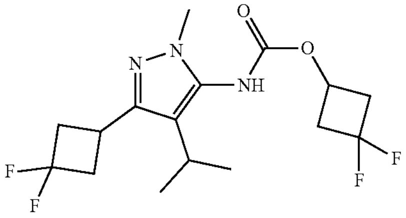 [SMILES: CC(C)c1c(C2CC(F)(F)C2)nn(C)c1NC(=O)OC1CC(F)(F)C1] | 3,3-difluorocyclobutyl (3-(3,3-difluorocyclobutyl)-4-isopropyl-1-methyl-1H-pyrazol-5-yl)carbamate |
| 302 | 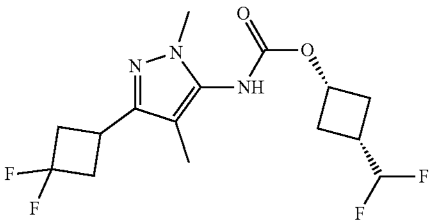 [SMILES: Cc1c(C2CC(F)(F)C2)nn(C)c1NC(=O)O[C@H]1C[C@@H](C(F)F)C1] | (1s,3s)-3-(difluoromethyl)cyclobutyl (3-(3,3-difluorocyclobutyl)-1,4-dimethyl-1H-pyrazol-5-yl)carbamate |
| 303 | 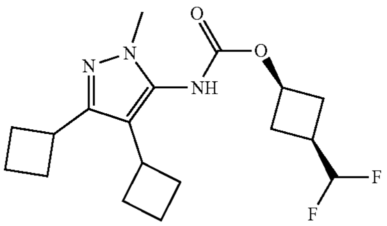 [SMILES: Cn1nc(C2CCC2)c(C2CCC2)c1NC(=O)O[C@H]1C[C@@H](C(F)F)C1] | (1s,3s)-3-(difluoromethyl)cyclobutyl (3,4-dicyclobutyl-1-methyl-1H-pyrazol-5-yl)carbamate |
| 304 | 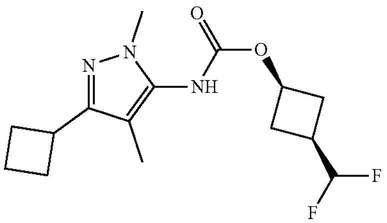 [SMILES: Cc1c(C2CCC2)nn(C)c1NC(=O)O[C@H]1C[C@@H](C(F)F)C1] | (1s,3s)-3-(difluoromethyl)cyclobutyl (3-cyclobutyl-1,4-dimethyl-1H-pyrazol-5-yl)carbamate |
| 305 | 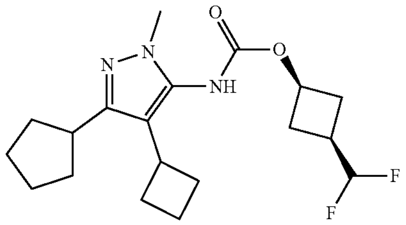 [SMILES: Cn1nc(C2CCCC2)c(C2CCC2)c1NC(=O)O[C@H]1C[C@@H](C(F)F)C1] | (1s,3s)-3-(difluoromethyl)cyclobutyl (4-cyclobutyl-3-cyclopentyl-1-methyl-1H-pyrazol-5-yl)carbamate |

-continued

| Cmpd # | Structure | Name |
|---|---|---|
| 306 | 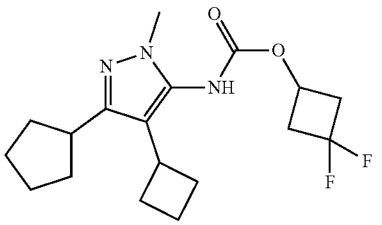 [SMILES: Cn1nc(C2CCCC2)c(C2CCC2)c1NC(=O)OC1CC(F)(F)C1] | 3,3-difluorocyclobutyl (4-cyclobutyl-3-cyclopentyl-1-methyl-1H-pyrazol-5-yl)carbamate |
| 307 | 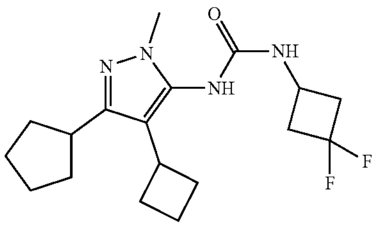 [SMILES: Cn1nc(C2CCCC2)c(C2CCC2)c1NC(=O)NC1CC(F)(F)C1] | 1-(4-cyclobutyl-3-cyclopentyl-1-methyl-1H-pyrazol-5-yl)-3-(3,3-difluorocyclobutyl)urea |
| 308 | 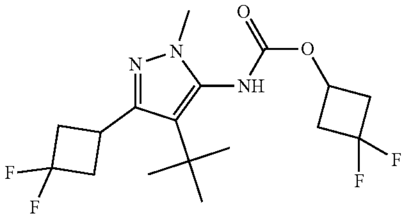 [SMILES: Cn1nc(C2CC(F)(F)C2)c(C(C)(C)C)c1NC(=O)OC1CC(F)(F)C1] | 3,3-difluorocyclobutyl (4-(tert-butyl)-3-(3,3-difluorocyclobutyl)-1-methyl-1H-pyrazol-5-yl)carbamate |
| 309 | 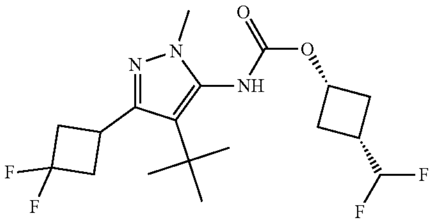 [SMILES: Cn1nc(C2CC(F)(F)C2)c(C(C)(C)C)c1NC(=O)O[C@H]1C[C@@H](C(F)F)C1] | (1s,3s)-3-(difluoromethyl)cyclobutyl (4-(tert-butyl)-3-(3,3-difluorocyclobutyl)-1-methyl-1H-pyrazol-5-yl)carbamate |
| 310 | 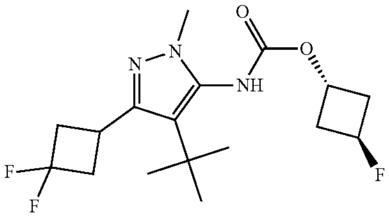 [SMILES: Cn1nc(C2CC(F)(F)C2)c(C(C)(C)C)c1NC(=O)O[C@H]1C[C@H](F)C1] | (1r,3r)-3-fluorocyclobutyl (4-(tert-butyl)-3-(3,3-difluorocyclobutyl)-1-methyl-1H-pyrazol-5-yl)carbamate |
| 311 | 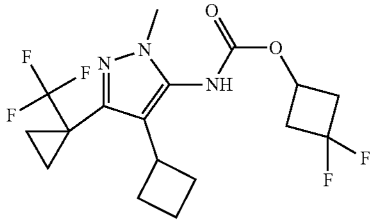 [SMILES: Cn1nc(C2(C(F)(F)F)CC2)c(C2CCC2)c1NC(=O)OC1CC(F)(F)C1] | 3,3-difluorocyclobutyl (4-cyclobutyl-1-methyl-3-(1-(trifluoromethyl)cyclopropyl)-1H-pyrazol-5-yl)carbamate |

-continued

| Cmpd # | Structure | Name |
|---|---|---|
| 312 | 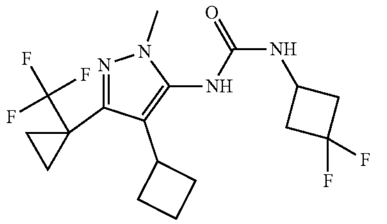 [SMILES: Cn1nc(C2(C(F)(F)F)CC2)c(C2CCC2)c1NC(=O)NC1CC(F)(F)C1] | 1-(4-cyclobutyl-1-methyl-3-(1-(trifluoromethyl)cyclopropyl)-1H-pyrazol-5-yl)-3-(3,3-difluoro-cyclobutyl)urea |
| 313 | 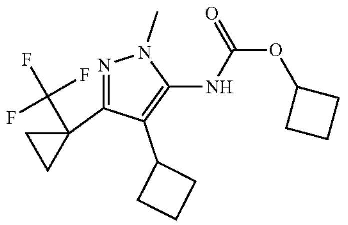 [SMILES: Cn1nc(C2(C(F)(F)F)CC2)c(C2CCC2)c1NC(=O)OC1CCC1] | cyclobutyl (4-cyclobutyl-1-meth-yl-3-(1-(trifluoromethyl)cyclo-propyl)-1H-pyrazol-5-yl)carbamate |
| 315 | 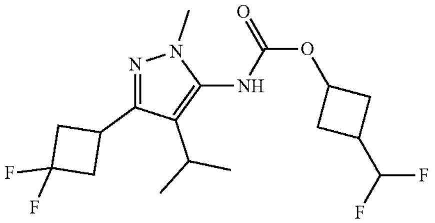 [SMILES: CC(C)c1c(C2CC(F)(F)C2)nn(C)c1NC(=O)OC1CC(C(F)F)C1] | 3-(difluoromethyl)cyclobutyl (3-(3,3-difluorocyclobutyl)-4-iso-propyl-1-methyl-1H-pyrazol-5-yl)carbamate |
| 316 | 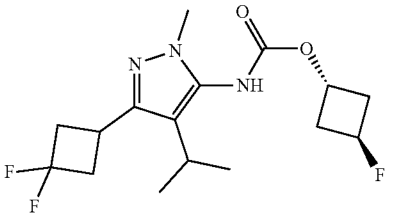 [SMILES: CC(C)c1c(C2CC(F)(F)C2)nn(C)c1NC(=O)O[C@H]1C[C@H](F)C1] | (1r,3r)-3-fluorocyclobutyl (3-(3,3-difluorocyclobutyl)-4-iso-propyl-1-methyl-1H-pyrazol-5-yl)carbamate |
| 320 | 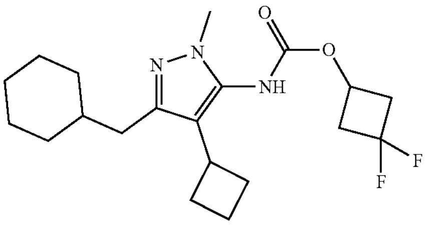 | 3,3-difluorocyclobutyl (4-cyclo-butyl-3-(cyclohexylmethyl)-1-methyl-1H-pyrazol-5-yl)carbamate |
| 323 | 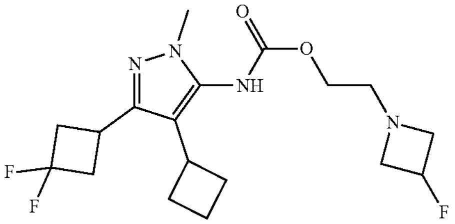 [SMILES: Cn1nc(C2CC(F)(F)C2)c(C2CCC2)c1NC(=O)OCCN1CC(F)C1] | 2-(3-fluoroazetidin-1-yl)ethyl (4-cyclobutyl-3-(3,3-difluorocyclo-butyl)-1-methyl-1H-pyrazol-5-yl)carbamate |

-continued

| Cmpd # | Structure | Name |
|---|---|---|
| 325 | 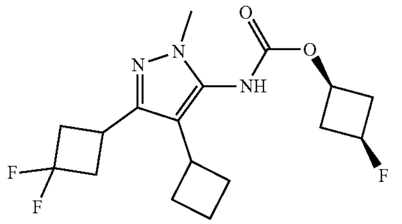 [SMILES: Cn1nc(C2CC(F)(F)C2)c(C2CCC2)c1NC(=O)O[C@H]1C[C@@H](F)C1] | (1s,3s)-3-fluorocyclobutyl (4-cyclobutyl-3-(3,3-difluorocyclo-butyl)-1-methyl-1H-pyrazol-5-yl)carbamate |
| 326 | 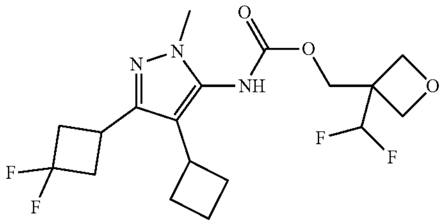 [SMILES: Cn1nc(C2CC(F)(F)C2)c(C2CCC2)c1NC(=O)OCC1(C(F)F)COC1] | (3-(difluoromethyl)oxetan-3-yl)methyl (4-cyclobutyl-3-(3,3-difluorocyclobutyl)-1-methyl-1H-pyrazol-5-yl)carbamate |
| 327 | 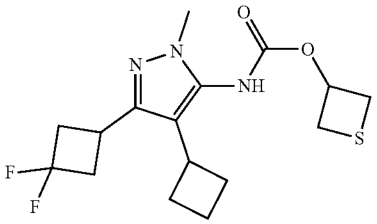 | thietan-3-yl (4-cyclobutyl-3-(3,3-difluorocyclobutyl)-1-methyl-1H-pyrazol-5-yl)carbamate |
| 328 | 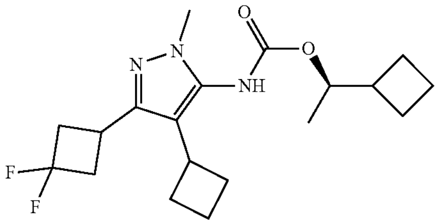 [SMILES: C[C@@H](OC(=O)Nc1c(C2CCC2)c(C2CC(F)(F)C2)nn1C)C1CCC1] | (R)-1-cyclobutylethyl (4-cyclo-butyl-3-(3,3-difluorocyclobutyl)-1-methyl-1H-pyrazol-5-yl)carbamate |
| 329 | 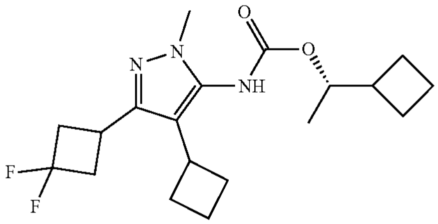 [SMILES: C[C@H](OC(=O)Nc1c(C2CCC2)c(C2CC(F)(F)C2)nn1C)C1CCC1] | (S)-1-cyclobutylethyl (4-cyclo-butyl-3-(3,3-difluorocyclobutyl)-1-methyl-1H-pyrazol-5-yl)carbamate |
| 332 | 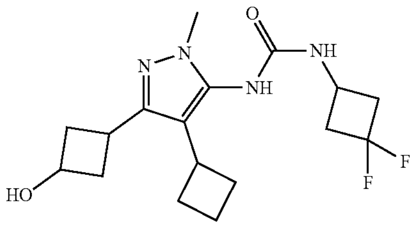 [SMILES: Cn1nc(C2CC(O)C2)c(C2CCC2)c1NC(=O)NC1CC(F)(F)C1] | 1-(4-cyclobutyl-3-(3-hydroxy-cyclobutyl)-1-methyl-1H-pyrazol-5-yl)-3-(3,3-difluorocyclobutyl)urea |

-continued

| Cmpd # | Structure | Name |
|---|---|---|
| 333 | 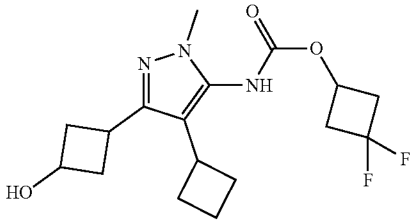 [SMILES: Cn1nc(C2CC(O)C2)c(C2CCC2)c1NC(=O)OC1CC(F)(F)C1] | 3,3-difluorocyclobutyl (4-cyclobutyl-3-(3-hydroxycyclobutyl)-1-methyl-1H-pyrazol-5-yl)carbamate |
| 334 | 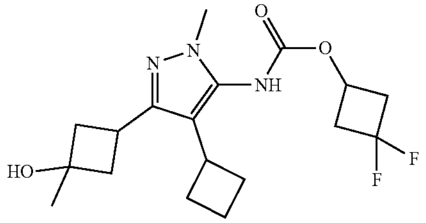 [SMILES: Cn1nc(C2CC(C)(O)C2)c(C2CCC2)c1NC(=O)OC1CC(F)(F)C1] | 3,3-difluorocyclobutyl (4-cyclobutyl-3-(3-hydroxy-3-methylcyclobutyl)-1-methyl-1H-pyrazol-5-yl)carbamate |
| 335 | 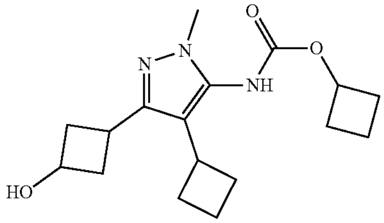 [SMILES: Cn1nc(C2CC(O)C2)c(C2CCC2)c1NC(=O)OC1CCC1] | cyclobutyl (4-cyclobutyl-3-(3-hydroxycyclobutyl)-1-methyl-1H-pyrazol-5-yl)carbamate |
| 336 | 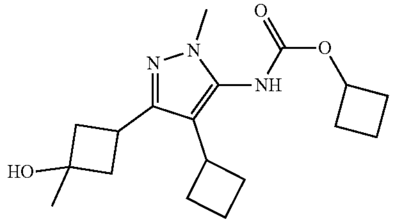 [SMILES: Cn1nc(C2CC(C)(O)C2)c(C2CCC2)c1NC(=O)OC1CCC1] | cyclobutyl (4-cyclobutyl-3-(3-hydroxy-3-methylcyclobutyl)-1-methyl-1H-pyrazol-5-yl)carbamate |
| 337 | 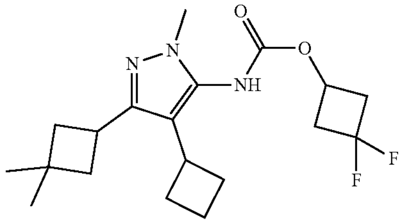 [SMILES: Cn1nc(C2CC(C)(C)C2)c(C2CCC2)c1NC(=O)OC1CC(F)(F)C1] | 3,3-difluorocyclobutyl (4-cyclobutyl-3-(3,3-dimethylcyclobutyl)-1-methyl-1H-pyrazol-5-yl)carbamate |
| 339 | 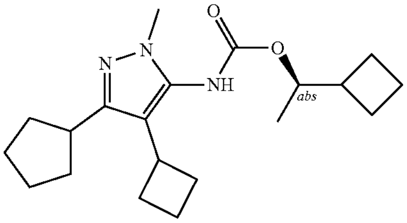 [SMILES: C[C@@H](OC(=O)Nc1c(C2CCC2)c(C2CCCC2)nn1C)C1CCC1] | (R)-1-cyclobutylethyl (4-cyclobutyl-3-cyclopentyl-1-methyl-1H-pyrazol-5-yl)carbamate |

-continued

| Cmpd # | Structure | Name |
|---|---|---|
| 342 | 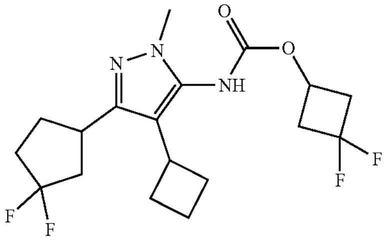 [SMILES: Cn1nc(C2CCC(F)(F)C2)c(C2CCC2)c1NC(=O)OC1CC(F)(F)C1] | 3,3-difluorocyclobutyl (4-cyclobutyl-3-(3,3-difluorocyclopentyl)-1-methyl-1H-pyrazol-5-yl)carbamate |
| 343 | 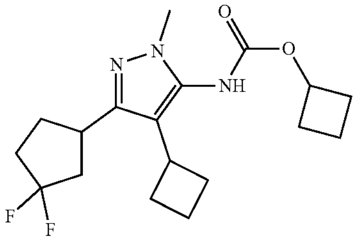 [SMILES: Cn1nc(C2CCC(F)(F)C2)c(C2CCC2)c1NC(=O)OC1CCC1] | cyclobutyl (4-cyclobutyl-3-(3,3-difluorocyclopentyl)-1-methyl-1H-pyrazol-5-yl)carbamate |
| 344 | 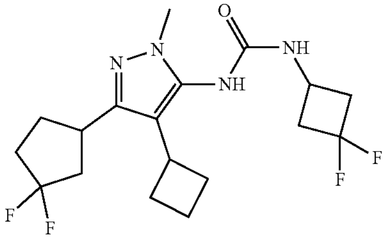 [SMILES: Cn1nc(C2CCC(F)(F)C2)c(C2CCC2)c1NC(=O)NC1CC(F)(F)C1] | 1-(4-cyclobutyl-3-(3,3-difluorocyclopentyl)-1-methyl-1H-pyrazol-5-yl)-3-(3,3-difluorocyclobutyl)urea |
| 346 | 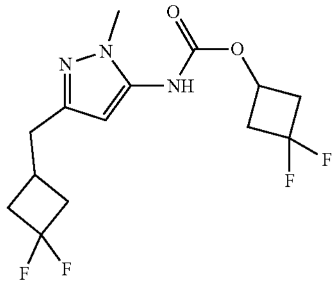 [SMILES: Cn1nc(CC2CC(F)(F)C2)cc1NC(=O)OC1CC(F)(F)C1] | 3,3-difluorocyclobutyl (3-((3,3-difluorocyclobutyl)methyl)-1-methyl-1H-pyrazol-5-yl)carbamate |
| 347 | 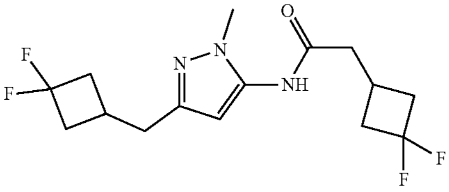 [SMILES: Cn1nc(CC2CC(F)(F)C2)cc1NC(=O)CC1CC(F)(F)C1] | 2-(3,3-difluorocyclobutyl)-N-(3-((3,3-difluorocyclobutyl)methyl)-1-methyl-1H-pyrazol-5-yl)acetamide |
| 348 | 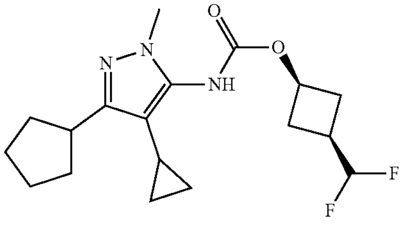 [SMILES: Cn1nc(C2CCCC2)c(C2CC2)c1NC(=O)O[C@H]1C[C@@H](C(F)F)C1] | (1s,3s)-3-(difluoromethyl)cyclobutyl (3-cyclopentyl-4-cyclopropyl-1-methyl-1H-pyrazol-5-yl)carbamate |

-continued

| Cmpd # | Structure | Name |
|---|---|---|
| 349 | 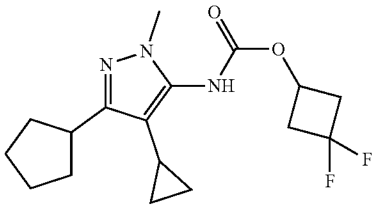 [SMILES: Cn1nc(C2CCCC2)c(C2CC2)c1NC(=O)OC1CC(F)(F)C1] | 3,3-difluorocyclobutyl (3-cyclo-pentyl-4-cyclopropyl-1-methyl-1H-pyrazol-5-yl)carbamate |
| 352 | 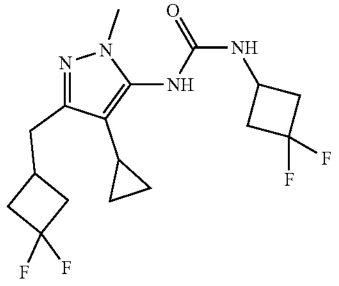 [SMILES: Cn1nc(CC2CC(F)(F)C2)c(C2CC2)c1NC(=O)NC1CC(F)(F)C1] | 1-(4-cyclopropyl-3-((3,3-difluorocyclobutyl)methyl)-1-methyl-1H-pyrazol-5-yl)-3-(3,3-difluorocyclobutyl)urea |
| 354 | 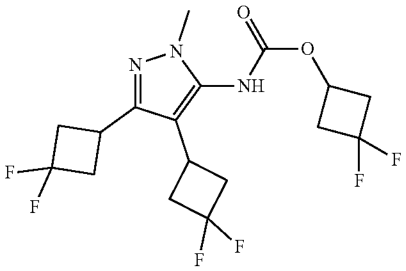 [SMILES: Cn1nc(C2CC(F)(F)C2)c(C2CC(F)(F)C2)c1NC(=O)OC1CC(F)(F)C1] | 3,3-difluorocyclobutyl (3,4-bis(3,3-difluorocyclobutyl)-1-methyl-1H-pyrazol-5-yl)carbamate |
| 355 | 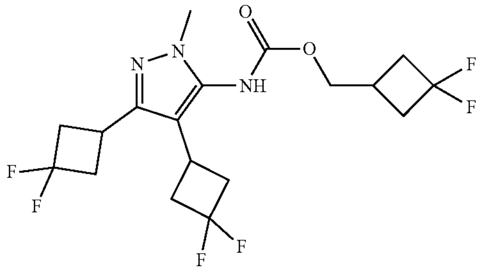 [SMILES: Cn1nc(C2CC(F)(F)C2)c(C2CC(F)(F)C2)c1NC(=O)OCC1CC(F)(F)C1] | (3,3-difluorocyclobutyl)methyl (3,4-bis(3,3-difluorocyclobutyl)-1-methyl-1H-pyrazol-5-yl)carbamate |
| 357 | 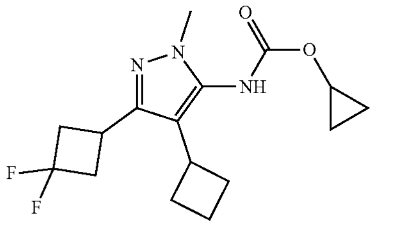 [SMILES: Cn1nc(C2CC(F)(F)C2)c(C2CCC2)c1NC(=O)OC1CC1] | cyclopropyl (4-cyclobutyl-3-(3,3-difluorocyclobutyl)-1-methyl-1H-pyrazol-5-yl)carbamate |
| 358 | 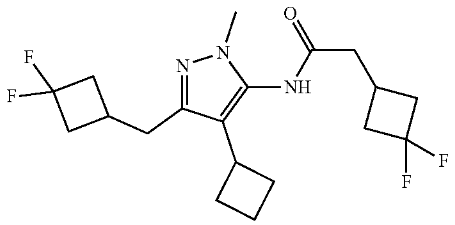 [SMILES: Cn1nc(CC2CC(F)(F)C2)c(C2CCC2)c1NC(=O)CC1CC(F)(F)C1] | N-(4-cyclobutyl-3-((3,3-difluoro-cyclobutyl)methyl)-1-methyl-1H-pyrazol-5-yl)-2-(3,3-difluoro-cyclobutyl)acetamide |

-continued

| Cmpd # | Structure | Name |
|---|---|---|
| 359 | 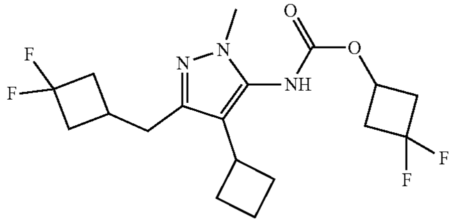 [SMILES: Cn1nc(CC2CC(F)(F)C2)c(C2CCC2)c1NC(=O)OC1CC(F)(F)C1] | 3,3-difluorocyclobutyl (4-cyclobutyl-3-((3,3-difluorocyclobutyl)methyl)-1-methyl-1H-pyrazol-5-yl)carbamate |
| 360 | 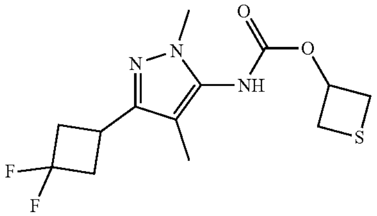 [SMILES: Cc1c(C2CC(F)(F)C2)nn(C)c1NC(=O)OC1CSC1] | thietan-3-yl (3-(3,3-difluorocyclobutyl)-1,4-dimethyl-1H-pyrazol-5-yl)carbamate |
| 362 | 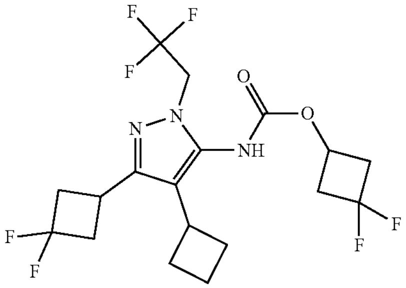 [SMILES: O=C(Nc1c(C2CCC2)c(C2CC(F)(F)C2)nn1CC(F)(F)F)OC1CC(F)(F)C1] | 3,3-difluorocyclobutyl (4-cyclobutyl-3-(3,3-difluorocyclobutyl)-1-(2,2,2-trifluoroethyl)-1H-pyrazol-5-yl)carbamate |
| 367 | 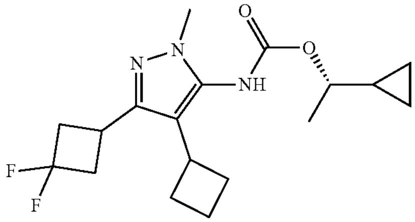 [SMILES: C[C@H](OC(=O)Nc1c(C2CCC2)c(C2CC(F)(F)C2)nn1C)C1CC1] | (S)-1-cyclopropylethyl (4-cyclobutyl-3-(3,3-difluorocyclobutyl)-1-methyl-1H-pyrazol-5-yl)carbamate |
| 368 | 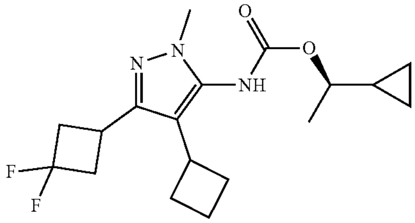 [SMILES: C[C@@H](OC(=O)Nc1c(C2CCC2)c(C2CC(F)(F)C2)nn1C)C1CC1] | (R)-1-cyclopropylethyl (4-cyclobutyl-3-(3,3-difluorocyclobutyl)-1-methyl-1H-pyrazol-5-yl)carbamate |
| 370 | 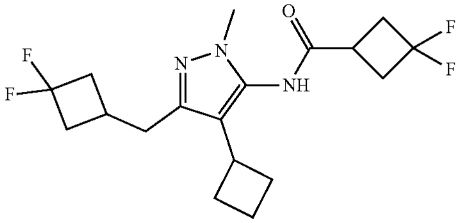 [SMILES: Cn1nc(CC2CC(F)(F)C2)c(C2CCC2)c1NC(=O)C1CC(F)(F)C1] | N-(4-cyclobutyl-3-((3,3-difluorocyclobutyl)methyl)-1-methyl-1H-pyrazol-5-yl)-3,3-difluorocyclobutane-1-carboxamide |

-continued

| Cmpd # | Structure | Name |
|---|---|---|
| 371 | 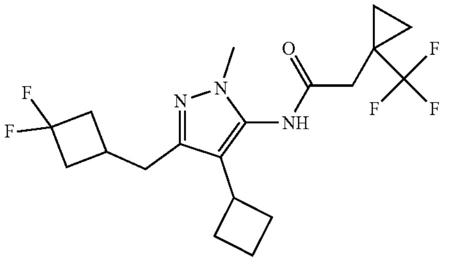 [SMILES: Cn1nc(CC2CC(F)(F)C2)c(C2CCC2)c1NC(=O)CC1(C(F)(F)F)CC1] | N-(4-cyclobutyl-3-((3,3-difluoro-cyclobutyl)methyl)-1-methyl-1H-pyrazol-5-yl)-2-(1-(trifluoro-methyl)cyclopropyl)acetamide |
| 373 | 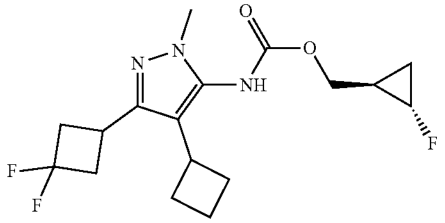 [SMILES: Cn1nc(C2CC(F)(F)C2)c(C2CCC2)c1NC(=O)OC[C@H]1C[C@@H]1F] | ((1R,2S)-2-fluorocyclopropyl)-methyl (4-cyclobutyl-3-(3,3-difluorocyclobutyl)-1-methyl-1H-pyrazol-5-yl)carbamate |
| 375 | 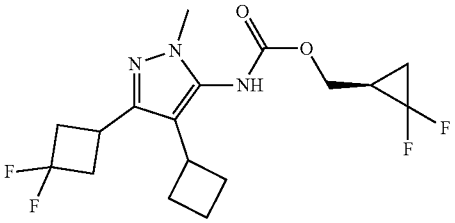 [SMILES: Cn1nc(C2CC(F)(F)C2)c(C2CCC2)c1NC(=O)OC[C@H]1CC1(F)F] | (R)-(2,2-difluorocyclopropyl)-methyl (4-cyclobutyl-3-(3,3-difluorocyclobutyl)-1-methyl-1H-pyrazol-5-yl)carbamate |
| 378 | 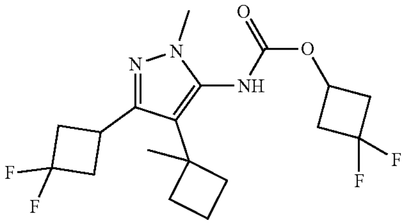 [SMILES: Cn1nc(C2CC(F)(F)C2)c(C2(C)CCC2)c1NC(=O)OC1CC(F)(F)C1] | 3,3-difluorocyclobutyl (3-(3,3-difluorocyclobutyl)-1-methyl-4-(1-methylcyclobutyl)-1H-pyrazol-5-yl)carbamate |
| 379 | 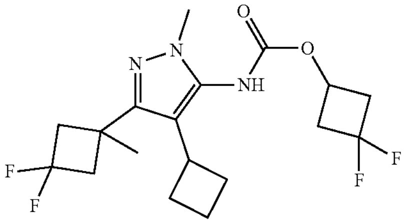 [SMILES: Cn1nc(C2(C)CC(F)(F)C2)c(C2CCC2)c1NC(=O)OC1CC(F)(F)C1] | 3,3-difluorocyclobutyl (4-cyclo-butyl-3-(3,3-difluoro-1-methyl-cyclobutyl)-1-methyl-1H-pyrazol-5-yl)carbamate |
| 380 | 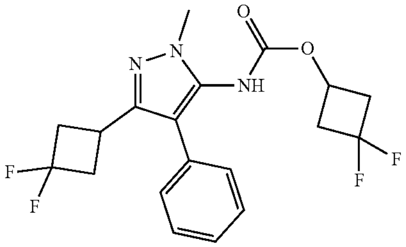 [SMILES: Cn1nc(C2CC(F)(F)C2)c(-c2ccccc2)c1NC(=O)OC1CC(F)(F)C1] | 3,3-difluorocyclobutyl (3-(3,3-difluorocyclobutyl)-1-methyl-4-phenyl-1H-pyrazol-5-yl)carbamate |

-continued

| Cmpd # | Structure | Name |
| --- | --- | --- |
| 383 | 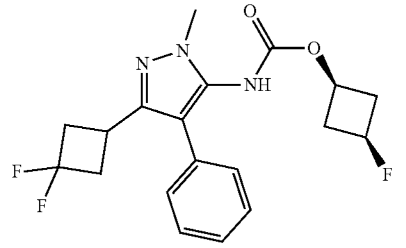 [SMILES: Cn1nc(C2CC(F)(F)C2)c(-c2ccccc2)c1NC(=O)O[C@H]1C[C@@H](F)C1] | (1s,3s)-3-fluorocyclobutyl (3-(3,3-difluorocyclobutyl)-1-methyl-4-phenyl-1H-pyrazol-5-yl)carbamate |
| 384 | 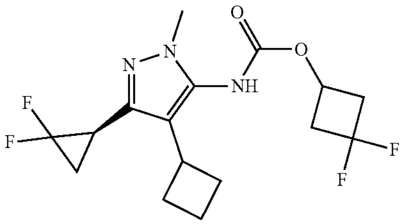 [SMILES: Cn1nc([C@H]2CC2(F)F)c(C2CCC2)c1NC(=O)OC1CC(F)(F)C1] | rac-3,3-difluorocyclobutyl (R)-(4-cyclobutyl-3-(2,2-difluoro-cyclopropyl)-1-methyl-1H-pyrazol-5-yl)carbamate |
| 386 | 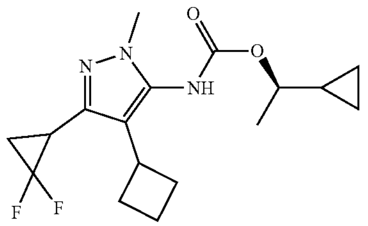 [SMILES: C[C@@H](OC(=O)Nc1c(C2CCC2)c(C2CC2(F)F)nn1C)C1CC1] | (R)-1-cyclopropylethyl (4-cyclo-butyl-3-(2,2-difluorocycloprop-yl)-1-methyl-1H-pyrazol-5-yl)carbamate |
| 387 | 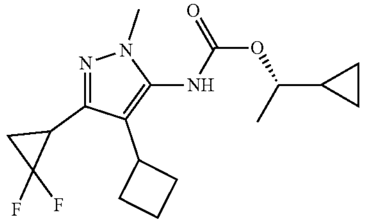 [SMILES: C[C@H](OC(=O)Nc1c(C2CCC2)c(C2CC2(F)F)nn1C)C1CC1] | (S)-1-cyclopropylethyl (4-cyclo-butyl-3-(2,2-difluorocycloprop-yl)-1-methyl-1H-pyrazol-5-yl)carbamate |
| 390 | 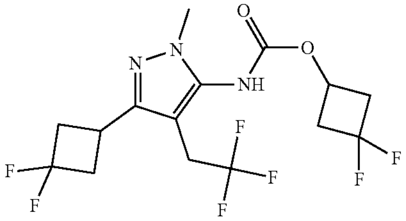 [SMILES: Cn1nc(C2CC(F)(F)C2)c(CC(F)(F)F)c1NC(=O)OC1CC(F)(F)C1] | 3,3-difluorocyclobutyl (3-(3,3-difluorocyclobutyl)-1-methyl-4-(2,2,2-trifluoroethyl)-1H-pyrazol-5-yl)carbamate |
| 392 | 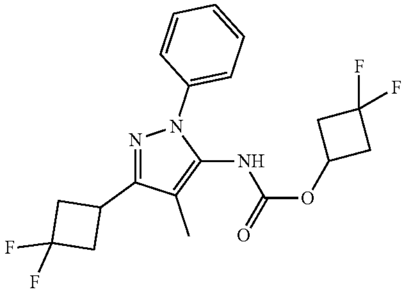 [SMILES: Cc1c(C2CC(F)(F)C2)nn(-c2ccccc2)c1NC(=O)OC1CC(F)(F)C1] | 3,3-difluorocyclobutyl (3-(3,3-difluorocyclobutyl)-4-methyl-1-phenyl-1H-pyrazol-5-yl)carbamate |

-continued

| Cmpd # | Structure | Name |
|---|---|---|
| 395 | 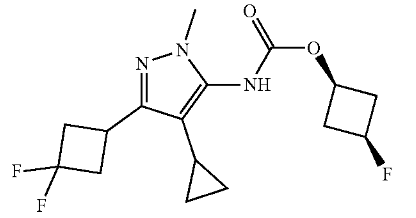 [SMILES: Cn1nc(C2CC(F)(F)C2)c(C2CC2)c1NC(=O)O[C@H]1C[C@@H](F)C1] | (1s,3s)-3-fluorocyclobutyl (4-cyclopropyl-3-(3,3-difluoro-cyclobutyl)-1-methyl-1H-pyrazol-5-yl)carbamate |
| 396 | 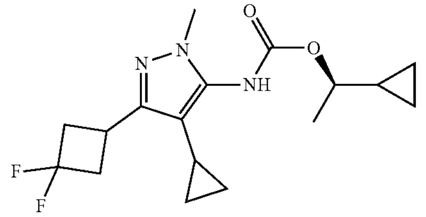 [SMILES: C[C@@H](OC(=O)Nc1c(C2CC2)c(C2CC(F)(F)C2)nn1C)C1CC1] | (R)-1-cyclopropylethyl (4-cyclo-propyl-3-(3,3-difluorocyclo-butyl)-1-methyl-1H-pyrazol-5-yl)carbamate |
| 398 | 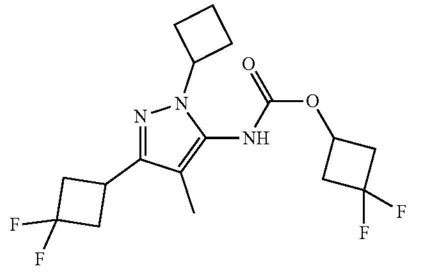 [SMILES: Cc1c(C2CC(F)(F)C2)nn(C2CCC2)c1NC(=O)OC1CC(F)(F)C1] | 3,3-difluorocyclobutyl (1-cyclo-butyl-3-(3,3-difluorocyclobutyl)-4-methyl-1H-pyrazol-5-yl)carbamate |
| 400 | 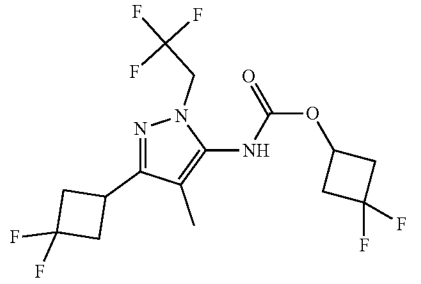 [SMILES: Cc1c(C2CC(F)(F)C2)nn(CC(F)(F)F)c1NC(=O)OC1CC(F)(F)C1] | 3,3-difluorocyclobutyl (3-(3,3-difluorocyclobutyl)-4-methyl-1-(2,2,2-trifluoroethyl)-1H-pyrazol-5-yl)carbamate |
| 406 | 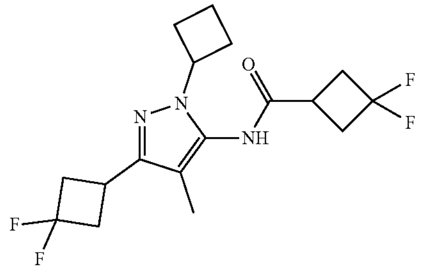 [SMILES: Cc1c(C2CC(F)(F)C2)nn(C2CCC2)c1NC(=O)C1CC(F)(F)C1] | N-(1-cyclobutyl-3-(3,3-difluoro-cyclobutyl)-4-methyl-1H-pyrazol-5-yl)-3,3-difluorocyclo-butane-1-carboxamide |
| 407 | 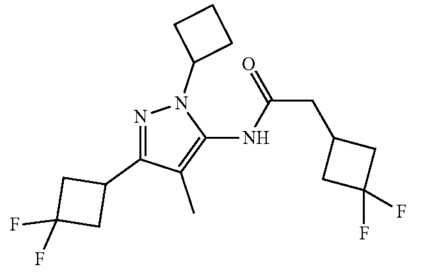 [SMILES: Cc1c(C2CC(F)(F)C2)nn(C2CCC2)c1NC(=O)CC1CC(F)(F)C1] | N-(1-cyclobutyl-3-(3,3-difluoro-cyclobutyl)-4-methyl-1H-pyrazol-5-yl)-2-(3,3-difluoro-cyclobutyl)acetamide |

-continued

| Cmpd # | Structure | Name |
|---|---|---|
| 412 | 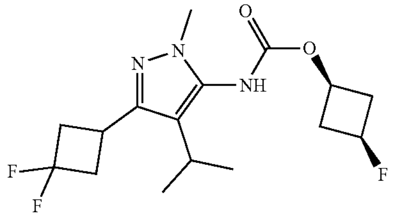 [SMILES: CC(C)c1c(C2CC(F)(F)C2)nn(C)c1NC(=O)O[C@H]1C[C@@H](F)C1] | (1s,3s)-3-fluorocyclobutyl (3-3,3-difluorocyclobutyl)-4-iso-propyl-1-methyl-1H-pyrazol-5-yl)carbamate |
| 416 | 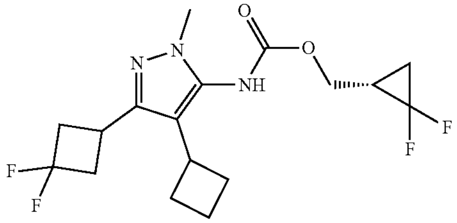 [SMILES: Cn1nc(C2CC(F)(F)C2)c(C2CCC2)c1NC(=O)OC[C@@H]1CC1(F)F] | (S)-(2,2-difluorocyclopropyl)-methyl (4-cyclobutyl-3-(3,3-difluorocyclobutyl)-1-methyl-1H-pyrazol-5-yl)carbamate |
| 417 | 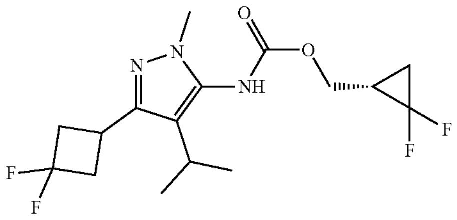 [SMILES: CC(C)c1c(C2CC(F)(F)C2)nn(C)c1NC(=O)OC[C@@H]1CC1(F)F] | (S)-(2,2-difluorocyclopropyl)-methyl (3-(3,3-difluorocyclo-butyl)-4-isopropyl-1-methyl-1H-pyrazol-5-yl)carbamate |
| 418 | 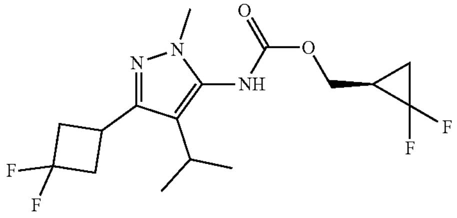 [SMILES: CC(C)c1c(C2CC(F)(F)C2)nn(C)c1NC(=O)OC[C@H]1CC1(F)F] | (R)-(2,2-difluorocyclopropyl)-methyl (3-(3,3-difluorocyclo-butyl)-4-isopropyl-1-methyl-1H-pyrazol-5-yl)carbamate |
| 420 | 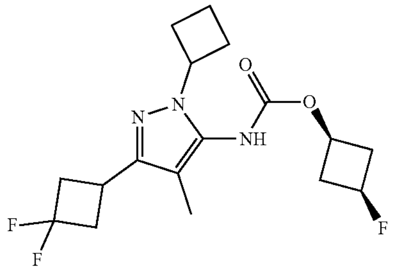 [SMILES: Cc1c(C2CC(F)(F)C2)nn(C2CCC2)c1NC(=O)O[C@H]1C[C@@H](F)C1] | (1s,3s)-3-fluorocyclobutyl (1-cyclobutyl-3-(3,3-difluorocyclo-butyl)-4-methyl-1H-pyrazol-5-yl)carbamate |
| 421 | 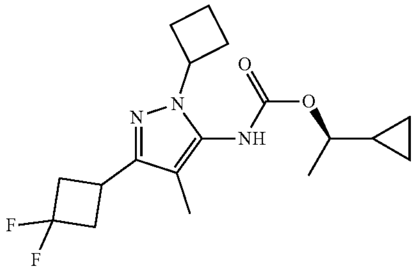 [SMILES: Cc1c(C2CC(F)(F)C2)nn(C2CCC2)c1NC(=O)O[C@H](C)C1CC1] | (R)-1-cyclopropylethyl (1-cyclo-butyl-3-(3,3-difluorocyclobutyl)-4-methyl-1H-pyrazol-5-yl)carbamate |

-continued

| Cmpd # | Structure | Name |
|---|---|---|
| 422 | 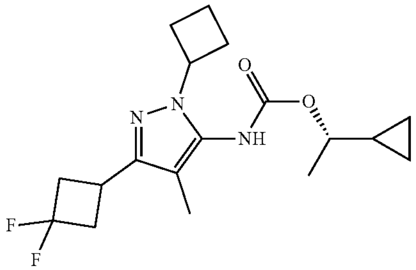 [SMILES: Cc1c(C2CC(F)(F)C2)nn(C2CCC2)c1NC(=O)O[C@@H](C)C1CC1] | (S)-1-cyclopropylethyl (1-cyclobutyl-3-(3,3-difluorocyclobutyl)-4-methyl-1H-pyrazol-5-yl)carbamate |
| 425 | 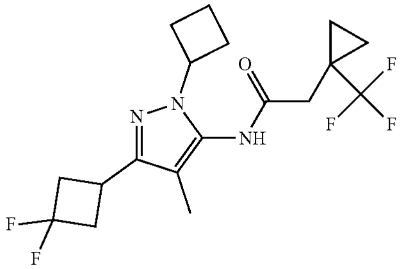 [SMILES: Cc1c(C2CC(F)(F)C2)nn(C2CCC2)c1NC(=O)CC1(C(F)(F)F)CC1] | N-(1-cyclobutyl-3-(3,3-difluorocyclobutyl)-4-methyl-1H-pyrazol-5-yl)-2-(1-(trifluoromethyl)cyclopropyl)acetamide |
| 426 | 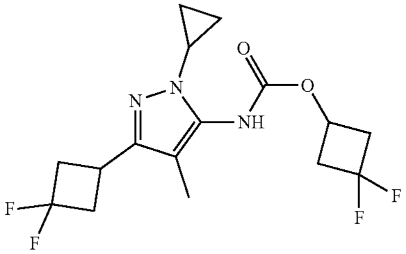 | 3,3-difluorocyclobutyl (1-cyclopropyl-3-(3,3-difluorocyclobutyl)-4-methyl-1H-pyrazol-5-yl)carbamate |
| 427 | 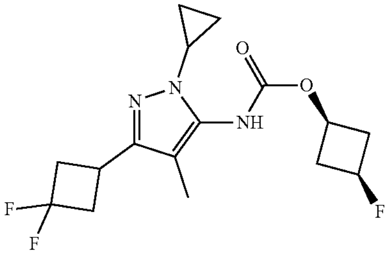 [SMILES: Cc1c(C2CC(F)(F)C2)nn(C2CC2)c1NC(=O)O[C@H]1C[C@@H](F)C1] | (1s,3s)-3-fluorocyclobutyl (1-cyclopropyl-3-(3,3-difluorocyclobutyl)-4-methyl-1H-pyrazol-5-yl)carbamate |
| 431 | 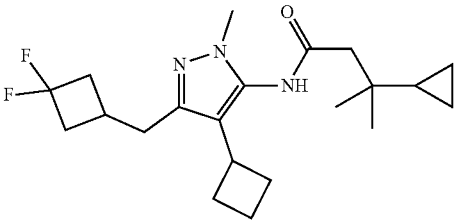 [SMILES: Cn1nc(CC2CC(F)(F)C2)c(C2CCC2)c1NC(=O)CC(C)(C)C1CC1] | N-(4-cyclobutyl-3-((3,3-difluorocyclobutyl)methyl)-1-methyl-1H-pyrazol-5-yl)-3-cyclopropyl-3-methylbutanamide |
| 432 | 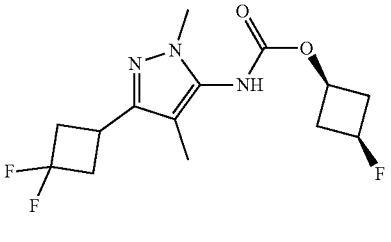 [SMILES: Cc1c(C2CC(F)(F)C2)nn(C)c1NC(=O)O[C@H]1C[C@@H](F)C1] | (1s,3s)-3-fluorocyclobutyl (3-(3,3-difluorocyclobutyl)-1,4-dimethyl-1H-pyrazol-5-yl)carbamate |

-continued

| Cmpd # | Structure | Name |
| --- | --- | --- |
| 433 | 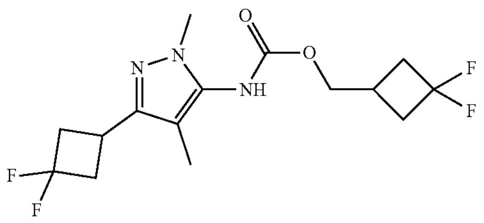 [SMILES: Cc1c(C2CC(F)(F)C2)nn(C)c1NC(=O)OCC1CC(F)(F)C1] | (3,3-difluorocyclobutyl)methyl (3-(3,3-difluorocyclobutyl)-1,4-dimethyl-1H-pyrazol-5-yl)carbamate |
| 440 | 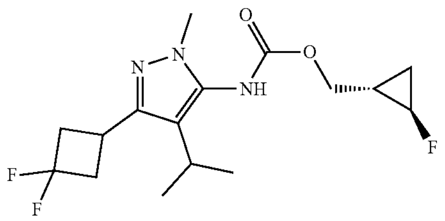 [SMILES: CC(C)c1c(C2CC(F)(F)C2)nn(C)c1NC(=O)OC[C@@H]1C[C@H]1F] | ((1S,2R)-2-fluorocyclopropyl)-methyl (3-(3,3-difluorocyclo-butyl)-4-isopropyl-1-methyl-1H-pyrazol-5-yl)carbamate |
| 441 | 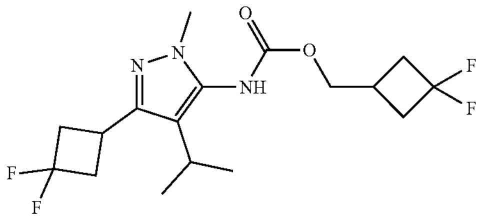 [SMILES: CC(C)c1c(C2CC(F)(F)C2)nn(C)c1NC(=O)OCC1CC(F)(F)C1] | (3,3-difluorocyclobutyl)methyl (3-(3,3-difluorocyclobutyl)-4-isopropyl-1-methyl-1H-pyrazol-5-yl)carbamate |
| 443 | 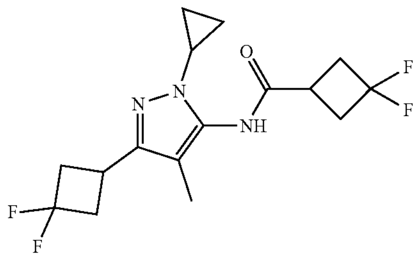 [SMILES: Cc1c(C2CC(F)(F)C2)nn(C2CC2)c1NC(=O)C1CC(F)(F)C1] | N-(1-cyclopropyl-3-(3,3-difluoro-cyclobutyl)-4-methyl-1H-pyrazol-5-yl)-3,3-difluorocyclobutane-1-carboxamide |
| 444 | 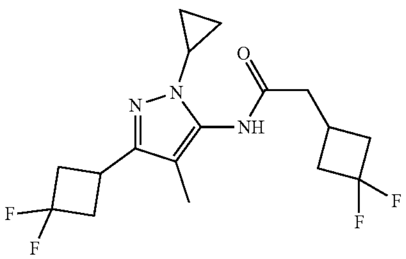 [SMILES: Cc1c(C2CC(F)(F)C2)nn(C2CC2)c1NC(=O)CC1CC(F)(F)C1] | N-(1-cyclopropyl-3-(3,3-difluoro-cyclobutyl)-4-methyl-1H-pyrazol-5-yl)-2-(3,3-difluorocyclo-butyl)acetamide |
| 445 | 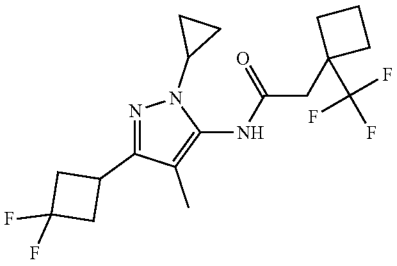 [SMILES: Cc1c(C2CC(F)(F)C2)nn(C2CC2)c1NC(=O)CC1(C(F)(F)F)CCC1] | N-(1-cyclopropyl-3-(3,3-difluoro-cyclobutyl)-4-methyl-1H-pyrazol-5-yl)-2-(1-(trifluoromethyl)cyclo-butyl)acetamide |

-continued

| Cmpd # | Structure | Name |
|---|---|---|
| 446 | 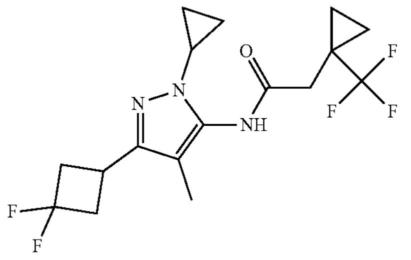 [SMILES: Cc1c(C2CC(F)(F)C2)nn(C2CC2)c1NC(=O)CC1(C(F)(F)F)CC1] | N-(1-cyclopropyl-3-(3,3-difluorocyclobutyl)-4-methyl-1H-pyrazol-5-yl)-2-(1-(trifluoromethyl)cyclopropyl)acetamide |
| 448 | 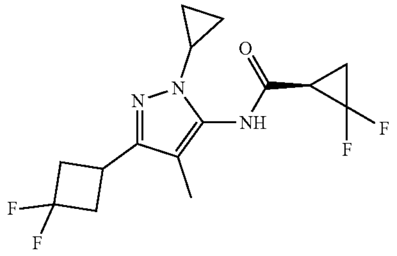 [SMILES: Cc1c(C2CC(F)(F)C2)nn(C2CC2)c1NC(=O)[C@H]1CC1(F)F] | (R)-N-(1-cyclopropyl-3-(3,3-difluorocyclobutyl)-4-methyl-1H-pyrazol-5-yl)-2,2-difluorocyclopropane-1-carboxamide |
| 449 | 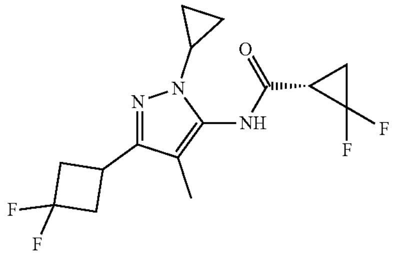 [SMILES: Cc1c(C2CC(F)(F)C2)nn(C2CC2)c1NC(=O)[C@@H]1CC1(F)F] | (S)-N-(1-cyclopropyl-3-(3,3-difluorocyclobutyl)-4-methyl-1H-pyrazol-5-yl)-2,2-difluorocyclopropane-1-carboxamide |
| 456 | 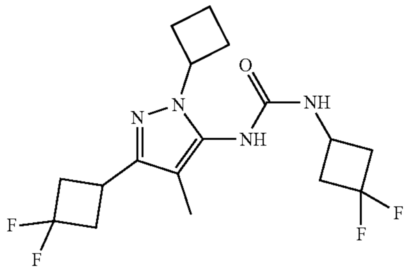 [SMILES: Cc1c(C2CC(F)(F)C2)nn(C2CCC2)c1NC(=O)NC1CC(F)(F)C1] | 1-(1-cyclobutyl-3-(3,3-difluorocyclobutyl)-4-methyl-1H-pyrazol-5-yl)-3-(3,3-difluorocyclobutyl)urea |
| 458 | 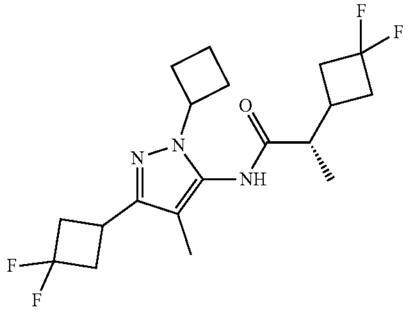 [SMILES: Cc1c(C2CC(F)(F)C2)nn(C2CCC2)c1NC(=O)[C@@H](C)C1CC(F)(F)C1] | (S)-N-(1-cyclobutyl-3-(3,3-difluorocyclobutyl)-4-methyl-1H-pyrazol-5-yl)-2-(3,3-difluorocyclobutyl)propenamide |

-continued

| Cmpd # | Structure | Name |
| --- | --- | --- |
| 459 | 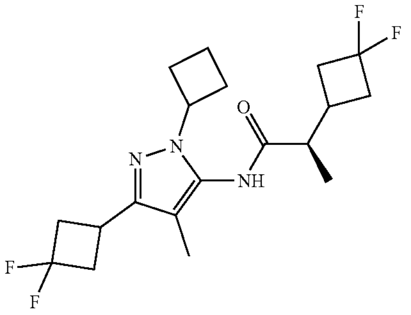 [SMILES: Cc1c(C2CC(F)(F)C2)nn(C2CCC2)c1NC(=O)[C@H](C)C1CC(F)(F)C1] | (R)-N-(1-cyclobutyl-3-(3,3-difluorocyclobutyl)-4-methyl-1H-pyrazol-5-yl)-2-(3,3-di-fluorocyclobutyl)propanamide |
| 460 | 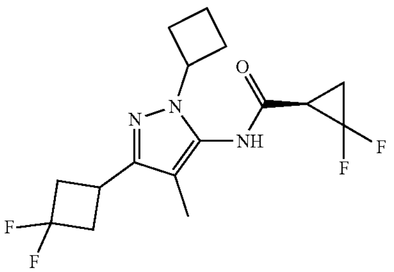 [SMILES: Cc1c(C2CC(F)(F)C2)nn(C2CCC2)c1NC(=O)[C@H]1CC1(F)F] | (R)-N-(1-cyclobutyl-3-(3,3-difluorocyclobutyl)-4-methyl-1H-pyrazol-5-yl)-2,2-difluoro-cyclopropane-1-carboxamide |
| 461 | 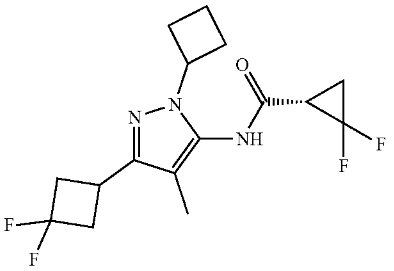 [SMILES: Cc1c(C2CC(F)(F)C2)nn(C2CCC2)c1NC(=O)[C@@H]1CC1(F)F] | (S)-N-(1-cyclobutyl-3-(3,3-difluorocyclobutyl)-4-methyl-1H-pyrazol-5-yl)-2,2-difluoro-cyclopropane-1-carboxamide |
| 462 | 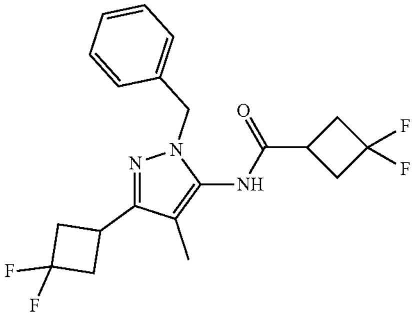 [SMILES: Cc1c(C2CC(F)(F)C2)nn(Cc2ccccc2)c1NC(=O)C1CC(F)(F)C1] | N-(1-benzyl-3-(3,3-difluoro-cyclobutyl)-4-methyl-1H-pyrazol-5-yl)-3,3-difluorocyclo-butane-1-carboxamide |
| 463 | 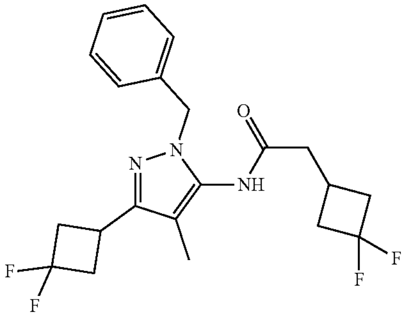 [SMILES: Cc1c(C2CC(F)(F)C2)nn(Cc2ccccc2)c1NC(=O)CC1CC(F)(F)C1] | N-(1-benzyl-3-(3,3-difluoro-cyclobutyl)-4-methyl-1H-pyrazol-5-yl)-2-(3,3-difluoro-cyclobutyl)acetamide |

-continued

| Cmpd # | Structure | Name |
|---|---|---|
| 464 | 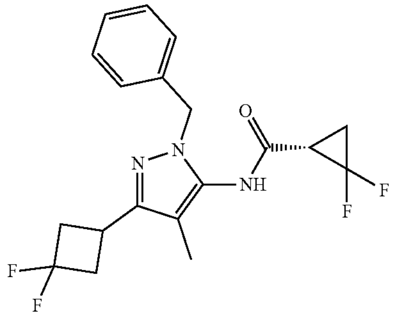 [SMILES: Cc1c(C2CC(F)(F)C2)nn(Cc2ccccc2)c1NC(=O)[C@@H]1CC1(F)F] | (S)-N-(1-benzyl-3-(3,3-difluoro-cyclobutyl)-4-methyl-1H-pyrazol-5-yl)-2,2-difluorocyclo-propane-1-carboxamide |
| 465 | 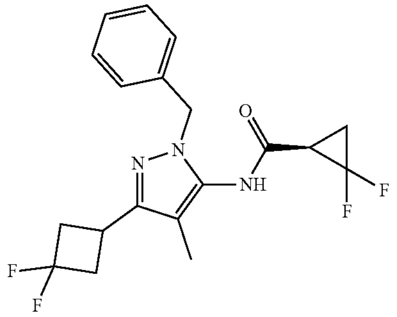 [SMILES: Cc1c(C2CC(F)(F)C2)nn(Cc2ccccc2)c1NC(=O)[C@H]1CC1(F)F] | (R)-N-(1-benzyl-3-(3,3-difluoro-cyclobutyl)-4-methyl-1H-pyrazol-5-yl)-2,2-difluoro-cyclopropane-1-carboxamide |
| 466 | 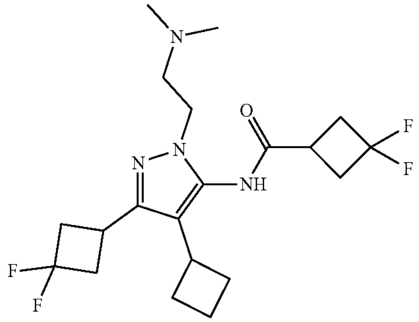 [SMILES: CN(C)CCn1nc(C2CC(F)(F)C2)c(C2CCC2)c1NC(=O)C1CC(F)(F)C1] | N-(4-cyclobutyl-3-(3,3-di-fluorocyclobutyl)-1-(2-(dimeth-ylamino)ethyl)-1H-pyrazol-5-yl)-3,3-difluorocyclobutane-1-carboxamide |
| 469 | 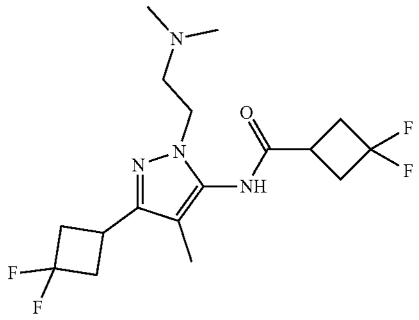 [SMILES: Cc1c(C2CC(F)(F)C2)nn(CCN(C)C)c1NC(=O)C1CC(F)(F)C1] | N-(3-(3,3-difluorocyclobutyl)-1-(2-(dimethylamino)ethyl)-4-methyl-1H-pyrazol-5-yl)-3,3-difluorocyclobutane-1-carboxamide |

-continued

| Cmpd # | Structure | Name |
|---|---|---|
| 470 | 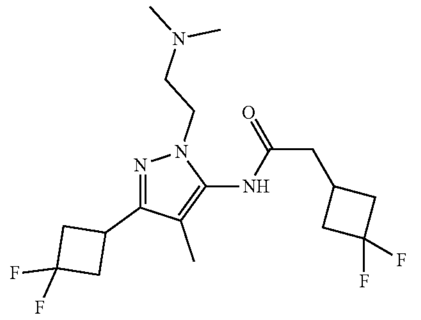 [SMILES: Cc1c(C2CC(F)(F)C2)nn(CCN(C)C)c1NC(=O)CC1CC(F)(F)C1] | 2-(3,3-difluorocyclobutyl)-N-(3-(3,3-difluorocyclobutyl)-1-(2-(dimethylamino)ethyl)-4-methyl-1H-pyrazol-5-yl)acetamide |
| 471 | 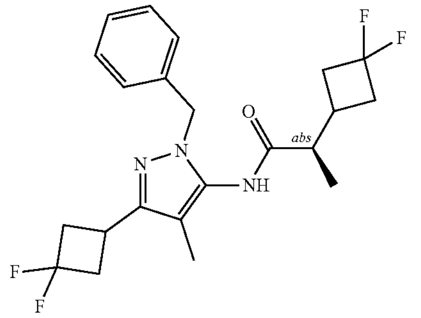 [SMILES: Cc1c(C2CC(F)(F)C2)nn(Cc2ccccc2)c1NC(=O)[C@H](C)C1CC(F)(F)C1] | (R)-N-(1-benzyl-3-(3,3-difluorocyclobutyl)-4-methyl-1H-pyrazol-5-yl)-2-(3,3-difluorocyclobutyl)propanamide |
| 472 | 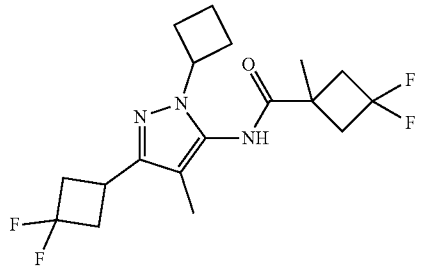 [SMILES: Cc1c(C2CC(F)(F)C2)nn(C2CCC2)c1NC(=O)C1(C)CC(F)(F)C1] | N-(1-cyclobutyl-3-(3,3-difluorocyclobutyl)-4-methyl-1H-pyrazol-5-yl)-3,3-difluoro-1-methylcyclobutane-1-carboxamide |
| 473 | 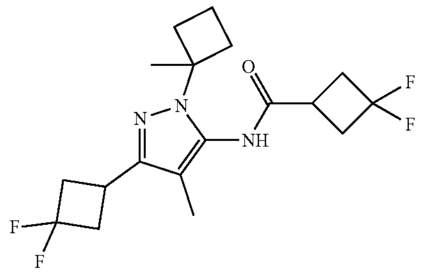 [SMILES: Cc1c(C2CC(F)(F)C2)nn(C2(C)CCC2)c1NC(=O)C1CC(F)(F)C1] | N-(3-(3,3-difluorocyclobutyl)-4-methyl-1-(1-methylcyclobutyl)-1H-pyrazol-5-yl)-3,3-difluorocyclobutane-1-carboxamide |
| 478 | 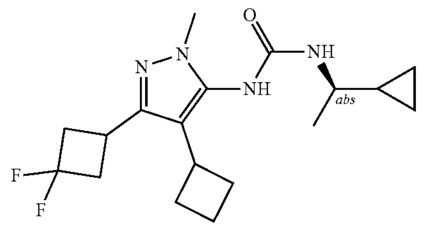 [SMILES: C[C@@H](NC(=O)Nc1c(C2CCC2)c(C2CC(F)(F)C2)nn1C)C1CC1] | (R)-1-(4-cyclobutyl-3-(3,3-difluorocyclobutyl)-1-methyl-1H-pyrazol-5-yl)-3-(1-cyclopropylethyl)urea |

-continued

| Cmpd # | Structure | Name |
|---|---|---|
| 479 | 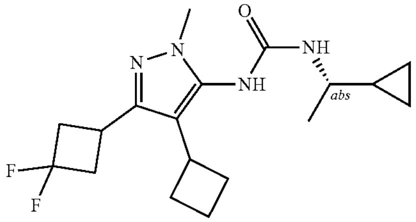 [SMILES: C[C@H](NC(=O)Nc1c(C2CCC2)c(C2CC(F)(F)C2)nn1C)C1CC1] | (S)-1-(4-cyclobutyl-3-(3,3-difluorocyclobutyl)-1-methyl-1H-pyrazol-5-yl)-3-(1-cyclopropylethyl)urea |
| 480 | 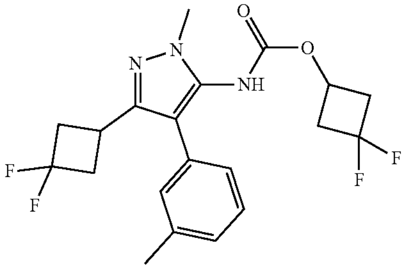 [SMILES: Cc1cccc(-c2c(C3CC(F)(F)C3)nn(C)c2NC(=O)OC2CC(F)(F)C2)c1] | 3,3-difluorocyclobutyl (3-(3,3-difluorocyclobutyl)-1-methyl-4-(m-tolyl)-1H-pyrazol-5-yl)carbamate |
| 481 | 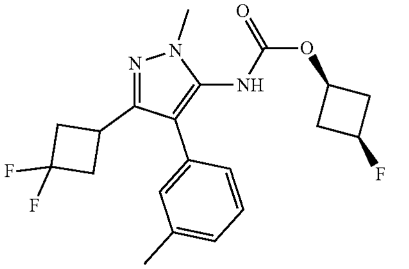 [SMILES: Cc1cccc(-c2c(C3CC(F)(F)C3)nn(C)c2NC(=O)O[C@H]2C[C@@H](F)C2)c1] | (1s,3s)-3-fluorocyclobutyl (3-(3,3-difluorocyclobutyl)-1-methyl-4-(m-tolyl)-1H-pyrazol-5-yl)carbamate |
| 482 | 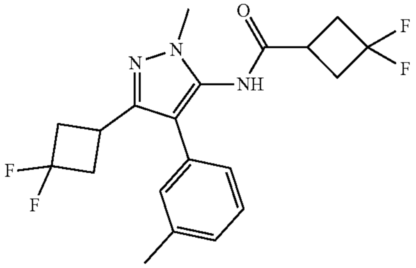 [SMILES: Cc1cccc(-c2c(C3CC(F)(F)C3)nn(C)c2NC(=O)C2CC(F)(F)C2)c1] | N-(3-(3,3-difluorocyclobutyl)-1-methyl-4-(m-tolyl)-1H-pyrazol-5-yl)-3,3-difluorocyclobutane-1-carboxamide |
| 483 | 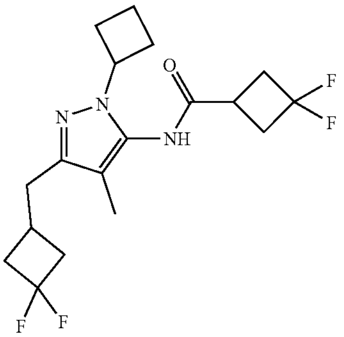 [SMILES: Cc1c(CC2CC(F)(F)C2)nn(C2CCC2)c1NC(=O)C1CC(F)(F)C1] | N-(1-cyclobutyl-3-((3,3-difluorocyclobutyl)methyl)-4-methyl-1H-pyrazol-5-yl)-3,3-difluorocyclobutane-1-carboxamide |

-continued

| Cmpd # | Structure | Name |
|---|---|---|
| 484 | 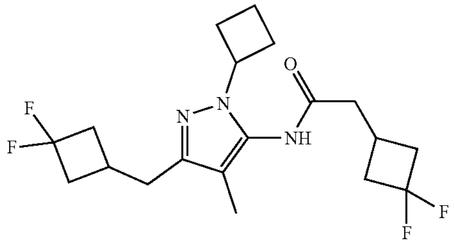 [SMILES: Cc1c(CC2CC(F)(F)C2)nn(C2CCC2)c1NC(=O)CC1CC(F)(F)C1] | N-(1-cyclobutyl-3-((3,3-difluoro-cyclobutyl)methyl)-4-methyl-1H-pyrazol-5-yl)-2-(3,3-difluoro-cyclobutyl)acetamide |
| 485 | 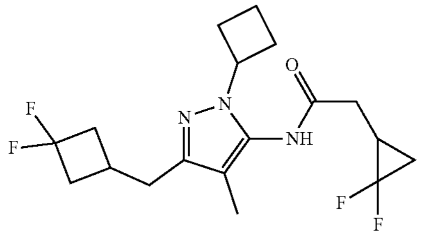 [SMILES: Cc1c(CC2CC(F)(F)C2)nn(C2CCC2)c1NC(=O)CC1CC1(F)F] | N-(1-cyclobutyl-3-((3,3-difluoro-cyclobutyl)methyl)-4-methyl-1H-pyrazol-5-yl)-2-(2,2-difluoro-cyclopropyl)acetamide |
| 488 | 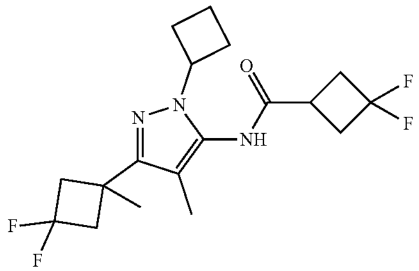 [SMILES: Cc1c(C2(C)CC(F)(F)C2)nn(C2CCC2)c1NC(=O)C1CC(F)(F)C1] | N-(1-cyclobutyl-3-(3,3-difluoro-1-methylcyclobutyl)-4-methyl-1H-pyrazol-5-yl)-3,3-difluoro-cyclobutane-1-carboxamide |
| 489 | 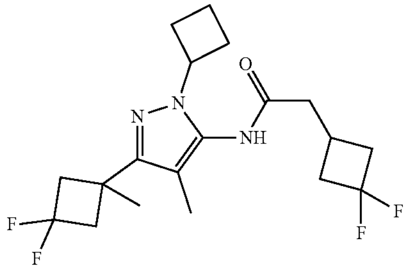 [SMILES: Cc1c(C2(C)CC(F)(F)C2)nn(C2CCC2)c1NC(=O)CC1CC(F)(F)C1] | N-(1-cyclobutyl-3-(3,3-difluoro-1-methylcyclobutyl)-4-methyl-1H-pyrazol-5-yl)-2-(3,3-difluoro-cyclobutyl)acetamide |
| 490 | 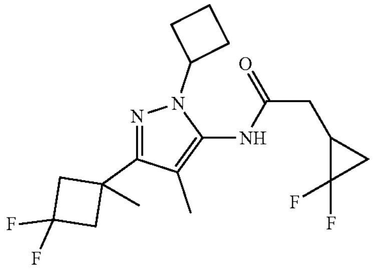 [SMILES: Cc1c(C2(C)CC(F)(F)C2)nn(C2CCC2)c1NC(=O)CC1CC1(F)F] | N-(1-cyclobutyl-3-(3,3-difluoro-1-methylcyclobutyl)-4-methyl-1H-pyrazol-5-yl)-2-(2,2-difluoro-cyclopropyl)acetamide |
| 491 | 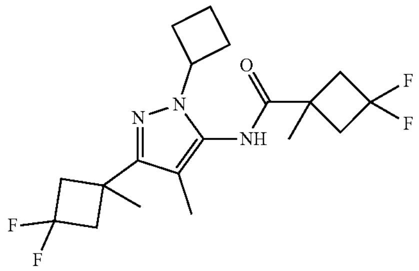 [SMILES: Cc1c(C2(C)CC(F)(F)C2)nn(C2CCC2)c1NC(=O)C1(C)CC(F)(F)C1] | N-(1-cyclobutyl-3-(3,3-difluoro-1-methylcyclobutyl)-4-methyl-1H-pyrazol-5-yl)-3,3-difluoro-1-methylcyclobutane-1-carboxamide |

-continued

| Cmpd # | Structure | Name |
|---|---|---|
| 492 | 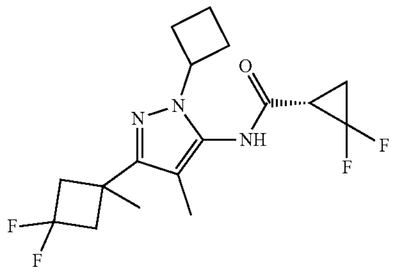 [SMILES: Cc1c(C2(C)CC(F)(F)C2)nn(C2CCC2)c1NC(=O)[C@@H]1CC1(F)F] | (S)-N-(1-cyclobutyl-3-(3,3-difluoro-1-methylcyclobutyl)-4-methyl-1H-pyrazol-5-yl)-2,2-difluorocyclopropane-1-carboxamide |
| 493 | 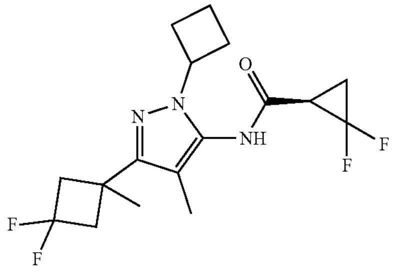 [SMILES: Cc1c(C2(C)CC(F)(F)C2)nn(C2CCC2)c1NC(=O)[C@H]1CC1(F)F] | (R)-N-(1-cyclobutyl-3-(3,3-difluoro-1-methylcyclobutyl)-4-methyl-1H-pyrazol-5-yl)-2,2-difluorocyclopropane-1-carboxamide |
| 494 | 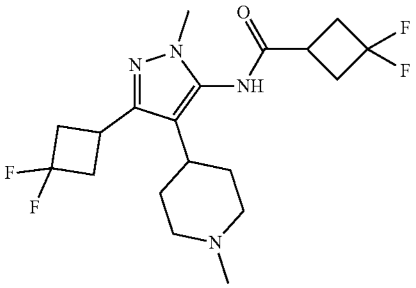 [SMILES: CN1CCC(c2c(C3CC(F)(F)C3)nn(C)c2NC(=O)C2CC(F)(F)C2)CC1] | N-(3-(3,3-difluorocyclobutyl)-1-methyl-4-(1-methylpiperidin-4-yl)-1H-pyrazol-5-yl)-3,3-difluorocyclobutane-1-carboxamide |
| 496 | 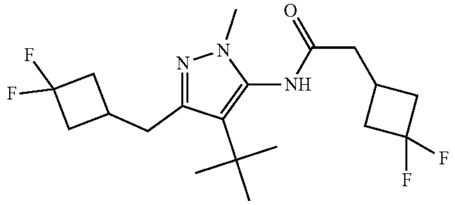 [SMILES: Cn1nc(CC2CC(F)(F)C2)c(C(C)(C)C)c1NC(=O)CC1CC(F)(F)C1] | N-(4-(tert-butyl)-3-((3,3-difluorocyclobutyl)methyl)-1-methyl-1H-pyrazol-5-yl)-2-(3,3-difluorocyclobutyl)acetamide |
| 498 | 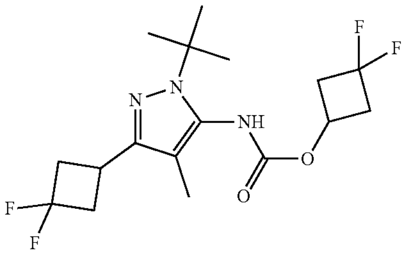 [SMILES: Cc1c(C2CC(F)(F)C2)nn(C(C)(C)C)c1NC(=O)OC1CC(F)(F)C1] | 3,3-difluorocyclobutyl (1-(tert-butyl)-3-(3,3-difluorocyclo-butyl)-4-methyl-1H-pyrazol-5-yl)carbamate |
| 501 | 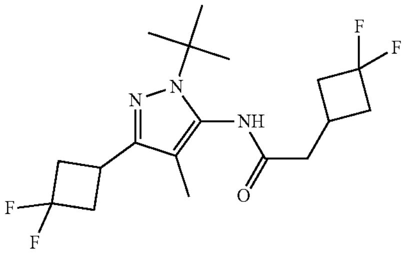 [SMILES: Cc1c(C2CC(F)(F)C2)nn(C(C)(C)C)c1NC(=O)CC1CC(F)(F)C1] | N-(1-(tert-butyl)-3-(3,3-difluoro-cyclobutyl)-4-methyl-1H-pyrazol-5-yl)-2-(3,3-difluoro-cyclobutyl)acetamide |

-continued

| Cmpd # | Structure | Name |
| --- | --- | --- |
| 504 | 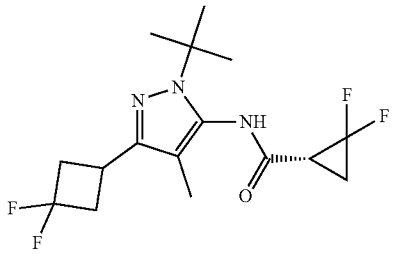 [SMILES: Cc1c(C2CC(F)(F)C2)nn(C(C)(C)C)c1NC(=O)[C@H]1CC1(F)F] | (R)-N-(1-(tert-butyl)-3-(3,3-difluorocyclobutyl)-4-methyl-1H-pyrazol-5-yl)-2,2-difluoro-cyclopropane-1-carboxamide |
| 514 | 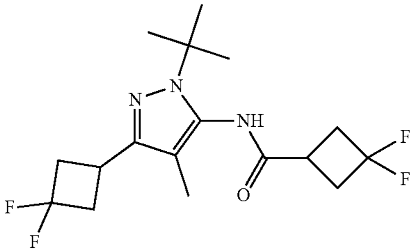 [SMILES: Cc1c(C2CC(F)(F)C2)nn(C(C)(C)C)c1NC(=O)C1CC(F)(F)C1] | N-(1-(tert-butyl)-3-(3,3-difluorocyclobutyl)-4-methyl-1H-pyrazol-5-yl)-3,3-difluoro-cyclobutane-1-carboxamide |
| 515 | 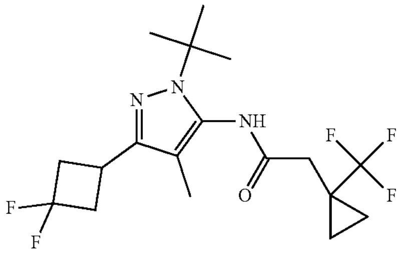 [SMILES: Cc1c(C2CC(F)(F)C2)nn(C(C)(C)C)c1NC(=O)CC1(C(F)(F)F)CC1] | N-(1-(tert-butyl)-3-(3,3-difluorocyclobutyl)-4-methyl-1H-pyrazol-5-yl)-2-(1-(trifluoro-methyl)cyclopropyl)acetamide |
| 521 | 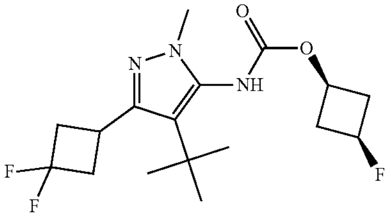 [SMILES: Cn1nc(C2CC(F)(F)C2)c(C(C)(C)C)c1NC(=O)O[C@H]1C[C@@H](F)C1] | (1s,3s)-3-fluorocyclobutyl (4-(tert-butyl)-3-(3,3-difluorocyclo-butyl)-1-methyl-1H-pyrazol-5-yl)carbamate |
| 523 | 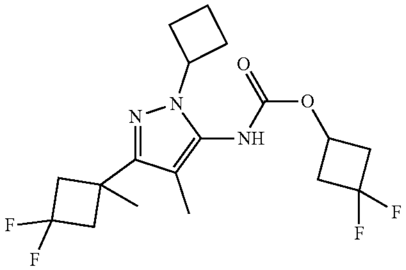 [SMILES: Cc1c(C2(C)CC(F)(F)C2)nn(C2CCC2)c1NC(=O)OC1CC(F)(F)C1] | 3,3-difluorocyclobutyl (1-cyclo-butyl-3-(3,3-difluoro-1-methyl-cyclobutyl)-4-methyl-1H-pyrazol-5-yl)carbamate |
| 524 | 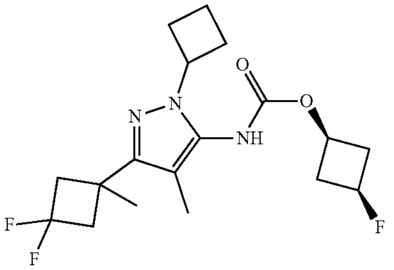 [SMILES: Cc1c(C2(C)CC(F)(F)C2)nn(C2CCC2)c1NC(=O)O[C@H]1C[C@@H](F)C1] | (1s,3s)-3-fluorocyclobutyl (1-cyclobutyl-3-(3,3-difluoro-1-methylcyclobutyl)-4-methyl-1H-pyrazol-5-yl)carbamate |

-continued

| Cmpd # | Structure | Name |
|---|---|---|
| 525 | 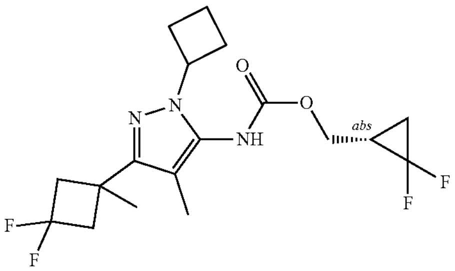 [SMILES: Cc1c(C2(C)CC(F)(F)C2)nn(C2CCC2)c1NC(=O)OC[C@@H]1CC1(F)F] | (S)-(2,2-difluorocyclopropyl)-methyl (1-cyclobutyl-3-(3,3-difluoro-1-methylcyclobutyl)-4-methyl-1H-pyrazol-5-yl)carbamate |
| 527 | 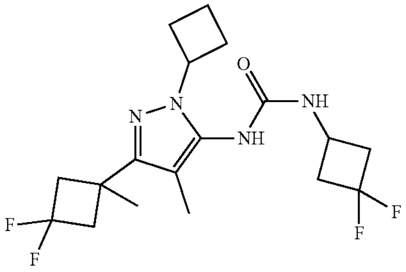 [SMILES: Cc1c(C2(C)CC(F)(F)C2)nn(C2CCC2)c1NC(=O)NC1CC(F)(F)C1] | 1-(1-cyclobutyl-3-(3,3-difluoro-1-methylcyclobutyl)-4-methyl-1H-pyrazol-5-yl)-3-(3,3-difluorocyclobutyl)urea |
| 528 | 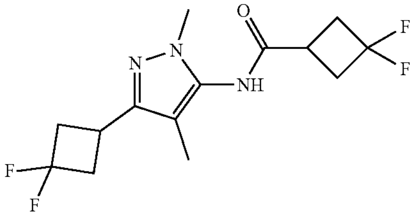 [SMILES: Cc1c(C2CC(F)(F)C2)nn(C)c1NC(=O)C1CC(F)(F)C1] | N-(3-(3,3-difluorocyclobutyl)-1,4-dimethyl-1H-pyrazol-5-yl)-3,3-difluorocyclobutane-1-carboxamide |
| 529 | 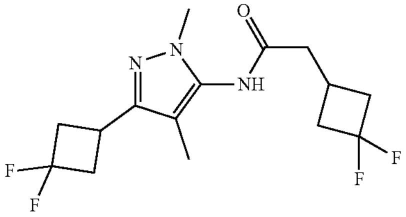 | 2-(3,3-difluorocyclobutyl)-N-(3-(3,3-difluorocyclobutyl)-1,4-dimethyl-1H-pyrazol-5-yl)acetamide |
| 530 | 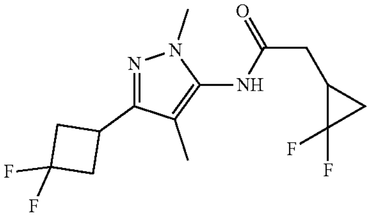 [SMILES: Cc1c(C2CC(F)(F)C2)nn(C)c1NC(=O)CC1CC1(F)F] | N-(3-(3,3-difluorocyclobutyl)-1,4-dimethyl-1H-pyrazol-5-yl)-2-(2,2-difluorocyclo-propyl)acetamide |
| 531 | 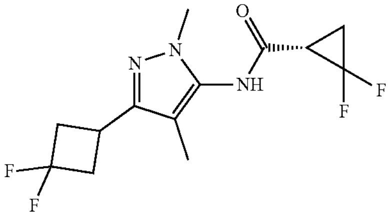 [SMILES: Cc1c(C2CC(F)(F)C2)nn(C)c1NC(=O)[C@@H]1CC1(F)F] | (S)-N-(3-(3,3-difluorocyclo-butyl)-1,4-dimethyl-1H-pyrazol-5-yl)-2,2-difluorocyclopropane-1-carboxamide |

-continued

| Cmpd # | Structure | Name |
|---|---|---|
| 532 | 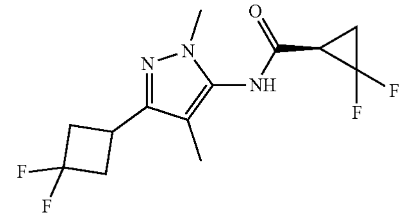 [SMILES: Cc1c(C2CC(F)(F)C2)nn(C)c1NC(=O)[C@H]1CC1(F)F] | (R)-N-(3-(3,3-difluorocyclobutyl)-1,4-dimethyl-1H-pyrazol-5-yl)-2,2-difluorocyclopropane-1-carboxamide |
| 533 | 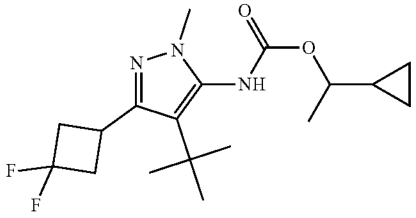 [SMILES: CC(OC(=O)Nc1c(C(C)(C)C)c(C2CC(F)(F)C2)nn1C)C1CC1] | 1-cyclopropylethyl (4-(tert-butyl)-3-(3,3-difluorocyclobutyl)-1-methyl-1H-pyrazol-5-yl)carbamate |
| 537 | 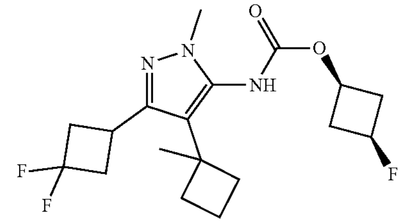 [SMILES: Cn1nc(C2CC(F)(F)C2)c(C2(C)CCC2)c1NC(=O)O[C@H]1C[C@@H](F)C1] | (1s,3s)-3-fluorocyclobutyl (3-(3,3-difluorocyclobutyl)-1-methyl-4-(1-methylcyclobutyl)-1H-pyrazol-5-yl)carbamate |
| 539 | 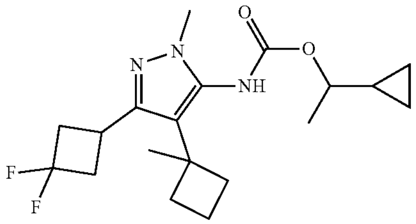 [SMILES: CC(OC(=O)Nc1c(C2(C)CCC2)c(C2CC(F)(F)C2)nn1C)C1CC1] | 1-cyclopropylethyl (3-(3,3-difluorocyclobutyl)-1-methyl-4-(1-methylcyclobutyl)-1H-pyrazol-5-yl)carbamate |
| 542 | 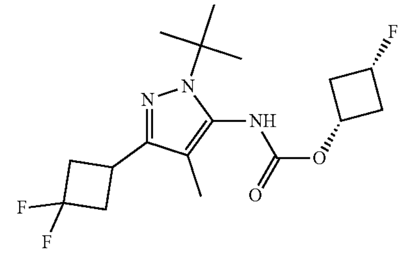 [SMILES: Cc1c(C2CC(F)(F)C2)nn(C(C)(C)C)c1NC(=O)O[C@H]1C[C@@H](F)C1] | (1s,3s)-3-fluorocyclobutyl (1-(tert-butyl)-3-(3,3-difluorocyclobutyl)-4-methyl-1H-pyrazol-5-yl)carbamate |
| 544 | 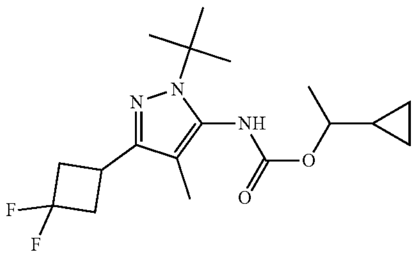 [SMILES: Cc1c(C2CC(F)(F)C2)nn(C(C)(C)C)c1NC(=O)OC(C)C1CC1] | 1-cyclopropylethyl (1-(tert-butyl)-3-(3,3-difluorocyclobutyl)-4-methyl-1H-pyrazol-5-yl)carbamate |

-continued

| Cmpd # | Structure | Name |
|---|---|---|
| 547 | 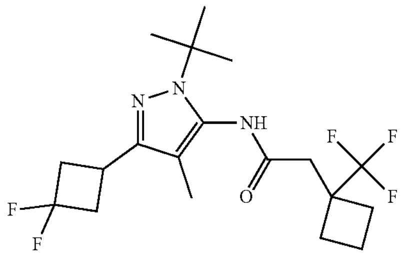 [SMILES: Cc1c(C2CC(F)(F)C2)nn(C(C)(C)C)c1NC(=O)CC1(C(F)(F)F)CCC1] | N-(1-(tert-butyl)-3-(3,3-difluoro-cyclobutyl)-4-methyl-1H-pyrazol-5-yl)-2-(1-(trifluoro-methyl)cyclobutyl)acetamide |
| 549 | 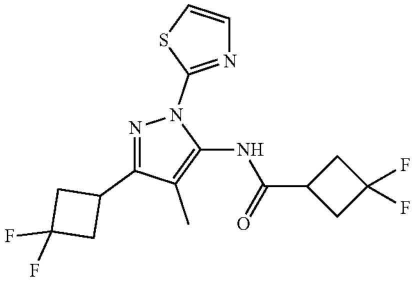 [SMILES: Cc1c(C2CC(F)(F)C2)nn(-c2nccs2)c1NC(=O)C1CC(F)(F)C1] | N-(3-(3,3-difluorocyclobutyl)-4-methyl-1-(thiazol-2-yl)-1H-pyrazol-5-yl)-3,3-difluorocyclo-butane-1-carboxamide |
| 550 | 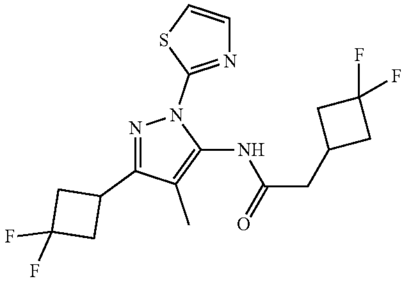 [SMILES: Cc1c(C2CC(F)(F)C2)nn(-c2nccs2)c1NC(=O)CC1CC(F)(F)C1] | 2-(3,3-difluorocyclobutyl)-N-(3-(3,3-difluorocyclobutyl)-4-meth-yl-1-(thiazol-2-yl)-1H-pyrazol-5-yl)acetamide |
| 551 | 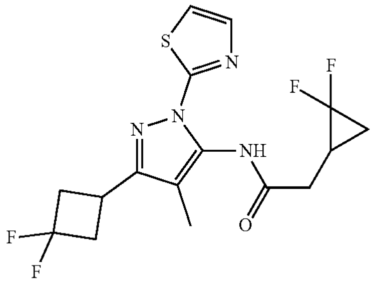 [SMILES: Cc1c(C2CC(F)(F)C2)nn(-c2nccs2)c1NC(=O)CC1CC1(F)F] | N-(3-(3,3-difluorocyclobutyl)-4-methyl-1-(thiazol-2-yl)-1H-pyrazol-5-yl)-2-(2,2-difluoro-cyclopropyl)acetamide |
| 552 | 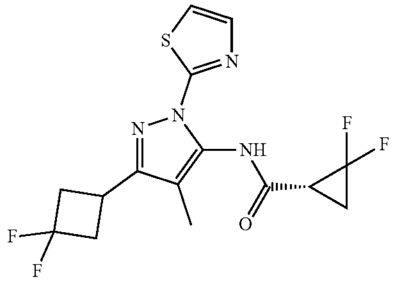 [SMILES: Cc1c(C2CC(F)(F)C2)nn(-c2nccs2)c1NC(=O)[C@H]1CC1(F)F] | (R)-N-(3-(3,3-difluorocyclobutyl)-4-methyl-1-(thiazol-2-yl)-1H-pyrazol-5-yl)-2,2-difluorocyclo-propane-1-carboxamide |

-continued

| Cmpd # | Structure | Name |
| --- | --- | --- |
| 553 | 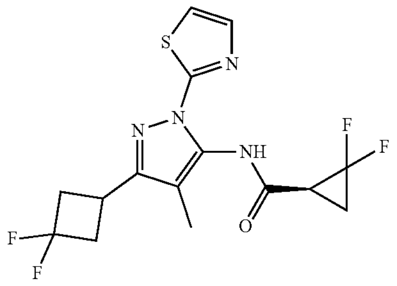 [SMILES: Cc1c(C2CC(F)(F)C2)nn(-c2nccs2)c1NC(=O)[C@@H]1CC1(F)F] | (S)-N-(3-(3,3-difluorocyclobutyl)-4-methyl-1-(thiazol-2-yl)-1H-pyrazol-5-yl)-2,2-difluorocyclo-propane-1-carboxamide |
| 554 | 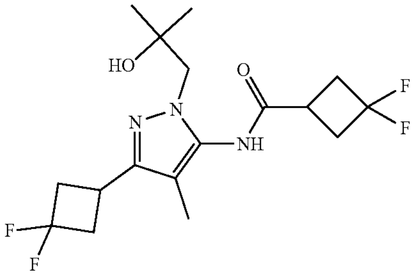 [SMILES: Cc1c(C2CC(F)(F)C2)nn(CC(C)(C)O)c1NC(=O)C1CC(F)(F)C1] | N-(3-(3,3-difluorocyclobutyl)-1-(2-hydroxy-2-methylpropyl)-4-methyl-1H-pyrazol-5-yl)-3,3-difluorocyclobutane-1-carboxamide |
| 555 | 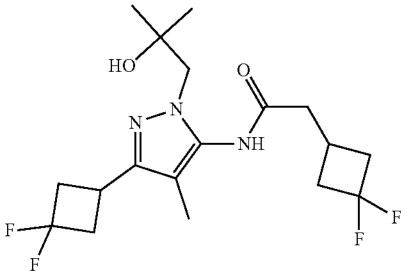 [SMILES: Cc1c(C2CC(F)(F)C2)nn(CC(C)(C)O)c1NC(=O)CC1CC(F)(F)C1] | 2-(3,3-difluorocyclobutyl)-N-(3-(3,3-difluorocyclobutyl)-1-(2-hydroxy-2-methylpropyl)-4-methyl-1H-pyrazol-5-yl)acetamide |
| 559 | 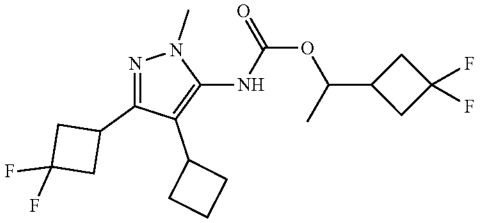 [SMILES: CC(OC(=O)Nc1c(C2CCC2)c(C2CC(F)(F)C2)nn1C)C1CC(F)(F)C1] | 1-(3,3-difluorocyclobutyl)ethyl (4-cyclobutyl-3-(3,3-difluoro-cyclobutyl)-1-methyl-1H-pyrazol-5-yl)carbamate |
| 560 | 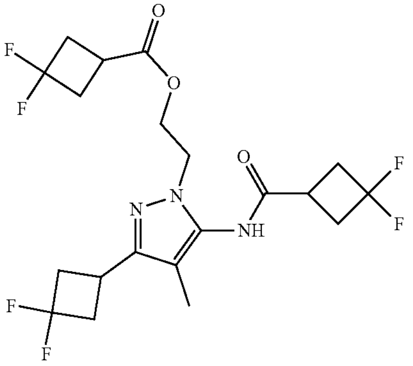 [SMILES: Cc1c(C2CC(F)(F)C2)nn(CCOC(=O)C2CC(F)(F)C2)c1NC(=O)C1CC(F)(F)C1] | 2-(5-(3,3-difluorocyclobutane-1-carboxamido)-3-(3,3-difluoro-cyclobutyl)-4-methyl-1H-pyrazol-1-yl)ethyl 3,3-difluoro-cyclobutane-1-carboxylate |

-continued

| Cmpd # | Structure | Name |
|---|---|---|
| 561 | 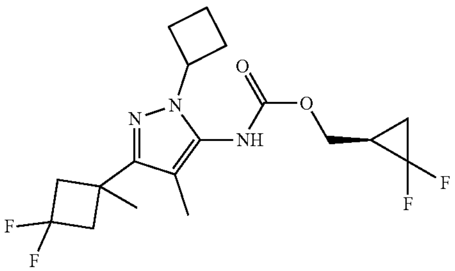 [SMILES: Cc1c(C2(C)CC(F)(F)C2)nn(C2CCC2)c1NC(=O)OC[C@H]1CC1(F)F] | (R)-(2,2-difluorocyclo-propyl)methyl (1-cyclobutyl-3-(3,3-difluoro-1-methylcyclobutyl)-4-methyl-1H-pyrazol-5-yl)carbamate |
| 562 | 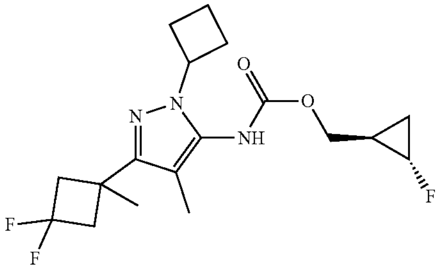 [SMILES: Cc1c(C2(C)CC(F)(F)C2)nn(C2CCC2)c1NC(=O)OC[C@H]1C[C@@H]1F] | ((1R,2S)-2-fluorocyclo-propyl)methyl (1-cyclobutyl-3-(3,3-difluoro-1-methylcyclobutyl)-4-methyl-1H-pyrazol-5-yl)carbamate |
| 564 | 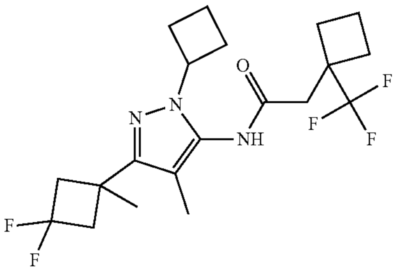 [SMILES: Cc1c(C2(C)CC(F)(F)C2)nn(C2CCC2)c1NC(=O)CC1(C(F)(F)F)CCC1] | N-(1-cyclobutyl-3-(3,3-difluoro-1-methylcyclobutyl)-4-methyl-1H-pyrazol-5-yl)-2-(1-(trifluoro-methyl)cyclobutyl)acetamide |
| 565 | 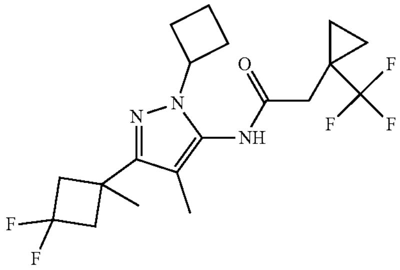 [SMILES: Cc1c(C2(C)CC(F)(F)C2)nn(C2CCC2)c1NC(=O)CC1(C(F)(F)F)CC1] | N-(1-cyclobutyl-3-(3,3-difluoro-1-methylcyclobutyl)-4-methyl-1H-pyrazol-5-yl)-2-(1-(trifluoro-methyl)cyclopropyl)acetamide |
| 568 | 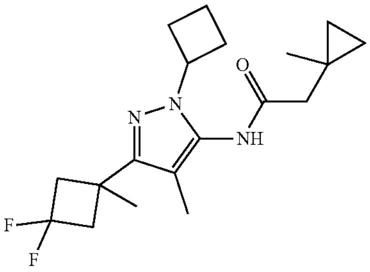 [SMILES: Cc1c(C2(C)CC(F)(F)C2)nn(C2CCC2)c1NC(=O)CC1(C)CC1] | N-(1-cyclobutyl-3-(3,3-difluoro-1-methylcyclobutyl)-4-methyl-1H-pyrazol-5-yl)-2-(1-methyl-cyclopropyl)acetamide |

-continued

| Cmpd # | Structure | Name |
|---|---|---|
| 569 | 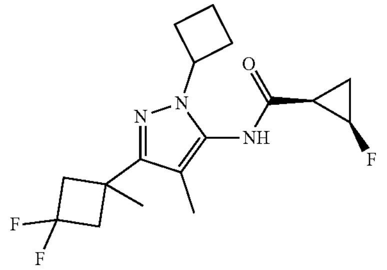 [SMILES: Cc1c(C2(C)CC(F)(F)C2)nn(C2CCC2)c1NC(=O)[C@H]1C[C@H]1F] | (1R,2R)-N-(1-cyclobutyl-3-(3,3-difluoro-1-methylcyclobutyl)-4-methyl-1H-pyrazol-5-yl)-2-fluorocyclopropane-1-carboxamide |
| 571 | 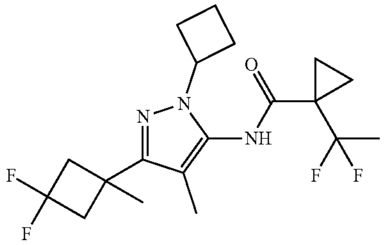 [SMILES: Cc1c(C2(C)CC(F)(F)C2)nn(C2CCC2)c1NC(=O)C1(C(C)(F)F)CC1] | N-(1-cyclobutyl-3-(3,3-difluoro-1-methylcyclobutyl)-4-methyl-1H-pyrazol-5-yl)-1-(1,1-difluoroethyl)cyclopropane-1-carboxamide |
| 574 | 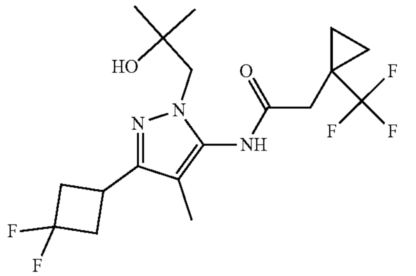 [SMILES: Cc1c(C2CC(F)(F)C2)nn(CC(C)(C)O)c1NC(=O)CC1(C(F)(F)F)CC1] | N-(3-(3,3-difluorocyclobutyl)-1-(2-hydroxy-2-methylpropyl)-4-methyl-1H-pyrazol-5-yl)-2-(1-(trifluoromethyl)cyclopropyl)acetamide. |

10. A pharmaceutical composition comprising the compound of claim 1, or a pharmaceutically acceptable salt thereof.

* * * * *